US010414825B2

(12) United States Patent
Flanagan et al.

(10) Patent No.: US 10,414,825 B2
(45) **Date of Patent: *Sep. 17, 2019**

(54) ANTI-MCAM ANTIBODIES AND ASSOCIATED METHODS OF USE

(71) Applicant: PROTHENA BIOSCIENCES LIMITED, Dublin (IE)

(72) Inventors: Kenneth Flanagan, Alameda, CA (US); Jeanne Baker, Redwood City, CA (US); Theodore A. Yednock, Forest Knolls, CA (US)

(73) Assignee: PROTHENA BIOSCIENCES LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/222,849

(22) Filed: Jul. 28, 2016

(65) Prior Publication Data

US 2017/0037144 A1 Feb. 9, 2017

Related U.S. Application Data

(63) Continuation of application No. 14/021,777, filed on Sep. 9, 2013, now Pat. No. 9,447,190.

(60) Provisional application No. 61/698,916, filed on Sep. 10, 2012, provisional application No. 61/797,179, filed on Nov. 30, 2012, provisional application No. 61/797,356, filed on Dec. 5, 2012.

(51) Int. Cl.

| | |
|---|---|
| ***C07K 16/00*** | (2006.01) |
| ***C07K 16/30*** | (2006.01) |
| ***C07K 16/28*** | (2006.01) |
| *A61K 39/00* | (2006.01) |

(52) U.S. Cl.

CPC ...... *C07K 16/3092* (2013.01); *C07K 16/2896* (2013.01); *C07K 16/30* (2013.01); *A61K 2039/505* (2013.01); *C07K 2317/24* (2013.01); *C07K 2317/30* (2013.01); *C07K 2317/56* (2013.01); *C07K 2317/565* (2013.01); *C07K 2317/567* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 5,859,205 | A | 1/1999 | Adair et al. | |
| 7,090,844 | B2 | 8/2006 | Bar-Eli et al. | |
| 7,456,260 | B2 | 11/2008 | Rybak | |
| 7,815,909 | B2 | 10/2010 | Heavner et al. | |
| 7,915,225 | B2 | 3/2011 | Finck | |
| 8,293,468 | B2 | 10/2012 | Prat et al. | |
| 9,017,682 | B2 | 4/2015 | Prat et al. | |
| 9,447,190 | B2 | 9/2016 | Flanagan et al. | |
| 10,059,761 | B2 | 8/2018 | Tam et al. | |
| 2003/0068319 | A1 | 4/2003 | Bar Eli | |
| 2003/0147809 | A1 | 8/2003 | Gudas | |
| 2006/0088523 | A1 | 4/2006 | Andya et al. | |
| 2007/0141057 | A1* | 6/2007 | Le | A61K 31/167 424/145.1 |
| 2011/0014183 | A1 | 1/2011 | Prat et al. | |
| 2011/0217237 | A1 | 9/2011 | Chen et al. | |
| 2013/0216556 | A1 | 8/2013 | Fowler et al. | |
| 2014/0227292 | A1 | 8/2014 | Flanagan et al. | |
| 2014/0314744 | A1 | 10/2014 | Flanagan et al. | |
| 2015/0218266 | A1 | 8/2015 | Prat et al. | |
| 2015/0239980 | A1 | 8/2015 | Flanagan et al. | |
| 2015/0259408 | A1 | 9/2015 | Tam et al. | |
| 2015/0259419 | A1 | 9/2015 | Liu et al. | |
| 2017/0002077 | A1 | 1/2017 | Tam et al. | |
| 2017/0002089 | A1 | 1/2017 | Liu | |
| 2017/0101470 | A1 | 4/2017 | Liu et al. | |
| 2017/0129954 | A1 | 5/2017 | Flanagan et al. | |
| 2017/0145109 | A1 | 5/2017 | Flanagan et al. | |
| 2017/0158755 | A1 | 6/2017 | Flanagan et al. | |
| 2018/0105602 | A1 | 4/2018 | Flanagan et al. | |
| 2018/0208646 | A1 | 7/2018 | Tam et al. | |

FOREIGN PATENT DOCUMENTS

| | | | |
|---|---|---|---|
| EP | 0 990 663 | A2 | 4/2000 |
| EP | 2234600 | B1 | 8/2014 |
| WO | WO 2003/057006 | A2 | 12/2002 |
| WO | WO 2003/057837 | A1 | 7/2003 |
| WO | WO 2003/057838 | A2 | 7/2003 |
| WO | WO 2007/058725 | A2 | 5/2007 |
| WO | WO 2009/028663 | A1 | 3/2009 |

(Continued)

OTHER PUBLICATIONS

Zhang et al. Generation and Characterization of a Panel of Monoclonal Antibodies Against Distinct Epitopes of Human CD146. Hybridoma; 27( 5):435-452, 2008. (Year: 2008).*

Hafner et al. Selection of mimotopes of the cell surface adhesion molecule Mel-CAM from a random pVIII-28aa phage peptide library. J. Invest Dermatol. 119:865-869, 2002 (Year: 2002).*

Stalin et al. Therapeutic and Diagnostic Antibodies to CD146: Thirty Years of Research on Its Potential for Detection and Treatment of Tumors. Antibodies 2017, 6, 17, pp. 1-13. (Year: 2017).*

U.S. Appl. No. 15/222,849 Requirement for Restriction/Election dated Nov. 16, 2017.

U.S. Appl. No. 15/222,848 Requirement for Restriction/Election dated Nov. 16, 2017.

(Continued)

*Primary Examiner* — Maher M Haddad

(74) *Attorney, Agent, or Firm* — Alston & Bird LLP

(57) ABSTRACT

Described herein are anti-MCAM antibodies and antigen binding fragments thereof that are capable of inhibiting the interaction between MCAM and its ligand, a protein comprising a laminin α-4 chain. These anti-MCAM antibodies and antigen binding fragments thereof may be useful for, for example, treating inflammatory conditions characterized by the infiltration of MCAM-expressing cells into a site of inflammation in the body.

25 Claims, 46 Drawing Sheets

Specification includes a Sequence Listing.

(56) References Cited

FOREIGN PATENT DOCUMENTS

| | | | |
|---|---|---|---|
| WO | WO 2009/054435 | A1 | 4/2009 |
| WO | WO 2009/064854 | A2 | 5/2009 |
| WO | WO 2009/093138 | A1 | 7/2009 |
| WO | WO 2011/100477 | A2 | 8/2011 |
| WO | WO 2012/024187 | A1 | 2/2012 |
| WO | WO 2012/170071 | A1 | 12/2012 |
| WO | WO 2012/170071 | A2 | 12/2012 |
| WO | WO 2013/164789 | A1 | 11/2013 |
| WO | WO 2013/186700 | A1 | 12/2013 |
| WO | WO 2014/039975 | A2 | 3/2014 |
| WO | WO 2014/039975 | A3 | 3/2014 |
| WO | WO 2015/061584 | A1 | 4/2015 |
| WO | WO 2015/136468 | A1 | 9/2015 |
| WO | WO 2015/136469 | A1 | 9/2015 |
| WO | WO 2015/136472 | A1 | 9/2015 |
| WO | WO 2015/136570 | A1 | 9/2015 |
| WO | WO 2017/046774 | A2 | 3/2017 |
| WO | WO 2017/046776 | A2 | 3/2017 |
| WO | WO 2017/149513 | A1 | 9/2017 |
| WO | WO 2017/208210 | A1 | 12/2017 |
| WO | WO 2018/223140 | A1 | 12/2018 |

OTHER PUBLICATIONS

U.S. Appl. No. 14/656,619 Notice of Allowance dated Nov. 2, 2017.

U.S. Appl. No. 15/125,570 Requirement for Restriction/Election dated Dec. 7, 2017.

U.S. Appl. No. 15/268,178 Requirement for Restriction/Election dated Dec. 7, 2017.

Awad, et al., "Cyclophosphamide in multiple sclerosis scientific rationale, history and novel treatment paradigms," *Ther Adv Neurol Disord,* 2(16) 357-368 (2009).

U.S. Appl. No. 14/124,620 Non/Final Office Action dated Jan. 19, 2018.

U.S. Appl. No. 14/656,619 Final Office Action dated Jun. 13, 2017.

Galvez, "Role of Th17 Cells in the Pathogenesis of Human IBD," *ISRN Inflammation,* vol. 201.4, Article ID 938461, 14 pages, retrieved from <http://dx.doi.org/10.1155/2014/928461> (2014).

Archelos, et al., "Inhibition of Experimental Autoimmune Encephalomyelitis by an Antibody to the Intercellular Adhesion Molecule ICAM-1," Ann Neurol, 34:145-154 (1993).

Bardin, et al., "Identification of the S-Endo 1 endothelial-associated antigen," *Biochem Biophys Res Commun,* 5;218(1):210-216, (Jan. 1996).

Bar-Eli, "Molecular mechanisms of melanoma metastasis," *J Cell Physiol,* 173(2):275-278, (Nov. 1997).

Bar-Eli, "Role of AP-2 in tumor growth and metastasis of human melanoma." *Cancer Metastasis Rev,*18(3):377-385, (1999).

Beutel, et al., "Possible Implications of MCAM Expression in Metastasis and Non-Metastatic of Primary Uveal Melanoma Patients," *Current Eye Research,* 34(11, 1004-1009, (2009).

Brucklacher-Waldert, et al., "Phenotypical and functional characterization of T helper 17 cells in multiple sclerosis," *Brain,* 132:3329-3341 (2009).

Bu, et al., "Anti-CD146 monoclonal antibody AA98 inhibits angiogenesis via suppression of nuclear factor-κB activation", *Mol Cancer Ther.,* 5(11)2872-2878 (Nov. 2006).

Chen, et al., "Is CD146 pivotal in neoplasm invasion and blastocyst embedding?" *Med Hypotheses,* 76(3):378-380, (Mar. 2001).

Dagur, et al., "MCAM-expressing CD4(+) T cells in Peripheral Blood Secrete IL-17A and are Significantly Elevated in Inflammatory Autoimmune Diseases," *J Autoimmun,* 37(4):319-27 (Dec. 2011).

Dehahn, et al., "The α4 laminin subunit regulates endothelial cell survival", Experimental Cell Research, 294:281-289, (2004).

Denton, et al., "A study of adhesion molecules as markers of progression in malignant melanoma," *J Pathol,* 167(2):187-191, (Jun. 1992).

Despoix, et al., "Mouse CD146/MCAM is a marker of natural killer cell maturation," *Eur J Immunol,* 38(10):2855-64 (2008).

Duan, et al., "Targeting endothelial CD146 attenuates neuroinflammation by limiting lymphocyte extravasation to the CNS," *Sci Rep.* 3:1687:1-11, (2013).

Duda, et al., "Differential CD146 expression on circulating versus tissue endothelial cells in rectal cancer patients: implications for circulating endothelial and progenitor cells as biomarkers for antiangiogenic therapy," *J Clin Oncol.,* 20;24(9):1449-53, (Mar. 20, 2006).

Dye, et al., "hShroom1 links a membrane bound protein to the actin cytoskeleton. Cell Mol Life Sci," 66(4):681-696, (Feb. 2009).

Dye, et al., "Melanoma Biomolecules: Independently Identified but Functionally Intertwined," *Front Oncol.,* 3:252:1-17, (Sep. 24, 2013).

Elmageed, et al., "Clinical significance of CD146 and latexin during different stages of thyroid cancer," *Mol Cell Biochem,* 381:95-103 (2013).

Elshal, et al., "A unique population of effector memory lymphocytes identified by CD146 having a distinct immunophenotypic and genomic profile," *BMC Immunol.,* 8:29:1-15, (Nov. 13, 2007).

Elshal, et al., "CD146 (Mel-CAM), an adhesion marker of endothelial cells, is a novel marker of lymphocyte subset activation in normal peripheral blood," *Blood,* 106(8):2923-2924, (Oct. 15, 2005).

EP Application No. 13836030.0 (Published as EP 2892562), Supplementary European Search Report and European Search Opinion, dated Apr. 4, 2016.

Feng, et al., "CD146 gene expression in clear cell renal cell carcinoma: a potential marker for prediction of early recurrence after nephrectomy," *Int Urol Nephrol,* 44:1663-1669 (2012).

Filshie, et al., "MUC18, a member of the immunoglobulin superfamily, is expressed on bone marrow fibroblasts and a subset of hematological malignancies," *Leukemia,* 12:414-421 (1998).

Flanagan, et al., "Laminin-411 Is a Vascular Ligand for MCAM and Facilitates TH17 Cell Entry into the CNS," *PLoS One,* vol. 7, Issue 7, (2012).

Flanagan, et al., "Laminin-411 Is a vascular ligand for MCAM and facilitates TH17 cell entry into the CNS," *PLoS One,* 7(7):1-11, (2012).

Freeman, et al., "Evaluation of a multi-marker immunomagnetic enrichment assay for the quantification of circulating melanoma cells," *J Transl Med.,* 10:192:1-9, (Sep. 15, 2012).

Geberhiwot, et al., "Rapid communication Erythromegakaryocytic Cells Synthesize Laminin-8 (α4β1γ1)", Experimental Cell Research, 254:189-195, (2000).

Gonzales, et al., "Structure and Function of a Vimentin-associated Matrix Adhesion in Endothelial Cells", Molecular biology of the Cell, vol. 12, 85-100 (Jan. 2001).

Gonzalez, et al., "Complex interactions between the laminin α4 subunit and integrins regulate endothelial cell behavior in vitro and angiogenesis in vivo", PNAS, vol. 99, No. 25, 16075-16080 (Dec. 10, 2002).

Gould Rothberg, et al., "Tissue biomarkers for prognosis in cutaneous melanoma: a systematic review and meta-analysis," *J Natl Cancer Inst,* 1;101(7):452-474, (Apr. 2009).

Grimm, et al., "Ectopic expression of carcinoembryonic antigen by a melanoma cell leads to changes in the transcription of two additional cell adhesion molecules," *Cancer Res.,* 55(15):3254-3257, (Aug. 1, 1995).

Guezguez, et al., "A dileucine motif targets MCAM-1 cell adhesion molecule to the basolateral membrane in MDCK cells," *FEBS Lett,* 580(15):3649-3656. (Jun. 26, 2006).

Guezguez, et al., "Dual role of Melanoma Cell Adhesion Molecule (MCAM)/CD146 in Lymphocyte Endothelium Interaction: MCAM/CD146 Promotes Rolling via Microvilli Induction in Lymphocyte and is an Endothelial Adhesion Receptor," *Journal of Immunology,* 179:6673-6685 (2007).

Guezguez, et al., "Dual role of melanoma cell adhesion molecule MCAM)/CD146 in lymphocyte endothelium interaction: MCAM/CD146 promotes rolling via microvilli induction in lymphocyte and is an endothelial adhesion receptor," *J Immunol.,* 79(10):6673-6685, (Nov. 15, 2007).

(56) References Cited

OTHER PUBLICATIONS

Hadjinicolaou, et al., "Relationship of CD146 expression to activation of circulating T cells: exploratory studies in healthy donors and patients with connective tissue disease," *Clin Exp Immunol.*, 174(1):73-88 (Oct. 2013).
Hansen, et al., "Laminin-8/9 is synthesized by a rat glomerular mesangial cells and is required for PDGF-induced mesangial cell migration", Kidney International, vol. 64, pp. 110-118, (2003).
Heimberger, et al., "Loss of the AP-2alpha transcription factor is associated with the grade of human gliomas," *Clin Cancer Res.*, 11(1):267-272, (Jan. 1, 2005).
Huang, et al., "LAMA4, highly expressed in human hepatocellular carcinoma from Chinese patients, is a novel marker of tumor invasion and metastasis", J. Cancer Res. Clin. Oncol., 134:705-714, (2008).
Hung, et al., "The motor protein KIF14 inhibits tumor growth and cancer metastasis in lung adenocarcinoma," *PLoS One,* 8(4):1-14, (Apr. 23, 2013).
Imbert, et al., "CD146 expression in human breast cancer cell lines induces phenotypic and functional changes observed in Epithelial to Mesenchymal Transition," *PLoS One,* 7(8):1-8, (2012).
Ishikawa, et al., "Monoclonal antibodies to human laminin α4 chain globular domain inhibit tumor cell adhesion and migration on laminins 411 and 421, and binding of α6β31 integrin and MCAM to α4-laminins", Matrix Biology, 36:5-14 (2014).
Jarasch, et al., "Developability Assessment During the Selection of Novel Therapeutic Antibodies", *Journal of Pharmaceutical Sciences,* 104:1855-1898 (2015).
Jean, et al., "Loss of AP-2 results in up-regulation of MCAM/MUC18 and an increase in tumor growth and metastasis of human melanoma cells," *J Biol Chem.*, 273(26):16501-16508, (Jun. 26, 1998).
Jean, et al., "Targeting the ATF-1/CREB transcription factors by single chain Fv fragment in human melanoma: potential modality for cancer therapy," *Crit Rev Immunol,* 21(1-3):275-86, (2001).
Jiang, et al., "CD146 is a coreceptor for VEGFR-2 in tumor angiogenesis. *Blood,"* 120(11):2330-2339, (Sep. 13, 2012).
Johnson, "Cell adhesion molecules in the development and progression of malignant melanoma," Cancer Metastasis Rev,18(3):345-357,(1998).
Johnson, "Cell adhesion molecules of the immunoglobulin supergene family and their role in malignant transformation and progression to metastatic disease," Cancer Metastasis Rev. 10(1):11-22, (May 1991).
Johnson, et al, "MUC18: A cell adhesion molecule with a potential role in tumor growth and tumor cell dissemination," *Curr Top Microbiol Immunol,* 213 ( Pt 1):95-105, (1996).
Johnson, et al., "Functional aspects of three molecules associated with metastasis development in human malignant melanoma," *Invasion Metastasis,* 9(6):338-350, (1989).
Johnson, et al., "Melanoma Progression-Associated Glycoprotein MUC18/MCAM Mediates Homotypic Cell Adhesion Through Interaction With a Heterophilic Ligand," *Int. J. Cancer,* 73:769-774 (1997).
Johnson, et al., "The progression associated antigen MUC18: a unique member of the immunoglobulin supergene family," *Melanoma Res,* 3(5):337-340, (Oct. 1993).
Kamiyama, et al., Coexpression of CCR6 and CD146 (MCAM) is a marker of effector memory T-helper 17 cells, J Dermatol. 39(10):838-842, (Oct. 2012).
Kapoor, et al., "CD146 expression and its close relationship to tumor progression in systemic malignancies besides gall bladder carcinomas," *Tumour Biol.,* 34(2):1273-4 (Apr. 2013).
Katagiri, et al., "Screening of integrin-binding peptides from the laminin α4 and α5 chain G domain peptide library", Archives of Biochemistry and Biophysics, 521:32-42, (2012).
Kraus, et al, "Analysis of the expression of intercellular adhesion molecule-1 and MUC18 on benign and malignant melanocytic lesions using monoclonal antibodies directed against distinct epitopes and recognizing denatured, non-glycosylated antigen," *Melanoma Res,* Suppl 2:S75-81, (Aug. 1997).
Kristiansen, et al., "Expression of the cell adhesion molecule CD146/MCAM in non-small cell lung cancer," *Anal Cell Pathol.,* 25(2):77-81, (2003).
Lai, et al., "Expression and distribution of MUC18 in human uveal melanoma," *Virchows Arch,* 451(5):967-76, (Nov. 2007).
Larochelle, et al., "Melanoma cell adhesion molecule identifies encephalitogenic T lymphocytes and promotes their recruitment to the central nervous system," *Brain,* 135(Pt 10):2906-2924, (Oct. 2012).
Larochelle, et al., "Melanoma Cell Adhesion Molecule-jPositive CD8 T Lymphocytes Mediate Central Nervous System Inflammation", 78(1):39-53 (2015).
Lehmann, et al., "MUC18, a marker of tumor progression in human melanoma, shows sequence similarity to the neural cell adhesion molecules of the immunoglobulin superfamily," *Proc Natl Acad Sci U S A,* 1989 (24):9891-9895, (Dec. 1986).
Lei, et al., "The multifaceted role of CD146/MCAM in the promotion of melanoma progression", *Cancer Cell International,* 15:3 1-11 (2015).
Leslie, et al., "Immunization against MUC18/MCAM, a novel antigen that drives melanoma invasion and metastasis," *Gene Ther,* 14(4):316-323, (Oct 5, 2006).
Leslie, et al., "Regulation of gene expression in melanoma: new approaches for treatment," *J Cell Biochem,* 94(1):25-38, (Jan. 2005).
Li, et al., "Increased expression of CD146 and microvessel density (MVD) in invasive micropapillary carcinoma of the breast: Comparative study with invasive ductal carcinoma-not otherwise specified," *Pathol Res Pract,* 207(12):739-746, (Dec. 15, 2011).
Li, et al., "Reciprocal regulation of MelCAM and AKT in human melanoma," *Oncogene,* 9;22(44):6891-6899. (Oct 2003).
Lian, et al., "Identification of an active site on the laminin α4 chain globular domain that binds to αvβ3 integrin and promotes angiogenesis", Biochemical and Biophysical Research Communications, 347:248-253, (2006).
Liu, et al., "Hypermethylation of MCAM gene is associated with advanced tumor stage in prostate cancer," *Prostate,* 68(4):418-426, (Mar. 1, 2008).
Ljubimova, et al., "Association between laminin-8 and glial tumor grade, recurrence, and patient survival," *Cancer,* 1;101(3):604-612, (Aug. 1, 2012).
Llie, et al., "Clinical value of circulating endothelial cells and of soluble CD146 levels in patients undergoing surgery for non-small cell lung cancer.," *Br J Cancer,* (Jan. 28, 2014).
Loricera, et al., "Tocilizumab in giant cell arteritis: Multicenter open-label study of 22 patients", *Seminars in Arthritis and Rheumotisum,* 44:717-723 (2015).
Luca, et al., "Direct correlation between MUC18 expression and metastatic potential of human melanoma cells," *Melanoma Res,* 3(1):35-41. (Feb. 1993).
Luca, et al., "Molecular changes in human melanoma metastasis," *Histol Histopathol,* 13(4):1225-1231, (Oct. 1998).
Luo, et al., "Recognition of CD146 as an ERM-binding protein offers novel mechanisms for melanoma cell migration," *Oncogene,* 31(3):306-321, (Jan. 19, 2012).
Ma, et al., "Synergistic killing effect between vorinostat and target of CD146 in malignant cells," *Clin Cancer Res,* 1;16(21):5165-5176, (Nov. 2010).
Maggi, et al., "CD161 is a marker of all human IL-17-producing T-cell subsets and is induced by RORC," *Eur J Immunol,* 40(8):2174-2181, (Aug. 2010).
Malpass, "Disease mechanisms in MS: Cell adhesion molecule MCAM on pathogenic T cells—a green light for CNS entry in multiple sclerosis," *Nat Rev Neurol,* 8(11):592, (Nov. 5, 2012).
Mantovani, "Inflaming metastasis," Nature, 457:36-37, (2009).
Matsuura, et al., "Localization of the Laminin αChain in the Skin and Identification of a Heparin-Dependent Cell Adhesion site within the Laminin α4 Chain C-Terminal LG 4 Module," The Journal of Investigative Dermatology, 122:614-620 (2004).

(56) References Cited

OTHER PUBLICATIONS

McGary, et al., "A fully human antimelanoma cellular adhesion molecule/MUC18 antibody inhibits spontaneous pulmonary metastasis of osteosarcoma cells in vivo," *Clin Cancer Res,* 15;9(17):6560-6566, (Dec. 2003).
McGary, et al., "Cellular adhesion pathways and metastatic potential of human melanoma," *Cancer Biol Ther,* 1(5):459-465, (Sep.-Oct. 2002).
Melnikova, et al., "Bioimmunotherapy for melanoma using fully human antibodies targeting MCAM/MUC18 and IL-8," *Pigment Cell Res,* 19(5):395-405, (Oct. 2006).
Mills, et al., "Fully human antibodies to MCAM/MUC18 inhibit tumor growth and metastasis of human melanoma," *Cancer Res,* 1;62(17):5106-5114, (Sep. 2002).
Minato, et al., "Comparative immunohistochemical analysis of IMP3, GLUT1, EMA, CD146, and desmin for distinguishing malignant mesothelioma from reactive mesothelial cells," *Am J Clin Pathol,* 141(1):85-93, (Jan. 2014).
Mintz-Weber, et al., "Identification of the elements regulating the expression of the cell adhesion molecule MCAM/MUC18. Loss of AP-2 is not required for MCAM expression in melanoma cell lines," *J Biol Chem,* 3;275(44):34672-34680, (Nov. 2000).
Neidhart, et al., "Synovial fluid CD146 (MUC18), a marker for synovial membrane angiogenesis in rheumatoid arthritis," *Arthritis Rheum,* 42(4):622-630, (Apr. 1999).
Nobbmann, et al., "Dynamic light scattering as a relative tool for assessing the molecular integrity and stability of monoclonal antibodies", *Biotechnology and Genetic Engineering Review,* vol. 24, 117-128 (2007).
Nyormoi, et al., "Transcriptional regulation of metastasis-related genes in human melanoma," *Clin Exp Metastasis,* 20(3):251-63, (2003).
Ody, et al., "Surface molecules involved in avian T-cell progenitor migration and differentiation," *Dev Immunol,* 7(2-4):267-277, (2007).
Oikawa, et al., "Melanoma cells produce multiple laminin isoforms and strongly migrate on α5 laminin(s) via several integrim receptors", Experimental Cell Research, 317:1110-1133, (2011).
Oka, et al., "The expression of CD146 predicts a poor overall survival in patients with adenocarcinoma of the lung," *Anticancer Res.,* 32(3):861-4 (2012).
Okazaki, et al., "CD146 and insulin-like growth factor 2 mRNA-binding protein 3 predict prognosis of asbestos-induced rat mesothelioma," *Cancer Sci,* 104(8):989-995, (Aug. 2013).
Okumura, et al., "Involvement of gicerin in the extension of microvilli," *Exp Cell Res,* 271(2):269-276, (Dec. 10, 2001).
Ouhtit, et al., "Towards understanding the mode of action of the multifaceted cell adhesion receptor CD146," *Biochim Biophys Acta,* 1795(2):130-136. (Apr. 2009).
Pacifico, et al., "Development of a tissue array for primary melanoma with long-term follow-up: discovering melanoma cell adhesion molecule as an important prognostic marker," *Plast Reconstr Surg.,* 115(2):367-75, (2005).
Pantel, et al., "Early metastasis of human solid tumours: expression of cell adhesion molecules," *Ciba Found Symp,* 189:157-170; (1995).
Pardo, et al., "The characterization of the invasion phenotype of uveal melanoma tumour cells shows the presence of MUC18 and HMG-1 metastasis markers and leads to the identification of DJ-1 as a potential serum biomarker," *Int J Cancer,* 1;119(5):1014-1022, (Sep. 2006).
PCT/IB2015/051785 International Preliminary Report on Patentability and Written Opinion dated Sep. 13, 2016.
PCT/IB2015/051785 International Search Report and Written Opinion dated Jul. 23, 2015.
PCT/IB2015/051786 International Preliminary Report on Patentability and Written Opinion dated Sep. 13, 2016.
PCT/IB2015/0517863 International Search Report and Written Opinion dated Aug. 26, 2015.
PCT/IB2015/0517863 Invitation to Pay Additional Fees and, Where Applicable, Protest Fee dated Jun. 17, 2015.
PCT/IB2015/051787 International Preliminary Report on Patentability and Written Opinion dated Sep. 13, 2016.
PCT/IB2015/051787 International Search Report and Written Opinion dated Jun. 22, 2015.
PCT/IB2015/051789 International Search Report and Written Opinion dated Aug. 13, 2015.
PCT/IB2015/051790 International Preliminary Report on Patentability and Written Opinion dated Sep. 13, 2016.
PCT/IB2015/051790 International Search Report and Written Opinion dated Jun. 25, 2015.
PCT/IB2016/055557 Invitation to Pay Additional Fees and, Where Applicable, Protest Fee dated Dec. 6, 2016.
PCT/US2012/000274 International Preliminary Report of Patentability and Written Opinion dated Dec. 10, 2013.
PCT/US2012/000274 International Search Report dated Sep. 26, 2012.
PCT/US2013/058773 International Search Report and Written Opinion dated Apr. 16, 2014.
PCT/US2013/058773 Invitation to Pay Additional Fees and, Where Applicable, Protest Fee dated Jan. 23, 2014.
PCT/US2013/058773 Preliminary report on Patentability dated Mar. 19, 2015.
Perego, et al., "Heterogeneous phenotype of human melanoma cells with in vitro and in vivo features of tumor-initiating cells," *J Invest Dermatol,* 130(7):1877-1886, (Jul. 2010).
Petajaniemi, et al., "Localization of laminin alpha4-chain in developing and adult human tissues," *J Histochem Cytochem,* 50(8):1113-1130, (Aug. 2002).
Pickl, et al., "MUC18/MCAM (CD146), an activation antigen of human T lymphocytes," *J Immunol,* 158(5):2107-2115, (Mar. 1, 1997).
Pierce, et al., "Expression of Laminin α3, α4, and α5 Chains by Alveolar Epithelial Cells and Fibroblasts", American Journal of Respiratory Cell and Molecular Biology, vol. 19, pp. 237-244 (1998).
Pires, et al., "Mel-CAM (CD146) expression in parotid mucoepidermoid carcinoma," *Oral Oncology,* 39:277-281 (2003).
Pujades, et al., "Melanoma Cell Adhesion Molecule (MCAM) expression in the myogenic lineage during early chick embryonic development," *Int J Dev Biol,* 46(2):263-266, (Mar. 2002).
Rapanotti, et al., "Blood MUC-18/MCAM expression in patients with melanoma: a suitable marker of poor outcome," *Br J Dermatol,* 169(1):221-222, (Jul. 2013).
Rapanotti, et al., "Melanoma-associated markers expression in blood: MUC-18 is associated with advanced stages in melanoma patients," *Br J Dermatol,* 160(2):338-344, (Feb. 2008).
Reboldi, et al., "C—C chemokine receptor 6—regulated entry of TH-17 cells into the CNS through the choroid plexus is required for the initiation of EAE," *Nat Immunol,* 10(5):514-523, (May 2009).
Reid, et al., "Markers of circulating tumour cells in the peripheral blood of patients with melanoma correlate with disease recurrence and progression," *Br J Dermatol,* 168(1):85-92. (Jan. 2013).
Rice, et al., "Anti-α4 integrin therapy for multiple sclerosis", *Neurology,* 64:1336-1342 (2005).
Roep, et al., "The problems and promises of research into human immunology and autoimmune disease", Nature Medicine, 18(1):48-53 (2012).
Romagnani, et al., "Properties and origin of human Th17 cells," *Mol Immunol,* 47(1):3-7, (Nov. 2009).
Rossi, et al., "Vascular inflammation in central nervous system diseases: adhesion receptors controlling leukocyte-endothelial interactions," Journal of Leukocyte Biology, 89:529-556 (2011).
Sato, et al., "Immunocytochemistry of CD146 is useful to discriminate between malignant pleural mesothelioma and reactive mesothelium," *Mod Pathol,* 23(11):1458-1466, (Nov. 2010).
Satyamoorthy, et al., "Mel-CAM-specific genetic suppressor elements inhibit melanoma growth and invasion through loss of gap junctional communication," *Oncogene,* 2;20(34):4676-4684, (Aug. 2001).
Schiano, et al., "Different expression of CD146 in human normal and osteosarcoma cell lines," *Med Oncol,* 29(4):2998-3002. (Dec. 2012).

(56) References Cited

OTHER PUBLICATIONS

Schlagbauer-Wadl, et al., "Influence of MUC18/MCAM/CD146 expression on human melanoma growth and metastasis in SCID mice," *Int J Cancer,* 11;81(6):951-955, (Jun. 1999).
Schrage, et al., "Murine CD146 is widely expressed on endothelial cells and is recognized by the monoclonal antibody ME-9F1," *Histochem Cell Biol,*129(4):441-451, (Apr. 2008).
Schwarz, et al., "Melanoma-associated adhesion molecule MUC18/ MCAM (CD146) and transcriptional regulator mader in normal human CNS," *Neuroimmunomodulation,* 5(5):270-276, (Sep.-Oct. 1998).
Sers, et al., "Genomic organization of the melanoma-associated glycoprotein MUC18: implications for the evolution of the immunoglobulin domains," *Proc Natl Acad Sci USA,* 15;90(18):8514-8518, (Sep. 1993).
Sers, et al., "MUC18, a melanoma-progression associated molecule, and its potential role in tumor vascularization and hematogenous spread," *Cancer Res,* 1;54(21):5689-5694. (Nov. 1994).
Shih et al., "A New Mel-Cam (CD146)-Specific Monoclonal Antibody, MN-4, On Paraffin-Embedded Tissue", *Modern Pathology,* 11(11):1098-1106, (1998).
Shih, "The role of CD146 (Mel-CAM) in biology and pathology," *J Pathol,* 189(1):4-11, (Sep. 1999).
Shih, et al., "Melanoma cell-cell interactions are mediated through heterophilic Mel-CAM/ligand adhesion," *Cancer Res,* 1;57(17):3835-3840, (Sep. 1997).
Shih, et al., "Regulation of Mel-CAM/MUC18 expression on melanocytes of different stages of tumor progression by normal keratinocytes," *Am J Pathol,* 145(4):837-845, (Oct. 1994).
Shih, et al., "The cell-cell adhesion receptor Mel-CAM acts as a tumor suppressor in breast carcinoma," *Am J Pathol,* 151(3):745-751, (Sep. 1997).
Sixt, et al., "Endothelial cell laminin isoforms, laminins 8 and 10, play decisive roles in T cell recruitment across the blood-brain barrier in experimental autoimmune encephalomyelitis," *J Cell Biol,* 28;153(5):933-946, (May 2001).
Solovey, et al., "Identification and functional assessment of endothelial P1H12," *J Lab Clin Med,* 138(5):322-331, (Nov. 2001).
Takaha, et al., "Expression of gicerin in development, oncogenesis and regeneration of the chick kidney," *Differentiation,* 58(5):313-320, (Jun. 1995).
Talts, et al., "Structural and Functional Analysis of the Recombinant G. Domain of the Laminin α4 Chain and its Proteolytic Processing in Tissues", The Journal of Biological Chemistry, vol. 275, No. 45, pp. 35192-35199, (Nov. 10, 2000).
Tian, et al., "CD146 protein as a marker to predict postoperative liver metastasis in colorectal cancer," *Cancer Biother Radiopharm,* 28(6):466-470, (Jul.-Aug. 2013).
Tsuchiya, et al., Gicerin, a cell adhesion molecule, promotes the metastasis of lymphoma cells of the chicken, *Cell Tissue Res,* 314(3):389-397, (Dec. 2003).
Tsukamoto, et al., "E. Gicerin, an Ig-superfamily cell adhesion molecule, promotes the invasive and metastatic activities of a mouse fibroblast cell line," *J Cell Physiol,* 197(1):103-109, (Oct. 2003).
Tsukamoto, et al., "Expression of gicerin enhances the invasive and metastatic activities of a mouse mammary carcinoma cell line," *Int J Oncol,* 23(6):1671-1677, (Dec. 2003).
Tsukamoto, et al., "Involvement of gicerin, a cell adhesion molecule, in development and regeneration of oviduct and metastasis of oviductal adenocarcinomas of the chicken," *Exp Cell Res,* 247(2):329-338, (Mar. 15, 1999).
Tsukamoto, et al., The role of gicerin, a novel cell adhesion molecule, in development, regeneration and neoplasia, *Histol Histopathol,* 16(2):563-571, (Apr. 2001).
U.S. Appl. No. 14/021,777 Final Office Action dated Jan. 29, 2016.
U.S. Appl. No. 14/021,777 Non-Final Office Action dated Sep. 16, 2015.
U.S. Appl. No. 14/021,777 Notice of Allowance dated Apr. 25, 2016.
U.S. Appl. No. 14/021,777 Restriction Requirement dated Apr. 14, 2015.
U.S. Appl. No. 14/124,620 Final Office Action dated Sep. 22, 2016.
U.S. Appl. No. 14/124,620 Non-Final Office Action dated Feb. 24, 2016.
U.S. Appl. No. 14/124,620 Restriction Requirement dated Sep. 23, 2015.
U.S. Appl. No. 14/427,290 Final Office Action dated Feb. 2, 2017.
U.S. Appl. No. 14/656,619 Non-Final Office Action dated Dec. 28, 2016.
U.S. Appl. No. 14/656,619 Restriction Requirement dated Aug. 11, 2016.
Vaninio, et al., "HEMCAM, an adhesion molecule expressed by c-kit+ hemopoietic progenitors," *J Cell Biol,* 135(6 Pt 1):1655-1668, (Dec. 1996).
Wang, et al., "A novel 'piipeline' system for downstream preparation of therapeutic monoclonal antibodies", *Biotechmol Lett,* 35:1411-1419, (2013).
Wang, et al., "CD146, a multi-functional molecule beyond adhesion," *Cancer Lett,* 330(2):150-162, (Apr. 28, 2013).
Wang, et al., "Identification of CD146 expression, angiogenesis, and lymphangiogenesis as progression, metastasis and poor-prognosis related markers for gallbladder adenocarcinoma," *Tumor biol.,* 33:173-182 (2012).
Waston-Hurst, et al., "The role of N-cadherin, MCAM and beta3 integrin in melanoma progression, proliferation, migration and invasion," *Cancer Biol Ther,* 5(10):1375-1382, (Oct. 2006).
Wellbrock, et al., "CD146: a new partner for VEGFR2," *Blood,* 13;120(11):2164-2165, (Sep. 2012).
Weninger, et al., "Keratinocytes express the CD146 (Muc18/S-endo) antigen in tissue culture and during inflammatory skin diseases," *J Invest Dermatol,* 115(2):219-224, (Aug. 2000).
Witze, et al., "Wnt5a control of cellpolarity and directional movement by polarized redistribution of adhesion receptors," *Science,* 320(5874):365-369, (Apr. 2008).
Wong, et al., "The role of immunoglobulin superfamily cell adhesion molecules in cancer metastasis," *Int J Cell Biol,* ;2012:340296, (2012).
Wu, et al., "Ectopical expression of human MUC18 increases metastasis of human prostate cancer cells," *Gene,* 327(2):201-213. (Mar. 2004).
Wu, et al., "Endothelial basement membrane laminin alpha5 selectively inhibits T lymphocyte extravasation into the brain," *Nat Med,* 15(5):519-27. (May 2009).
Wu, et al., "Enforced expression of MCAM/MUC18 increases invitro motility and invasiveness and in vivo metastasis of two mouse melanoma K1735 sublines in a syngeneic mouse model," *Mol Cancer Res,* 6(11):1666-1677 (Nov. 2008).
Wu, et al., "Enforced expression of METCAM/MUC18 increases tumorigenesis of human prostate cancer LNCaP cells in nude mice," *J Urol,* 185(4):1504-1512, (Apr. 2011).
Wu, et al., "Expression of a human cell adhesion molecule, MUC18, in prostate cancer cell lines and tissues," *Prostate,* 48(4):305-315 (Sep. 2001).
Wu, et al., "MCAM is a novel metastasis marker and regulates spreading, apoptosis and invasion of ovarian cancer cells," *Tumour Biol,* 33(5):1619-1628, (Oct. 2012).
Xie, et al., "Expression of MCAM/MUC18 by human melanoma cells leads to increased tumor growth and metastasis," *Cancer Res,* 1;57(11):2295-2303, (Jun. 1997).
Yamashita, et al., "Cryptic fragment α4 LEG4-5 derived from laminin α4 chain inhibits de novo adipogenesis by modulating the effect of fibroblast growth factor-2", Develop. Growth Differ., 50:97-107 (2008).
Yan, et al., "A novel anti-CD146 monoclonal antibody, AA98, inhibits angiogenesis and tumor growth," *Blood,* 1;102(1):184-191, (Jul. 2003).
Yang, et al., "Isolation and characterization of mouse MUC18 cDNA gene, and correlation of MUC18 expression in mouse melanoma cell lines with metastatic ability," *Gen,* 265(1-2):133-45, (Mar. 2001).

(56) References Cited

OTHER PUBLICATIONS

Yousif, et al., "Laminin isoforms in endothelial and perivascular basement membranes," *Cell Adh Migr,* 7(1):101-110, (Jan.-Feb. 2013).
Yun et al: "A Novel Antibody AA98 $V_H$/L Directed Against CD146 Efficiently Inhibits Angiogenesis", Anticancer Research, 27(6B):4219-4224, (2007).
Zabouo, et al., "CD146 expression is associated with a poor prognosis in human breast tumors and with enhanced motility in breast cancer cell lines," *Breast Cancer Res,* 11(1):R1, (2009).
Zeng, et al., "CD146, an epithelial-mesenchymal transition inducer, is associated with triple-negative breast cancer," *Proc Natl Acad Sci U S A,* 24;109(4):1127-1132, (Jan. 2012).
Zeng, et al., "Up-regulation of METCAM/MUC18 promotes motility, invasion, and tumorigenesis of human breast cancer cells," *BMC Cancer,* 30;11:113, (Mar. 2011).
Zhang, et al., "CD146 is a potential marker for the diagnosis of malignancy in cervical and endometrial cancer," *Oncol Lett,* 5(4):1189-1194, (Apr. 2013).
Zhang, et al., "Generation and characterization of a panel of monoclonal antibodies against distinct epitopes of human CD146," *Hybridoma* (*Larchmt*), 27(5):345-52, (Oct. 2008).
Zheng, et al., "Endothelial CD146 is required for in vitro tumor-induced angiogenesis: The role of a disulfide bond in signaling and dimerization," *The International Journal of Biochemistry & Cell Biology,* 41:2163-2172 (2009).
Zigler, et al., "Expression of Id-1 is regulated by MCAM/MUC18: a missing link in melanoma progression," *Cancer Res,* 15;71(10):3494-3504 (May 2011).
Zigler, et al., "Tumor immunotherapy in melanoma: strategies for overcoming mechanisms of resistance and escape," *Am J Clin Dermatol,* 9(5):307-311, (2008).
U.S. Appl. No. 14/656,596 Restriction Requirement dated Feb. 14, 2017.
PCT/IB2016/055559 International Preliminary Report on Patentability and Written Opinion dated Mar. 31, 2017.
PCT/IB2016/055559 Invitation to Pay Additional Fees, and, Where Applicable, Protest Fee dated Dec. 5, 2016.
PCT/IB2016/055557 International Search Report and Written Opinion dated Apr. 7, 2017.
U.S. Appl. No. 14/656,596 Restriction Requirement dated May 11, 2017.
PCT/IB2017/051264 Invitation to Pay Additional Fees and, Where Applicable, Protest Fee dated May 22, 2017.
Mukhopadhyay, "Granulomatous Lung Disease," *Arch Pathol Lab Med,* vol. 134, pp. 667-690, (May 2010).
PCT/IB2017/05142 Invitation to Pay Additional Fees and, Where Applicable, Protest Fee dated Jun. 2, 2017.
Flanagan, "Prothena to Present Precinical Data for PRX003 at 2016 AAAAI Annual Meeting," (Mar. 6, 2016).
U.S. Appl. No. 14/656,596 Non-Final Office Action dated Aug. 2017.
PCT/IB2017/05142 International Search Report and Written Opinion dated Aug. 8, 2017.
Wouters, et al., "Blau Syndrome, the prototypic auto-inflammatory granulomatous disease," *Pediatrk Pheumotology,* 12:33 (2014).
PCT/IB2017051264 International Search Report and Written Opinion dated Aug. 8, 2017.
PCT/IB2017/053289 International Search Report and Written Opinion dated Aug. 8, 2017.
Flanagan, "Anti-Mcam Monoclonal Antibody PRX003 Inhibits the Unique Migratory Potential of Pathogenic IL-17-Producing T Cellls," *J Allergy Clin Immunol,* AB190 Abstract, (Fed 2016).
Prothena, "Prothena Reports Results of Phase 1 Single Ascending Dose Study of PRX003, Demonstrating Target Engagement of the Novel Anti-MCAM Antibody for Inflammatory Disease", Jun. 9, 2016, Retrieved from the Internet: URL:http://files.shareholder.com/downloads/AMDA-1GZ5QD/4888716237x0x895935/C88913509-F11C-4742-PFFD-AD031305F573/PRTA_News_2016_6_9_General_Releases.pdf retrieved on Jul. 31, 2017.
Koller, et al., "OPO205 Clinical and Preclinical Assessment of the Anti-MCAM Monoclonal Antibody PRX003, A Potential Novel Treatment for Th17-Mediated Inflammatory Disease," *Annals of the Rheumatic Diseases,* vol. 75, No. Suppl 2, (Jun. 2016).
Kinney, et al., "Clinical Assessment of the Monoclonal Antibody, PRX003, a Potential Novel Treatment for Th17-Mediated Inflammatory Disease," *Arthritis Rgeumatol,* vol. 68, No. Suppl 10, (Sep. 28, 2016).
Abaza, et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," *Journal of Protein Chemistry,* vol. 11, No. 5, pp. 433-444, (1992).
Hafner, et al., "Selection of Mimotopes of the Cell Surface Adhersion Molecule Mel-CAM from a Random pVIII-28aa Phage Peptide Library," *The Journal of Investigative Dermatology,* vol. 119, No. 4, pp. 865-869, (Oct. 2002).
PCT/IB2015/051789 International Preliminary Report of Patentability and Written Opinion dated Sep. 10, 2016.
PCT/IB2016/055557 International Preliminary Report on Patentability dated Mar. 29, 2018.
PCT/IB2016/055559 International Preliminary Report on Patentability dated Mar. 29, 2018.
PCT/IB2017/051402 International Search Report and Written Opinion dated Aug. 8, 2017.
Rose, "Prothena Ends An early Stage Psoriasis Drug After Data Failed to Wow its Researchers," *Filter News,* pp. 1-6, (Sep. 29, 2017).
Rose, Prothena Reports Results from Phase 1b Multiple Ascending Dose Study of PRX003 in Patients with Psoriasis,Press Release, Sep. 28, 2017.
Taylor, "Prothena scratches MCAM psoriasis antibody after negative trial," *Gene Therapy & Immunotherapy;* Alphabetical Glossary of Terms, revised 22nd Edition, Sep. 29, 2017.
U.S. Appl. No. 14/124,620 Non-Final Office Action dated May 23, 2018.
U.S. Appl. No. 14/656,596 Non/Final Office Action dated Feb. 1, 2018.
U.S. Appl. No. 14/656,619 Notice of Allowance dated Feb. 27, 2018.
U.S. Appl. No. 15/125,270 Non-Final Office Action dated Apr. 27, 2018.
U.S. Appl. No. 15/125,570 Non-Final Office Action dated Apr. 27, 2018.
U.S. Appl. No. 15/222,484 Non-Final Office Action dated Apr. 27, 2018.
U.S. Appl. No. 15/222,849 Non-Final Office Action dated May 4, 2018.
U.S. Appl. No. 15/268,178 Non-Final Office Action dated Apr. 27, 2018.
U.S. Appl. No. 15/268,295 Restriction Requirement dated Mar. 12, 2018.
Vajdos, et al., "Comprehensive functinal Maps of the Antigen-binding Site of an Anti-ErbB2 Antibody Obtained with Shotgun Scanning Mutagenesis," *J. Mol. Biol.,* 320, 415-428, (2002).
Van Regenmortel, "Mapping Epitope Structure and Activity: From One-Dimensional Prediction to Four-Dimensional Description of Antigenic Specificity," *Methods: A Comparison to Methods in Enzymology,* 9(3), 465-472, (1996).
Wu, et al., "Relationship of CD146 expression to secretion of interleukin (IL)-17, IL-22 and interferon-y by CD4+ T cells in patients with inflammatory arthritis," *Clin Exp Immunol.,* 179(3): 378-391, (2015).
Zhang, et al., "Elevated Levels of soluble and Neurtrophil CD 146 in Active Systemic Vasculitis," *Science,* vol. 40, No. 6, pp. 351-356, (Jun. 2009).
U.S. Appl. No. 15/125,568 Restriction Requirement dated Sep. 21, 2018.
U.S. Appl. No. 15/125,570 Final Office Action dated Sep. 24, 2018.
PCT/IB2017/051402 International Preliminary Report on Patentability dated Sep. 20, 2018.
PCT/IB2017/051400 International Preliminary Report on Patentability dated Sep. 20, 2018.

(56) References Cited

OTHER PUBLICATIONS

Dajur, et al., "Secretion of interleukin-17 by CD8+ T cells expressing CD146 (MCAM)," *Clinical Immunology,* 152, 36-47, (2014).
Mayer, et al., "Sarcoidosis and Chronic Beryllium Disease: Similarities and Differences," *Semin Respir Crit Care Med,* 35:316-329, (2014).
Li, et al., "D38. Flying: Reaching New Heights in Sarconidosis," *American Journal of Respiratory and Critical Care Medicine,* 191, A5822, (2015).
PCT/US2013/058773 International Preliminary Report on Patentability dated Mar. 10, 2015.
U.S. Appl. No. 14/124,620 Final Office Action dated Oct. 16, 2018.
U.S. Appl. No. 14/124,620 Advisory Action dated Jan. 25, 2019.
U.S. Appl. No. 15/125,570 Advisory Action dated Jan. 31, 2019.
U.S. Appl. No. 15/222,848 Final Office Action dated Oct. 26, 2018.
U.S. Appl. No. 15/726,170 Non-Final Office Action dated Jan. 15, 2019.
PCT/US2012/000274 filed Jun. 6, 2012.
U.S. Appl. No. 61/527,481, filed Aug. 25, 2011.
U.S. Appl. No. 61/493,780, filed Jun. 6, 2011.
PCT/US2013/058773 filed Sep. 9, 2013.
U.S. Appl. No. 61/698,916, filed Sep. 10, 2012.
U.S. Appl. No. 61/797,179, filed Nov. 30, 2012.
U.S. Appl. No. 61/797,356, filed Dec. 5, 2012.
U.S. Appl. No. 14/427,290, filed Mar. 10, 2015.
PCT/IB2015/051789 filed Mar. 12, 2015.
U.S. Appl. No. 61/952,129, filed Mar. 12, 2014.
U.S. Appl. No. 62/023,753, filed Jul. 11, 2014.
U.S. Appl. No. 62/068,286, filed Oct. 24, 2014.
U.S. Appl. No. 62/086,600, filed Dec. 2, 2014.
PCT/IB2015/051790 filed Mar. 12, 2015.
U.S. Appl. No. 61/952,132, filed Mar. 12, 2014.
U.S. Appl. No. 62/023,760, filed Jul. 11, 2014.
U.S. Appl. No. 62/068,349, filed Oct. 24, 2014.
U.S. Appl. No. 14/656,501, filed Mar. 12, 2015.
PCT/IB2015/051786 filed Mar. 12, 2015.
U.S. Appl. No. 61/952,123, filed Mar. 12, 2014.
U.S. Appl. No. 62/023,698, filed Jul. 11, 2014.
U.S. Appl. No. 62/068,438, filed Oct. 24, 2014.
PCT/IB2015/051787 filed Mar. 12, 2105.
U.S. Appl. No. 61/952,116, filed Mar. 12, 2014.
U.S. Appl. No. 61/952,833, filed Mar. 13, 2014.
U.S. Appl. No. 62/023,724, filed Jul. 11, 2014.
U.S. Appl. No. 62/068,419, filed Oct. 24, 2014.
PCT/IB2016/055559 filed Sep. 16, 2016.
U.S. Appl. No. 62/219,599, filed Sep. 16, 2015.
PCT/IB2016/055557 filed Sep. 16, 2016.
U.S. Appl. No. 62/219,611, filed Sep. 16, 2015.
U.S. Appl. No. 62/303,360, filed Mar. 3, 2016.
U.S. Appl. No. 62/303,369, filed Mar. 3, 2016.
U.S. Appl. No. 62/306,060, filed Mar. 9, 2016.
U.S. Appl. No. 62/345,732, filed Jun. 3, 2016.
U.S. Appl. No. 14/656,596, filed Mar. 12, 2015.
U.S. Appl. No. 15/268,178, filed Sep. 12, 2016.
U.S. Appl. No. 15/268,295, filed Sep. 12, 2016.
PCT/IB2017/051264 filed Mar. 3, 2017.
PCT/IB2017/051402 filed Mar. 9, 2017; and.
PCT/IB2017/053289 filed Jun. 2, 2017.
U.S. Appl. No. 61/952,835, filed Mar. 13, 2014.
U.S. Appl. No. 62/023,577, filed Jul. 11, 2014; and.
PCT/IB2015/051785 filed Mar. 12, 2015.
Brevini, et al., "No shortcuts to pig embryonic stem cells," Theriogenology, 74(4):544-550, (2010).
Cao, et al., "Isolation and Culture of Primary Bovine Embryonic Stem Cell Colonies by a Novel Method," J. Exp. Zool. A. Ecol. Genet. Physiol., 311(5):368-376, (2009).
Dennis, "Welfare Issues of Genetically Modified Animals," ILAR J., 43(2):100-109, (2002).
Paris, et al., "Equine embryos and embryonic stem cells: Defining reliable marker of pluripotency," Theriogenology, 74(4):516-524, (2010).
Zhou, et al., "Developing tTa Transgenic Rats for Inducible and Reversible Gene Expression," Int. J. Biol. Sci., 5(2):171-181, (2009).
Houdebine, "Methods to Generate Transgenic Animals," Genetic Engineering in Livestock: New Applications and Interdisciplinary Perspectives, Ed. Engelhard, et al., Springer-Verlag Berlin Heidelberg, pp. 31-48, (2009).

* cited by examiner

5' ATGAGGGTCCAGATTCAGTTTCTGGGGCTCCTTCTGCTCTGGACATCAGTTGTCCAGTGTGATGTCCAGATGACCCAGTCTCCATCTTAT 90
0
0 Signal peptide
M R V Q I Q F L G L L L L W T S V V Q C D V Q M T Q S P S Y
0 1 2 3 4 5 6 7 8 9 10 11 12 13 14 15 16 17 18 19 20 21 22 23 24 25 26 27 28 29 30

5' CTTGCTACGTCTCCTGGAGAGAGTGTTTCCATCAGTTGCAAGGCAAGTAAAAACATTGACACATACTTAGCCTGGTATCAGGAGAAACCT 180
0
0 CDR1 (SEQ ID NO:3)
L A T S P G E S Y S I S C K A S K N I D T Y L A W Y Q E K P
0 31 32 33 34 35 36 37 38 39 40 41 42 43 44 45 46 47 48 49 50 51 52 53 54 55 56 57 58 59 60

5' GGGAAAACGAATAAGCTTCTTATCTACTCTGGGTCAACTTTGCAATCTGGAACTCCATCGAGATTCAGTGGCAGTGGATCTGGTACAGAT 270
0
0 CDR2 (SEQ ID NO: 4)
G K T N K L L I Y S G S T L Q S G T P S R F S G S G S G T D
0 61 62 63 64 65 66 67 68 69 70 71 72 73 74 75 76 77 78 79 80 81 82 83 84 85 86 87 88 89 90

FIG. 6A

5' CAAATGACCAGTCTGAGGCCTGAGGACACGGCCACTTATTATTGTGCAAGACATCGGGGGTATAGTACGAATTTTTATCACGACGTTTTGGATGCCTGGG 400
3' GTTTACTGGTCAGACTCCGGACTCCTGTGCCGGTGAATAATAACACGTTCTGTAGCCCCCATATCATGCTTAAAAATAGTGCTGCAAAACCTACGGACCC

CDR3 (SEQ ID NO: 10)

Q M T S L R P E D T A T Y Y C A R H R G Y S T N F Y H D V L D A W
101 102 103 104 105 106 107 108 109 110 111 112 113 114 115 116 117 118 119 120 121 122 123 124 125 126 127 128 129 130 131 132 133

5' GTCAAGGAGCTTTAGTCACTGTCTCCTCAGCTGAAACAACAGCCCCATCTGTCTATCCACTGGCTCCTGGAACTGCTCTCAAA (SEQ ID NO: 6) 483
3' CAGTTCCTCGAAATCAGTGACAGAGGAGTCGACTTTGTTGTCGGGGTAGACAGATAGGTGACCGAGGACCTTGACGAGAGTTT

CDR3

G Q G A L V T V S S A E T T A P S V Y P L A P G T A L K (SEQ ID NO: 7)
134 135 136 137 138 139 140 141 142 143 144 145 146 147 148 149 150 151 152 153 154 155 156 157 158 159 160 161

FIG. 6B (Cont'd)

Figure 9A:
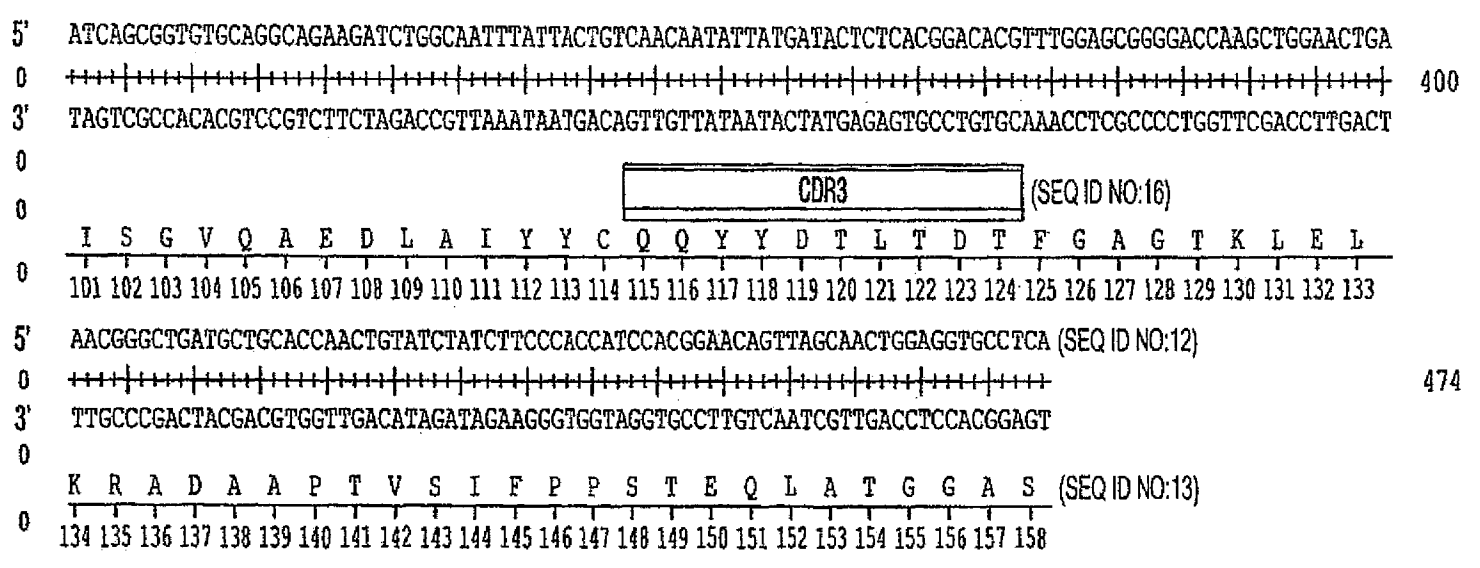

5' ATCAGCGGTGTGCAGGCAGAAGATCTGGCAATTTATTACTGTCAACAATATTATGATACTCTCACGGACACGTTTGGAGCGGGGACCAAGCTGGAACTGA 0 400

3' TAGTCGCCACACGTCCGTCTTCTAGACCGTTAAATAATGACAGTTGTTATAATACTATGAGAGTGCCTGTGCAAACCTCGCCCCTGGTTCGACCTTGACT

0

0 CDR3 (SEQ ID NO:16)

I S G V Q A E D L A I Y Y C Q Q Y Y D T L T D T F G A G T K L E L 0 101 102 103 104 105 106 107 108 109 110 111 112 113 114 115 116 117 118 119 120 121 122 123 124 125 126 127 128 129 130 131 132 133

5' AACGGGCTGATGCTGCACCAACTGTATCTATCTTCCCACCATCCACGGAACAGTTAGCAACTGGAGGTGCCTCA (SEQ ID NO:12)

0 474

3' TTGCCCGACTACGACGTGGTTGACATAGATAGAAGGGTGGTAGGTGCCTTGTCAATCGTTGACCTCCACGGAGT

0

K R A D A A P T V S I F P P S T E Q L A T G G A S (SEQ ID NO:13)

Figure 9B:
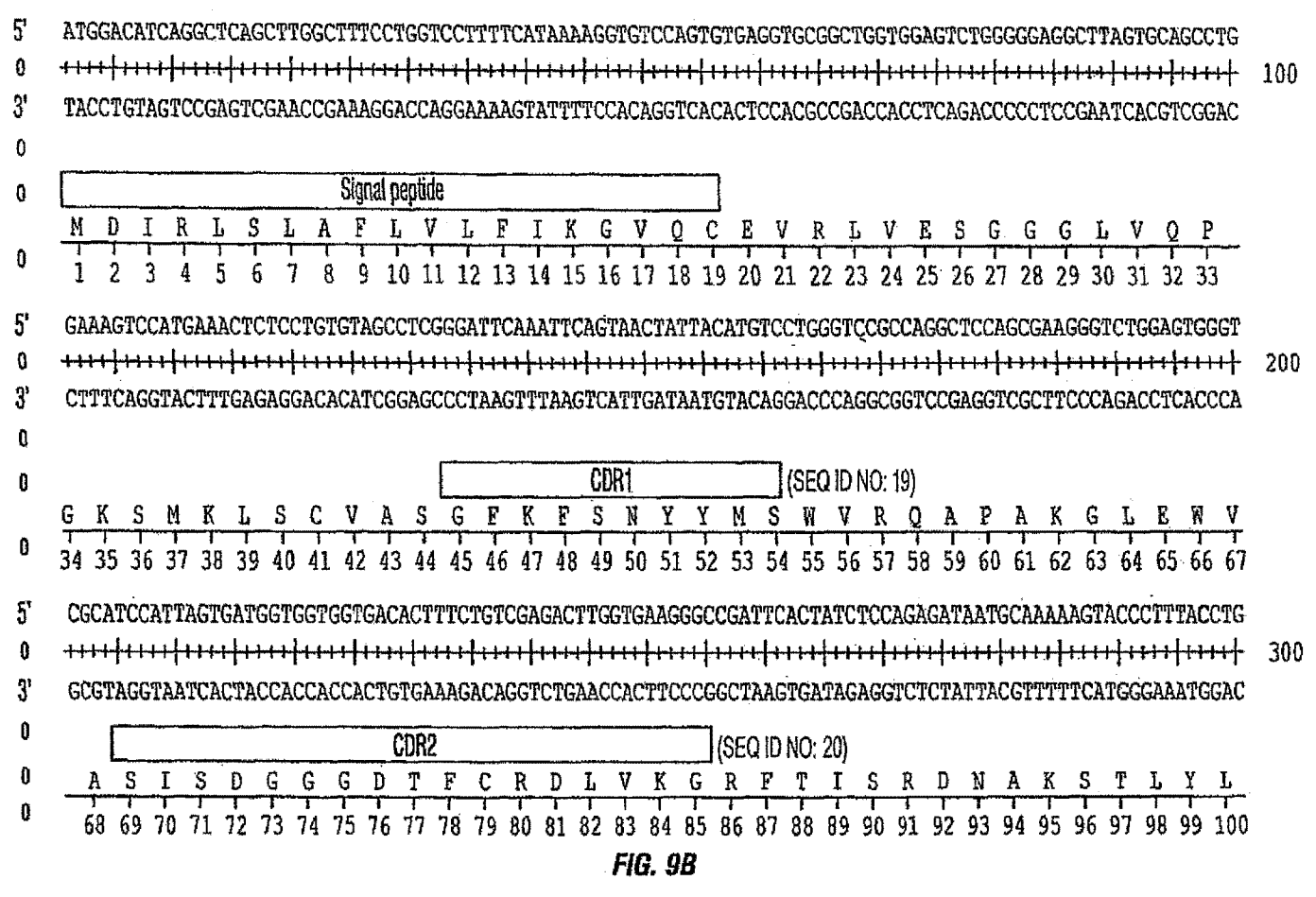

5' ATGGACATCAGGCTCAGCTTGGCTTTCCTGGTCCTTTTCATAAAAGGTGTCCAGTGTGAGGTGCGGCTGGTGGAGTCTGGGGGAGGCTTAGTGCAGCCTG 0 100

3' TACCTGTAGTCCGAGTCGAACCGAAAGGACCAGGAAAAGTATTTTCCACAGGTCACACTCCACGCCGACCACCTCAGACCCCCTCCGAATCACGTCGGAC

0

0 Signal peptide

M D I R L S L A F L V L F I K G V Q C E V R L V E S G G G L V Q P 0 1 2 3 4 5 6 7 8 9 10 11 12 13 14 15 16 17 18 19 20 21 22 23 24 25 26 27 28 29 30 31 32 33

5' GAAAGTCCATGAAACTCTCCTGTGTAGCCTCGGGATTCAAATTCAGTAACTATTACATGTCCTGGGTCCGCCAGGCTCCAGCGAAGGGTCTGGAGTGGGT 0 200

3' CTTTCAGGTACTTTGAGAGGACACATCGGAGCCCTAAGTTTAAGTCATTGATAATGTACAGGACCCAGGCGGTCCGAGGTCGCTTCCCAGACCTCACCCA

0

0 CDR1 (SEQ ID NO: 19)

G K S M K L S C V A S G F K F S N Y Y M S W V R Q A P A K G L E W V 0 34 35 36 37 38 39 40 41 42 43 44 45 46 47 48 49 50 51 52 53 54 55 56 57 58 59 60 61 62 63 64 65 66 67

5' CGCATCCATTAGTGATGGTGGTGGTGACACTTTCTGTCGAGACTTGGTGAAGGGCCGATTCACTATCTCCAGAGATAATGCAAAAAGTACCCTTTACCTG 0 300

3' GCGTAGGTAATCACTACCACCACCACTGTGAAAGACAGGTCTGAACCACTTCCCGGCTAAGTGATAGAGGTCTCTATTACGTTTTTCATGGGAAATGGAC

0 CDR2 (SEQ ID NO: 20)

```
5'  CAAATGGACAGTCTGAGGCCTGAGGACACGGCCACTTATTACTGTGCAAGACGGGGAGCAGCTATGGGGGTGTTATGGATGCCTGGGGTCAAGGAACTT  400
    +----+----+----+----+----+----+----+----+----+----+----+----+----+----+----+----+----+----+----+----+
3'  GTTTACCTGTCAGACTCCGGACTCCTGTGCCGGTGAATAATGACACGTTCTGCCCCTCGTCGATACCCCACAATACCTACGGACCCCAGTTCCTTGAA

    Q   M   D   S   L   R   P   E   D   T   A   T   Y   Y   C   A   R   R   G   A   A   M   G   G   V   M   D   A   W   G   Q   G   T
   101 102 103 104 105 106 107 108 109 110 111 112 113 114 115 116 117 118 119 120 121 122 123 124 125 126 127 128 129 130 131 132 133
                                                                          [========== CDR3 ==========] (SEQ ID NO: 21)

5'  CAGTCACTGTCTCCTCAGCTGAAACAACAGCCCCATCTGTCTATCCACTGGCTCCTGGAACTGCTCTCA (SEQ ID NO: 17)  469
    +----+----+----+----+----+----+----+----+----+----+----+----+----+---+
3'  GTCAGTGACAGAGGAGTCGACTTTGTTGTCGGGGTAGACAGATAGGTGACCGAGGACCTTGACGAGAGT

    S   V   T   V   S   S   A   E   T   T   A   P   S   V   Y   P   L   A   P   G   T   A   L  (SEQ ID NO: 18)
   134 135 136 137 138 139 140 141 142 143 144 145 146 147 148 149 150 151 152 153 154 155 156
```

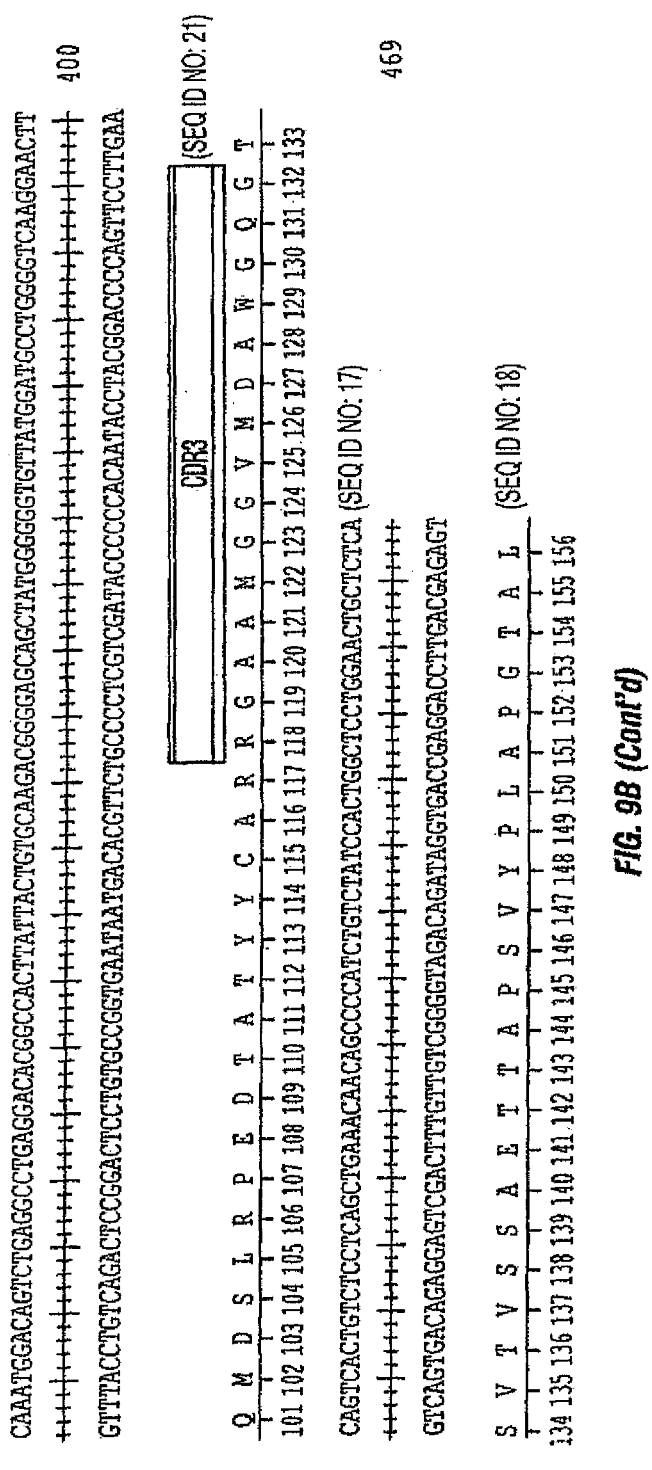

FIG. 9B (Cont'd)

A1 - FL protein, clone 15, B1 - FL protein, SP2 media, C1 - Ig1 domain, clone 15, D1 - Ig1 domain, SP2 media E1 - Ig2 domain, clone 15, F1 - Ig2 domain, SP2 media, G1 - Ig1-2A domain, clone 15, H1 - Ig1-2A domain, SP2 media A1- FL protein, clone 17, B1 - FL protein, SP2 media, C1 - Ig1 domain, clone 17, D1 - Ig1 domain, SP2 media E1- Ig2 domain, clone 17, F1 - Ig2 domain, SP2 media, G1 - Ig1-2A domain, clone 17, H1 - Ig1-2A domain, SP2 media MGLPRLVCAFLLAACCCCPRVAGVPGEAEQPAPELVEVEVGSTALLKCGLSQSQGNLSHVDWFSVHKEKR
TLIFRVRQGQGQSEPGEYEQRLSLQDRGATLALTQVTPQDERIFLCQGKRPRSQEYRIQLRVYKAPEEPN
IQVNPLGIPVNSKEPEEVATCVGRNGYPIPQVIWYKNGRPLKEEKNRVHIQSSQTVESSGLYTLQSILKA
QLVKEDKDAQFYCELNYRLPSGNHMKESREVTVPVFYPTEKVWLEVEPVGMLKEGDRVEIRCLADGNPPP
HFSISKQNPSTREAEEETTNDNGVLVLEPARKEHSGRYECQAWNLDTMISLLSEPQELLVNYVSDVRVSP
AAPERQEGSSLTLTCEAESSQDLEFQWLREETDQVLERGPVLQLHDLKREAGGGYRCVASVPSIPGLNRT
QLVKLAIFGPPWMAFKERKVWVKENMVLNLSCEASGHPRPTISWNVNGTASEQDQDPQRVLSTLNVLVTP
ELLETGVECTASNDLGKNTSILFLELVNLTTLTPDSNTTTGLSTSTASPHTRANSTSTERKLPEPESRGV
VIVAVIVCILVLAVLGAVLYFLYKKGKLPCRRSGKQEITLPPSRKTELVVEVKSDKLPEEMGLLQGSSGD
KRAPGDQGEKYIDLRH (SEQ ID NO: 11)

FIG. 11A

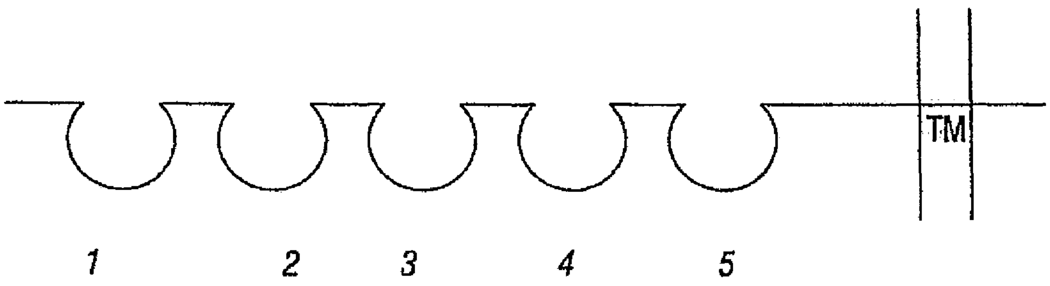

FIG. 11B

```
malssawrsv lplwllwsaa csraasgddn afpfdiegss avgrqdppet seprvalgrl ppaaekcnag
ffhtlsgecv pcdcngnsne cldgsgycvh cqrnttgehc ekcldgyigd sirgapqfcq pcpcplphla
nfaescyrkn gavrcicnen yagpncerca pgyygnplli gstckkcdcs gnsdpnlife dcdevtgqcr
nclrnttgfk cercapgyyg dariakncav cncgggpcds vtgecleegf epptgmdcpt iscdkcvwdl
tddlrlaals ieegksgvls vssgaaahrh vneinatiyl lktklseren qyalrkiqin naentmksll
sdveelveke nqasrkgqlv qkesmdtinh asqlveqahd mrdkiqeinn kmlyygeehe lspkeisekl
vlaqkmleei rsrqpfftqr elvdeeadea yellsqaesw qrlhnetrtl fpvvleqldd ynaklsdlqe
aldqalnyvr daedmnrata arqrdhekqq ervreqmevv nmslstsads lttprltlse lddiiknasg
iyaeidgaks elqvklsnls nlshdlvqea idhaqdlqqe anelsrklhs sdmnglvqka ldasnvyeni
vnyvseanet aefalnttdr iydavsgidt qiiyhkdese nllnqarelq akaesssdea vadtsrrvgg
alarksalkt rlsdavkqlq aaergdaqqr lgqsrlitee anrttmevqq atapmannlt nwsqnlqhfd
ssayntavns ardavrnlte vvpqlldqlr tveqkrpasn vsasiqrire liaqtrsvas kiqvsmmfdg
qsavevhsrt smddlkafts lslymkppvk rpeltetadq filylgskna kkeymglaik ndnlvyvynl
gtkdveipld skpvsswpay fsivkiervg khgkvfltvp slsstaeekf ikkgefsgdd slldldpedt
vfyvggvpsn fklptslnlp gfvgclelat lnndvislyn fkhiynmdps tsvpcardkl aftqsraasy
ffdgsgyavv rditrrgkfg qvtrfdievr tpadnglill mvngsmffrl emrngylhvf ydfgfsggpv
hledtlkkaq indakyheis iiyhndkkmi lvvdrrhvks mdnekmkipf tdiyiggapp eilqsralra
hlpldinfrg cmkgfqfqkk dfnlleqtet lgvgygcped slisrrayfn gqsfiasiqk isffdgfegg
fnfrtlqpng llfyyasgsd vfsisldngt vimdvkgikv qsvdkqyndg lshfvissvs ptryelivdk
srvgsknptk gkieqtqase kkfyfggspi saqyanftgc isnayftrvd rdvevedfqr ytekvhtsly
ecpiessplf llhkkgknls kpkasqnkkg gkskdapswd pvalklpern tprnshchls nspraiehay
qyggtansrq efehlkgdfg aksqfsirlr trsshgmify vsdqeendfm tlflahgrlv ymfnvghkkl
kirsqekynd glwhdvifir erssgrlvid glrvleeslp pteatwkikg piylggvapg kavknvqins
iysfsgclsn lqlngasits asqtfsvtpc fegpmetgty fsteggyvvl desfniglkf eiafevrprs
ssgtlvhghs vngeylnvhm kngqvivkvn ngirdfstsv tpkqslcdgr whritvirds nvvqldvdse
vnhvvgplnp kpidhrepvf vggvpesllt prlapskpft gcirhfvidg hpvsfskaal vsgavsinsc
paa (SEQ ID NO:27)
```

FIG. 12A malssawrsv lplwllwsaa csraasgddn afpfdiegss avgrqdppet seprvalgrl ppaaekcnag
ffhtlsgecv pcdcngnsne cldgsgycvh cqrnttgehc ekcldgyigd sirgapqfcq pcpcplphla
nfaescyrkn gavrcicnen yagpncerca pgyygnplli gstckkcdcs gnsdpnlife dcdevtgqcr
nclrnttgfk cercapgyyg dariakncav cncgggpcds vtgecleegf epptgcdkcv wdltddlrla
alsieegksg vlsvssgaaa hrhvneinat iyllktklse renqyalrki qinnaentmk sllsdveelv
ekenqasrkg qlvqkesmdt inhasqlveq ahdmrdkiqe innkmlyyge ehelspkeis eklvlaqkml
eeirsrqpff tqrelvdeea deayellsqa eswqrlhnet rtlfpvvleq lddynaklsd lqealdqaln
yvrdaedmnr ataarqrdhe kqqervreqm evvnmslsts adslttprlt lselddiikn asgiyaeidg
akselqvkls nlsnlshdlv qeaidhaqdl qqeanelsrk lhssdmnglv qkaldasnvy enivnyvsea
netaefalnt tdriydavsg idtqiiyhkd esenllnqar elqakaesss deavadtsrr vggalarksa
lktrlsdavk qlqaaergda qqrlgqsrli teeanrttme vqqatapman nltnwsqnlq hfdssaynta
vnsardavrn ltevvpqlld qlrtveqkrp asnvsasiqr ireliaqtrs vaskiqvsmm fdgqsavevh
srtsmddlka ftslslymkp pvkrpeltet adqfilylgs knakkeymgl aikndnlvyv ynlgtkdvei
pldskpvssw payfsivkie rvgkhgkvfl tvpslsstae ekfikkgefs gddslldldp edtvfyvggv
psnfklptsl nlpgfvgcle latlnndvis lynfkhiynm dpstsvpcar dklaftqsra asyffdgsgy
avvrditrrg kfgqvtrfdi evrtpadngl illmvngsmf frlemrngyl hvfydfgfsg gpvhledtlk
kaqindakyh eisiiyhndk kmilvvdrrh vksmdnekmk ipftdiyigg appeilqsra lrahlpldin
frgcmkgfqf qkkdfnlleq tetlgvgygc pedslisrra yfngqsfias iqkisffdgf eggfnfrtlq
pngllfyyas gsdvfsisld ngtvimdvkg ikvqsvdkqy ndglshfvis svsptryeli vdksrvgskn
ptkgkieqtq asekkfyfgg spisaqyanf tgcisnayft rvdrdveved fqrytekvht slyecpiess
plfllhkkgk nlskpkasqn kkggkskdap swdpvalklp erntprnshc hlsnspraie hayqyggtan
srqefehlkg dfgaksqfsi rlrtrsshgm ifyvsdqeen dfmtlflahg rlvymfnvgh kklkirsqek
yndglwhdvi firerssgrl vidglrvlee slppteatwk ikgpiylggv apgkavknvq insiysfsgc
lsnlqlngas itsasqtfsv tpcfegpmet gtyfsteggy vvldesfnig lkfeiafevr prsssgtlvh
ghsvngeyln vhmkngqviv kvnngirdfs tsvtpkqslc dgrwhritvi rdsnvvqldv dsevnhvvgp
lnpkpidhre pvfvggvpes lltprlapsk pftgcirhfv idghpvsfsk aalvsgavsi nscpaa
(SEQ ID NO: 28)

Clone 1174.1.3 – Variable Light Chain (Nucleic Acid Sequence)

GACATTGTGCTGACACAGTCTCCTGCTTCCTTAGCTGTATCTCTGGGGCAGAGGG
CCACCATCTCATGCAGGGCCAGCAAAAGTGTCAGTACATCTGGCTATAGTTATATG
TACTGGTACCAACAGAAACCAGGACAGCCACCCAAACTCCTCATCTATCTTGCATC
CAACCTAGAATCTGGGGTCCCTGCCAGGTTCAGTGGCAGTGGGTCTGGGACAGAC
TTCACCCTCAACATCCATCCTGTGGAGGAGGAGGATGCTGCAACCTATTACTGTCA
ACACAGTAGGGAGCTTCCATTCACGTTCGGCTCGGGGACAAAGTTGGAAATAAAA
C (SEQ ID NO:29)

Clone 1174.1.3 – Variable Light Chain (Amino Acid Sequence)

DIVLTQSPASLAVSLGQRATISCRASKSVSTSGYSYMYWYQQKPGQPPKLLIYIASNLE
SGVPARFSGSGSGTDFTLNIHPVEEEDAATYYCQHSRELPFTFGSGTKLEIK (SEQ
ID NO:30)

Clone 1174.1.3 – CDR-L1 (Amino Acid Sequence)

RASKSVSTSGYSYMY (SEQ ID NO:31)

Clone 1174.1.3 – CDR-L2 (Amino Acid Sequence)

ASNLES (SEQ ID NO:32)

Clone 1174.1.3 – CDR-L3 (Amino Acid Sequence)

QHSRELPFT (SEQ ID NO:33)

Figure 14

Clone 1174.1.3 – Variable Heavy Chain (Nucleic Acid Sequence)

CAGATTCAGTTGGTGCAGTCTGGACCTGAGCTGAAGAAGCCTGGAGAGACAGTCA
AGATCTCCTGCAAGGCTTCTGGGTATACCTTCACAAACTATGGAATGAACTGGGTG
AAGCAGGCTCCAGGAAAGGGTTTAAAGTGGATGGGCTGGATAAACACCTACACTG
GAGAGCCAACATATGCTGATGACTTCAAGGGACGGTTTGCCTTGTCTTTGGAAACC
TCTGCCAGCACTGCCTATTTGCAGATCAACAACCTCAAAAATGAGGACATGGCTAC
ATATTTCTGTGCAAGATATAGGTATAATAAATACGAGAGGGCTATGGACTACTGGG
GTCAAGGAACCTCAGTCACCGTCTCCTCA (SEQ ID NO:34)

Clone 1174.1.3 – Variable Heavy Chain (Amino Acid Sequence)

QIQLVQSGPELKKPGETVKISCKASGYTFTNYGMNWVKQAPGKGLKWMGWINTYTGE
PTYADDFKGRFALSLETSASTAYLQINNLKNEDMATYFCARYRYNKYERAMDYWGQG
TSVTVSS (SEQ ID NO:35)

Clone 1174.1.3 – CDR-H1 (Amino Acid Sequence)

GYTFTNYGMN (SEQ ID NO:36)

Clone 1174.1.3 – CDR-H2 (Amino Acid Sequence)

WINTYTGEPTYADDFKG (SEQ ID NO:37)

Clone 1174.1.3 – CDR-H3 (Amino Acid Sequence)

YRYNKYERAMDY (SEQ ID NO:38)

Figure 15

Clone 1414.1.2 – Variable Light Chain (Nucleic Acid Sequence)

GACATTGTGATGTCACAGTCTCCATCCTCCCTGGCTGTGTCAGCAGGAGAGAAGG
TCACTATGAGCTGCAAATCCAGTCAGAGTCTGCTCAACAGTAGCACCCGAAAGAAC
TTCTTGGCTTGGTACCAGCAGAAACCAGGGCAGTCTCCTAAACTGCTGATCTACTG
GGCATCCACTAGGGAATCTGGGGTCCCTGATCGCTTCACAGGCAGTGGATCTGGG
ACAGATTTCACTCTCACCATCAGCAGTGTGCAGGCTGAAGACCTGGCAGTTTATTA
CTGCAAGCAATCTTATAATCGGTACACGTTCGGAGGGGGGACCAAGCTGGAAATA
AAACG (SEQ ID NO:39)

Clone 1414.1.2 – Variable Light Chain (Amino Acid Sequence)

DIVMSQSPSSLAVSAGEKVTMSCKSSQSLLNSSTRKNFLAWYQQKPGQSPKLLIYWA
STRESGVPDRFTGSGSGTDFTLTISSVQAEDLAVYYCKQSYNRYTFGGGTKLEIK
(SEQ ID NO:40)

Clone 1414.1.2 – CDR-L1 (Amino Acid Sequence)

KSSQSLLNSSTRKNFLA (SEQ ID NO:41)

Clone 1414.1.2 – CDR-L2 (Amino Acid Sequence)

WASTRES (SEQ ID NO:42)

Clone 1414.1.2 – CDR-L3 (Amino Acid Sequence)

KQSYNRYT (SEQ ID NO:43)

Figure 16

Clone 1414.1.2 – Variable Heavy Chain (Nucleic Acid Sequence)

GAGATCCAGCTGCAGCAGACTGGACCTGAGCTGGTGAAGCCTGGGGCTTCAGTG
AAGATATCCTGCAAGGCTTCTGGTTATTCATTCACTGACTACATCATGCTCTGGGTG
AAGCAGAGCCATGGAAAGAGCCTTGAGTGGATTGGAAATATTAATCCTTACTCTGG
TAGTAGTGGCTACAATCTGAAGTTCAAGGGCAAGGCCaCATTGACTGTAGACAAAT
CTTCCAGCACAGCCTACATGCAGCTCAACAGTCTGACATCTGAGGACTCTGCAGTC
TATTACTGTGCAAGAGGGAAGGACTTTGCTATGGACTACTGGGGTCAAGGAACCT
CAGTCACCGTCTCCTCA (SEQ ID NO:44)

Clone 1414.1.2 – Variable Heavy Chain (Amino Acid Sequence)

EIQLQQTGPELVKPGASVKISCKASGYSFTDYIMLWVKQSHGKSLEWIGNINPYSGSS
GYNLKFKGKATLTVDKSSSTAYMQLNSLTSEDSAVYYCARGKDFAMDYWGQGTSVTV
SS (SEQ ID NO:45)

Clone 1414.1.2 – CDR-H1 (Amino Acid Sequence)

GYSFTDYIML (SEQ ID NO:46)

Clone 1414.1.2 – CDR-H2 (Amino Acid Sequence)

NINPYSGSSGYNLKFKG (SEQ ID NO:47)

Clone 1414.1.2 – CDR-H3 (Amino Acid Sequence)

GKDFAMD (SEQ ID NO:48)

Figure 17

Clone 1415.1.1 – Variable Light Chain (Nucleic Acid Sequence)

GACATTGTGATGACTCAGTCTCCAGCCACCCTGTCTGTGACTCCAGGAGATAGAGT
CTCTCTTTCATGCAGGGCCAGCCAGAGTATTAGCGACTACTTACACTGGTATCAAC
AAAAATCACATGAGTCTCCAAGGCTTCTCATCAAATATGCTTCCCAATCCATCTCTG
GGATCCCCTCCAGGTTCAGTGGCAGTGGATCAGGGTCAGATTTCACTCTCAGTATC
AACAGTGTGGAACCTGAAGATGTTGGAGTGTATTACTGTCAAAATGGTCACAACTT
TCCTCGGACGTTCGGTGGAGGCACCAAGCTGGAAATCAAAC (SEQ ID NO:49)

Clone 1415.1.1 – Variable Light Chain (Amino Acid Sequence)

DIVMTQSPATLSVTPGDRVSLSCRASQSISDYLHWYQQKSHESPRLLIKYASQSISGIP
SRFSGSGSGSDFTLSINSVEPEDVGVYYCQNGHNFPRTFGGGTKLEIK (SEQ ID NO:50)

Clone 1415.1.1 – CDR-L1 (Amino Acid Sequence)

RASQSISDYLH (SEQ ID NO:51)

Clone 1415.1.1 – CDR-L2 (Amino Acid Sequence)

YASQSIS (SEQ ID NO:52)

Clone 1415.1.1 – CDR-L3 (Amino Acid Sequence)

QNGHNFPRT (SEQ ID NO:53)

Figure 18

Clone 1415.1.1 – Variable Heavy Chain (Nucleic Acid Sequence)

CAGGTCCAACTGCAGCAGCCTGGGGCTGAGCTTGTGCAGCCTGGGGCTCCAGTG
AAGCTGTCCTGCAAGGCTTCTGGCTACATTTTCACCAGCTACTGGATGAACTGGGT
GAAGCAGAGGCCTGGACGAGGCCTCGAGTGGATTGGAAGGATTGATCCTTCCGAT
AGTAAAATTCACTACAATCAAAAGTTCAAAGACAAGGCCACACTGACTGTAGACAG
ATCCTCCAGCACAGCCTACATCCAACTCGGCAGCCTGACATCTGAGGACTCTGCG
GTCTATTATTGTGCAAAAGAGGGGGGTTTACGACGGGGGGACTATGCTATGGACT
ACTGGGGTCAAGGAACCTCAGTCACCGTCTCCTCA (SEQ ID NO:54)

Clone 1415.1.1 – Variable Heavy Chain (Amino Acid Sequence)

QVQLQQPGAELVQPGAPVKLSCKASGYIFTSYWMNWVKQRPGRGLEWIGRIDPSDS
KIHYNQKFKDKATLTVDRSSSTAYIQLGSLTSEDSAVYYCAKEGGLRRGDYAMDYWG
QGTSVTVSS (SEQ ID NO:55)

Clone 1415.1.1 – CDR-H1 (Amino Acid Sequence)

GYIFTSYWMN (SEQ ID NO:56)

Clone 1415.1.1 – CDR-H2 (Amino Acid Sequence)

RIDPSDSKIHYNQKFKD (SEQ ID NO:57)

Clone 1415.1.1 – CDR-H3 (Amino Acid Sequence)

EGGLRRGDYAMDY (SEQ ID NO:58)

Figure 19

Clone 1749.1.3 – Variable Light Chain (Nucleic Acid Sequence)

GACATTGTGATGTCACAGTCTCCATCCTCCCTGGCTGTGTCAGCAGGAGAGAAGG
TCACTATGAACTGCAAATCCAGTCGGAGTCTGCTCAACAGTAGAATCCGAAAGAAC
TACTTGGCTTGGTACCAGCAGAAACCAGGGCAGTCTCCTAAACTGCTGATCTACTG
GGCATCCACTAGGGAATCTGGGGTCCCTGATCGCTTCACAGGCAGTGGATCTGGG
ACAGATTTCACTCTCACCATCAGCAGTGTGCAGGCTGAAGACCTGGCAGTTTATTA
CTGCAAGCAATCTTATAATCTGCTCACGTTCGGTGCTGGGACCAAGCTGGAGCTG
AAAC (SEQ ID NO:59)

Clone 1749.1.3 – Variable Light Chain (Amino Acid Sequence)

DIVMSQSPSSLAVSAGEKVTMNCKSSRSLLNSRIRKNYLAWYQQKPGQSPKLLIYWAS
TRESGVPDRFTGSGSGTDFTLTISSVQAEDLAVYYCKQSYNLLTFGAGTKLELK
(SEQ ID NO:60)

Clone 1749.1.3 – CDR-L1 (Amino Acid Sequence)

KSSRSLLNSRIRKNYLA (SEQ ID NO:61)

Clone 1749.1.3 – CDR-L2 (Amino Acid Sequence)

WASTRES (SEQ ID NO:62)

Clone 1749.1.3 – CDR-L3 (Amino Acid Sequence)

KQSYNLLT (SEQ ID NO:63)

Figure 20

Clone 1749.1.3 – Variable Heavy Chain (Nucleic Acid Sequence)

GACGTGAAGCTGGTGGAGTCTGGGGGAGACTTAGTGAAGCCTGGAGGGTCCCTG
AAACTCTCCTGTGCAGCCTCTGGATTCACtTTCAGTAGCTATATCATGTCTTGGGTT
CGTCAGACTCCGGAGAAGAGGCTGGAGTGGGTCGCAACCATTAGTAGTGGTGGTA
GTTCCACCTACTATCCAGACAGTGTGAAGGGCCGATTCACcATCTCCAGAGACAAT
GCCAAGAACACCCTGTACCTGCAAATGAGCAGTCTGAAGTCTGAGGACACAGCCA
TGTATTACTGTACAAGAGATGATGATTACGACGTAAAGGTATTTGCTTACTGGGGC
CAAGGGACTCTGGTCACTGTCTCTGCA (SEQ ID NO:64)

Clone 1749.1.3 – Variable Heavy Chain (Amino Acid Sequence)

DVKLVESGGDLVKPGGSLKLSCAASGFTFSSYIMSWVRQTPEKRLEWVATISSGGSST
YYPDSVKGRFTISRDNAKNTLYLQMSSLKSEDTAMYYCTRDDDYDVKVFAYWGQGTL
VTVSA (SEQ ID NO:65)

Clone 1749.1.3 – CDR-H1 (Amino Acid Sequence)

GFTFSSYIMS (SEQ ID NO:66)

Clone 1749.1.3 – CDR-H2 (Amino Acid Sequence)

TISSGGSSTYYPDSVKG (SEQ ID NO:67)

Clone 1749.1.3 – CDR-H3 (Amino Acid Sequence)

DDDYDVKVFAY (SEQ ID NO:68)

Figure 21A

Clone 2120.4.19 – Variable Light Chain (Nucleic Acid Sequence)

GATATCCGGATGACTCAGTCTCCTTCACTCCTGTCTGCATCTGTGGGGGACAGAGT
CACTCTCAACTGCAAAGCAAGTCAGAATATTTATAACAGCTTAGCCTGGTATCAGC
AAAAGCTTGGAGAAGGTCCCAAAGTCCTGATTTTTAATGCAAACAGTTTGCAAACG
GGCATCCCATCAAGGTTCAGTGGCAGTGGATCTGGTACAGATTTCACACTCACCAT
CAGCAGCCTGCAGCCTGAAGATTTTGCCACATATTTCTGCCAGCAGTTTTATAGCG
GGTACACGTTTGGAGCTGGGACCAAGCTGGAACTGAAAC (SEQ ID NO:69)

Clone 2120.4.19 – Variable Light Chain (Amino Acid Sequence – Version 1)

DIRMTQSPSLLSASVGDRVTLNCKASQNIYNSLAWYQQKLGEGPKVLIFNANSLQTGIP
SRFSGSGSGTDFTLTISSLQPEDFATYFCQQFYSGYTFGAGTKLELK (SEQ ID NO:70)

Clone 2120.4.19 – Variable Light Chain (Amino Acid Sequence – Version 2)

DIQVTQSPSLLSASVGDRVTLNCKASQNIYNSLAWYQQKLGEGPKVLIFNANSLQTGIP
SRFSGSGSGTDFTLTISSLQPEDFATYFCQQFYSGYTFGAGTKLELK (SEQ ID NO:71)

Clone 2120.4.19 – Variable Light Chain (Amino Acid Sequence – Version 3)

DIVLTQSPSLLSASVGDRVTLNCKASQNIYNSLAWYQQKLGEGPKVLIFNANSLQTGIP
SRFSGSGSGTDFTLTISSLQPEDFATYFCQQFYSGYTFGAGTKLELK (SEQ ID NO:72)

Clone 2120.4.19 – CDR-L1 (Amino Acid Sequence)

KASQNIYNSLA (SEQ ID NO:73)

Figure 21B

Clone 2120.4.19 – CDR-L2 (Amino Acid Sequence)

NANSLQT (SEQ ID NO:74)

Clone 2120.4.19 – CDR-L3 (Amino Acid Sequence)

QQFYSGYT (SEQ ID NO:75)

Figure 22

Clone 2120.4.19 - Variable Heavy Chain (Nucleic Acid Sequence)

CAGGTGCAGCTGAAGGAGTCAGGACCTGGTCTGGTGCAGCCCTCACAGACCCTG
TCTCTCACCTGCACTGTCTCTGGATTCTCATTAACCAGCAATGGTGTAAGCTGGGT
TCGCCAGCCTCCAGGAAAGGGTCTGGAGTGGATTGCAGCAATATCATCTGGTGGA
ACCACATATTATAATTCAGCGTTCAAATCCCGACTGAGCATCAGCAGGAACACCTC
CAAGAGCCAAGTTCTCTTAAAAATGAACAGTCTGCAAACTGAAGACACAGCCATGT
ACTTCTGTGCCAGACGGTATGGGTACGGGTGGTACTTTGACTTCTGGGGCCCAGG
AACCATGGTCACAGTCTCCTCA (SEQ ID N0:76)

Clone 2120.4.19 - Variable Heavy Chain (Amino Acid Sequence)

QVQLKESGPGLVQPSQTLSLTCTVSGFSLTSNGVSWVRQPPGKGLEWIAAISSGGTT
YYNSAFKSRLSISRNTSKSQVLLKMNSLQTEDTAMYFCARRYGYGWYFDFWGPGTM
VTVSS (SEQ ID NO:77)

Clone 2120.4.19 - CDR-H1 (Amino Acid Sequence)

GFSLTSNGVS (SEQ ID NO:78)

Clone 2120.4.19 - CDR-H2 (Amino Acid Sequence)

AISSGGTTYYNSAFKS (SEQ ID NO:79)

Clone 2120.4.19 - CDR-H3 (Amino Acid Sequence)

RYGYGWYFDF (SEQ ID N0:80)

Figure 23A

Clone 2107.4.10 – Variable Light Chain (Nucleic Acid Sequence – Version 1)

GACATCCGGGTGACTCAGTCTCCTTCACTCCTGTCTGCATCTGTGGGAGACAGAG
TCACTCTCAACTGCAAAGGAAGTCAGAATATTTATAAGAGCTTAGCCTGGTTTCGG
CTAAAGCGTGGAGAAGCTCCCAAGCTCCTGATTTATGATGCAAACAGTTTGCAAAC
GGGCATCCCATCAAGGTTCAGTGGCAGTGGATCTGGTACAGATTTCACACTCACC
ATCACCAGCCTACAGCCTGAAGATGTTGCCACATATTTCTGCCAGCAGTATTATAG
CGGTTACACGTTTGGAGCTGGGACCAAGCTGGAACTGAAA (SEQ ID NO:81)

Clone 2107.4.10 – Variable Light Chain (Nucleic Acid Sequence – Version 2)

GACATCCAGGTGACTCAGTCTCCTTCACTCCTGTCTGCATCTGTGGGAGACAGAGT
CACTCTCAACTGCAAAGGAAGTCAGAATATTTATAAGAGCTTAGCCTGGTTTCGGC
TAAAGCGTGGAGAAGCTCCCAAGCTCCTGATTTATGATGCAAACAGTTTGCAAACG
GGCATCCCATCAAGGTTCAGTGGCAGTGGATCTGGTACAGATTTCACACTCACCAT
CACCAGCCTACAGCCTGAAGATGTTGCCACATATTTCTGCCAGCAGTATTATAGCG
GTTACACGTTTGGAGCTGGGACCAAGCTGGAACTGAAA (SEQ ID NO:82)

Clone 2107.4.10 – Variable Light Chain (Amino Acid Sequence – Version 1)

DIRVTQSPSLLSASVGDRVTLNCKGSQNIYKSLAWFRLKRGEAPKLLIYDANSLQTGIP
SRFSGSGSGTDFTLTITSLQPEDVATYFCQQYYSGYTFGAGTKLELK (SEQ ID NO:83)

Clone 2107.4.10 – Variable Light Chain (Amino Acid Sequence – Version 2)

DIQVTQSPSLLSASVGDRVTLNCKGSQNIYKSLAWFRLKRGEAPKLLIYDANSLQTGIP
SRFSGSGSGTDFTLTITSLQPEDVATYFCQQYYSGYTFGAGTKLELK (SEQ ID NO:84)

Clone 2107.4.10 – CDR-L1 (Amino Acid Sequence)

KGSQNIYKSLA (SEQ ID NO:85)

Figure 23B

Clone 2107.4.10 – CDR-L2 (Amino Acid Sequence)

DANSLQT (SEQ ID NO:86)

Clone 2107.4.10 – CDR-L3 (Amino Acid Sequence)

QQYYSGYT (SEQ ID NO:87)

Figure 24

Clone 2107.4.10 – Variable Heavy Chain (Nucleic Acid Sequence)

CAGGTGCAGCTGAAGGAGTCAGGACCTGGTCTGGTGCAGTCCTCACAGACCCTGT
CTCTCACCTGCACTGTCTCTGGATTCTCATTAACCAGTAATGGTGTAAGCTGGGTT
CGCCAGCCTCCAGGAAAGGGTCTGGAGTGGATTGCAGCAATATCAAGTGGTGGAA
GCACATATTATAATTCAGCGTTCAAATCCCGACTGAGCATCAGCAGGAACACCTCC
AAGAGCCAAGTTCTCTTAAAAATGAACAGTCTGCAAACTGAAGACACAGGCATGTA
CTTCTGTGCCAGACATAGACCGTTCTACTTTGATTACTGGGGCCAAGGAGTCATGG
TCACAGTCTCCTCA (SEQ ID NO:88)

Clone 2107.4.10 – Variable Heavy Chain (Amino Acid Sequence)

QVQLKESGPGLVQSSQTLSLTCTVSGFSLTSNGVSWVRQPPGKGLEWIAAISSGGST
YYNSAFKSRLSISRNTSKSQVLLKMNSLQTEDTGMYFCARHRPFYFDYWGQGVMVTV
SS (SEQ ID NO:89)

Clone 2107.4.10 – CDR-H1 (Amino Acid Sequence)

GFSLTSNGVS (SEQ ID NO:90)

Clone 2107.4.10 – CDR-H2 (Amino Acid Sequence)

AISSGGSTYYNSAFKS (SEQ ID NO:91)

Clone 2107.4.10 – CDR-H3 (Amino Acid Sequence)

HRPFYFDY (SEQ ID NO:92)

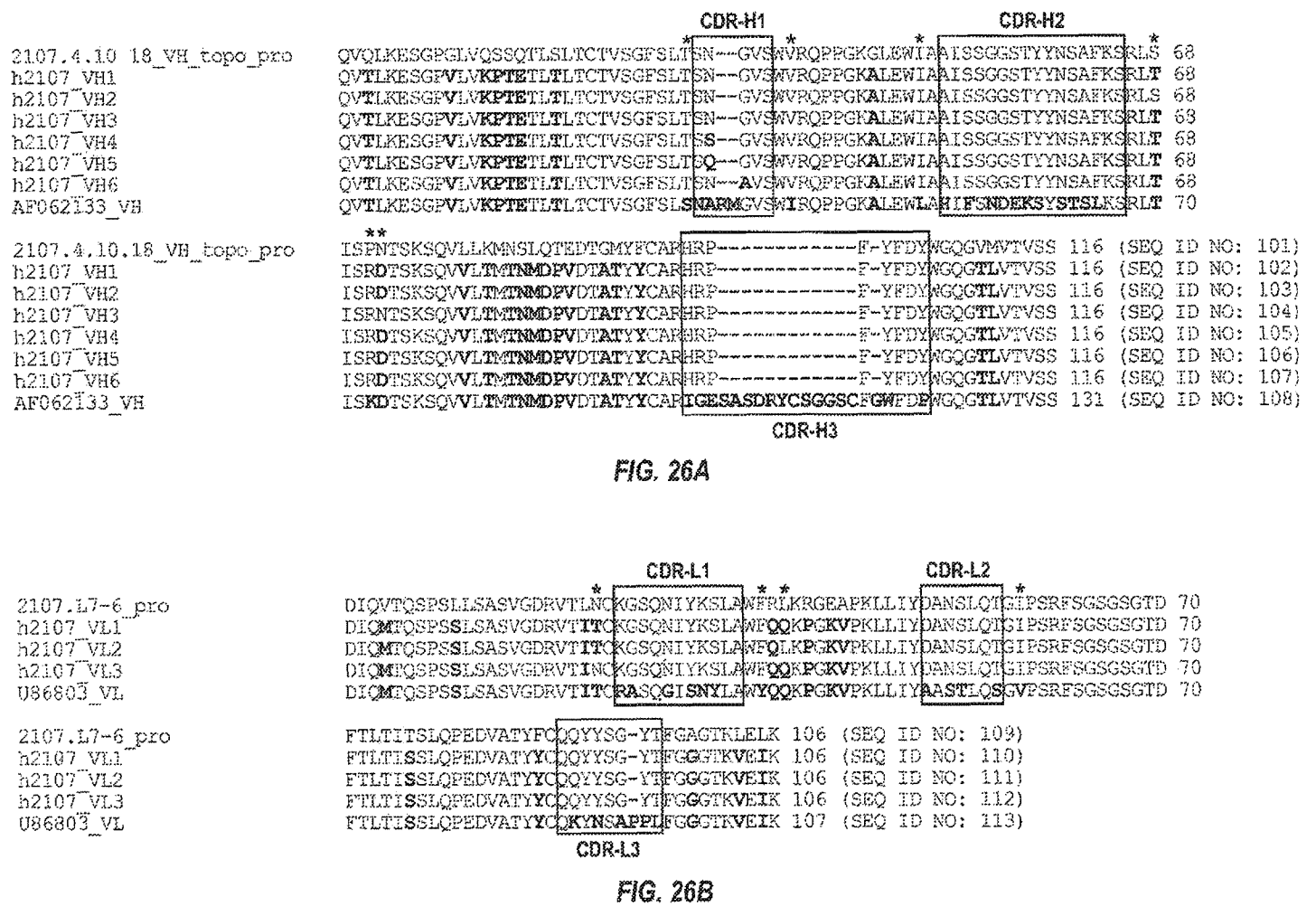

```
                                                          CDR-H1             CDR-H2
                                                         *     *      *                     *
2107.4.10 18_VH_topo_pro  QVQLKESGPGLVQSSQTLSLTCTVSGFSLTSN--GVSWVRQPPGKGLEWIAAISSGGSTYYNSAFKSRLS 68
h2107_VH1                 QVTLKESGPVLVKPTETLTLTCTVSGFSLTSN--GVSWVRQPPGKALEWIAAISSGGSTYYNSAFKSRLT 68
h2107_VH2                 QVTLKESGPVLVKPTETLTLTCTVSGFSLTSN--GVSWVRQPPGKALEWIAAISSGGSTYYNSAFKSRLS 68
h2107_VH3                 QVTLKESGPVLVKPTETLTLTCTVSGFSLTSN--GVSWVRQPPGKALEWIAAISSGGSTYYNSAFKSRLT 68
h2107_VH4                 QVTLKESGPVLVKPTETLTLTCTVSGFSLTSS--GVSWVRQPPGKALEWIAAISSGGSTYYNSAFKSRLT 68
h2107_VH5                 QVTLKESGPVLVKPTETLTLTCTVSGFSLTSQ--GVSWVRQPPGKALEWIAAISSGGSTYYNSAFKSRLT 68
h2107_VH6                 QVTLKESGPVLVKPTETLTLTCTVSGFSLTSN--AVSWVRQPPGKALEWIAAISSGGSTYYNSAFKSRLT 68
AF062133_VH               QVTLKESGPVLVKPTETLTLTCTVSGFSLSNARMGVSWIRQPPGKALEWLAHIFSNDEKSYSTSLKSRLT 70

                           **
2107.4.10.18_VH_topo_pro  ISPNTSKSQVLLKMNSLQTEDTGMYFCARHRP-------------F-YFDYWGQGVMVTVSS 116 (SEQ ID NO: 101)
h2107_VH1                 ISRDTSKSQVVLTMTNMDPVDTATYYCARHRP-------------F-YFDYWGQGTLVTVSS 116 (SEQ ID NO: 102)
h2107_VH2                 ISRDTSKSQVVLTMTNMDPVDTATYYCARHRP-------------F-YFDYWGQGTLVTVSS 116 (SEQ ID NO: 103)
h2107_VH3                 ISRNTSKSQVVLTMTNMDPVDTATYYCARHRP-------------F-YFDYWGQGTLVTVSS 116 (SEQ ID NO: 104)
h2107_VH4                 ISRDTSKSQVVLTMTNMDPVDTATYYCARHRP-------------F-YFDYWGQGTLVTVSS 116 (SEQ ID NO: 105)
h2107_VH5                 ISRDTSKSQVVLTMTNMDPVDTATYYCARHRP-------------F-YFDYWGQGTLVTVSS 116 (SEQ ID NO: 106)
h2107_VH6                 ISRDTSKSQVVLTMTNMDPVDTATYYCARHRP-------------F-YFDYWGQGTLVTVSS 116 (SEQ ID NO: 107)
AF062133_VH               ISKDTSKSQVVLTMTNMDPVDTATYYCARIGESASDRYCSGGSCFGWFDPWGQGTLVTVSS 131 (SEQ ID NO: 108)
                                                            CDR-H3
```

*FIG. 26A*

```
                                                 CDR-L1                      CDR-L2
                                         *              * *                     *
2107.L7-6_pro    DIQVTQSPSLLSASVGDRVTLNCKGSQNIYKSLAWFRLKRGEAPKLLIYDANSLQTGIPSRFSGSGSGTD 70
h2107_VL1        DIQMTQSPSSLSASVGDRVTITCKGSQNIYKSLAWFQQKPGKVPKLLIYDANSLQTGIPSRFSGSGSGTD 70
h2107_VL2        DIQMTQSPSSLSASVGDRVTITCKGSQNIYKSLAWFQLKPGKVPKLLIYDANSLQTGIPSRFSGSGSGTD 70
h2107_VL3        DIQMTQSPSSLSASVGDRVTINCKGSQNIYKSLAWFQQKPGKVPKLLIYDANSLQTGIPSRFSGSGSGTD 70
U86803_VL        DIQMTQSPSSLSASVGDRVTITCRASQGISNYLAWYQQKPGKVPKLLIYAASTLQSGVPSRFSGSGSGTD 70

2107.L7-6_pro    FTLTITSLQPEDVATYFCQQYYSG-YTFGAGTKLELK 106 (SEQ ID NO: 109)
h2107_VL1        FTLTISSLQPEDVATYYCQQYYSG-YTFGGGTKVEIK 106 (SEQ ID NO: 110)
h2107_VL2        FTLTISSLQPEDVATYYCQQYYSG-YTFGGGTKVEIK 106 (SEQ ID NO: 111)
h2107_VL3        FTLTISSLQPEDVATYYCQQYYSG-YTFGGGTKVEIK 106 (SEQ ID NO: 112)
U86803_VL        FTLTISSLQPEDVATYYCQKYNSAPPLFGGGTKVEIK 107 (SEQ ID NO: 113)
                                   CDR-L3
```

*FIG. 26B*

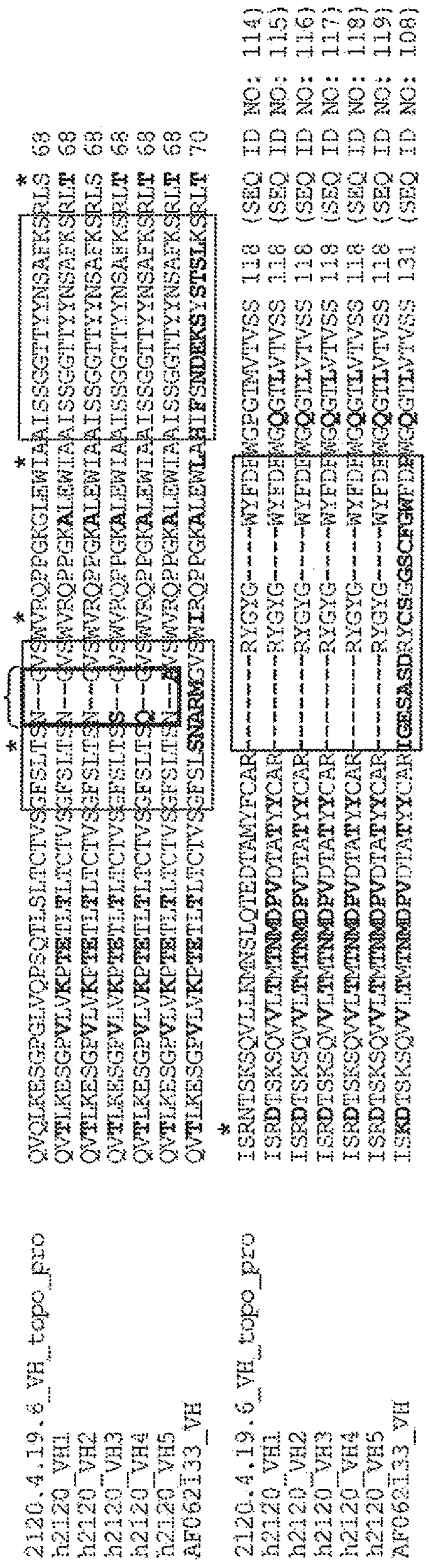

FIG. 27A

```
2120.4.19.6_VH_topo_pro
h2120_VH1     QVQLKESGPGLVQPSQTLSLTCTVS GFSLTSN--VSWVRQPPGKGLEWLAAISSGGTTYYNSAFKSRLS 68
h2120_VH2     QVTLKESGPVLVKPTETLTLTCTVS GFSLIEN--VSWVRQPPGKALEWLAAISSGGTTYYNSAFKSRLS 68
h2120_VH3     QVTLKESGPVLVKPTETLTLTCTVS GFSLITS--VSWVRQPPGKALEWLAAISSGGTTYYNSAFKSRLT 68
h2120_VH4     QVTLKESGPVLVKPTETLTLTCTVS GFSLITS--VSWVRQPPGKALEWLAAISSGGTTYYNSAFKSRLT 68
h2120_VH5     QVTLKESGPVLVKPTETLTLTCTVS GFSLITQ--VSWVRQPPGKALEWLAAISSGGTTYYNSAFKSRLT 68
AF062133_VH   QVTLKESGPVLVKPTETLTLTCTVS GFSLSNARMGVSWIRQPPGKALEWLARIFSNDEKSYSTIKSRLT 70

2120.4.19.6_VH_topo_pro
h2120_VH1     ISRNTSKSQVLLNMSLQTEDTAMYFCAR -----RYGYG-------WYFDF-WGPGTMVTVSS 118  (SEQ ID NO: 114)
h2120_VH2     ISRDTSKSQVVLTMTNMDPVDTATYYCAR -----RYGYG-------WYFDF-MGQGTLVTVSS 118  (SEQ ID NO: 115)
h2120_VH3     ISRDTSKSQVVLTMTNMDPVDTATYYCAR -----RYGYG-------WYFDF-MGQGTLVTVSS 118  (SEQ ID NO: 116)
h2120_VH4     ISRDTSKSQVVLTMTNMDPVDTATYYCAR -----RYGYG-------WYFDF-MGQGTLVTVSS 118  (SEQ ID NO: 117)
h2120_VH5     ISRDTSKSQVVLTMTNMDPVDTATYYCAR -----RYGYG-------WYFDF-MGQGTLVTVSS 118  (SEQ ID NO: 118)
AF062133_VH   ISKDTSKSQVVLTMTNMDPVDTATYYCAR GESASDRYCSGGSCFWFDFWGQGTLVTVSS 131  (SEQ ID NO: 108)
```

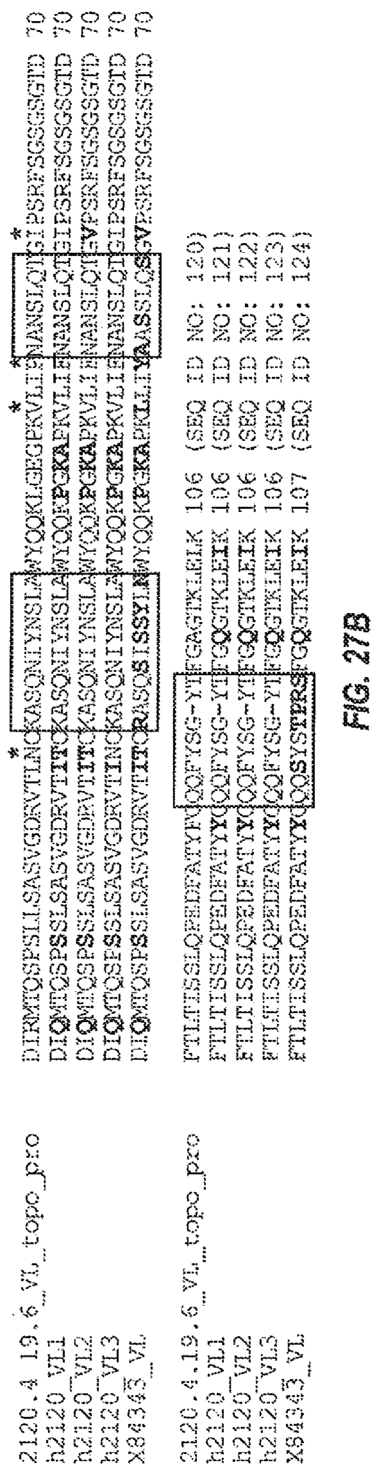

FIG. 27B

```
2120.4.19.6_VL_topo_pro
h2120_VL1     DIRMTQSPSSILSASVGDKVTLNC KASQNIYNSLAWYQQKLGEGPKVLI YNANSLQTG IPSRFSGSGSGTD 70
h2120_VL2     DIQMTQSPSSLSASVGDRVTITC KASQNIYNSLAWYQQKPGKAPKVLI YNANSLQTG IPSRFSGSGSGTD 70
h2120_VL3     DIQMTQSPSSLSASVGDRVTITC KASQNIYNSLAWYQQKPGKAPKVLI YNANSLQTG IPSRFSGSGSGTD 70
h2120_VL4     DIQMTQSPSSLSASVGDRVTITC KASQNIYNSLAWYQQKPGKAPKVLI YNANSLQTG IPSRFSGSGSGTD 70
h2120_VL5     DIQMTQSPSSLSASVGDRVTITC KASQNIYNSLAWYQQKPGKAPKLLI YAASSLQS VPSRFSGSGSGTD 70
X84343_VL     DIQMTQSPSSLSASVGDRVTITC RASQSISSYLNWYQQKPGKAPKLLI YAASSLQS VPSRFSGSGSGTD 70

2120.4.19.6_VL_topo_pro
h2120_VL1     FTLTISSLQPEDFATYYC QQFYSG--YTF GAGTKLELK 106  (SEQ ID NO: 120)
h2120_VL2     FTLTISSLQPEDFATYYC QQFYSG--YTF GQGTKLEIK 106  (SEQ ID NO: 121)
h2120_VL3     FTLTISSLQPEDFATYYC QQFYSG--YTF GQGTKLEIK 106  (SEQ ID NO: 122)
h2120_VL4     FTLTISSLQPEDFATYYC QQFYSG--YTF GQGTKLEIK 106  (SEQ ID NO: 123)
h2120_VL5     FTLTISSLQPEDFATYYC QQFYSG--YTF RSFGQGTKLEIK 106  (SEQ ID NO: 124)
X84343_VL     FTLTISSLQPEDFATYYC QQSYSTPRS FGQGTKLEIK 107  (SEQ ID NO: 107)
```

ANTI-MCAM ANTIBODIES AND ASSOCIATED METHODS OF USE

CROSS-REFERENCES TO RELATED APPLICATIONS

This application is a continuation of U.S. application Ser. No. 14/021,777 filed Sep. 9, 2013, now U.S. Pat. No. 9,447,190, which claims priority to U.S. Provisional Application No. 61/698,916, filed Sep. 10, 2012, U.S. Provisional Application No. 61/797,179, filed Nov. 30, 2012, and U.S. Provisional Application No. 61/797,356, filed Dec. 15, 2012, each of the aforementioned applications is incorporated in its entirety herein for all purposes.

REFERENCE TO A SEQUENCE LISTING

This application includes an electronic sequence listing in a file named "481511_SEQLST.TXT," created on Jul. 22, 2016 and containing 144,258 bytes, which is incorporated by reference.

FIELD OF THE INVENTION

The present invention is directed to antibodies that bind to melanoma cell adhesion molecule (MCAM) which are capable of blocking the interaction between MCAM and its ligand, the laminin alpha-4 chain. The present invention is also directed to methods of use of the novel anti-MCAM antibodies described herein.

REFERENCE TO A "SEQUENCE LISTING", A TABLE, OR A COMPUTER PROGRAM LISTING

The Sequence Listing written in file 436599SEQLIST.txt was created on Sep. 16, 2013 for "ANTI-MCAM ANTIBODIES AND ASSOCIATED METHODS OF USE" is 144,190 bytes. The information contained in this file is hereby incorporated by reference.

BACKGROUND

A novel subset of CD4+ T cells, termed TH17 cells (T helper 17 cells), has been implicated in the pathogenesis of a number of autoimmune diseases, particularly those neuroinflammatory conditions involving CNS infiltration of T cells, such as multiple sclerosis and the animal model, experimental autoimmune encephalomyelitis (EAE). See, e.g., Cua et al., *Nature* 421: 744-748 (2003); see also Ivonov et al., *Cell* 126: 1121-1133 (2006). Much attention on the enhanced pathogenicity of TH17 cells has focused on their ability to secrete a number of select cytokines including IL-17 and IL-22. However, the role of these TH17 cytokines themselves has been called into question, as a conditional knockout of IL-17 is insufficient to affect EAE progression. See, e.g., Haak et al., *J. Clin. Invest.* 119: 61-69 (2009); see also Kreymborg et al., *J. Immunol.* 179: 8098-8104 (2007). Although IL-17 affects such vital aspects of EAE as endothelial cell permeability, TH17 cells appear to do more than just produce any one cytokine. The molecular determinants of the pathogenic function of TH17 cells remain elusive.

The pathogenicity of TH17 cells can be partially explained by their unique migration pattern as evidenced by their expression of chemokine receptors. See, e.g., Kim, *Inflamm. Allergy Drug Targets* 8: 221-228 (2009). It has been established that IL-17 producing cells are enriched within the CCR6+ population of CD4+ T cells, likely conferring a unique migration pattern throughout the vasculature. See, e.g., Acosta-Rodriguez et al., *Nat. Immunol.* 8:639-646 (2007). In fact, CCR6 expression on T cells is required for T cell migration into the CNS and the progression of EAE. Reboldi et al., *Nat. Immunol.* 10: 514-523 (2009). A hypothesis has arisen of two waves of T cells, the first a small population of CCR6 expressing TH17 cells that accumulates and recruits a broader second wave of T cells with a more diverse chemokine receptor repertoire. The anatomical site of this infiltration has been suggested to be the choroid plexus due to the constitutive expression of CCL20, a known ligand of CCR6. Ransohoff et al., *Nat. Rev. Immunol.* 3: 569-581 (2003). The implication has been made that the true pathogenic function of TH17 cells lies in their specific recruitment and infiltration of tissue.

Thus, there is still a need in the art to identify molecules that are involved in the infiltration of TH17 cells into CNS and contribute to their pathogenicity. These molecules can be targets to design therapeutic agents for neuroinflammatory conditions, such as multiple sclerosis (MS) and Parkinson's disease, as well as other TH17-mediated inflammatory conditions not associated with the central nervous system. There is also a need to identify novel antibodies that can bind to and are capable of reducing, interfering, or otherwise blocking the interaction between MCAM expressed on the surface of TH17 and its identified ligand.

SUMMARY OF THE INVENTION

TH17 cells play a significant role in the pathogenesis of various autoimmune diseases, particularly those displaying neuroinflammatory conditions involving T cells' infiltration into CNS. It has been newly discovered that (1) MCAM is selectively enriched on TH17 cells; and (2) MCAM interacts with a laminin $\alpha 4$ chain, such as, for example, the $\alpha 4$ chain of laminin 411, present in the endothelial basement membrane. An MCAM antagonist, e.g., a monoclonal antibody, capable of inhibiting MCAM's binding to a molecule containing a laminin $\alpha 4$ chain, such as, for example, a laminin 411 molecule, may inhibit the migration of TH17 cells into CNS, and thus can be used as a therapeutic agent to prevent or treat diseases displaying TH17-mediated neuroinflammatory conditions. MCAM antagonists, such as an MCAM monoclonal antibody or an antigen-binding fragment thereof, may also be useful to prevent or treat and TH17-mediated disease, including for example, autoimmune disease, for example, multiple sclerosis, inflammatory bowel disease, psoriasis, and rheumatoid arthritis.

The present invention is directed to novel antibodies that are capable of binding to MCAM protein on the surface of cells and, in turn, that are capable of interfering with the interaction of MCAM with its ligand, a protein comprising a laminin alpha-4 chain. Optionally, the antibody is a monoclonal antibody, antibody fragment, chimeric antibody, humanized antibody, single-chain antibody or antibody that competitively inhibits the binding of an anti-MCAM antibody to its respective antigenic epitope.

In other embodiments, the invention provides vectors comprising DNA encoding any of the herein described antibodies and host cells comprising such vectors, wherein such host cells may be CHO cells, *E. coli* cells, or yeast cells. A process for producing any of the herein described antibodies is further provided and comprises the steps of culturing host cells under conditions suitable for expression of the desired antibody, and recovering the desired antibody from the cell culture.

In one embodiment, the present invention is directed to an isolated anti-MCAM antibody, or antigen binding fragment thereof, wherein the antibody or antigen binding fragment thereof comprises three light chain hypervariable regions (HVR-L1, HVR-L2, and HVR-L3) and three heavy chain hypervariable regions (HVR-H1, HVR-H2, and HVR-H3), and wherein:

(a) HVR-L1 comprises the amino acid sequence of SEQ ID NO:31, HVR-L2 comprises the amino acid sequence of SEQ ID NO:32, HVR-L3 comprises the amino acid sequence of SEQ ID NO:33, HVR-H1 comprises the amino acid sequence of SEQ ID NO:36, HVR-H2 comprises the amino acid sequence of SEQ ID NO:37, and HVR-H3 comprises the amino acid sequence of SEQ ID NO:38;

(b) HVR-L1 comprises the amino acid sequence of SEQ ID NO:41, HVR-L2 comprises the amino acid sequence of SEQ ID NO:42, HVR-L3 comprises the amino acid sequence of SEQ ID NO:43, HVR-H1 comprises the amino acid sequence of SEQ ID NO:46, HVR-H2 comprises the amino acid sequence of SEQ ID NO:47, and HVR-H3 comprises the amino acid sequence of SEQ ID NO:48;

(c) HVR-L1 comprises the amino acid sequence of SEQ ID NO:51, HVR-L2 comprises the amino acid sequence of SEQ ID NO:52, HVR-L3 comprises the amino acid sequence of SEQ ID NO:53, HVR-H1 comprises the amino acid sequence of SEQ ID NO:56, HVR-H2 comprises the amino acid sequence of SEQ ID NO:57, and HVR-H3 comprises the amino acid sequence of SEQ ID NO:58;

(d) HVR-L1 comprises the amino acid sequence of SEQ ID NO:61, HVR-L2 comprises the amino acid sequence of SEQ ID NO:62, HVR-L3 comprises the amino acid sequence of SEQ ID NO:63, HVR-H1 comprises the amino acid sequence of SEQ ID NO:66, HVR-H2 comprises the amino acid sequence of SEQ ID NO:67, and HVR-H3 comprises the amino acid sequence of SEQ ID NO:68;

(e) HVR-L1 comprises the amino acid sequence of SEQ ID NO:73, HVR-L2 comprises the amino acid sequence of SEQ ID NO:74, HVR-L3 comprises the amino acid sequence of SEQ ID NO:75, HVR-H1 comprises the amino acid sequence of SEQ ID NO:78, HVR-H2 comprises the amino acid sequence of SEQ ID NO:79, and HVR-H3 comprises the amino acid sequence of SEQ ID NO:80; or (f) HVR-L1 comprises the amino acid sequence of SEQ ID NO:85, HVR-L2 comprises the amino acid sequence of SEQ ID NO:86, HVR-L3 comprises the amino acid sequence of SEQ ID NO:87, HVR-H1 comprises the amino acid sequence of SEQ ID NO:90, HVR-H2 comprises the amino acid sequence of SEQ ID NO:91, and HVR-H3 comprises the amino acid sequence of SEQ ID NO:92.

In certain embodiments, the anti-MCAM antibody may be a chimeric or humanized antibody. In another embodiment, the anti-MCAM antibody may be an IgG1 antibody which may optionally be produced in bacteria or CHO cells.

In yet another embodiment, the present invention is directed to an isolated anti-MCAM antibody, or antigen binding fragment thereof, said antibody or antigen binding fragment thereof comprising a light chain variable region and a heavy chain variable region, wherein:

(a) the light chain variable region comprises the amino acid sequence of SEQ ID NO:30 and the heavy chain variable region comprises the amino acid sequence of SEQ ID NO:35;

(b) the light chain variable region comprises the amino acid sequence of SEQ ID NO:40 and the heavy chain variable region comprises the amino acid sequence of SEQ ID NO:45;

(c) the light chain variable region comprises the amino acid sequence of SEQ ID NO:50 and the heavy chain variable region comprises the amino acid sequence of SEQ ID NO:55;

(d) the light chain variable region comprises the amino acid sequence of SEQ ID NO:60 and the heavy chain variable region comprises the amino acid sequence of SEQ ID NO:65;

(e) the light chain variable region comprises the amino acid sequence of any one of SEQ ID NOS:70, 71, or 72 and the heavy chain variable region comprises the amino acid sequence of SEQ ID NO:77; or (f) the light chain variable region comprises the amino acid sequence of any one of SEQ ID NOS:83 or 84 and the heavy chain variable region comprises the amino acid sequence of SEQ ID NO:89.

In certain embodiments, the anti-MCAM antibody may be a chimeric or humanized antibody. In another embodiment, the anti-MCAM antibody may be an IgG1 antibody which may optionally be produced in bacteria or CHO cells.

In yet another embodiment, the present invention is directed to an isolated anti-MCAM antibody, or antigen binding fragment thereof, that binds substantially the same epitope as, or competes for binding with, any of the anti-MCAM antibodies described herein.

In yet other embodiments, the present invention is directed to an isolated anti-MCAM antibody, or antigen binding fragment thereof, that blocks the interaction between an MCAM protein comprising the amino acid sequence of SEQ ID NO:22 and a protein comprising a laminin α-4 chain. Another embodiment of the present invention is directed to an isolated anti-MCAM antibody, or antigen binding fragment thereof, that blocks the interaction between an MCAM protein comprising the amino acid sequences of SEQ ID NOS:22 and 23 and a protein comprising a laminin α-4 chain. A further embodiment of the present invention is directed to an isolated anti-MCAM antibody or antigen binding fragment thereof which does not block the interaction between an MCAM protein consisting of the amino acid sequence of SEQ ID NO:22 and a protein comprising a laminin α-4 chain. Yet another embodiment of the present invention is directed to an isolated anti-MCAM antibody, or antigen binding fragment thereof, that blocks the interaction between an MCAM protein comprising the amino acid sequences of SEQ ID NOS:22, 23, and 24 and a protein comprising a laminin α-4 chain. Further embodiments of the present invention are directed to isolated anti-MCAM antibodies, or antigen binding fragments thereof, that bind to antigenic epitopes defined by domains 1 and 2, or domain 3 of the human MCAM protein. In a preferred embodiment, the anti-MCAM antibody or fragment thereof does not bind to a protein consisting of amino acids 19-129 of the human MCAM protein.

Yet other embodiments of the present invention are directed to pharmaceutical compositions comprising any of the herein described antibodies, or antigen binding fragment thereof, and articles of manufacture comprising the same.

Other embodiments of the present invention are directed to the use of an anti-MCAM antibody, or antigen binding fragment thereof, in the manufacture of a medicament for the treatment of an inflammatory disorder characterized by infiltration of MCAM-expressing cells into a site of inflammation in the body. In certain embodiments, the inflammatory disorder may be a central nervous system (CNS) inflammatory disorder characterized by infiltration of MCAM-expressing cells into the CNS.

The invention also provides for the use of an anti-MCAM antibody, or antigen binding fragment thereof, in the manufacture of a medicament for the treatment of multiple sclerosis, Parkinson's disease. The invention also provides for the use of an anti-MCAM antibody, or antigen binding fragment thereof, in the manufacture of a medicament for the treatment of allergic contact dermatitis. The invention also provides for the use of an anti-MCAM antibody, or antigen binding fragment thereof, in the manufacture of a medicament for the treatment of, psoriasis. The invention also provides for the use of an anti-MCAM antibody, or antigen binding fragment thereof, in the manufacture of a medicament for the treatment of psoriatic arthritis. The invention also provides for the use of an anti-MCAM antibody, or antigen binding fragment thereof, in the manufacture of a medicament for the treatment of cancer, for example, a solid tumor, such as a melanoma. The invention also provides for the use of an anti-MCAM antibody, or antigen binding fragment thereof, in the manufacture of a medicament for the treatment of sarcoidosis.

Another embodiment of the present invention is directed to a method for the treatment of an inflammatory disorder characterized by infiltration of MCAM-expressing cells to a site of inflammation, the method comprising administering to a mammalian subject in need thereof an effective amount of an anti-MCAM antibody or antigen binding fragment thereof that inhibits the binding of MCAM to a protein comprising a laminin α-4 chain. In certain embodiments, the mammalian subject may be a human and the MCAM-expressing cells may be TH17 cells.

In another aspect, the present invention provides an isolated h1749 anti-MCAM antibody, or antigen binding fragment thereof. In one embodiment, the antibody or antigen binding fragment thereof comprises three light chain hypervariable regions (HVR-L1, HVR-L2, and HVR-L3) and three heavy chain hypervariable regions (HVR-H1, HVR-H2, and HVR-H3), wherein HVR-L1 comprises the amino acid sequence of SEQ ID NO: 61, HVR-L2 comprises the amino acid sequence of SEQ ID NO:62, HVR-L3 comprises the amino acid sequence of SEQ ID NO:63, HVR-H1 comprises the amino acid sequence of SEQ ID NO:66, HVR-H2 comprises the amino acid sequence of SEQ ID NO:67, HVR-H3 comprises the amino acid sequence of SEQ ID NO:68. In another embodiment, the isolated anti-MCAM antibody, or antibody binding fragment thereof, further comprises a heavy chain framework region 2 (FR2) comprising the amino acid sequence of SEQ ID NO: 128.

In one other aspect, the present invention provides an isolated h2107 anti-MCAM antibody, or antigen binding fragment thereof. In one embodiment, the isolated anti-MCAM antibody, or antigen binding fragment thereof, comprises three light chain hypervariable regions (HVR-L1, HVR-L2, and HVR-L3) and three heavy chain hypervariable regions (HVR-H1, HVR-H2, and HVR-H3), wherein HVR-L1 comprises the amino acid sequence of SEQ ID NO:85, HVR-L2 comprises the amino acid sequence of SEQ ID NO:86, HVR-L3 comprises the amino acid sequence of SEQ ID NO:87, HVR-H1 comprises the amino acid sequence of SEQ ID NO:90, HVR-H2 comprises the amino acid sequence of SEQ ID NO:91, and HVR-H3 comprises the amino acid sequence of SEQ ID NO:92. In another embodiment, the isolated anti-MCAM antibody, or antibody binding fragment thereof, further comprises a heavy chain framework region 2 (FR2) comprising the amino acid sequence of SEQ ID NO:134 and/or a heavy chain framework region 3 (FR3) comprising the amino acid sequence of SEQ ID NO:137. In one other embodiment, the isolated anti-MCAM antibody, or antibody binding fragment thereof, further comprises a light chain framework region 2 (FR2) comprising the amino acid sequence of SEQ ID NO:146; and/or a light chain framework region 3 (FR3) comprising the amino acid sequence of SEQ ID NO:144.

In one additional aspect, the present invention provides an isolated h2120 anti-MCAM antibody, or antigen binding fragment thereof. In one embodiment, the antibody or antigen binding fragment thereof comprises three light chain hypervariable regions (HVR-L1, HVR-L2, and HVR-L3) and three heavy chain hypervariable regions (HVR-H1, HVR-H2, and HVR-H3), wherein HVR-L1 comprises the amino acid sequence of SEQ ID NO:73, HVR-L2 comprises the amino acid sequence of SEQ ID NO:74, HVR-L3 comprises the amino acid sequence of SEQ ID NO:75, HVR-H1 comprises the amino acid sequence of SEQ ID NO:141, HVR-H2 comprises the amino acid sequence of SEQ ID NO:79, and HVR-H3 comprises the amino acid sequence of SEQ ID NO:80. In another embodiment, the isolated anti-MCAM antibody, or antibody binding fragment thereof, comprises a heavy chain framework region 2 (FR2) comprising the amino acid sequence of SEQ ID NO:134 and/or a heavy chain framework region 3 (FR3) comprising the amino acid sequence of SEQ ID NO:135. In one other embodiment, the isolated anti-MCAM antibody, or antibody binding fragment thereof, further comprises a light chain framework region 1 (FR1) comprising the amino acid sequence of SEQ ID NO:147; a light chain framework region 2 (FR2) comprising the amino acid sequence of SEQ ID NO:148; a light chain framework region 3 (FR3) comprising the amino acid sequence of SEQ ID NO:149; or any combination thereof.

Additional embodiments of the present invention will be evident to those of ordinary skill in the art based upon the teachings of the present specification.

BRIEF DESCRIPTION OF THE DRAWINGS

FIGS. 1A and 1B depict the presence of MCAM in IL-17-producing human CD4+ cells. FIG. 1A depicts the microarray analysis showing that MCAM is an up-regulated gene in both circulating and activated TH17 cells. FIG. 1B depicts the cell sorting results showing that MCAM exist almost exclusively in a small population of memory T cells (CD45RO+ T cells). FIG. 1C depicts the cell sorting results showing that MCAM is enriched in IL-17-producing human CD4+ T cells.

FIG. 2A depicts MCAM expressing T cells as effector memory T cells (CCR6+ while CCR7−).

FIG. 3A depicts the effects of various cytokines on IL-17 production in MCAM positive T cells. FIG. 3B depicts the percentage of cells expressing MCAM following stimulation by various cytokines. FIGS. 3C, 3D, and 3E depict the levels of IL-17 (FIG. 3C), IL-22 (FIG. 3D), and CCL20 (FIG. 3E) in both MCAM positive and MCAM negative cells after stimulations with various cytokines. FIG. 3F depicts the intracellular levels of FOXP3 in both MCAM positive and MCAM negative cells after stimulations with various cytokines.

FIG. 4A depicts co-localization of the MCAM ligand and laminin on the choroid plexus of healthy mice. FIG. 4B depicts absence of MCAM staining on the choroid plexus of healthy mice (4',6-diamidino-2-phenylindole (DAPI) was used as a counterstain). FIG. 4C depicts the presence of MCAM on vascular endothelial cells within healthy mouse brain (DAPI was used as a counterstain). FIG. 4D depicts the expression pattern of the MCAM ligand by staining healthy mouse spinal cord sections with MCAM-Fc protein. FIG. 4E depicts co-localization of the MCAM ligand and laminin on healthy mouse spinal cord. FIG. 4F depicts the extracellular matrix (ECM) localization of the MCAM ligand. CD31 staining was used to show that MCAM staining is exterior to the endothelial cell layer within the vasculature. FIG. 4G depicts the localization of the MCAM ligand within EAE lesions. MCAM-Fc is shown to colocalize with laminin within the endothelial cell basement membrane, but not within the parenchymal basement membrane. FIG. 4H depicts co-localization of the MCAM ligand and laminin 411 (or laminin alpha-4 chain).

FIG. 5A depicts specific binding of MCAM antibodies to human and mouse MCAM. FIG. 5B depicts blockage of MCAM-Fc's binding to tissues by MCAM antibodies. FIG. 5C depicts inhibition of the interaction between human MCAM and its ligand laminin 411 by a monoclonal antibody.

FIG. 6A depicts the light chain variable region of clone 17 monoclonal antibody. FIG. 6A discloses the nucleic acid sequence encoding the light chain variable region (SEQ ID NO:1) and the amino acid sequence of the light chain variable region (SEQ ID NO:2), in order of appearance. The three hypervariable regions are also indicated as CDRL1 (SEQ ID NO:3), CDRL2 (SEQ ID NO:4), and CDRL3 (SEQ ID NO:5). FIG. 6B discloses the nucleic acid sequence encoding the heavy chain variable region (SEQ ID NO:6) and the amino acid sequence of the heavy chain variable region (SEQ ID NO:7), in order of appearance. The three hypervariable regions are also indicated as CDRH1 (SEQ ID NO:8), CDRH2 (SEQ ID NO:9), and CDRH3 (SEQ ID NO:10).

FIG. 7A depicts absence of MCAM on T cells from naive mouse.

FIG. 9A depicts the light chain variable region of clone 15 monoclonal antibody. FIG. 9A discloses the nucleic acid sequence encoding the light chain variable region (SEQ ID NO:12) and the amino acid sequence of the light chain variable region (SEQ ID NO:13), in order of appearance. The three hypervariable regions are also indicated as CDRL1 (SEQ ID NO:14), CDRL2 (SEQ ID NO:15), and CDRL3 (SEQ ID NO:16). FIG. 9B depicts the heavy chain variable region clone 15 monoclonal antibody. FIG. 9B discloses the nucleic acid sequence encoding the heavy chain variable region (SEQ ID NO:17) and the amino acid sequence of the heavy chain variable region (SEQ ID NO:18), in order of appearance. The three hypervariable regions are also indicated as CDRH1 (SEQ ID NO:19), CDRH2 (SEQ ID NO:20), and CDRH3 (SEQ ID NO:21).

FIGS. 11A, B depict the amino acid sequence (A) (SEQ ID NO:11—Accession No. CAA48332) and structure (B) for human MCAM. In FIG. 11A, the amino acid residue positions corresponding to the five immunoglobulin domains of human MCAM are as follows—1: amino acid residues 19-129; 2: amino acid residues 139-242; 3: amino acid residues 244-321; 4: amino acid residues 335-424; and 5: amino acid residues 430-510) (SEQ ID NOS:22-26), which are also depicted schematically in FIG. 11B.

FIGS. 12A, B show the amino acid sequences for two α4-chain isoforms of human laminin 411. FIG. 12A shows the amino acid sequence corresponding to GenBank Accession No. NP001098676 (SEQ ID NO:27) and FIG. 12B shows the amino acid sequence corresponding to GenBank Accession No. NP001098677 (SEQ ID NO:28).

FIG. 13 depicts the light chain variable region of clone 1174.1.3 monoclonal antibody. FIG. 13 discloses the nucleic acid sequence encoding the light chain variable region (SEQ ID NO:29) and the amino acid sequence of the light chain variable region (SEQ ID NO:30), in order of appearance. The three hypervariable regions are also indicated as CDRL1 (SEQ ID NO:31), CDRL2 (SEQ ID NO:32), and CDRL3 (SEQ ID NO:33).

FIG. 14 depicts the heavy chain variable region clone 1174.1.3 monoclonal antibody. FIG. 14 discloses the nucleic acid sequence encoding the heavy chain variable region (SEQ ID NO:34) and the amino acid sequence of the heavy chain variable region (SEQ ID NO:35), in order of appearance. The three hypervariable regions are also indicated as CDRH1 (SEQ ID NO:36), CDRH2 (SEQ ID NO:37), and CDRH3 (SEQ ID NO:38).

FIG. 15 depicts the light chain variable region of clone 1414.1.2 monoclonal antibody. FIG. 15 discloses the nucleic acid sequence encoding the light chain variable region (SEQ ID NO:39) and the amino acid sequence of the light chain variable region (SEQ ID NO:40), in order of appearance. The three hypervariable regions are also indicated as CDRL1 (SEQ ID NO:41), CDRL2 (SEQ ID NO:42), and CDRL3 (SEQ ID NO:43).

FIG. 16 depicts the heavy chain variable region clone 1414.1.2 monoclonal antibody. FIG. 16 discloses the nucleic acid sequence encoding the heavy chain variable region (SEQ ID NO:44) and the amino acid sequence of the heavy chain variable region (SEQ ID NO:45), in order of appearance. The three hypervariable regions are also indicated as CDRH1 (SEQ ID NO:46), CDRH2 (SEQ ID NO:47), and CDRH3 (SEQ ID NO:48).

FIG. 17 depicts the light chain variable region of clone 1415.1.1 monoclonal antibody. FIG. 17 discloses the nucleic acid sequence encoding the light chain variable region (SEQ ID NO:49) and the amino acid sequence of the light chain variable region (SEQ ID NO:50), in order of appearance. The three hypervariable regions are also indicated as CDRL1 (SEQ ID NO:51), CDRL2 (SEQ ID NO:52), and CDRL3 (SEQ ID NO:53).

FIG. 18 depicts the heavy chain variable region clone 1415.1.1 monoclonal antibody. FIG. 18 discloses the nucleic acid sequence encoding the heavy chain variable region (SEQ ID NO:54) and the amino acid sequence of the heavy chain variable region (SEQ ID NO:55), in order of appearance. The three hypervariable regions are also indicated as CDRH1 (SEQ ID NO:56), CDRH2 (SEQ ID NO:57), and CDRH3 (SEQ ID NO:58).

FIG. 19 depicts the light chain variable region of clone 1749.1.3 monoclonal antibody. FIG. 19 discloses the nucleic acid sequence encoding the light chain variable region (SEQ ID NO:59) and the amino acid sequence of the light chain variable region (SEQ ID NO:60), in order of appearance. The three hypervariable regions are also indicated as CDRL1 (SEQ ID NO:61), CDRL2 (SEQ ID NO:62), and CDRL3 (SEQ ID NO:63).

FIG. 20 depicts the heavy chain variable region clone 1749.1.3 monoclonal antibody. FIG. 20 discloses the nucleic acid sequence encoding the heavy chain variable region (SEQ ID NO:64) and the amino acid sequence of the heavy chain variable region (SEQ ID NO:65), in order of appearance. The three hypervariable regions are also indicated as CDRH1 (SEQ ID NO:66), CDRH2 (SEQ ID NO:67), and CDRH3 (SEQ ID NO:68).

FIGS. 21A, B depict different versions of the light chain variable region of clone 2120.4.19 monoclonal antibody. FIG. 21A-B discloses one version of the nucleic acid sequence encoding a light chain variable region (SEQ ID NO:69), the amino acid sequence of version 1 of the light chain variable region (SEQ ID NO:70), the amino acid sequence of version 2 of the light chain variable region (SEQ ID NO:71), and the amino acid sequence of version 3 of the light chain variable region (SEQ ID NO:72). The three hypervariable regions are also indicated as CDRL1 (SEQ ID NO:73), CDRL2 (SEQ ID NO:74), and CDRL3 (SEQ ID NO:75).

FIG. 22 depicts the heavy chain variable region clone 2120.4.19 monoclonal antibody. FIG. 22 discloses the nucleic acid sequence encoding the heavy chain variable region (SEQ ID NO:76) and the amino acid sequence of the heavy chain variable region (SEQ ID NO:77), in order of appearance. The three hypervariable regions are also indicated as CDRH1 (SEQ ID NO:78), CDRH2 (SEQ ID NO:79), and CDRH3 (SEQ ID NO:80).

FIGS. 23A, B depict different versions of the light chain variable region of clone 2107.4.10 monoclonal antibody. FIGS. 23A-B discloses the nucleic acid sequence encoding version 1 of a light chain variable region (SEQ ID NO:81), the nucleic acid sequence encoding version 2 of a light chain variable region (SEQ ID NO:83), the amino acid sequence of version 1 of the light chain variable region (SEQ ID NO:82), and the amino acid sequence of version 2 of the light chain variable region (SEQ ID NO:84). The three hypervariable regions are also indicated as CDRL1 (SEQ ID NO:85), CDRL2 (SEQ ID NO:86), and CDRL3 (SEQ ID NO:87).

FIG. 24 depicts the heavy chain variable region clone 2107.4.10 monoclonal antibody. FIG. 24 discloses the nucleic acid sequence encoding the heavy chain variable region (SEQ ID NO:88) and the amino acid sequence of the heavy chain variable region (SEQ ID NO:89), in order of appearance. The three hypervariable regions are also indicated as CDRH1 (SEQ ID NO:90), CDRH2 (SEQ ID NO:91), and CDRH3 (SEQ ID NO:92).

FIG. 26A shows the alignment of sequences of the variable heavy chains for the following: murine 2107.4.10.18 anti-MCAM antibody (2107.4.10.18_VH_topo_pro; SEQ ID NO:101); 2107 VH1 humanized anti-MCAM antibody (h2107VH1; SEQ ID NO:102); 2107 VH2 humanized anti-MCAM antibody (h2107VH2; SEQ ID NO:103); 2107 VH3 humanized anti-MCAM antibody (h2107VH3; SEQ ID NO:104); 2107 VH4 humanized anti-MCAM antibody (h2107VH4; SEQ ID NO:105); 2107 VH5 humanized anti-MCAM antibody (h2107VH5; SEQ ID NO:106); 2107 VH6 humanized anti-MCAM antibody (h2107VH6; SEQ ID NO:107); and heavy chain human variable AF062133 IGHV2-26*01 sequence used as the framework donor (AF062133_VH; SEQ ID NO:108). Kabat numbering is used and hypervariable regions (HVRs) grafted from the murine 2107.4.10.18 antibody to the variable heavy chain variable AF062133 IGHV2-26*01 framework are boxed in both FIG. 26A. The S30T, I37V, L48I and K71R mutations combined with (i) mutations of the boxed N/D residues between CDR-H2 and CDR-H3 (D78N) restores murine N-glycosylation; or a mutation in an N-G sequence in CDR-H1, e.g., N32S (VH4); N32Q (VH5); or G33A (VH6)), provides an N deamidation mutant. The bolded amino acid residues in the humanized antibody sequences differ from the corresponding residues in the murine antibody sequence. The position of canonical and interface amino acid residues that may affect CDR contact or CDR structure are indicated by an asterisk.

FIG. 26B shows the alignment of sequences of the variable light chains for the following: murine 2107_L7-6 anti-MCAM antibody (2107_L7-6_pro; SEQ ID NO:109); 2107 VL1 humanized anti-MCAM antibody (h2107VL1; SEQ ID NO:110); 2107 VL2 humanized anti-MCAM antibody (h2107VL2; SEQ ID NO:111); 2107 VL3 humanized anti-MCAM antibody (h2107VL3 SEQ ID NO:112); and light chain human variable U86803 IGKV1-27*01 sequence used as the framework donor (U86803_VL SEQ ID NO:113). Kabat numbering is used and hypervariable regions (HVRs) grafted from the murine 2107_L7-6 antibody to the variable light chain variable U86803 IGKV1-27*01 framework are boxed. The bolded amino acid residues in the humanized antibody sequences differ from the corresponding residues in the murine antibody sequence.

The position of canonical and interface amino acid residues that may affect CDR contact or CDR structure are indicated by an asterisk.

FIG. 27A shows the alignment of sequences of the variable heavy chains for the following: murine 2120.4.19.6 anti-MCAM antibody (2120.4.19.6_VH_topo_pro; SEQ ID NO:114); 2120 VH1 humanized anti-MCAM antibody (h2120VH1; SEQ ID NO:115); 2120 VH2 humanized anti-MCAM antibody (h2120VH2; SEQ ID NO:116); 2120 VH3 humanized anti-MCAM antibody (h2120VH3; SEQ ID NO:117); 2120 VH4 humanized anti-MCAM antibody (h2120VH4; SEQ ID NO:118); 2120 VH5 humanized anti-MCAM antibody (h2120VH5; SEQ ID NO:119); and heavy chain human variable AF062133 IGHV2-26*01 sequence used as the framework donor (AF062133_VH; SEQ ID NO:108). Kabat numbering is used and hypervariable regions (HVRs) grafted from the murine 2120.4.19.6 antibody to the variable heavy chain variable AF062133 IGHV2-26*01 framework are boxed. The S30T, I37V, L48I and K71R mutations combined with (i) mutations of the boxed N/D residues in CDR-H1, e.g., N32S (VH3); N32Q (VH4); or G33A (VH5)), provides an N deamidation mutant. The bolded amino acid residues in the humanized antibody sequences differ from the corresponding residues in the murine antibody sequence. The position of canonical and interface amino acid residues that may affect CDR contact or CDR structure are indicated by an asterisk. Residues where mutations were focused due to the presence of N-deamination sites or N-glycosylation sites are shown in the bracketed box.

FIG. 27B shows the alignment of sequences of the variable light chains for the following: murine 2120.4.19.6 anti-MCAM antibody (2120.4.19.6_VL_topo_pro; SEQ ID NO:120); 2120 VL1 humanized anti-MCAM antibody (h2120VL1 SEQ ID NO:121); 2120 VL2 humanized anti-MCAM antibody (h2120VL2 SEQ ID NO:122); 2120 VL3 humanized anti-MCAM antibody (h2120VL3 SEQ ID NO:123); and light chain human variable X84343 IGKV2-26*01 sequence used as the framework donor (X84343_VL SEQ ID NO:124). Kabat numbering is used and hypervariable regions (HVRs) grafted from the murine 2120.4.19.6 antibody to the variable light chain variable X84343 IGKV2-26*01 framework are boxed. The bolded amino acid residues in the humanized antibody sequences differ from the corresponding residues in the murine antibody sequence. The position of canonical and interface amino acid residues that may affect CDR contact or CDR structure are indicated by an asterisk.

Figure 28A:
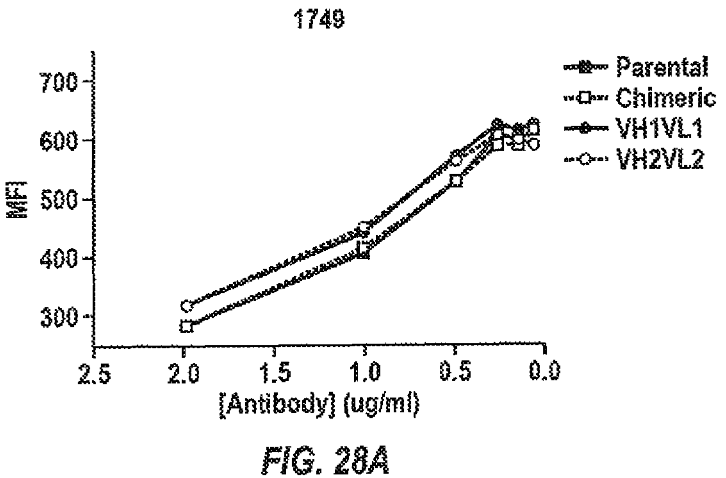
Figure 28B:
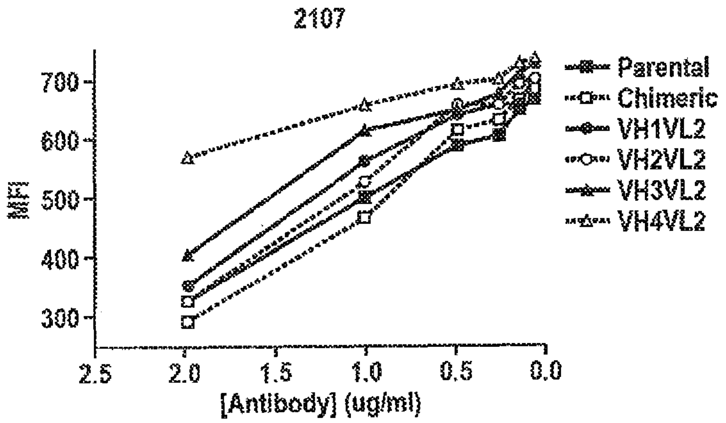
Figure 28C:
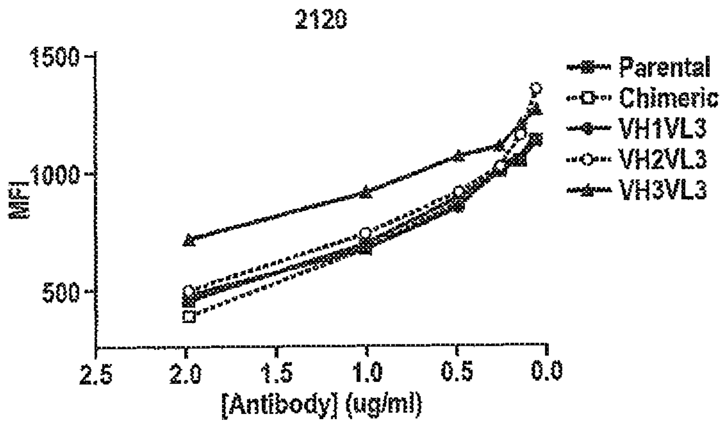

FIG. 28A-C compare the blocking of various 1749, 2120, and 2107 antibodies respectively of MCAM binding to laminin 411.

Figure 29A:
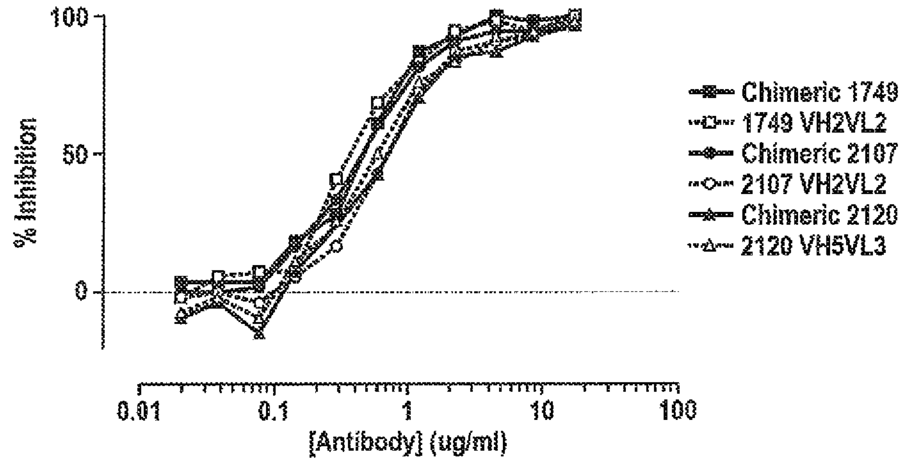

FIGS. 29A, B shows the % inhibition for certain humanized anti-MCAM antibodies as compared to chimeric anti-MCAM antibodies.

Figure 30:
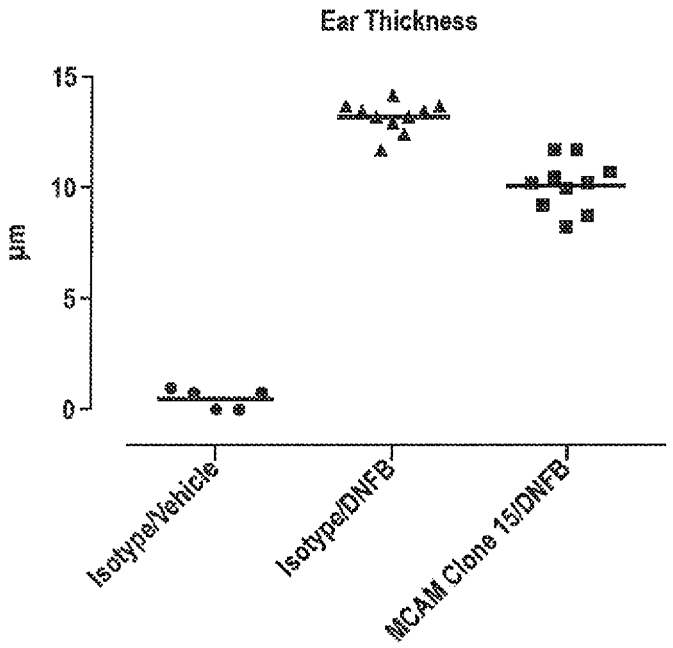

FIG. 30: Treatment with an anti-MCAM antibody reduces inflammation in model of skin inflammation.

Figure 31A:
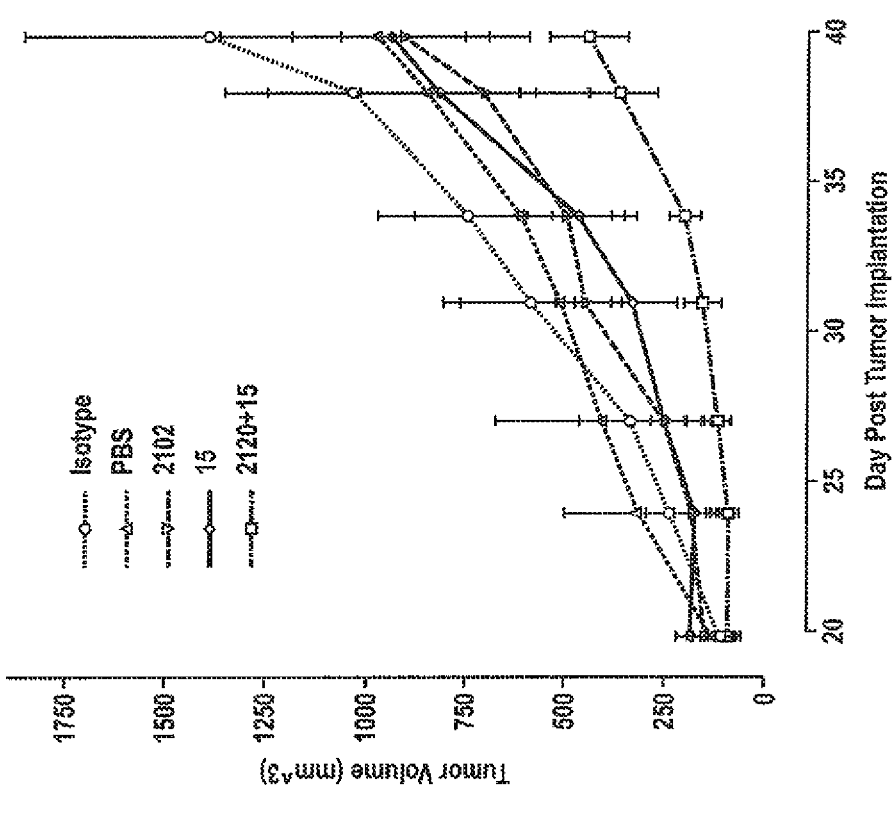

FIGS. 31A, B: Anti-MCAM antibodies inhibit melanoma growth by volume (A) and weight (B) in xenograft model.

DETAILED DESCRIPTION

1. Definitions and Abbreviations

1.1. Definitions

An "individual" or "subject" as used herein may be any of mammalian animals (e.g., domesticated animals), including human, dog, cat, cattle, horse, goat, pig, swine, sheep, monkey, guinea pig, rat, and mouse. In one embodiment, the individual or subject can be a human.

"MCAM" (melanoma cell adhesion molecule, also known as CD146 and MUC18) refers to a cell surface glycoprotein belonging to the immunoglobulin superfamily involved in cell adhesion, and in cohesion of the endothelial monolayer at intercellular junctions in vascular tissue. It also promotes tumor progression of many cancers, such as solid tumors, including melanoma and prostate cancer. It is known to interact in a homotypic/homophilic manner and may also bind to other ligands. The human MCAM has the amino acid sequence of SEQ ID NO: 11 (FIG. 11A), which includes five immunoglobulin domains (1: amino acid residues 19-129; 2: amino acid residues 139-242; 3: amino acid residues 244-321; 4: amino acid residues 335-424; and 5: amino acid residues 430-510) shown as SEQ ID NOS:22-26, which are also depicted schematically in FIG. 11B.

A "laminin α4 chain" refers to one of the polypeptide chains found in laminin molecules, which are expressed in the basal lamina (of the basement membrane), a protein network foundation for most cells and organs. Laminins are known to bind to cell membranes through plasma membrane molecules and contribute to cell attachment. The laminin α4 chain typically forms a complex with a laminin β-chain, and a laminin γ-chain. The laminin α4 chain is found in numerous laminin molecules including, without limitation, laminin 411 (laminin 8 or α4β1γ1); laminin 421 (laminin 9 or α4β2γ1), and laminin 423 (laminin 14 or α4β2γ3). There are two main isoforms of the human laminin α4-chain: GenBank Accession Nos. NP001098676 and NP001098677 as shown in FIGS. 12A-B (amino acid sequences SEQ ID NOS:27-28). "Laminin 411" refers to a trimeric polypeptide complex made up of three polypeptide subunits or chains: α4-chain, a β1-chain, and a γ1-chain.

The term "antagonist" is used in the broadest sense, and includes any molecule that partially or fully blocks, inhibits, or neutralizes a qualitative biological activity of an MCAM polypeptide. For the purpose of the present invention, the biological activity preferably is the ability to inhibit the ability of MCAM (i) to specifically bind its ligand: a laminin α4 chain, e.g., the α4 chain of laminin 411; and/or (ii) to facilitate an MCAM-expressing cell, e.g., a TH17 cell, to infiltrate into or migrate to a subject's tissue. Antagonists of MCAM can be identified, for example, based upon their ability to inhibit or block the specific binding of MCAM to its ligand: a laminin α4 chain, e.g., the α4 chain of laminin 411. MCAM antagonists specifically include, without limitation, antibodies (e.g., antagonist or neutralizing antibodies), including chimeric, humanized and human antibodies and their functional fragments, small molecules, ribozymes, aptamers, peptides, and nucleic acids that encode polypeptide antagonists or antagonist antibodies.

The term "MCAM antagonist antibody" refers to an antibody which inhibits or neutralizes the activity of MCAM. Such an antibody specifically binds to a polypeptide target involved in the infiltration of an MCAM-expressing cell into the CNS, e.g., MCAM or a laminin α4 chain (e.g., the α4 chain of laminin 411).

A "blocking" antibody, "neutralizing" antibody, or "antagonist" antibody is one which inhibits or reduces a biological activity of the antigen it binds. Such antibodies may substantially or completely inhibit the biological activity of the antigen.

The terms "specifically binds" or "binds specifically" as used herein means that one member of a specific binding pair will not show any statistically significant binding to molecules other than its specific binding partner. A binding partner may show at least 1000 times the affinity of binding (measured as an apparent association constant) for its specific binding pair partner than a non-specific binding partner. For example, antibodies that bind to MCAM with a binding affinity of $10^7$ mole/L or more, typically $10^8$ mole/L or more, are said to bind specifically to MCAM.

The terms “biological activity” and “biologically active” with regard to MCAM refer to its ability to specifically bind its ligand (a laminin α4 chain, e.g., the α4 chain of laminin 411) and/or to facilitate the infiltration of MCAM-expressing cells, e.g., TH17 cells, into the CNS.

The term an “MCAM-expressing cell” refers to a cell of the immune system that expresses MCAM. For example, MCAM expression is enriched on memory T lymphocytes, e.g., TH17 cells.

The term “binding molecule” as used herein refers to a molecule that specifically binds to a target. The term specifically includes, without limitation, antibodies and antibody fragments (e.g. those comprising one or more of the CDRs described herein), and peptide and non-peptide small molecules.

“Antibodies” (Abs) and “immunoglobulins” (Igs) are glycoproteins having some common structural characteristics. While antibodies exhibit binding specificity to a specific antigen, immunoglobulins include both antibodies and other antibody-like molecules which lack antigen specificity. Polypeptides of the latter kind can be, for example, produced at low levels by the lymph system and at increased levels by myelomas.

The term “antibody” used herein may encompass intact monoclonal antibodies, polyclonal antibodies, multispecific antibodies (e.g. bispecific antibodies) formed from at least two intact antibodies, and antibody fragments, so long as they exhibit the desired biological activity. The term “antigen-binding fragment” of an antibody refers to a portion of the full-length immunoglobulin molecule that specifically binds to the antigen. An antigen-binding fragment of an antibody thus includes an antigen-binding heavy chain, light chain, heavy chain-light chain dimer, Fab fragment, $F(ab')_2$ fragment, Fv fragment, single chain Fv (scFv), diabodies, linear antibodies, and multispecific antibodies formed from antibody fragment(s).

The term “monoclonal antibody” as used herein refers to an antibody from a population of substantially homogeneous antibodies, i.e., the individual antibodies comprising the population are substantially similar and bind the same epitope(s), except for possible variants that may arise during production of the monoclonal antibody, such variants generally being present in minor amounts. Such monoclonal antibody typically includes an antibody comprising a variable region that binds a target, wherein the antibody was obtained by a process that includes the selection of the antibody from a plurality of antibodies. For example, the selection process can be the selection of a unique clone from a plurality of clones, such as a pool of hybridoma clones, phage clones or recombinant DNA clones. It should be understood that the selected antibody can be further altered, for example, to improve affinity for the target, to humanize the antibody, to improve its production in cell culture, to reduce its immunogenicity in vivo, to create a multispecific antibody, etc., and that an antibody comprising the altered variable region sequence is also a monoclonal antibody of this invention. In addition to their specificity, the monoclonal antibody preparations are advantageous in that they are typically uncontaminated by other immunoglobulins. The modifier “monoclonal” indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981), recombinant DNA methods (see, e.g., U.S. Pat. No. 4,816,567), phage display technologies (see, e.g., Clackson et al., Nature, 352:624-628 (1991); Marks et al., J. Mol. Biol., 222:581-597 (1991); Sidhu et al., J. Mol. Biol. 338(2):299-310 (2004); Lee et al., J. Mol. Biol. 340 (5):1073-1093 (2004); Fellouse, Proc. Nat. Acad. Sci. USA 101(34):12467-12472 (2004); and Lee et al. J. Immunol. Methods 284(1-2):119-132 (2004) and technologies for producing human or human-like antibodies from animals that have parts or all of the human immunoglobulin loci or genes encoding human immunoglobulin sequences (see, e.g., WO98/24893, WO/9634096, WO/9633735, and WO/91 10741, Jakobovits et al., Proc. Natl. Acad. Sci. USA, 90:2551 (1993); Jakobovits et al., Nature, 362:255-258 (1993); Bruggemann et al., Year in Immune, 7:33 (1993); U.S. Pat. Nos. 5,545,806, 5,569,825, 5,591,669 (all of GenPharm); U.S. Pat. No. 5,545,807; WO 97/17852, U.S. Pat. Nos. 5,545,807; 5,545,806; 5,569,825; 5,625,126; 5,633,425; and 5,661,016, and Marks et al., Bio/Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); and Lonberg and Huszar, Intern. Rev. Immunol., 13: 65-93 (1995).

The monoclonal antibodies herein specifically include “chimeric” antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 (1984)). Chimeric antibodies of interest herein include “primatized” antibodies comprising variable domain antigen-binding sequences derived from a non-human primate (e.g. Old World Monkey, Ape etc) and human constant region sequences, as well as “humanized” antibodies.

“Humanized” forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

An "intact antibody" herein is one which comprises two antigen binding regions, and an Fc region. Preferably, the intact antibody has a functional Fc region.

An "antibody (or any other binding molecule) that binds to the same epitope" as a reference antibody (or any other binding molecule) refers to an antibody (or any other binding molecule) that blocks binding of the reference antibody (or any other binding molecule) to its antigen in a competition assay by 50% or more, and conversely, the reference antibody (or any other binding molecule) blocks binding of the antibody to its antigen in a competition assay by 50% or more.

An "affinity matured" antibody is one with one or more alterations in one or more hypervariable regions thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

The "light chains" of antibodies from any vertebrate species can be assigned to one of two clearly distinct types, called κ and λ, based on the amino acid sequences of their constant domains. Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions (HVRs) both in the light-chain and heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

"Fv" is the minimum antibody fragment which contains a complete antigen-recognition and binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Hypervariable region" or "HVR" refers to the amino acid residues of an antibody that are responsible for antigen-binding. The hypervariable region generally comprises amino acid residues from a "complementarity determining region" or "CDR" (Kabat et al., Sequences of Proteins of Immunological Interest, $5^{th}$ Ed. Public Health Service, National Institutes of Health, Bethesda, Md. (1991)) and/or those residues from a "hypervariable loop" (Chothia and Lesk, *J. Mol. Biol.* 196: 901-917 (1987)).

The term "complementarity determining regions" or "CDRs" when used herein refers to parts of immunological receptors that make contact with a specific ligand and determine its specificity. The CDRs of immunological receptors are the most variable part of the receptor protein, giving receptors their diversity, and are carried on six loops at the distal end of the receptor's variable domains, three loops coming from each of the two variable domains of the receptor.

The term "epitope" is used to refer to binding sites for (monoclonal or polyclonal) antibodies on protein antigens. Typically, an epitope refers to a unit of structure conventionally bound by an immunoglobulin VH-VL pair. Epitopes define the minimum binding site for an antibody, and thus represent the target of specificity of an antibody. Epitopes can be linear or conformational, and can be as small as three amino acids.

A "small molecule" is defined herein to have a molecular weight below about 600, preferably below about 1000 daltons. Generally, a small molecule is a non-peptide small organic molecule.

"Isolated," when used to describe the various polypeptides, proteins and antibodies disclosed herein, means polypeptide, protein or antibody that has been identified and separated and/or recovered from a component of its natural environment. Contaminant components of its natural environment are materials that would typically interfere with diagnostic or therapeutic uses for the polypeptide, protein or antibody, and may include enzymes, hormones, and other proteinaceous or non-proteinaceous solutes. In preferred embodiments, the polypeptide, protein or antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide, protein or antibody includes polypeptide, protein or antibody in situ within recombinant cells, since at least one component of the associated natural environment will not be present. Ordinarily, however, isolated polypeptide, protein or antibody will be prepared by at least one purification step.

The terms "affinity", "binding affinity" and "$K_d$" refer to the equilibrium dissociation constant (expressed in units of concentration) associated with each MCAM binding molecule—target complex, such as between an anti-MCAM antibody and MCAM. The binding affinity is directly related to the ratio of the off-rate constant (generally reported in units of inverse time, e.g., $seconds^{-1}$) to the on-rate constant (generally reported in units of concentration per unit time, e.g., molar/second). The binding affinity may be determined by, for example, an ELISA assay, kinetic exclusion assay or surface plasmon resonance. It is noted that certain epitopes can occur repetitively (multivalent) on a cell surface and that the dissociation constant (koff) for the binding of an antibody to a repetitive epitope may be greatly diminished over the dissociation constant for the reaction of the same antibody with the corresponding ligand in univalent form. The diminished dissociation constant arises because when one antibody-ligand bond dissociates, other bonds hold the bivalent (or multivalent) antibody to the multivalent ligand, allowing the dissociated bond to form again. The dissociation constant for the reaction between bivalent (or multivalent) Ab and multivalent ligand has been termed the functional affinity to contrast it with intrinsic affinity, which is the association constant for an antibodies representative individual site.

The terms "dissociation", "dissociation rate" and "$k_{off}$" as used herein, are intended to refer to the off rate constant for dissociation of a binding molecule, such as an antibody, from the binding molecule/target, e.g. antibody/antigen complex.

The terms "association", "association rate" and "$k_{on}$" as used herein, are intended to refer to the on rate constant for association of a binding molecule with a target, such as an antibody with an antigen, to form a complex.

The terms "effective concentration" and "$EC_{50}$" as used herein, are intended to refer to the concentration of a binding molecule (e/g/ antibody) capable of interacting with sufficient quantities of target molecules to produce an effect on approximately 50% of the treated cells.

As used herein, "treatment" (and grammatical variations thereof such as "treat" or "treating") refers to clinical intervention in an attempt to alter the natural course of the individual being treated, and can be performed either for prophylaxis/prevention, or during the course of clinical pathology. The term refers to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

"Chronic" administration refers to administration of the agent(s) in a continuous mode as opposed to an acute mode, so as to maintain the desired effect for an extended period of time.

"Intermittent" administration is treatment that is not consecutively done without interruption, but rather is cyclic in nature.

An "effective amount" refers to an amount effective, at dosages and for periods of time necessary, to achieve the desired prophylactic or therapeutic result. An effective amount refers to the amount of active compound or pharmaceutical agent that elicits the biological or medicinal response in a tissue, system, animal, individual or human that is being sought by a researcher, veterinarian, medical doctor or other clinician, which includes one or more of the following:

(A) preventing the disease; for example, preventing an inflammatory disease, such as a neuroinflammatory disease, condition or disorder in an individual that may be predisposed to the disease, condition or disorder but does not yet experience or display the pathology or symptoms of the disease, (B) inhibiting the disease; for example, inhibiting an inflammatory disease, such as a neuroinflammatory disease, condition or disorder in an individual that is experiencing or displaying the pathology or symptoms of the disease, condition or disorder (i.e., arresting further development of the pathology and/or symptoms), and (C) ameliorating the disease; for example, ameliorating an inflammatory disease, such as a neuroinflammatory disease, condition or disorder in an individual that is experiencing or displaying the pathology or symptoms of the disease, condition or disorder (i.e., reversing the pathology and/or symptoms).

Unless defined otherwise, all technical and scientific terms used herein have the same meaning as commonly understood by one of ordinary skill in the art. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted. Before the present methods, kits and uses therefore are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein, the singular forms "a", "and", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth. Throughout this specification and claims, the word "comprise," or variations such as "comprises" or "comprising," will be understood to imply the inclusion of a stated integer or group of integers but not the exclusion of any other integer or group of integers.

1.2. Abbreviations

| | |
|---|---|
| Abs | antibodies |
| CDR | complementarity determining region |
| CFA | complete Freund's adjuvant |
| CFSE | carboxyfluorescein succinimidyl ester |
| CNS | central nervous system |
| DAPI | 4',6-diamidino-2-phenylindole |
| DN | dopamine-containing neuron |
| EAE | experimental autoimmune encephalomyelitis |
| ECM | extracellular matrix |
| FACS | fluorescence Activated cell sorting |
| FR | Framework Region |
| IFA | incomplete Freund's adjuvant |
| Igs | immunoglobulins |
| MCAM | melanoma cell adhesion molecule |
| MOG | myelin oligodendrocyte glycoprotein (MOG) |
| MS | multiple sclerosis |
| PD | Parkinson's disease |
| PMA | phorbol myristate acetate |

2. MCAM

MCAM (melanoma cell adhesion molecule) is a cell-surface glycoprotein originally identified as a melanoma antigen, whose expression is associated with tumor progression and the development of metastatic potential. MCAM is a 113 kDa cell surface integral membrane glycoprotein composed of a signal peptide, five immunoglobulin-like domains (1, 2, 3, 4, and 5; or V-V-C2-C2-C2), a transmembrane region, and a short cytoplasmic tail. See, e.g., Lehmann et al., *Proc. Nat'l Acad. Sci. USA* 86: 9891-9895 (1989) and FIG. 11B. MCAM is a member of the immunoglobulin superfamily and has significant sequence homology to a number of cell adhesion molecules of the Ig superfamily, including BEN (Pourquie et al., *Proc. Nat'l Acad. Sci. USA* 89: 5261-5265 (1992)), neural-cell adhesion molecule (N-CAM) (Owens et al., *Proc. Nat'l Acad. Sci. USA* 84: 294-298 (1987)), myelin-associated glycoprotein (MAG) (Lai et al., *Proc. Nat'l Acad. Sci. USA* 84: 4337-4341 (1987)), deleted in colorectal cancer protein (DCC) (Hedrick et al., *Genes Devel.* 8: 1174-1183 (1994)), and gicerin (Taira et al., *Neuron* 12: 861-872 (1994)). The expression of MCAM has been detected in relatively limited spectrum of normal human tissues and in a variety of malignant neoplasms. In normal adult tissues, MCAM is expressed on endothelial cells, smooth muscle cells (Shih et al., *Lab. Invest.* 75: 377-388 (1996); Sers et al., *Cancer Res.* 54: 5689-5694 (1994)), a subpopulation of activated T lymphocytes (Pickl et al., *J. Immunol.* 158: 2107-2115 (1997)), and intermediate trophoblasts (Shih et al., supra). MCAM is also expressed on a variety of malignant neoplasms including smooth muscle neoplasms (Leiomyomas and leiomyosarcomas), tumors of vascular origin (angiosarcomas and Kaposi's sarcomas), placental site trophoblastic tumors, choriocarcinomas, and melanomas (Shih et al., *Clinical Cancer Res.* 2: 569-575 (1996); Holzmann et al., *Int. J. Cancer* 39: 466-471 (1987)). The expression of MUC18 correlates directly with the metastatic potential of human melanoma cells (Bar-Eli, *Cancer Metastasis,* 18: 377-385 (1999)).

A number of studies have identified MCAM as a marker of tumor progression and metastasis in melanomas. The expression of MCAM is absent in normal melanocytes and benign nevi but prominent on many primary melanomas and in most metastatic lesions (Lehmann et al., supra; Shih et al., supra). MCAM expression correlates well with tumor vertical thickness and metastasis formation, and greater than 80% of metastatic lesions express MCAM (Lehmann et al., supra; Xie et al., *Cancer Res.* 57: 2295-2303 (1997); and Shih et al., supra). Modulators of MCAM have been generated to treat melanomas. See, e.g., U.S. Pat. No. 7,067,131. Recently, MCAM modulation has been suggested to identify and select inflammatory cytokine-secreting T cells or their precursors to treat various inflammatory conditions. See, e.g., U.S. Published Patent Application No. 2011/0014183.

3. Neuroinflammatory Conditions, Multiple Sclerosis, and Parkinson Disease

A neuroinflammatory condition refers to a condition associated with inflammation of the nervous system, in an embodiment the central nervous system (CNS), and which is associated with cell/tissue damage. It is typically characterized by, for example, increased glial activation, increased pro-inflammatory cytokine/chemokine levels (e.g., TNFα, INFγ, IL-1β), increased blood-brain-barrier permeability, and/or increased immune cell (e.g., leukocyte) recruitment/invasion to the CNS. It may refer to, for example, chronic neuroinflammation, such as an inflammation associated with chronic activation of cells of the immune system (i.e., autoimmune-associated neuroinflammation). Such chronic neuroinflammation can be observed in, for example, multiple sclerosis (MS). Additionally, Parkinson's disease (PD) is a neurodegenerative disease displaying neuroinflammation, for example, activated microglia and infiltrating T cells.

Multiple sclerosis, as a progressive neurological autoimmune disease, results from chronic, pathological inflammation (Yednock et al., *Nature* 356: 63-66 (1992); Baron et al., *J. Exp. Med.* 177: 57-68 (1993)). MS affects an estimated 250,000 to 350,000 people in the United States. Multiple sclerosis is thought to be the result of a specific autoimmune reaction wherein certain leukocytes attack and initiate the destruction of myelin, the insulating sheath covering nerve fibers. The onset of MS may be dramatic or so mild as to not cause a patient to seek medical attention. The most common symptoms include weakness in one or more limbs, visual blurring due to optic neuritis, sensory disturbances, diplopia, and ataxia. The course of disease may be stratified into three general categories: (1) relapsing MS, (2) chronic progressive MS, and (3) inactive MS.

Relapsing MS is generally characterized by recurrent attacks of neurologic dysfunction. MS attacks generally evolve over days to weeks and may be followed by complete, partial, or no recovery. Recovery from attacks generally occurs within weeks to several months from the peak of symptoms, although rarely some recovery may continue for 2 or more years.

Chronic progressive MS results in gradually progressive worsening without periods of stabilization or remission. This form develops in patients with a prior history of relapsing MS, although in 20% of patients, no relapses can be recalled. Acute relapses also may occur during the progressive course of MS.

A third form is inactive MS. Inactive MS is characterized by fixed neurologic deficits of variable magnitude. Most patients with inactive MS have an earlier history of relapsing MS. The course of MS is also dependent on the age of the patient. For example, favorable prognostic factors include early onset (excluding childhood), a relapsing course and little residual disability 5 years after onset. By contrast, poor prognosis is associated with a late age of onset (i.e., age 40 or older) and a progressive course. These variables are interdependent, since chronic progressive MS tends to begin at a later age that relapsing MS. Disability from chronic progressive MS is usually due to progressive paraplegia or quadriplegia in individual patients.

Parkinson's disease (PD) is a progressive neurodegenerative disease displaying primary clinical features of motor abnormalities, e.g., resting tremor, bradykinesia, and rigidity. PD is characterized by the loss of dopamine-containing neuron (DN) cells in the substantia nigra parts compacta (Forno, *J. Neurophthol. Exp. Neurol.* 55: 259-272 (1996)). One of the hallmarks of PD is neuroinflammation characterized by activated microglia and infiltrating T cells. Although studies have suggested various mechanisms for PD, such as mitochonodrial dysfunction, oxidative stress, and impairment of protein degradation machinery, the cause of PD remains elusive (Dauer et al., *Neuron* 39: 889-909 (2003)). Recent findings have indicated that both innate and adaptive immunity may play important roles in the pathogenesis of PD (Stone et al., *Antioxid. Redox. Signal.* 11: 2151-2166 (2009)). Particularly, it has been shown in the animal model of PD that both activated microglia and T lymphocytes contribute significantly to neurodegeneration. See, e.g., Brochard et al., *J. Clin. Invest.* 119: 182-192 (2009). It has been hypothesized that CD4 positive T cells (e.g., proinflammatory T17 cells) mediate cytotoxicity by activating microglia in PD and/or exert a direct toxic effect on substantia nigra DNs (Appel, *J. Clin. Invest.* 119: 13-15 (2009)).

4. Autoimmune Diseases

An autoimmune disease herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and autoimmune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, diabetic retinopathy, diabetic nephropathy, diabetic large-artery disorder, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis, large-vessel vasculitis (including polymyalgia rheumatica and giant-cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behçet's disease/syndrome, Castleman's syndrome, Goodpasture's syndrome, Reynaud's syndrome, Sjögren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, lymphoid interstitial pneumonitis (LIP), bronchiolitis obliterans (non-transplant) vs NSIP, Guillain-Barré syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia areata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis.

5. Cancer

Cancer or a cancerous condition is the physiological condition in mammals that is typically characterized by unregulated cell growth/proliferation. Included in this definition are benign and malignant cancers, as well metastatic cancers. Also included are solid tumors and hematopoietic malignancies. Metastatic cancer refers to a cancer that has spread from the place where it first started to another place in the body. Tumors formed by metastatic cancer cells are called a metastatic tumor or a metastasis (which is also used to refer to the process by which cancer cells spread to other parts of the body). In general, metastatic cancer has the same name and same type of cancer cells as the original, or primary, cancer. Metastatic cancer includes prostate cancer, lung cancer, and pancreas cancer. By prostate cancer or conditions related to prostate cancer is meant the malignant growth of abnormal cells in the prostate gland, capable of invading and destroying other prostate cells, and spreading (metastasizing) to other parts of the body, including bones, lungs, liver, and lymph nodes. By lung cancer or conditions related to lung cancer is meant the malignant growth of abnormal cells in the lungs, capable of invading and destroying other lung cells, and spreading (metastasizing) to other parts of the body, including the adrenal gland, and liver. By pancreatic cancer or conditions related to pancreatic cancer is meant the malignant growth of abnormal cells in the pancreas, capable of invading and destroying other pancreas cells, and spreading (metastasizing) to other parts of the body, including the liver, lungs, and peritoneum.

6. MCAM Antagonists

The present invention provides antagonists of MCAM. Such antagonists encompass those that directly act upon MCAM (e.g., an anti-MCAM antibody) and those that indirectly affect MCAM activity (e.g., an anti-laminin α4 chain antibody). Such antagonists are useful, for example, for treating a central nervous system (CNS) inflammatory disorder characterized by infiltration of MCAM-expressing cells into the CNS. In one embodiment, a composition comprising an MCAM antagonist is useful for reducing inflammation in a mammalian subject. In another embodiment, such a composition is useful for partially or fully inhibiting CNS infiltration of MCAM-expressing cells. Examples of MCAM antagonists include, without limitation, antagonist or neutralizing antibodies or antibody fragments against one or more domains, e.g., an immunoglobulin domain of a native sequence MCAM polypeptide or a domain of a native sequence laminin α4 chain polypeptide (e.g., the α4 chain of laminin 411), small molecules, ribozymes, aptamers, peptides, and nucleic acids that encode polypeptide antagonists or antagonist antibodies. Reference to "an" antagonist encompasses a single antagonist. In one embodiment, the MCAM antagonists are antibodies including, without limitation, chimeric, humanized and human antibodies and their functional fragments.

In a preferred embodiment, the laminin α4 chain is an α4 chain of laminin 411. In another preferred embodiment, the MCAM antagonist blocks the interaction of an MCAM domain comprising the amino acid sequence of SEQ ID NO:22 and/or SEQ ID NO:23 with a laminin α4 chain.

6.1 Screening Assays to Identify MCAM Antagonists

The present invention includes screening assays to identify MCAM antagonists, which find utility in the treatment of inflammatory conditions characterized by infiltration of MCAM-expressing cells into the central nervous system (CNS).

In one aspect, the invention concerns a method for identifying an inhibitor of CNS infiltration by MCAM-expressing cells comprising the steps of: (a) incubating a population of cells expressing a laminin α4 chain, e.g., an α4 chain of laminin 411, with MCAM, in the presence or absence of a candidate molecule; (b) monitoring the level of binding of MCAM to the cells; and (c) identifying said candidate molecule as an inhibitor of CNS infiltration by MCAM-expressing cells if the level of MCAM binding is lower in the presence than in the absence of said candidate molecule. In one embodiment, the candidate molecule is selected from the group consisting of a small molecule, a peptide, a polypeptide, and an antibody. Those of ordinary skill in the art will appreciate that other types of candidate molecule may be suitable. In another embodiment, the level of binding of MCAM is monitored by known techniques including, without limitation, fluorescent microscopy, FACS, and ELISA. In one other embodiment, the cells expressing a laminin α4 chain are endothelial cells. In a preferred embodiment, the laminin α4 chain is an α4 chain of laminin 411.

Screening assays for antagonist drug candidates may be designed to identify compounds that bind or complex with MCAM (including a subunit or other fragment thereof) or with an MCAM ligand, such as a laminin α4 chain (e.g., an α4 chain of laminin 411), or otherwise interfere with the interaction of MCAM with other cellular proteins, thereby interfering with the interaction of MCAM with its ligand, e.g., a laminin α4 chain. The screening assays provided herein include assays amenable to high-throughput screening of chemical libraries, making them particularly suitable for identifying small molecule drug candidates. Generally, binding assays and activity assays are provided.

The assays can be performed in a variety of formats, including, without limitation, protein-protein binding assays, biochemical screening assays, immunoassays, and cell-based assays, which are well characterized in the art.

All assays for antagonists and agonists are common in that they call for contacting the drug candidate with an MCAM polypeptide, or an MCAM ligand polypeptide, e.g., a laminin α4 chain, or a fragment of such polypeptides (specifically including MCAM and laminin α4 chains) under conditions and for a time sufficient to allow these two components to interact.

For example, human MCAM is a 646 amino acid polypeptide, the sequence of which is available from the GenBank database under Accession Number AAA20922.1 (CAA48332) (SEQ ID NO:11; FIG. 11A). Amino acid sequences for human laminin α4-chain are available from the GenBank database under Accession Nos. NP001098676 and NP001098677 (SEQ ID NOS: 27-28; FIGS. 12A-B). The making of antibodies or small molecules binding to such polypeptides is well within the skill of the ordinary artisan.

In binding assays, the interaction is binding, and the complex formed can be isolated or detected in the reaction mixture. In a particular embodiment, either the MCAM or MCAM ligand polypeptide or the drug candidate is immobilized on a solid phase, e.g., on a microtiter plate, by covalent or non-covalent attachments. Non-covalent attachment generally is accomplished by coating the solid surface with a solution of the MCAM or MCAM ligand polypeptide and drying. Alternatively, an immobilized antibody, e.g., a monoclonal antibody, specific for the MCAM or MCAM ligand polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound is a polypeptide which interacts with but does not bind to MCAM or the MCAM ligand polypeptide, its interaction with the respective polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245-246 (1989); Chien et al., Proc. Natl. Acad. Sci. USA, 88:9578-9582 (1991)) as disclosed by Chevray and Nathans, Proc. Natl. Acad. Sci. USA, 89: 5789-5793 (1991).

Compounds that interfere with the interaction of MCAM and other extracellular components, in particular an MCAM ligand polypeptide, can be tested as follows. Usually a reaction mixture is prepared containing MCAM and the extracellular component (e.g., MCAM ligand such as a laminin α4 chain, e.g., an α4 chain of laminin 411) under conditions and for a time allowing for the interaction of the two products. To test the ability of a candidate compound to inhibit the interaction of MCAM and its ligand, the reaction is run in the absence and in the presence of the test compound. In addition, a placebo may be added to a third reaction mixture, to serve as positive control. Since MCAM has been shown to specifically bind its ligand, e.g., a laminin α4 chain, the ability of the test compound to inhibit the MCAM/MCAM ligand interaction can, for example, be tested by measuring the degree of binding between MCAM and its ligand in the absence and presence of the test compound. If the degree of MCAM binding to its ligand is lower in the absence of the candidate compound than in its presence, the candidate compound is an MCAM antagonist by the definition of the present invention.

An alternate screening protocol involves the use of a population of cells expressing a laminin α4 chain, e.g., an α4 chain of laminin 411, which can be incubated with MCAM, in the presence and absence of a test compound, and binding of MCAM to the cell population monitored, e.g. by fluorescent microscopy (exemplified in Example 5). Other methods of monitoring will be appreciated by those skilled in the art, including fluorescence-activated cell sorting (FACS) and enzyme-linked immunosorbent assay (ELISA). If the binding of MCAM to the cell population in the presence of the test compound is lower than in its absence, the test compound is an MCAM antagonist.

The MCAM antagonists identified based upon their ability to inhibit the binding of MCAM to its ligand, e.g., a laminin α4 chain, are drug candidates for the treatment of neuroinflammatory conditions characterized by infiltration of MCAM-expressing cells into the CNS.

It is emphasized that the screening assays specifically discussed herein are for illustration only. A variety of other assays, which can be selected depending on the type of the antagonist candidates screened (e.g. polypeptides, peptides, non-peptide small organic molecules, aptamers, ribozymes, nucleic acid, etc.) are well known to those skilled in the art and are equally suitable for the purposes of the present invention.

6.2 Antibodies

In one aspect, an MCAM antagonist is an anti-MCAM antibody or an anti-laminin α4 chain, e.g., α4 chain of laminin 411, antibody, or an antigen-binding fragment thereof. In some embodiments, an anti-MCAM antibody is a blocking antibody that fully or partially blocks the interaction of MCAM with its ligand, a laminin α4 chain. In other embodiments, an anti-laminin α4 chain antibody is a blocking antibody that fully or partially blocks the interaction of a laminin α4 chain with MCAM. In certain embodiments, the anti-MCAM antibody binds to the extracellular domain of MCAM which interacts with its ligand, a laminin α4 chain. In a preferred embodiment, the laminin α4 chain is an α4 chain of laminin 411.

In one embodiment, an anti-MCAM antibody specifically or selectively binds to an MCAM fragment comprising or having the amino acid sequence of position 19 to position 129 of SEQ ID NO: 11 (SEQ ID NO:22). In another embodiment, an anti-MCAM antibody specifically or selectively binds to an MCAM fragment comprising or having the amino acid sequence of position 139 to position 242 of SEQ ID NO: 11 (SEQ ID NO:23). In one other embodiment, an anti-MCAM antibody specifically or selectively binds to an MCAM fragment comprising the amino acid sequences of SEQ ID NOS:22 and 23.

In a preferred embodiment, the antagonist antibody blocks the interaction of an MCAM domain comprising the amino acid sequence of SEQ ID NO:22 and/or SEQ ID NO:23 with a laminin α4 chain.

In one other embodiment, the anti-MCAM antibody or antibody fragment comprises the following hypervariable regions (HVRs):

a) HVR-L1 shown as SEQ ID NO:3;
b) HVR-L2 shown as SEQ ID NO:4;
c) HVR-L3 shown as SEQ ID NO:5;
d) HVR-H1 shown as SEQ ID NO:8;
e) HVR-H2 shown as SEQ ID NO:9; and/or
f) HVR-H3 shown as SEQ ID NO:10.

In another embodiment, the anti-MCAM antibody or antibody fragment comprises a light chain variable domain shown as SEQ ID NO:2 and/or a heavy chain variable domain shown as SEQ ID NO:7.

In other embodiments, the anti-MCAM antibody or antibody fragment comprises the following hypervariable regions (HVRs):

a) HVR-L1 shown as SEQ ID NO:14;
b) HVR-L2 shown as SEQ ID NO:15;
c) HVR-L3 shown as SEQ ID NO:16;
d) HVR-H1 shown as SEQ ID NO:19;
e) HVR-H2 shown as SEQ ID NO:20; and/or
f) HVR-H3 shown as SEQ ID NO:21.

In one other embodiment, the anti-MCAM antibody or antibody fragment comprises a light chain variable domain shown as SEQ ID NO:13 and/or a heavy chain variable domain shown as SEQ ID NO:18.

In one other embodiment, the anti-MCAM antibody or antibody fragment comprises the following hypervariable regions (HVRs):

a) HVR-L1 shown as SEQ ID NO:31;
b) HVR-L2 shown as SEQ ID NO:32;
c) HVR-L3 shown as SEQ ID NO:33;
d) HVR-H1 shown as SEQ ID NO:36;
e) HVR-H2 shown as SEQ ID NO:37; and/or
f) HVR-H3 shown as SEQ ID NO:38.

In another embodiment, the anti-MCAM antibody or antibody fragment comprises a light chain variable domain shown as SEQ ID NO:30 and/or a heavy chain variable domain shown as SEQ ID NO:35.

In other embodiments, the anti-MCAM antibody or antibody fragment comprises the following hypervariable regions (HVRs):

a) HVR-L1 shown as SEQ ID NO:41;
b) HVR-L2 shown as SEQ ID NO:42;
c) HVR-L3 shown as SEQ ID NO:43;
d) HVR-H1 shown as SEQ ID NO:46;
e) HVR-H2 shown as SEQ ID NO:47; and/or
f) HVR-H3 shown as SEQ ID NO:48.

In one other embodiment, the anti-MCAM antibody or antibody fragment comprises a light chain variable domain shown as SEQ ID NO:40 and/or a heavy chain variable domain shown as SEQ ID NO:45.

In other embodiments, the anti-MCAM antibody or antibody fragment comprises the following hypervariable regions (HVRs):

a) HVR-L1 shown as SEQ ID NO:51;
b) HVR-L2 shown as SEQ ID NO:52;
c) HVR-L3 shown as SEQ ID NO:53;
d) HVR-H1 shown as SEQ ID NO:56;
e) HVR-H2 shown as SEQ ID NO:57; and/or
f) HVR-H3 shown as SEQ ID NO:58.

In one other embodiment, the anti-MCAM antibody or antibody fragment comprises a light chain variable domain shown as SEQ ID NO:50 and/or a heavy chain variable domain shown as SEQ ID NO:55.

In other embodiments, the anti-MCAM antibody or antibody fragment comprises the following hypervariable regions (HVRs):

a) HVR-L1 shown as SEQ ID NO:61;
b) HVR-L2 shown as SEQ ID NO:62;
c) HVR-L3 shown as SEQ ID NO:63;
d) HVR-H1 shown as SEQ ID NO:66;
e) HVR-H2 shown as SEQ ID NO:67; and/or
f) HVR-H3 shown as SEQ ID NO:68.

In another embodiment, the anti-MCAM antibody or antibody fragment further comprises a heavy chain framework region 2 (FR2) comprising the amino acid sequence of SEQ ID NO: 128.

In one other embodiment, the anti-MCAM antibody or antibody fragment comprises a light chain variable domain shown as SEQ ID NO:60 and/or a heavy chain variable domain shown as SEQ ID NO:65.

In other embodiments, the anti-MCAM antibody or antibody fragment comprises the following hypervariable regions (HVRs):

a) HVR-L1 shown as SEQ ID NO:73;
b) HVR-L2 shown as SEQ ID NO:74;
c) HVR-L3 shown as SEQ ID NO:75;
d) HVR-H1 shown as SEQ ID NO:78;
e) HVR-H2 shown as SEQ ID NO:79; and/or
f) HVR-H3 shown as SEQ ID NO:80.

In one other embodiment, the anti-MCAM antibody or antibody fragment comprises a light chain variable domain shown as any one of SEQ ID NOS:70, 71, or 72 and/or a heavy chain variable domain shown as SEQ ID NO:77.

In other embodiments, the anti-MCAM antibody or antibody fragment comprises the following hypervariable regions (HVRs):

a) HVR-L1 shown as SEQ ID NO:85;
b) HVR-L2 shown as SEQ ID NO:86;
c) HVR-L3 shown as SEQ ID NO:87;
d) HVR-H1 shown as SEQ ID NO:90;
e) HVR-H2 shown as SEQ ID NO:91; and/or
f) HVR-H3 shown as SEQ ID NO:92.

In another embodiment, the anti-MCAM antibody or antibody fragment further comprises (a) a heavy chain framework region 2 (FR2) comprising the amino acid sequence of SEQ ID NO: 134; (b) a heavy chain framework region 3 (FR3) comprising the amino acid sequence of SEQ ID NO:137; (c) a light chain framework region 2 (FR2) comprising the amino acid sequence of SEQ ID NO:146; and/or (d) a light chain framework region 3 (FR3) comprising the amino acid sequence of SEQ ID NO:144.

In one other embodiment, the anti-MCAM antibody or antibody fragment comprises a light chain variable domain shown as any one of SEQ ID NOS:83 or 84 and/or a heavy chain variable domain shown as SEQ ID NO:89.

In other embodiments, the anti-MCAM antibody or antibody fragment comprises the following hypervariable regions (HVRs):

a) HVR-L1 shown as SEQ ID NO:73;
b) HVR-L2 shown as SEQ ID NO:74;
c) HVR-L3 shown as SEQ ID NO:75;
d) HVR-H1 shown as SEQ ID NO:141;
e) HVR-H2 shown as SEQ ID NO:79; and/or
f) HVR-H3 shown as SEQ ID NO:80.

In another embodiment, the anti-MCAM antibody or antibody fragment further comprises (a) a heavy chain framework region 2 (FR2) comprising the amino acid sequence of SEQ ID NO: 134; (b) a heavy chain framework region 3 (FR3) comprising the amino acid sequence of SEQ ID NO:135; (c) a light chain framework region 1 (FR1) comprising the amino acid sequence of SEQ ID NO:147; (d) a light chain framework region 2 (FR2) comprising the amino acid sequence of SEQ ID NO:148; and/or (e) a light chain framework region 3 (FR3) comprising the amino acid sequence of SEQ ID NO:149.

In another aspect, the present invention provides MCAM antagonists that bind to substantially the same epitope as, or compete for binding with, an anti-MCAM antibody described herein. In one embodiment, the MCAM antagonist binds to substantially the same epitope as, or competes for binding with, an anti-MCAM antibody comprising the following HVRs:

a) HVR-L1 shown as SEQ ID NO:3;
b) HVR-L2 shown as SEQ ID NO:4;
c) HVR-L3 shown as SEQ ID NO:5;
d) HVR-H1 shown as SEQ ID NO:8;
e) HVR-H2 shown as SEQ ID NO:9; and/or
f) HVR-H3 shown as SEQ ID NO:10.

In another embodiment, the MCAM antagonist binds to substantially the same epitope as, or competes for binding with, an anti-MCAM antibody comprising a light chain variable domain shown as SEQ ID NO:2 and/or a heavy chain variable domain shown as SEQ ID NO:7.

In one other embodiment, the MCAM antagonist binds to substantially the same epitope as, or competes for binding with, an anti-MCAM antibody comprising the following HVRs:

a) HVR-L1 shown as SEQ ID NO:14;
b) HVR-L2 shown as SEQ ID NO:15;
c) HVR-L3 shown as SEQ ID NO:16;
d) HVR-H1 shown as SEQ ID NO:19;
e) HVR-H2 shown as SEQ ID NO:20; and/or
f) HVR-H3 shown as SEQ ID NO:21.

In another embodiment, the MCAM antagonist binds to substantially the same epitope as, or competes for binding with, an anti-MCAM antibody comprising a light chain variable domain shown as SEQ ID NO:13 and/or a heavy chain variable domain shown as SEQ ID NO:18.

In one other embodiment, the MCAM antagonist binds to substantially the same epitope as, or competes for binding with, an anti-MCAM antibody comprising the following HVRs:

a) HVR-L1 shown as SEQ ID NO:31;
b) HVR-L2 shown as SEQ ID NO:32;
c) HVR-L3 shown as SEQ ID NO:33;
d) HVR-H1 shown as SEQ ID NO:36;
e) HVR-H2 shown as SEQ ID NO:37; and/or
f) HVR-H3 shown as SEQ ID NO:38.

In another embodiment, the MCAM antagonist binds to substantially the same epitope as, or competes for binding with, an anti-MCAM antibody comprising a light chain variable domain shown as SEQ ID NO:30 and/or a heavy chain variable domain shown as SEQ ID NO:35.

In one other embodiment, the MCAM antagonist binds to substantially the same epitope as, or competes for binding with, an anti-MCAM antibody comprising the following HVRs:

a) HVR-L1 shown as SEQ ID NO:41;
b) HVR-L2 shown as SEQ ID NO:42;
c) HVR-L3 shown as SEQ ID NO:43;
d) HVR-H1 shown as SEQ ID NO:46;
e) HVR-H2 shown as SEQ ID NO:47; and/or
f) HVR-H3 shown as SEQ ID NO:48.

In another embodiment, the MCAM antagonist binds to substantially the same epitope as, or competes for binding with, an anti-MCAM antibody comprising a light chain variable domain shown as SEQ ID NO:40 and/or a heavy chain variable domain shown as SEQ ID NO:45.

In one other embodiment, the MCAM antagonist binds to substantially the same epitope as, or competes for binding with, an anti-MCAM antibody comprising the following HVRs:

a) HVR-L1 shown as SEQ ID NO:51;
b) HVR-L2 shown as SEQ ID NO:52;
c) HVR-L3 shown as SEQ ID NO:53;
d) HVR-H1 shown as SEQ ID NO:56;
e) HVR-H2 shown as SEQ ID NO:57; and/or
f) HVR-H3 shown as SEQ ID NO:58.

In another embodiment, the MCAM antagonist binds to substantially the same epitope as, or competes for binding with, an anti-MCAM antibody comprising a light chain variable domain shown as SEQ ID NO:50 and/or a heavy chain variable domain shown as SEQ ID NO:55.

In one other embodiment, the MCAM antagonist binds to substantially the same epitope as, or competes for binding with, an anti-MCAM antibody comprising the following HVRs:

a) HVR-L1 shown as SEQ ID NO:61;
b) HVR-L2 shown as SEQ ID NO:62;
c) HVR-L3 shown as SEQ ID NO:63;
d) HVR-H1 shown as SEQ ID NO:66;
e) HVR-H2 shown as SEQ ID NO:67; and/or
f) HVR-H3 shown as SEQ ID NO:68.

In another embodiment, the MCAM antagonist binds to substantially the same epitope as, or competes for binding with, an anti-MCAM antibody comprising a light chain variable domain shown as SEQ ID NO:60 and/or a heavy chain variable domain shown as SEQ ID NO:65.

In one other embodiment, the MCAM antagonist binds to substantially the same epitope as, or competes for binding with, an anti-MCAM antibody comprising the following HVRs:

a) HVR-L1 shown as SEQ ID NO:73;
b) HVR-L2 shown as SEQ ID NO:74;
c) HVR-L3 shown as SEQ ID NO:75;
d) HVR-H1 shown as SEQ ID NO:78;
e) HVR-H2 shown as SEQ ID NO:79; and/or
f) HVR-H3 shown as SEQ ID NO:80.

In another embodiment, the MCAM antagonist binds to substantially the same epitope as, or competes for binding with, an anti-MCAM antibody comprising a light chain variable domain shown as any one of SEQ ID NOS:70, 71, or 72 and/or a heavy chain variable domain shown as SEQ ID NO:77.

In one other embodiment, the MCAM antagonist binds to substantially the same epitope as, or competes for binding with, an anti-MCAM antibody comprising the following HVRs:

a) HVR-L1 shown as SEQ ID NO:85;
b) HVR-L2 shown as SEQ ID NO:86;
c) HVR-L3 shown as SEQ ID NO:87;
d) HVR-H1 shown as SEQ ID NO:90;
e) HVR-H2 shown as SEQ ID NO:91; and/or
f) HVR-H3 shown as SEQ ID NO:92.

In another embodiment, the MCAM antagonist binds to substantially the same epitope as, or competes for binding with, an anti-MCAM antibody comprising a light chain variable domain shown as any one of SEQ ID NOS:83 or 84 and/or a heavy chain variable domain shown as SEQ ID NO:89.

Figure 25A:
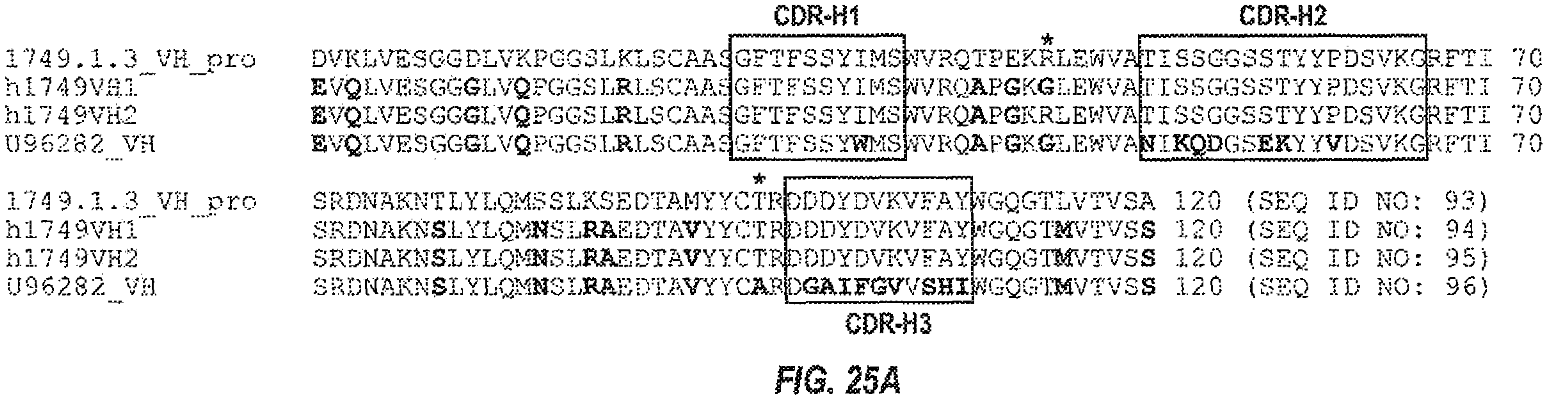
FIG. 25A shows the alignment of sequences of the variable heavy chains for the following: murine 1749.1.3 anti-MCAM antibody (1749.1.3_VH_pro; SEQ ID NO:93); 1749 VH1 humanized anti-MCAM antibody (h1749VH1; SEQ ID NO:94); 1749 VH2 humanized anti-MCAM antibody (h1749VH2; SEQ ID NO:95); and heavy chain human variable IGHV3-7*02 sequence used as the framework donor (U96282_VH; SEQ ID NO:96). Kabat numbering is used and hypervariable regions (HVRs) grafted from the murine 1749.1.3 antibody to the variable heavy chain variable IGHV3-7*02 framework are boxed. The bolded amino acid residues in the humanized antibody sequences differ from the corresponding residues in the murine antibody sequence. The position of canonical and interface amino acid residues that may affect CDR contact or CDR structure are indicated by an asterisk.
Figure 25B:
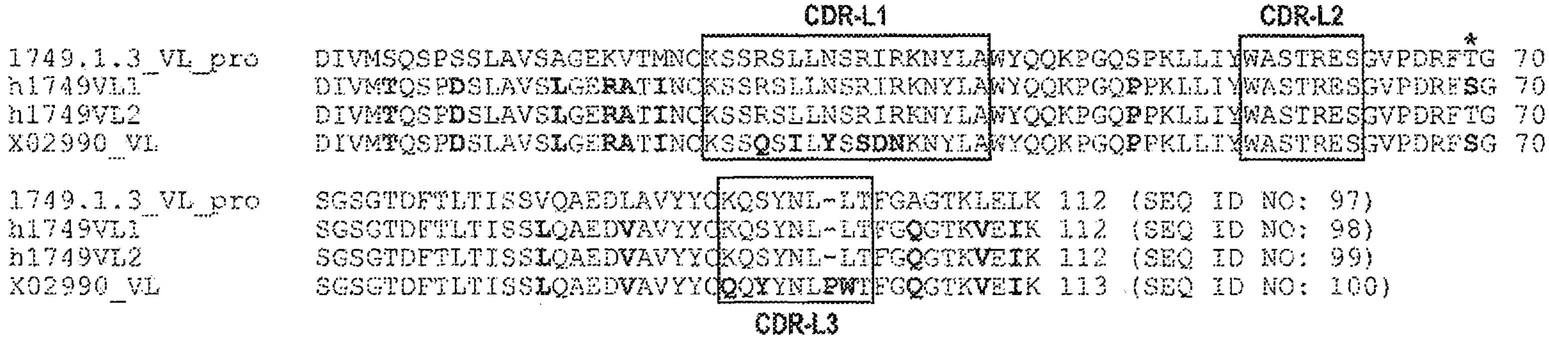
FIG. 25B shows the alignment of sequences of the variable light chains for the following: murine 1749.1.3 anti-MCAM antibody (1749.1.3_VL_pro; SEQ ID NO:97); 1749 VL1 humanized anti-MCAM antibody (h1749VL1 SEQ ID NO:98); 1749 VL2 humanized anti-MCAM antibody (h1749VL2 SEQ ID NO:99); and light chain human variable X02990 IGKV4-1*01 sequence used as the framework donor (X02990_VL SEQ ID NO:100). Kabat numbering is used and hypervariable regions (HVRs) grafted from the murine 1749.1.3 antibody to the variable light chain variable X02990 IGKV4-1*01 framework are boxed. The bolded amino acid residues in the humanized antibody sequences differ from the corresponding residues in the murine antibody sequence. The position of canonical and interface amino acid residues that may affect CDR contact or CDR structure are indicated by an asterisk.

In an embodiment, the invention provides humanized antibodies. In some embodiments, the humanized antibody comprises a heavy chain variable domain sequence selected from the group consisting of SEQ ID NO: 94 and SEQ ID NO: 95 (FIG. 25A; h1749). In some embodiments, the humanized antibody comprises a light chain variable domain sequence selected from the group consisting of SEQ ID NO: 98 and SEQ ID NO: 99 (FIG. 25B; h1749). In another embodiment, the humanized antibody comprises a heavy chain variable domain sequence SEQ ID NO: 94 and a light chain variable domain sequence selected from the group consisting of SEQ ID NO: 98 and SEQ ID NO:99. In another embodiment, the humanized antibody comprises a heavy chain variable domain sequence SEQ ID NO: 95 and a light chain variable domain sequence selected from the group consisting of SEQ ID NO: 98 and SEQ ID NO:99.

In some embodiments, the humanized antibody comprises a heavy chain variable domain sequence selected from the group consisting of SEQ ID NO: 102, SEQ ID NO: 103, SEQ ID NO: 104, SEQ ID NO: 105, SEQ ID NO: 106, and SEQ ID NO: 107 (FIG. 26A; h2107). In some embodiments, the humanized antibody comprises a light chain variable domain sequence selected from the group consisting of SEQ ID NO: 110, SEQ ID NO: 111, and SEQ ID NO: 112 (FIG. 26B; h2107). In another embodiment, the humanized antibody comprises a light chain variable domain sequence SEQ ID NO: 111 and a heavy chain variable domain sequence selected from the group consisting of SEQ ID NO: 102, SEQ ID NO: 103, SEQ ID NO: 104, and SEQ ID NO: 105. In one other embodiment, the humanized antibody comprises a heavy chain variable domain sequence SEQ ID NO: 102 and a light chain variable domain sequence selected from the group consisting of SEQ ID NO: 110 and SEQ ID NO: 112. In one embodiment, the humanized antibody comprises a heavy chain variable domain sequence SEQ ID NO: 106 and a light chain variable domain sequence selected from the group consisting of SEQ ID NO: 110, SEQ ID NO: 111, and SEQ ID NO: 112. In one embodiment, the humanized antibody comprises a heavy chain variable domain sequence SEQ ID NO: 107 and a light chain variable domain sequence selected from the group consisting of SEQ ID NO: 110, SEQ ID NO: 111, and SEQ ID NO: 112.

In some embodiments, the humanized antibody comprises a heavy chain variable domain sequence selected from the group consisting of SEQ ID NO: 115, SEQ ID NO: 116, SEQ ID NO: 117, SEQ ID NO: 118, and SEQ ID NO: 119 (FIG. 27A; h2120). In some embodiments, the humanized antibody comprises a light chain variable domain sequence selected from the group consisting of SEQ ID NO: 121, SEQ ID NO: 122, and SEQ ID NO: 123 (FIG. 27B; h2120). In another embodiment, the humanized antibody comprises a light chain variable domain sequence SEQ ID NO: 123 and a heavy chain variable domain sequence selected from the group consisting of SEQ ID NO: 115, SEQ ID NO: 116, and SEQ ID NO: 117. In one other embodiment, the humanized antibody comprises a light chain variable domain sequence SEQ ID NO: 123 and a heavy chain variable domain sequence selected from the group consisting of SEQ ID NO: 108 and SEQ ID NO: 109. In one embodiment, the humanized antibody comprises a heavy chain variable domain sequence SEQ ID NO: 115 and a light chain variable domain sequence selected from the group consisting of SEQ ID NO: 121 and SEQ ID NO: 122.

In one embodiment, the invention provides an isolated humanized h1749 anti-MCAM antibody, or antigen binding fragment thereof, comprising two heavy chains (VH1 and VH2) and two light chains (VL1 and VL2). The VH1 heavy chain comprises SEQ ID NO: 94, three heavy chain hypervariable regions (HVR-HC) comprising SEQ ID NOs: 66, 67, and 68, respectively, and four heavy chain frame work regions (FR-HC) comprising SEQ ID NOs: 155, 125, 126, and 127, respectively. The VH2 heavy chain of h1749 comprises SEQ ID NO: 95, three heavy chain hypervariable regions (HVR-HC) comprising SEQ ID NOs: 66, 67, and 68, respectively, and four heavy chain frame work regions (FR-HC) comprising SEQ ID NOs: 155, 128, 126, and 127, respectively. The VL1 light chain of h1749 comprises SEQ ID NO: 98, three light chain hypervariable regions (HVR-LC) comprising SEQ ID NOs: 61, 62, and 63, respectively, and four light chain frame work regions (FR-LC) comprising SEQ ID NOs: 128, 129, 130, and 131, respectively. The VL2 light chain of h1749 comprises SEQ ID NO: 99, three light chain hypervariable regions (HVR-LC) comprising SEQ ID NOs: 61, 62, and 63, respectively, and four light chain frame work regions (FR-LC) comprising SEQ ID NOs: 128, 129, 132, and 131, respectively.

In another embodiment, the invention provides an isolated humanized h2107 anti-MCAM antibody, or antigen binding fragment thereof, comprising six heavy chains (VH1, VH2, VH3, VH4, VH5, and VH6) and three light chains (VL1, VL2, and VL3). The VH1 heavy chain comprises SEQ ID NO: 102, three heavy chain hypervariable regions (HVR-HC) comprising SEQ ID NOs: 90 or 151, 91, and 92, respectively, and four heavy chain frame work regions (FR-HC) comprising SEQ ID NOs: 133, 134, 135, and 136, respectively. The VH2 heavy chain of h2107 comprises SEQ ID NO: 103, three heavy chain hypervariable regions (HVR-HC) comprising SEQ ID NOs: 90 or 151, 91, and 92, respectively, and four heavy chain frame work regions (FR-HC) comprising SEQ ID NOs: 133, 134, 137, and 136, respectively. The VH3 heavy chain of h2107 comprises SEQ ID NO: 104, three heavy chain hypervariable regions (HVR-HC) comprising SEQ ID NOs: 90 or 151, 91, and 92, respectively, and four heavy chain frame work regions (FR-HC) comprising SEQ ID NOs: 133, 134, 138, and 136, respectively. The VH4 heavy chain of h2107 comprises SEQ ID NO: 105, three heavy chain hypervariable regions (HVR-HC) comprising SEQ ID NOs: 139 or 152, 91, and 92, respectively, and four heavy chain frame work regions (FR-HC) comprising SEQ ID NOs: 133, 134, 135, and 136, respectively. The VH5 heavy chain of h2107 comprises SEQ ID NO: 106, three heavy chain hypervariable regions (HVR-HC) comprising SEQ ID NOs: 140, 91, 92, respectively, and four heavy chain frame work regions (FR-HC) comprising SEQ ID NOs: 133, 134, 135, and 136, respectively. The VH6 heavy chain of h2107 comprises SEQ ID NO: 107, three heavy chain hypervariable regions (HVR-HC) comprising SEQ ID NOs: 141, 91, and 92, respectively, and four heavy chain frame work regions (FR-HC) comprising SEQ ID NOs: 133, 134, 135, and 136, respectively.

The VL1 light chain of h2107 comprises SEQ ID NO: 110, three light chain hypervariable regions (HVR-LC) comprising SEQ ID NOs: 85, 86, and 87, respectively, and four light chain frame work regions (FR-LC) comprising SEQ ID NOs: 142, 143, 144, and 145, respectively. The VL2 light chain of h2107 comprises SEQ ID NO: 111, three light chain hypervariable regions (HVR-LC) comprising SEQ ID NOs: 85, 86, and 87, respectively, and four light chain frame work regions (FR-LC) comprising SEQ ID NOs: 142, 146, 144, and 145, respectively. The VL3 light chain of h2107 comprises SEQ ID NO: 112, three light chain hypervariable regions (HVR-LC), comprising SEQ ID NOs: 85, 86, and 87, respectively, and four light chain frame work regions (FR-LC) comprising SEQ ID NOs: 147, 143, 144, and 145, respectively.

In another embodiment, the invention provides an isolated humanized h2120 anti-MCAM antibody, or antigen binding fragment thereof, comprising five heavy chains (VH1, VH2, VH3, VH4, and VH5) and three light chains (VL1, VL2, and VL3). The VH1 heavy chain comprises SEQ ID NO: 115, three heavy chain hypervariable regions (HVR-HC) comprising SEQ ID NOs: 78, 79, and 153, respectively, and four heavy chain frame work regions (FR-HC) comprising SEQ ID NOs: 133, 134, 135, and 136, respectively. The VH2 heavy chain of h2120 comprises SEQ ID NO: 116, three heavy chain hypervariable regions (HVR-HC) comprising SEQ ID NOs: 78, 79, and 153, respectively, and four heavy chain frame work regions (FR-HC) comprising SEQ ID NOs: 133, 134, 138, and 136, respectively. The VH3 heavy chain of h2120 comprises SEQ ID NO: 117, three heavy chain hypervariable regions (HVR-HC) comprising SEQ ID NOs: 139, 79, and 153, respectively, and four heavy chain frame work regions (FR-HC) comprising SEQ ID NOs: 133, 134, 135, and 136, respectively. The VH4 heavy chain of h2120 comprises SEQ ID NO: 118, three heavy chain hypervariable regions (HVR-HC) comprising SEQ ID NOs: 140, 79, and 153, respectively, and four heavy chain frame work regions (FR-HC) comprising SEQ ID NOs: 133, 134, 135, and 136, respectively. The VH5 heavy chain of h2120 comprises SEQ ID NO: 119, three heavy chain hypervariable regions (HVR-HC) comprising SEQ ID NOs: 141, 79, and 153, respectively, and four heavy chain frame work regions (FR-HC) comprising SEQ ID NOs: 133, 134, 135, and 136, respectively.

The VL1 light chain of h2120 comprises SEQ ID NO: 121, three light chain hypervariable regions (HVR-LC) comprising SEQ ID NOs: 73, 74, and 75, respectively, and four light chain frame work regions (FR-LC) comprising SEQ ID NOs: 142, 148, 149, and 150, respectively. The VL2 light chain of h2120 comprises SEQ ID NO: 122, three light chain hypervariable regions (HVR-LC) comprising SEQ ID NOs: 73, 74, and 75, respectively, and four light chain frame work regions (FR-LC) comprising SEQ ID NOs: 142, 148, 154, and 150, respectively. The VL3 light chain of h2120 comprises SEQ ID NO: 123, three light chain hypervariable regions (HVR-LC) comprising SEQ ID NOs: 73, 74, and 75, respectively, and four light chain frame work regions (FR-LC) comprising SEQ ID NOs: 147, 148, 149, and 150, respectively.

In some embodiments, the invention provides an antibody that binds to MCAM, wherein the antibody comprises a heavy chain variable domain having at least 90%, at least 91%, at least 92%, at least 93%, at least 94%, at least 95%, at least 96%, at least 97%, at least 98%, or at least 99% sequence identity to an amino acid sequence selected from SEQ ID NO: 94, SEQ ID NO: 95, SEQ ID NO: 102, SEQ ID NO: 103, SEQ ID NO: 104; SEQ ID NO: 105, SEQ ID NO: 106, SEQ ID NO: 107, SEQ ID NO: 115, SEQ ID NO: 116, SEQ ID NO: 117, SEQ ID NO: 118, and SEQ ID NO: 119. In some embodiments, the anti-MCAM antibody comprises a light chain variable domain having at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NO: 98, SEQ ID NO: 99, SEQ ID NO: 110, SEQ ID NO: 111, SEQ ID NO: 112, SEQ ID NO: 121, SEQ ID NO: 122, and SEQ ID NO: 123. In some embodiment, the antibody comprises a heavy chain variable domain having at least 90%, at least 91%, at least 92%, at least 93%, at least 94%, at least 95%, at least 96%, at least 97%, at least 98%, or at least 99% sequence identity to an amino acid sequence selected from SEQ ID NO: 94, SEQ ID NO: 95, SEQ ID NO: 102, SEQ ID NO: 103, SEQ ID NO: 104; SEQ ID NO: 105, SEQ ID NO: 106, SEQ ID NO: 107, SEQ ID NO: 115, SEQ ID NO: 116, SEQ ID NO: 117, SEQ ID NO: 118, and SEQ ID NO: 119, and the antibody further comprises a light chain variable domain having at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NO: 98, SEQ ID NO: 99, SEQ ID NO: 110, SEQ ID NO: 111, SEQ ID NO: 112, SEQ ID NO: 121, SEQ ID NO: 122, and SEQ ID NO: 123.

In some embodiments, the invention provides an antibody that is a variant of any of the above antibodies having one or more amino acid substitutions, deletions, insertions or modifications, and which retains a biological function of the antibody. In some embodiments, the invention provides an antibody that binds to MCAM expressed on the cell surface and inhibits the binding of MCAM to laminin 411. In some embodiments, the anti-MCAM antibody binds to MCAM expressed on the cell surface and inhibits disease progression. In some embodiments, the progression of an autoimmune disease is inhibited. In one embodiment, the progression of multiple sclerosis is inhibited. In some embodiments, the invention provides an antibody that is a variant of any one of the above antibodies having improvements in one or more of a property such as binding affinity, specificity, thermostability, expression level, effector function, glycosylation, reduced immunogenicity, or solubility as compared to the unmodified antibody.

In other embodiments, the anti-MCAM antibody binds to MCAM expressed on the cell surface and inhibits progression of a metastatic cancer. In one embodiment, the metastatic cancer is selected from the group consisting of prostate cancer, lung cancer, and pancreatic cancer.

The invention herein includes the production and use of MCAM antagonist antibodies. Exemplary methods for generating antibodies are described in more detail herein. MCAM antibodies can include, but are not limited to, polyclonal, monoclonal, multispecific, human, humanized, primatized, or chimeric antibodies, single chain antibodies (e.g., scFv), Fab fragments, F(ab') fragments, fragments produced by a Fab expression library, anti-idiotypic (anti-Id) antibodies (including, e.g., anti-Id antibodies to antibodies of the present embodiments), and epitope-binding fragments of any of the above. Human antigen-binding antibody fragments include, but are not limited to, Fab, Fab' and $F(ab')_2$, Fd, single-chain Fvs (scFv), single-chain antibodies, disulfide-linked Fvs (sdFv), and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included are antigen-binding fragments that can comprise any combination of variable region(s) with a hinge region, CH1, CH2, and CH3 domains. The antibodies may be from any animal origin including birds and mammals. Typically, the antibodies are from human or other primates, murine (e.g., mouse and rat), donkey, sheep, monkey, rabbit, goat, guinea pig, pig, camel, horse, or chicken (or other avian). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example in, U.S. Pat. No. 5,939,598.

In another embodiment, the MCAM antibody can be a monoclonal antibody. In yet a further embodiment, the antibody may be chemically modified, e.g., by pegylation. Additionally, other antibodies can be identified using techniques available in the art. For example, antibodies capable of specifically binding to MCAM can be produced using phage display technology. Antibody fragments that selectively bind to MCAM can then be isolated. Exemplary methods for producing such antibodies via phage display are disclosed, for example, in U.S. Pat. No. 6,225,447, for example.

Monoclonal antibodies can also be produced using the conventional hybridoma methods. These methods have been widely applied to produce hybrid cell lines that secrete high levels of monoclonal antibodies against many specific antigens, and can also be used to produce monoclonal antibodies capable of specifically binding to MCAM. For example, mice (e.g., Balb/c mice) can be immunized with an antigenic MCAM epitope by intraperitoneal injection. After sufficient time has passed to allow for an immune response, the mice are sacrificed, and the spleen cells obtained and fused with myeloma cells, using techniques well known in the art. The resulting fused cells, hybridomas, are then grown in a selective medium, and the surviving cells grown in such medium using limiting dilution conditions. After cloning and recloning, hybridomas can be isolated for secreting antibodies (for example, of the IgG or IgM class or IgG1 subclass) that selectively bind to MCAM. To produce agents specific for human use, the isolated monoclonal can then be used to produce chimeric and humanized antibodies.

MCAM antagonist antibodies are selected using an antigen derived from a mammalian species. Preferably the antigen is human MCAM or a laminin α4 chain, e.g., α4 chain of laminin 411. However, polypeptides from other species such as murine MCAM or laminin α4 chain can also be used as the target antigen. The antigens from various mammalian species may be isolated from natural sources. In other embodiments, the antigen is produced recombinantly or made using other synthetic methods known in the art. The antibody selected will normally have a sufficiently strong binding affinity for the antigen. For example, the antibody may bind human MCAM or a laminin α4 chain, e.g., an α4 chain of laminin 411 with a $K_d$ value of no more than about 5 nM, preferably no more than about 2 nM, and more preferably no more than about 500 pM. Antibody affinities may be determined by a surface plasmon resonance based assay (such as the BIAcore assay as described in Examples); enzyme-linked immunoabsorbent assay (ELISA); and competition assays (e.g. RIA's), for example.

Also, the antibody may be subject to other biological activity assays, e.g., in order to evaluate its effectiveness as a therapeutic. Such assays are known in the art and depend on the target antigen and intended use for the antibody. Examples include the experimental autoimmune encephalomyelitis (EAE) (as described in Example 7 below), and in vitro and in vivo assays described herein for identifying MCAM antagonists.

To screen for antibodies which bind to a particular epitope on the antigen of interest, a routine cross-blocking assay such as that described in Antibodies, A Laboratory Manual, Cold Spring Harbor Laboratory, Ed Harlow and David Lane (1988), can be performed. Alternatively, epitope mapping, e.g. as described in Champe et al. (1995) J. Biol. Chem. 270:1388-1394, can be performed to determine whether the antibody binds an epitope of interest.

In a preferred embodiment, the antagonist antibodies are selected using a unique phage display approach. The approach involves generation of synthetic antibody phage libraries based on single framework template, design of sufficient diversities within variable domains, display of polypeptides having the diversified variable domains, selection of candidate antibodies with high affinity to target antigen, and isolation of the selected antibodies. Details of the phage display methods can be found, for example, in WO03/102157 published Dec. 11, 2003. The antibody generated from phage libraries can be further modified to generate antibody mutants with improved physical, chemical and or biological properties over the parent antibody. Where the assay used is a biological activity assay, the antibody mutant preferably has a biological activity in the assay of choice which is at least about 10 fold better, preferably at least about 20 fold better, more preferably at least about 50 fold better, and sometimes at least about 100 fold or 200 fold better, than the biological activity of the parent antibody in that assay. For example, an anti-MCAM antibody mutant preferably has a binding affinity for MCAM which is at least about 10 fold stronger, preferably at least about 20 fold stronger, more preferably at least about 50 fold stronger, and sometimes at least about 100 fold or 200 fold stronger, than the binding affinity of the parent anti-MCAM antibodies, such as clone 15 or 17 antibodies.

Chimeric and humanized antibodies can be produced from non-human antibodies, and can have the same or similar binding affinity as the antibody from which they are produced. Exemplary techniques for producing chimeric antibodies include splicing the genes from, e.g., a mouse antibody molecule of appropriate antigen specificity together with genes from a human antibody molecule of appropriate biological activity. See, e.g., Morrison et al., 1984 *Proc. Nat'l. Acad. Sci. USA* 81: 6851; Neuberger et al., 1984 *Nature* 312: 604; and Takeda et al., 1985 *Nature* 314: 452. For example, a nucleic acid encoding a variable (V) region of a mouse monoclonal antibody can be joined to a nucleic acid encoding a human constant (C) region, e.g., IgG1 or IgG4. The resulting antibody is thus a species hybrid, generally with the antigen binding domain from the non-human antibody and the C or effector domain from a human or primate antibody.

Humanized antibodies are antibodies with variable regions that are primarily from a human antibody (i.e., the acceptor antibody), but which have complementarity determining regions substantially from a non-human antibody (the donor antibody). See, e.g., Queen et al., *Proc. Nat'l. Acad. Sci USA* 86: 10029-10033 (1989); WO 90/07861, U.S. Pat. Nos. 7,435,802, 6,054,297; 5,693,761; 5,585,089; 5,530,101; and 5,224,539. The constant region or regions of these antibodies are generally also from a human antibody. The human variable domains are typically chosen from human antibodies having sequences displaying a high homology with the desired non-human variable region binding domains. The heavy and light chain variable residues can be derived from the same antibody, or a different human antibody. In addition, the sequences can be chosen as a consensus of several human antibodies, such as described in WO 92/22653.

A "Primatized™ antibody" is a recombinant antibody containing primate variable sequences or antigen binding portions, and human constant domain sequences. See e.g., Newman, *Bio/Technology,* 1992, 10: 1455-60. Primatization of antibodies results in the generation of antibodies that contain primate (e.g., monkey) variable domains and human constant sequences. See, e.g., U.S. Pat. No. 6,113,898. This technique modifies antibodies such that they are not rejected upon administration in humans because they are antigenic.

This technique relies on immunization of cynomolgus monkeys with human antigens or receptors. This technique was developed to create high affinity monoclonal antibodies directed to human cell surface antigens.

In another aspect, specific amino acids within the human variable region can be selected for substitution based on the predicted conformation and antigen binding properties. This can be determined using techniques such as computer modeling, prediction of the behavior and binding properties of amino acids at certain locations within the variable region, and observation of effects of substitution. For example, when an amino acid differs between a non-human variable region and a human variable region, the human variable region can be altered to reflect the amino acid composition of the non-human variable region. In a specific embodiment, the antibodies used in the chronic dosage regime can be humanized antibodies as disclosed in U.S. Pat. No. 5,840,299. In another embodiment, transgenic mice containing human antibody genes can be immunized with an antigenic MCAM structure and hybridoma technology can be used to generate human antibodies that selectively bind to MCAM.

Chimeric, human and/or humanized antibodies can be produced by using recombinant expression, e.g., expression in human hybridomas (Cole et al., *Monoclonal Antibodies and Cancer Therapy*, Alan R. Liss, p. 77 (1985)), in myeloma cells, or in Chinese hamster ovary (CHO) cells. Alternatively, antibody coding sequences can be incorporated into transgenes for introduction into the genome of a transgenic animal and subsequent expression in the milk of the transgenic animal. See, e.g., U.S. Pat. No. 6,197,946. Exemplary suitable transgenes include, but are not limited to, transgenes having a promoter and/or enhancer from a mammary gland specific gene, for example casein or β-lactoglobulin.

6.3 Antibody Variants

In addition to the MCAM antagonist antibodies described herein, it is contemplated that variants of such antibodies can be prepared. Anti-MCAM antagonist antibody variants can be prepared by introducing appropriate nucleotide changes into the encoding DNA, and/or by synthesis of the desired antibody. Those skilled in the art will appreciate that amino acid changes may alter post-translational processes of the anti-MCAM antibody, such as changing the number or position of glycosylation sites.

Variations in the MCAM antagonist antibodies described herein, can be made, for example, using any of the techniques and guidelines for conservative and non-conservative mutations set forth, for instance, in U.S. Pat. No. 5,364,934. Variations may be a substitution, deletion or insertion of one or more codons encoding the antibody that results in a change in the amino acid sequence as compared with the native sequence antibody. Optionally the variation is by substitution of at least one amino acid with any other amino acid in one or more of the domains of the MCAM antagonist antibody. Guidance in determining which amino acid residue may be inserted, substituted or deleted without adversely affecting the desired activity may be found by comparing the sequence of the MCAM antagonist antibody with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Covalent modifications of anti-MCAM antibodies are included within the scope of this invention. Covalent modifications include reacting targeted amino acid residues of an anti-MCAM antibody with an organic derivatizing agent that is capable of reacting with selected side chains or the N- or C-terminal residues of the anti-MCAM antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

In one aspect, the MCAM antagonist antibodies of the present invention comprise one or more deamidation mutations in the amino acid sequence. The deamidation of amino acid residues is a common structural modification in recombinant polypeptides, which can lead to the formation of iso-aspartic acid resulting in decreased stability. Deamidation may be associated with glycine (G)-asparginine (N) sequences, including G-N and N-G sequences. In one embodiment, the antibody comprises a deamidation mutation. In another embodiment, the deamidation mutation is the substitution of an N amino acid residue or a G amino acid residue. In some embodiments, the substitution is selected from the group consisting of N→S, N→A, and G→Q. In one embodiment, the deamidation mutation is located at Kabat residue N32 or G33.

Other types of covalent modification of the anti-MCAM antibody included within the scope of this invention include altering the native glycosylation pattern of the antibody or polypeptide (Beck et al., Curr. Pharm. Biotechnol. 9: 482-501, 2008; Walsh, Drug Discov. Today 15: 773-780, 2010), and linking the antibody to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

In one aspect, the MCAM antagonist antibodies of the present invention comprise one or more glycosylation mutations in the amino acid sequence. The mutation may remove or restore/introduce a glycosylation site. Generally, the glycosylation mutation is associated with an asparginine (N) residue. In one embodiment, the antibody comprises a glycosylation mutation. In another embodiment, the glycosylation mutation is the introduction of an N amino acid residue. In some embodiments, the introduction is the replacement of an aspartic acid (D) residue with an N residue (D→N). In one embodiment, the mutation is located at Kabat residue 72.

MCAM antagonist antibody fragments are provided herein. Such fragments may be truncated at the N-terminus or C-terminus, or may lack internal residues, for example, when compared with a full length native antibody. Certain fragments lack amino acid residues that are not essential for a desired biological activity of the MCAM antagonist antibody.

MCAM antagonist antibody fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-MCAM antagonist antibody fragments share at least one biological and/or immunological activity with a native MCAM antagonist antibody disclosed herein.

In particular embodiments, conservative substitutions of interest are shown in Table 1 below under the heading of preferred substitutions. If such substitutions result in a change in biological activity, then more substantial changes, as further described below in reference to amino acid classes, are introduced and the products screened.

Substantial modifications in function or immunological identity of the MCAM antagonist antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

TABLE 1

| Original Residue | Exemplary Substitutions | Preferred Substitutions |
|---|---|---|
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the MCAM antagonist antibody variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science, 244:1081-1085 (1989)]. Alanine is also typically preferred because it is the most common amino acid. Further, it is frequently found in both buried and exposed positions [Creighton, The Proteins, (W.H. Freeman & Co., N.Y.); Chothia, J. Mol. Biol., 150:1 (1976)]. If alanine substitution does not yield adequate amounts of variant, an isoteric amino acid can be used.

Any cysteine residue not involved in maintaining the proper conformation of the MCAM antagonist antibody also may be substituted, generally with serine, to improve the oxidative stability of the molecule and prevent aberrant crosslinking. Conversely, cysteine bond(s) may be added to the MCAM antagonist antibody to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human MCAM or laminin 411 polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Preferred affinity matured antibodies have an affinity which is five times, more preferably 10 times, even more preferably 20 or 30 times greater than the starting antibody (generally murine, humanized or human) from which the matured antibody is prepared.

Nucleic acid molecules encoding amino acid sequence variants of the MCAM antagonist antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the MCAM antagonist antibody.

Also included in the invention are antibodies that bind to the same epitope as the antibodies described herein. For example, antibodies of the invention specifically bind to an epitope that includes one or more amino acid residues on human MCAM (Accession No. AAA20922.1/CAA48332). In some embodiments, antibodies of the invention specifically bind MCAM, wherein the antibody binds to an epitope on human MCAM (e.g., Accession No. AAA20922.1/CAA48332).

Those skilled in the art will recognize that it is possible to determine, without undue experimentation, if a monoclonal antibody (e.g., fully human monoclonal antibody) has the same specificity as a monoclonal antibody of the invention by ascertaining whether the former prevents the latter from binding to MCAM. If the monoclonal antibody being tested competes with the monoclonal antibody of the invention, as shown by a decrease in binding by the monoclonal antibody of the invention, then the two monoclonal antibodies bind to the same, or a closely related, epitope.

An alternative method for determining whether a monoclonal antibody has the specificity of monoclonal antibody of the invention is to pre-incubate the monoclonal antibody of the invention with MCAM (e.g., an MCAM-Fc molecule exemplified in the Examples) and then add the monoclonal antibody being tested to determine if the monoclonal antibody being tested is inhibited in its ability to bind MCAM. If the monoclonal antibody being tested is inhibited then, in all likelihood, it has the same, or functionally equivalent, epitopic specificity as the monoclonal antibody of the invention.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889-7893 (1993).

In a further embodiment, the invention comprises a binding agent that binds to essentially the same epitope as any of the antibodies disclosed herein. In one embodiment, the binding agent is capable of binding to MCAM protein on the surface of cells. In some embodiments, the binding agent inhibits the interaction of MCAM (e.g., cell surface MCAM) with its ligand, a protein comprising a laminin alpha-4 chain. In some embodiments, the binding agent is an antibody or a functional fragment thereof.

In one embodiment, the invention provides a binding agent capable of binding to MCAM, wherein any one of the antibodies disclosed above displaces the binding agent in a competitive binding assay. In some embodiments, the binding agent is an antibody, or a functional fragment thereof. In another embodiment, the invention provides a binding agent capable of binding to MCAM, wherein the binding agent displaces any one of the antibodies disclosed above in a competitive binding assay. In some embodiments, the binding agent is an antibody, or a functional fragment thereof.

In other embodiments, the binding agent is an alternative binding agent. These alternative binding agents may include, for example, any of the engineered protein scaffolds known in the art. Such scaffolds include, for example, anticalins, which are based upon the lipocalin scaffold, a protein structure characterized by a rigid beta-barrel that supports four hypervariable loops which form the ligand binding site. Novel binding specificities are engineered by targeted random mutagenesis in the loop regions, in combination with functional display and guided selection (Skerra (2008) FEBS J. 275: 2677-2683). Other suitable scaffolds may include, for example, adnectins, or monobodies, based on the tenth extracellular domain of human fibronectin III (Koide and Koide (2007) Methods Mol. Biol. 352: 95-109); affibodies, based on the Z domain of staphylococcal protein A (Nygren et al. (2008) FEBS J. 275: 2668-2676)); DARPins, based on ankyrin repeat proteins (Stumpp et al. (2008) Drug. Discov. Today 13: 695-701); fynomers, based on the SH3 domain of the human Fyn protein kinase (Grabulovski et al. (2007) J. Biol. Chem. 282: 3196-3204); affitins, based on Sac7d from Sulfolobus acidolarius (Krehenbrink et al. (2008) J. Mol. Biol. 383: 1058-1068); affilins, based on human y-B-crystallin (Ebersbach et al. (2007) J. Mol. Biol. 372: 172-185); avimers, based on the A domains of membrane receptor proteins (Silverman et al. (2005) Biotechnol. 23: 1556-1561); cysteine-rich knottin peptides (Kolmar (2008) FEBS J. 275: 2684-2690); and engineered Kunitz-type inhibitors (Nixon and Wood (2006) Curr. Opin. Drug. Discov. Dev. 9: 261-268). For review, see Gebauer and Skerra (2009) Curr. Opin. Chem. Biol. 13: 245-255. In other embodiments, the binding agent is an anticalin, an adnectin, an affibody, a DARPin, a fynomer, an affitin, an affilin, an avimer, a cysteine-rich knottin peptide, or an engineered Kunitz-type inhibitor.

7. Methods of Use

The present invention provides MCAM antagonists as therapeutic agents for neuroinflammatory conditions, cancer, and autoimmune diseases. For the prevention, treatment or reduction in the severity of a given disease or condition, the appropriate dosage of a compound of the invention will depend on the type of disease or condition to be treated, as defined above, the severity and course of the disease or condition, whether the agent is administered for preventive or therapeutic purposes, previous therapy, the patient's clinical history and response to the compound, and the discretion of the attending physician. The compound is suitably administered to the patient at one time or over a series of treatments. Preferably, it is desirable to determine the dose-response curve and the pharmaceutical composition of the invention first in vitro, and then in useful animal models prior to testing in humans.

In one aspect, the present invention provides a method for inhibiting or blocking the interaction of MCAM expressed on T cells and laminin α4 chain, e.g., an α4 chain of laminin 411, comprising treating the T cells with an MCAM antagonist (as described herein), thereby inhibiting the interaction of MCAM with laminin α4 chain. In one embodiment, the laminin α4 chain is expressed on the surface of a cell, e.g., an endothelial cell. In a preferred embodiment, the MCAM antagonist is an anti-MCAM antibody. In another embodiment, the T cells are TH17 cells. In one other embodiment, the treatment with an MCAM antagonist is performed in vivo. In yet another embodiment, the treatment is performed in a mammalian subject. In one embodiment, the mammalian subject is a human.

In another aspect, the present invention provides a method for inhibiting or preventing extravasation of MCAM-expressing T cells into the central nervous system (CNS) comprising treating the T cells with an MCAM antagonist (as described herein), thereby inhibiting or preventing the extravasation of MCAM-expressing T cells into the CNS. In one embodiment, the MCAM antagonist blocks the interaction of MCAM with laminin $\alpha$4 chain, e.g., an $\alpha$4 chain of laminin 411. In a preferred embodiment, the MCAM antagonist is an anti-MCAM antibody. In one other embodiment, the laminin $\alpha$4 chain is expressed on the surface of a cell, e.g., an endothelial cell. In another embodiment, the T cells are TH17 cells. In one other embodiment, the treatment with an MCAM antagonist is performed in vivo. In yet another embodiment, the treatment is performed in a mammalian subject. In one embodiment, the mammalian subject is a human.

In one other aspect, the present invention provides methods of treatment for a neuroinflammatory condition, a cancerous condition, or an autoimmune disease. In one embodiment, the method comprises administering to a mammalian subject in need a therapeutically effective amount of an MCAM antagonist. In another aspect, the invention provides a method for the delaying or slowing down of the progression of a neuroinflammatory condition, a cancerous condition, or an autoimmune disease. In one embodiment, the method comprises administering to subject diagnosed with the condition or disease, an effective amount of an MCAM antagonist. In another aspect, the invention provides a method for preventing indicia of a neuroinflammatory condition, cancerous condition, or an autoimmune disease. In one embodiment, the method comprises administering an effective amount of an MCAM antagonist to a subject at risk of the condition or disease, wherein the MCAM antagonist is effective against the development of indicia of the condition or disease. In one additional aspect, the present invention provides methods of treatment for a metastatic cancer.

In one embodiment, the present invention provides an MCAM antagonist for use as a medicament for, or for the treatment of a disease, condition or disorder described herein. In another embodiment, the present invention provides the use of an MCAM antagonist for the manufacture of a medicament for treating a disease, condition or disorder described herein. In one other embodiment, the present invention provides the use of an MCAM antagonist described herein, in the manufacture of a medicament for the treatment of a central nervous system (CNS) inflammatory disorder characterized by infiltration of MCAM-expressing cells into the CNS.

7.1 Neuroinflammatory Conditions

In one aspect, the MCAM antagonists provide a preventative or prophylactic effect against the development of, or the progression of, clinical and/or histological and/or biochemical and/or pathological indicia (including both symptoms and signs) of neuroinflammatory conditions in a subject. In one embodiment, the neuroinflammatory condition is characterized by CNS inflammation and/or cell/tissue damage. In one embodiment, the indicia include increased glial activation, increased pro-inflammatory cytokine/chemokine levels (e.g., TNF$\alpha$, INF$\gamma$, IL-1$\beta$), increased blood-brain-barrier permeability, and/or increased immune cell (e.g., leukocyte) recruitment/invasion to the CNS. In another embodiment, the neuroinflammation is progressive or chronic neuroinflammation associated with chronic activation of cells of the immune system (i.e., autoimmune-associated neuroinflammation). Chronic neuroinflammation conditions include, without limitation, relapsing multiple sclerosis (MS), chronic progressive MS, inactive MS, and Parkinson's disease (PD). In another embodiment, the subject is at risk for a neuroinflammatory condition. In general, a subject at risk will previously have had a neuroinflammatory condition as described herein, or will have a genetic predisposition for neuroinflammatory condition.

The efficacy of the treatment of neuroinflammatory conditions can be measured by various assessments commonly used in evaluating neuroinflammatory condition. For example, CNS health can be evaluated by testing for MS symptoms including, but not limited to, impaired vision (e.g., blurred or double vision, red-green color distortion, or blindness); muscle weakness in the extremities; impaired coordination and balance; partial or complete paralysis, paresthesias, transitory abnormal sensory feelings (e.g., numbness, prickling, or "pins and needles" sensations); pain; speech impediments; tremors; dizziness; hearing loss; cognitive impairments (e.g., difficulties with concentration, attention, memory, and poor judgment); and depression. MS testing may also include a lumbar puncture (spinal tap) for cerebrospinal fluid (CSF) tests (e.g., CSF oligoclonal banding suggesting inflammation of the CNS); a magnetic resonance imaging (MRI) scan of the head or spine; and a nerve function test (e.g., evoked potential test).

CNS health may also be evaluated by testing for PD symptoms including, but not limited to, tremor (e.g., trembling in hands, arms, legs, jaw, and face); rigidity or stiffness of the limbs and trunk; bradykinesia or slowness of movement; postural instability or impaired balance and coordination; depression and other emotional changes; difficulty in swallowing, chewing, and speaking; urinary problems or constipation; skin problems; sleep disruptions; and brain scans or other tests to rule out other diseases.

7.2 Autoimmune Diseases

For autoimmune diseases, the term "treatment" refers to both therapeutic treatment and prophylactic or preventative measures for an autoimmune disease, wherein the object is to prevent or slow down (lessen) the targeted pathologic condition or disorder. Those in need of treatment include those already with an autoimmune disease as well as those prone to have an autoimmune disease or those in whom the autoimmune disease is to be prevented.

In one aspect, the MCAM antagonists provide a preventative or prophylactic effect against the development of, or the progression of, clinical and/or histological and/or biochemical and/or pathological indicia (including both symptoms and signs) of autoimmune disease in a subject. In another embodiment, the subject is at risk for autoimmune disease or an autoimmune disease flare-up. In general, a subject at risk will previously have had autoimmune disease and/or one or more autoimmune disease flare-ups, or will have a genetic predisposition for an autoimmune disease.

7.3 Metastatic Cancers

For metastatic cancer, the term "treatment" refers to both therapeutic treatment and prophylactic or preventative measures for a metastatic cancer, wherein the object is to prevent or slow down (lessen) the targeted pathologic condition or disorder. Those in need of treatment include those already with a metastatic cancer as well as those prone to have a metastatic cancer or those in whom the metastatic cancer is to be prevented.

In one aspect, the MCAM antagonists provide a preventative or prophylactic effect against the development of, or the progression of, clinical and/or histological and/or biochemical and/or pathological indicia (including both symptoms and signs) of a metastatic cancer in a subject. In one embodiment, the metastatic cancer is selected from the group consisting of prostate cancer, lung cancer, and pancreas cancer.

7.4 Combination Therapy

Antibodies of the invention can be used either alone or in combination with other compositions in a therapy. For instance, an antibody of the invention may be co-administered with at least one additional therapeutic agent. In certain embodiments, an additional therapeutic agent is one or more of the following disease-modifying agents: teriflunomide, interferon beta-1a, interferon beta-1b, glatiramer acetate, fingolimod, and mitoxantrone. In another embodiment, an additional therapeutic agent is an agent which treats an acute exacerbation of a disease. In one embodiment, the additional therapeutic agent for acute exacerbation is one or more corticosteroids. In one other embodiment, the one or more corticosteroids are selected from the group consisting of prednisone, methylprednisolone, and dexamethasone. In another embodiment, the disease is multiple sclerosis and the acute exacerbation is a relapse or attack (e.g., inflammation of the CNS).

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent.

8. Pharmaceutical Compositions

MCAM antagonist antibodies specifically binding MCAM or a laminin α4 chain, e.g., an α4 chain of laminin 411, as well as other MCAM antagonist molecules identified by the screening assays disclosed hereinbefore, can be administered for the treatment of various disorders, in particular neuroinflammatory diseases or diseases benefiting from the inhibition of the infiltration of MCAM-expressing cells into the CNS, in the form of pharmaceutical compositions.

In one aspect, the present invention concerns pharmaceutical compositions comprising an antibody, or antigen binding fragment thereof, as described herein. In one embodiment, the pharmaceutical composition comprises (i) an isolated anti-MCAM antibody, or antigen binding fragment thereof, that binds to an immunoglobulin domain of MCAM comprising the amino acid sequence shown as SEQ ID NO:22;

(ii) an isolated anti-MCAM antibody, or antigen binding fragment thereof, that binds to an immunoglobulin domain of MCAM comprising the amino acid sequence shown as SEQ ID NO:23; or (iii) an isolated anti-MCAM antibody, or antigen binding fragment thereof, that binds to a domain of MCAM comprising the amino acid sequences shown as SEQ ID NOS: 22 and 23.

In another embodiment, the pharmaceutical composition comprises an isolated anti-MCAM antibody, or antigen binding fragment thereof, comprising the following hypervariable regions (HVRs):

(i) an HVR-L1 comprising the amino acid sequence KASKNIDTYLA (SEQ ID NO:3);

(ii) an HVR-L2 comprising the amino acid sequence SGSTL (SEQ ID NO:4);

(iii) an HVR-L3 comprising the amino acid sequence QQHNEYPLT (SEQ ID NO:5);

(iv) an HVR-H1 comprising the amino acid sequence GFTFSNYYMA (SEQ ID NO:8)

(v) an HVR-H2 comprising the amino acid sequence SISFEGNRNHYGDSVK (SEQ ID NO:9); and/or (vi) an HVR-H3 comprising the amino acid sequence HRGYSTNFYHDVLDAWGQG (SEQ ID NO:10).

In one other embodiment, the pharmaceutical composition comprises an isolated anti-MCAM antibody, or antigen binding fragment thereof, comprising the following hypervariable regions (HVRs):

(i) an HVR-L1 comprising the amino acid sequence KSSQSLLYSGTQKNYLA (SEQ ID NO:14);

(ii) an HVR-L2 comprising the amino acid sequence WASTRQS (SEQ ID NO:15);

(iii) an HVR-L3 comprising the amino acid sequence QQYYDTLTDT (SEQ ID NO:16);

(iv) an HVR-H1 comprising the amino acid sequence GFKFSNYYMS (SEQ ID NO:19);

(v) an HVR-H2 comprising the amino acid sequence SISDGGGDTFCRDLVKG (SEQ ID NO:20); and/or (vi) an HVR-H3 comprising the amino acid sequence RGAAMGGVMDAWGQG (SEQ ID NO:21).

In another embodiment, the pharmaceutical composition comprises an isolated anti-MCAM antibody, or antigen binding fragment thereof, comprising the following hypervariable regions (HVRs):

(i) an HVR-L1 comprising the amino acid sequence of SEQ ID NO:31;

(ii) an HVR-L2 comprising the amino acid sequence of SEQ ID NO:32;

(iii) an HVR-L3 comprising the amino acid sequence of SEQ ID NO:33;

(iv) an HVR-H1 comprising the amino acid sequence of SEQ ID NO:36;

(v) an HVR-H2 comprising the amino acid sequence of SEQ ID NO:37; and/or (vi) an HVR-H3 comprising the amino acid sequence of SEQ ID NO:38.

In another embodiment, the pharmaceutical composition comprises an isolated anti-MCAM antibody, or antigen binding fragment thereof, comprising the following hypervariable regions (HVRs):

(i) an HVR-L1 comprising the amino acid sequence of SEQ ID NO:41;

(ii) an HVR-L2 comprising the amino acid sequence of SEQ ID NO:42;

(iii) an HVR-L3 comprising the amino acid sequence of SEQ ID NO:43;

(iv) an HVR-H1 comprising the amino acid sequence of SEQ ID NO:46;

(v) an HVR-H2 comprising the amino acid sequence of SEQ ID NO:47; and/or (vi) an HVR-H3 comprising the amino acid sequence of SEQ ID NO:48.

In another embodiment, the pharmaceutical composition comprises an isolated anti-MCAM antibody, or antigen binding fragment thereof, comprising the following hypervariable regions (HVRs):

(i) an HVR-L1 comprising the amino acid sequence of SEQ ID NO:51;

(ii) an HVR-L2 comprising the amino acid sequence of SEQ ID NO:52;

(iii) an HVR-L3 comprising the amino acid sequence of SEQ ID NO:53;

(iv) an HVR-H1 comprising the amino acid sequence of SEQ ID NO:56;

(v) an HVR-H2 comprising the amino acid sequence of SEQ ID NO:57; and/or (vi) an HVR-H3 comprising the amino acid sequence of SEQ ID NO:58.

In another embodiment, the pharmaceutical composition comprises an isolated anti-MCAM antibody, or antigen binding fragment thereof, comprising the following hypervariable regions (HVRs):

(i) an HVR-L1 comprising the amino acid sequence of SEQ ID NO:61;

(ii) an HVR-L2 comprising the amino acid sequence of SEQ ID NO:62;

(iii) an HVR-L3 comprising the amino acid sequence of SEQ ID NO:63;

(iv) an HVR-H1 comprising the amino acid sequence of SEQ ID NO:66;

(v) an HVR-H2 comprising the amino acid sequence of SEQ ID NO:67; and/or (vi) an HVR-H3 comprising the amino acid sequence of SEQ ID NO:68.

In another embodiment, the pharmaceutical composition comprises an isolated anti-MCAM antibody, or antigen binding fragment thereof, comprising the following hypervariable regions (HVRs):

(i) an HVR-L1 comprising the amino acid sequence of SEQ ID NO:73;

(ii) an HVR-L2 comprising the amino acid sequence of SEQ ID NO:74;

(iii) an HVR-L3 comprising the amino acid sequence of SEQ ID NO:75;

(iv) an HVR-H1 comprising the amino acid sequence of SEQ ID NO:78;

(v) an HVR-H2 comprising the amino acid sequence of SEQ ID NO:79; and/or (vi) an HVR-H3 comprising the amino acid sequence of SEQ ID NO:80.

In another embodiment, the pharmaceutical composition comprises an isolated anti-MCAM antibody, or antigen binding fragment thereof, comprising the following hypervariable regions (HVRs):

(i) an HVR-L1 comprising the amino acid sequence of SEQ ID NO:85;

(ii) an HVR-L2 comprising the amino acid sequence of SEQ ID NO:86;

(iii) an HVR-L3 comprising the amino acid sequence of SEQ ID NO:87;

(iv) an HVR-H1 comprising the amino acid sequence of SEQ ID NO:90;

(v) an HVR-H2 comprising the amino acid sequence of SEQ ID NO:91; and/or (vi) an HVR-H3 comprising the amino acid sequence of SEQ ID NO:92.

In another embodiment, the pharmaceutical composition comprises an isolated anti-MCAM antibody, or antigen binding fragment thereof, comprising (a) a light chain variable domain comprising the amino acid sequence shown as SEQ ID NO:2 and a heavy chain variable domain comprising the amino acid sequence shown as SEQ ID NO:7;

(b) a light chain variable domain comprising the amino acid sequence shown as SEQ ID NO:13 and a heavy chain variable domain comprising the amino acid sequence shown as SEQ ID NO:18;

(c) a light chain variable domain comprising the amino acid sequence shown as SEQ ID NO:30 and a heavy chain variable domain comprising the amino acid sequence shown as SEQ ID NO:35;

(d) a light chain variable domain comprising the amino acid sequence shown as SEQ ID NO:40 and a heavy chain variable domain comprising the amino acid sequence shown as SEQ ID NO:45;

(e) a light chain variable domain comprising the amino acid sequence shown as SEQ ID NO:50 and a heavy chain variable domain comprising the amino acid sequence shown as SEQ ID NO:55;

(f) a light chain variable domain comprising the amino acid sequence shown as SEQ ID NO:60 and a heavy chain variable domain comprising the amino acid sequence shown as SEQ ID NO:65;

(g) a light chain variable domain comprising the amino acid sequence shown as any one of SEQ ID NOS:70, 71, or 72 and a heavy chain variable domain comprising the amino acid sequence shown as SEQ ID NO:77; or (h) a light chain variable domain comprising the amino acid sequence shown as any one of SEQ ID NOS:83 or 84 and a heavy chain variable domain comprising the amino acid sequence shown as SEQ ID NO:89.

In yet another embodiment, the pharmaceutical composition comprises an isolated anti-MCAM antibody, or antigen binding fragment thereof, which binds to substantially the same epitope as an antibody described herein. In one other embodiment, the pharmaceutical composition comprises an isolated anti-MCAM antibody, or antigen binding fragment thereof, that competes for binding to human MCAM with an antibody described herein. In additional embodiments, the present invention provides the use of an anti-MCAM antibody, or antigen binding fragment thereof, as described herein, in the manufacture of a medicament for the treatment of a central nervous system (CNS) inflammatory disorder characterized by infiltration of MCAM-expressing cells into the CNS.

The compounds of the invention for prevention or treatment of a neuroinflammatory condition or autoimmune disease are typically administered by intravenous injection. Other methods administration by also be used, which includes but is not limited to, topical, parenteral, subcutaneous, intraperitoneal, intrapulmonary, intranasal, ocular, intraocular, intravitreal, intralesional, intracerobrospinal, intra-articular, intrasynovial, intrathecal, oral, topical, or inhalation administration. Parenteral infusions include intramuscular, intravenous, intraarterial, intraperitoneal, or subcutaneous administration. In addition, the compounds described herein are administered to a human subject, in accord with known methods, such as intravenous administration as a bolus or by continuous infusion over a period of time.

The present invention provides dosages for the MCAM antagonist-based therapeutics. For example, depending on the type and severity of the disease, about 1 μg/kg to 15 mg/kg (e.g. 0.1-20 mg/kg) of polypeptide is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The MCAM antagonist (including MCAM antagonist antibody) compositions herein will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antagonist to be administered will be governed by such considerations, and is the minimum amount necessary to prevent, ameliorate, or treat a given disease or condition.

In some embodiments, the composition is used to prevent the occurrence or reoccurrence of the disease or condition disease in the subject. In one embodiment, the present invention can be used for increasing the duration of survival of a human patient susceptible to or diagnosed with the disease or condition disease. Duration of survival is defined as the time from first administration of the drug to death.

Therapeutic formulations are prepared using standard methods known in the art by mixing the active ingredient having the desired degree of purity with optional physiologically acceptable carriers, excipients or stabilizers (see, e.g., Alfonso R Gennaro (ed), Remington: The Science and Practice of Pharmacy, formerly Remington's Pharmaceutical Sciences 20th ed., Lippincott, Williams & Wilkins, 2003, incorporated herein by reference in its entirety). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations.

Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

9. Articles of Manufacture and Kits

The instant invention further includes kits comprising the MCAM antagonists of the invention and related materials, such as instructions for use. The instructions for use may contain, for example, instructions for administration of the MCAM antagonists and optionally one or more additional agents. The invention also provides kits for the treatment of a central nervous system (CNS) inflammatory disorder characterized by infiltration of MCAM-expressing cells into the CNS. The disorders include, without limitation, neuroinflammatory conditions, such as, for example, multiple sclerosis and Parkinson's disease, and autoimmune disease. The kits of the invention comprise one or more containers of at least one MCAM antagonist, preferably an antibody, in combination with a set of instructions, generally written instructions, relating to the use and dosage of the MCAM antagonist for the treatment of the disorder. The instructions included with the kit generally include information as to dosage, dosing schedule, and route of administration for the treatment of the target disorder, such as a neuroinflammatory condition or an autoimmune disease. The containers of MCAM antagonist(s) may be unit doses, bulk packages (e.g., multi-dose packages), or sub-unit doses.

In one aspect, the present invention provides a kit comprising an MCAM antagonist as described herein and instructions for use in the treatment of a central nervous system (CNS) inflammatory disorder characterized by infiltration of MCAM-expressing cells into the CNS. In one embodiment, the present invention provides a kit for the treatment of a central nervous system (CNS) inflammatory disorder characterized by infiltration of MCAM-expressing cells into the CNS, said kit comprising: (a) a container comprising an MCAM antagonist antibody; and (b) a label or instructions for administering said antibody to treat said CNS inflammatory disorder. Preferably, the CNS inflammatory disorder is a neuroinflammatory condition or an autoimmune disease. In one embodiment, the CNS inflammatory disorder is multiple sclerosis or Parkinson's disease.

Also provided is an article of manufacture for therapeutic use, comprising a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an MCAM antagonist of the invention. The label or package insert indicates that the composition is used for treating the particular condition. The label or package insert will further comprise instructions for administering the antibody composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

All patents, patent applications, and literature references cited in the present specification are hereby incorporated by reference in their entirety.

EXAMPLES

The following examples are not to be interpreted as limiting, but are exemplary means of using the methods disclosed.

Materials and Methods

Animals and Manipulation of Cells

SJL mice (Jackson), 8-16 week old, were immunized with PLP 139-151 peptide emulsified in CFA. The commercial kit, EK-0122 (Hooke Laboratories) was used for this immunization experiment. For some experiments, spleens were removed 11 days later and processed into a single cell suspension. For some experiments, splenocytes were processed for in vitro analysis as described below. For EAE studies, mice were injected on days 5, 9, 13, and 17 after PLP immunization with either PBS, isotype control antibody (BioXcell), or anti-MCAM clone 17. Progression of the disease was monitored daily and scored in a blinded fashion by standard techniques. Mice were sacrificed 35 days after PLP immunization, and brains and spinal cords were analyzed for infiltration of immune cells.

For analysis of MCAM-Fc binding to EAE tissues, 8-16 week old C57BL6 mice were immunized with myelin oligodendrocyte glycoprotein (MOG) 35-55 emulsified in CFA. The commercial kit, EK-0111 (Hooke laboratories) was used for this immunization experiment. The immunized animals were sacrificed at the peak of disease. Brains and spinal cords were snap frozen in OCT (optimal cutting temperature media) and analyzed by fluorescent microscopy as described below.

Flow Cytometry/Marker Staining and Detection/FACS Protocols

Buffy coats were obtained from healthy human donors (Stanford Blood Center, Palo Alto, Calif.) and CD4 T cells were negatively enriched using RosetteSep (Stem Cell Technologies). Where indicated, CD4+/CD45RO+ memory T cells were further negatively purified using magnetic beads (Miltenyi Biotec). T cells were plated ($2\times10^5$ cells/well) in anti-CD3 (5 μg/ml, BD Pharmingen) coated 96 well U bottom plates in RPMI containing 10% heat-inactivated FCS (HyClone Laboratories), penicillin, streptomycin, L-glutamine, anti-IFNγ (5 μg/ml; R&D Systems), anti-IL4 (0.5 μg/ml, R&D Systems), and anti-CD28 (2 μg/ml; BD Pharmingen) for five days. Where indicated, TGFβ (2 ng/ml, unless otherwise indicated), IL12, IL1β, and/or IL-23 (all at 20 ng/ml) were added. All cytokines were obtained from R&D Systems. Analysis of intracellular cytokines occurred following five hours in the presence of PMA (50 ng/ml) and Ionomycin (500 ng/ml; both from Sigma-Aldrich) and GolgiStop (BD Pharmingen). Surface staining with anti-MCAM (Pharmingen) was followed by fixation, permeabilization, and staining with anti-IL-17A (Ebioscience), IL-22 (R&D Systems), CCL20 (R&D Systems) and/or FOXP3 using a FOXP3 staining kit (Biolegend). In some experiments, unmanipulated whole blood was stained for surface expression with anti-CCR7, anti-CCR6, anti-integrin alpha 4, anti-integrin beta 7, or anti-integrin beta 1 (all from BD Pharmingen).

Antibody Generation/Characterization

For the generation of antibodies capable of binding to murine MCAM, MCAM-Fc was generated by fusing the extracellular domain of murine MCAM to human IgG and produced in CHO cells using standard techniques. Lou/M rats were immunized with 100 μg of MCAM-Fc protein in CFA (1:1 volume). Rats were boosted two times at two week intervals with MCAM-Fc protein in incomplete Freund's adjuvant (IFA) (1:1 volume). Hybridomas were generated from immunized rats using standard protocols and clones were selected by Clonepix. CHO cells were transfected with the full length murine MCAM gene and selected for stable expression using neomycin and standard techniques. Parental CHO cells (MCAM negative) were fluorescently labeled with carboxyfluorescein succinimidyl ester (CFSE) using standard techniques and mixed at a 1:1 ratio with unlabeled MCAM transfected CHO cells. Hybridoma supernatants were incubated with this mixture of cells for 30 minutes and binding of potential MCAM specific antibodies was detected with a fluorescently labeled anti-rat secondary antibody (Jackson Immuno) by flow cytometry.

Supernatants from hybridomas that screened positive for MCAM specific antibodies were pre-incubated with fluorescently labeled mouse MCAM-Fc protein (5 μg/mL) for 30 minutes before addition to the laminin α4 expressing cell line WM2664 and neutralization of binding of the MCAM-Fc protein to the cell line was determined by flow cytometry.

For the generation of rat antibodies capable of binding to human MCAM, hMCAM-Fc was generated by fusing the extracellular domain of human MCAM to human IgG and produced in CHO cells using standard techniques. Lou/M rats were immunized with 250 μg of hMCAM-Fc protein in CFA (1:1 volume). Rats were boosted two times at two week intervals with hMCAM-Fc protein in incomplete Freund's adjuvant (IFA) (1:1 volume). Hybridomas were generated from immunized rats using standard protocols and clones were selected by Clonepix. CHO cells were transfected with the full length human MCAM gene and selected for stable expression using neomycin and standard techniques. Parental CHO cells (MCAM negative) were fluorescently labeled with carboxyfluorescein succinimidyl ester (CFSE) using standard techniques and mixed at a 1:1 ratio with unlabeled human MCAM transfected CHO cells. Hybridoma supernatants were incubated with this mixture of cells for 30 minutes and binding of potential human MCAM specific antibodies was detected with a fluorescently labeled anti-rat secondary antibody (Jackson Immuno) by flow cytometry.

For the generation of mouse antibodies capable of binding to human MCAM, hMCAM-Fc was generated by fusing the extracellular domain of human MCAM to human IgG and produced in CHO cells using standard techniques. Balb/c mice were immunized with 50 μg of hMCAM-Fc protein in CFA (1:1 volume). Mice were boosted two times at two week intervals with hMCAM-Fc protein in incomplete Freund's adjuvant (IFA) (1:1 volume). Hybridomas were generated from immunized mice using standard protocols and clones were selected by Clonepix. CHO cells were transfected with the full length human MCAM gene and selected for stable expression using neomycin and standard techniques. Parental CHO cells (MCAM negative) were fluorescently labeled with carboxyfluorescein succinimidyl ester (CFSE) using standard techniques and mixed at a 1:1 ratio with unlabeled human MCAM transfected CHO cells.

Hybridoma supernatants were incubated with this mixture of cells for 30 minutes and binding of potential human MCAM specific antibodies was detected with a fluorescently labeled anti-mouse secondary antibody (Jackson Immuno) by flow cytometry.

Supernatants from hybridomas that screened positive for human MCAM specific antibodies were pre-incubated with fluorescently labeled hMCAM-Fc protein (5 µg/mL) for 30 minutes before addition to the laminin α4 expressing cell line WM2664 and neutralization of binding of the hMCAM-Fc protein to the cell line was determined by flow cytometry.

Nucleic Acid and Protein Manipulation

For microarray experiments, human CD4+ T cells were isolated as above, stained for CD161 and CCR6 (both from BD Pharmingen), and sorted into CD4+/CD161−/CCR6− (non-TH17) and CD4+/CD161+/CCR6+ (TH17) cells from three independent healthy donors. RNA was isolated from half of the cells from each donor immediately (circulating) and the other half was stimulated with plate bound anti-CD3 and soluble anti-CD28 as above, in the absence of exogenous cytokines for four days (activated) before RNA isolation. RNA was amplified (Nugen) and hybridized on Human U133 Plus 2.0 Array (Affymetrix). All microarray experiments were performed at Expression Analysis, Inc. (Durham, N.C.).

For determination of CDRs, total RNA was isolated from hybridoma cells using RNAquous-4PCR kit (Ambion), and was used for cDNA synthesis. First and second strand cDNA was synthesized using methods modified from Marathon cDNA amplification (Clontech) with the cDNA adaptor ligated to the 5'-end of the obtained dscDNA. The reverse specific primer was designed based on the specific antibody isotype constant region sequence for both heavy and light chains, and was used along with the adaptor primer in the PCR amplification of both VL and VH fragments using Pfu Ultra DNA polymerase (Stratagene). The amplified PCR product was cloned into pCR-Blunt-TOPO (Invitrogen), and the nucleotide sequence was determined. Identical VL and VH sequences (those of clone 17) were identified from at least 3 out of 5 individual clones for both light and heavy chains.

For determination of IL-17 concentrations in the supernatant, ELISA was performed using a commercial kit (R&D Systems).

Fluorescence Microscopy/Standard Immunofluorescent Methods

Tissues from EAE induced mice were snap frozen in OCT and sectioned at 10 µM. Sections were fixed in cold acetone and stained with directly conjugated anti-pan-laminin (Novus Biologicals), MCAM-Fc, anti-CD31 (BD Pharmingen), or anti-laminin α4 (Novus biological). In some experiments, MCAM-Fc was preincubated with anti-MCAM antibodies prior to addition to tissues to ascertain neutralization of MCAM binding to its ligand on tissues.

Mouse Polarization Experiment

Splenocytes from mice immunized with PLP in CFA for 11 days were isolated and cultured in the presence of PLP (5 µg/mL, Hooke Laboratories). Where indicated, human TGFβ (5 ng/ml) and/or murine IL-23 (20 ng/mL), and murine IL-1β (20 ng/mL) were added for five days in RPMI containing 10% heat-inactivated FCS (HyClone Laboratories), penicillin, streptomycin, L-glutamine, anti-IFNγ (5 µg/ml; R&D Systems), anti-IL4 (0.5 µg/ml, R&D Systems) and β-ME (50 µM). All cytokines were from R&D Systems. Cells were stained with anti-CD4, anti-NK1.1 (both from BD Pharmingen) and anti-MCAM generated as described above.

Example 1. MCAM is a Gene Up-Regulated in IL-17-Producing Human CD4+ T Cells

To identify novel targetable molecules associated with TH17 cell infiltration of the CNS, human CD4+ T cells from three healthy donors were enriched by magnetic negative selection as described in Materials and Methods above. After the enriched human CD4+ T cells were stained for surface expression of CD161 and CCR6, cells were FACS sorted into two populations: CCR6−/CD161− (representing circulating non-TH17 cells) and CCR6+/CD161+ (representing circulating TH17 cells) as described in Materials and Methods above. RNA was isolated immediately from half of the cells in each population as described in Materials and Methods above. The other half was put into culture with plate-bound anti-CD3 and soluble anti-CD28, without exogenous cytokines, for four days to obtain activated non-TH17 cells and activated TH17 cells, respectively. RNA was similarly isolated from these two types of activated cells. RNA was subject to microarray analysis as described in Materials and Methods above to identify genes specifically expressed in TH17 cells.

Figure 1A:
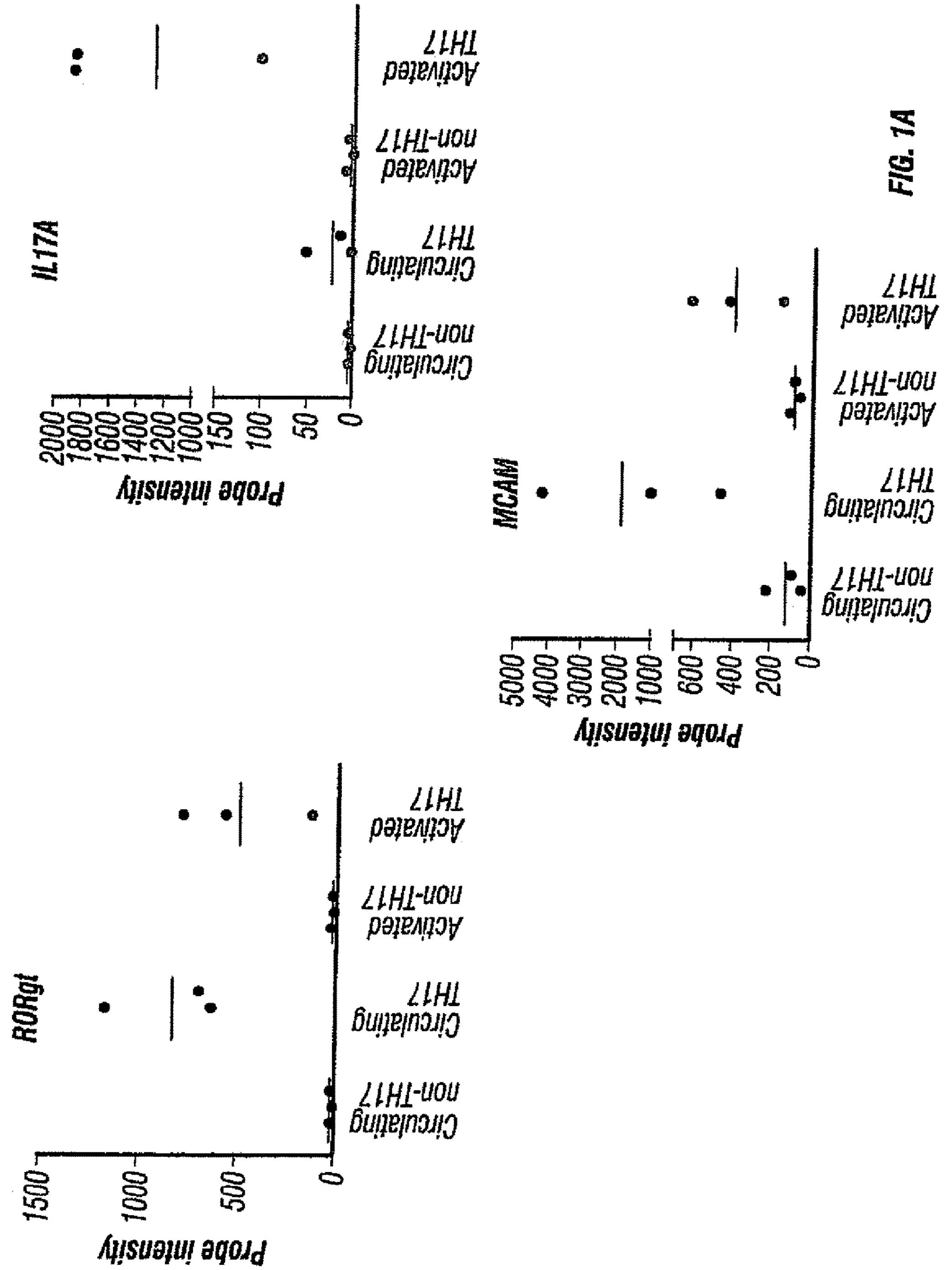
FIGS. 1A-C.

As shown in FIG. 1A, RORγt, a known TH17 transcription factor, was up-regulated in both circulating and activated TH17 cells, while IL-17, as an activated TH17 marker, was nearly exclusively expressed in the activated TH17 population. These results indicate that the above procedures of separation and activation were successful. Microarray analysis identified MCAM as an up-regulated gene in both circulating and activated TH17 cells—a profile similar to that of RORγt (FIG. 1A).

Figure 1B:
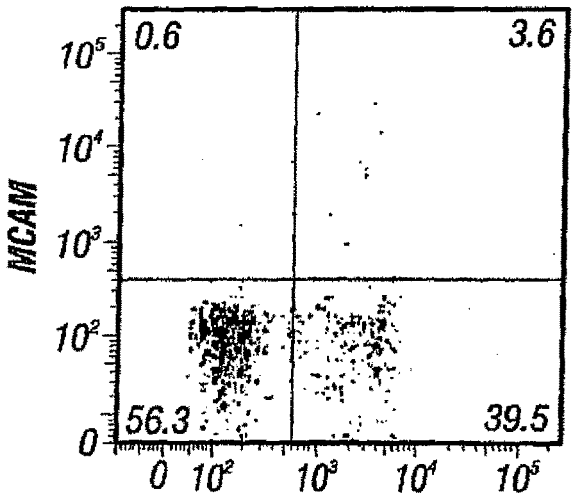
Figure 1C:
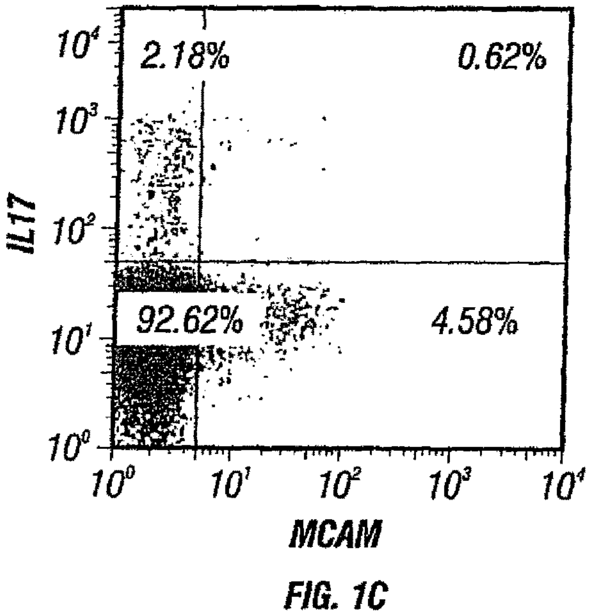

MCAM expressing T cells have been described previously as having enriched expression among T cell clones generated from multiple sclerosis patients, and are particularly prominent at sites of inflammation. See, e.g., Brucklacher-Waldert et al., *Brian* 132: 3329-3341 (2009); see also Pickl et al., *J. Immunol.* 158: 2107-2115 (1997). Here, the MCAM protein was found to be present on the surface of a small population of CD4+ T cells (typically 3-5% of healthy donors). MCAM protein was also found to exist nearly entirely within the CD45RO+ memory population of T cells (FIG. 1B). The human CD4+ T cells were isolated as above, and stimulated for four hours with phorbol myristate acetate (PMA)/Ionomycin. The stimulated CD4+ T cells were analyzed for intracellular IL-17 and surface MCAM levels as described in Materials and Methods above. As shown in FIG. 1C, although the majority of T cells producing IL-17 under these conditions were MCAM negative, MCAM protein was enriched on IL-17-producing cells. Only 2.3% of MCAM negative cells (2.18%/(2.18%+92.62%)) stained positive for IL-17; while 11.9% of MCAM expressing cells (0.62%/(0.62%+4.58%)) were IL-17 positive. Given these data, MCAM is enriched in IL-17-producing human CD4+ T cells.

Furthermore, when CD4+/CD45RO+ memory T cells were separated into purified populations of MCAM positive and MCAM negative cells and stimulated in vitro with anti-CD3 and anti-CD28, the MCAM positive population produced nearly ten times as much IL-17 (data not shown). The majority of the potential IL-17 production was found to be from the small population of T cells expressing MCAM. In one donor, only the MCAM positive population produced detectable levels of IL-17. Thus, the majority of the potential IL-17 production is from the small population of T cells expressing MCAM.

Example 2. MCAM Expressing T Cells are Effector Memory T Cells Having a Unique Integrin Expression Profile The CD45RO+ memory population of human CD4 T cells can be segregated into (1) effector memory cells with tissue tropism, and (2) central memory cells with lymphoid tissue homing based upon expression of CCR7. See, e.g., Sallusto et al., *Nature* 401: 708-712 (1999).

Figure 2A:
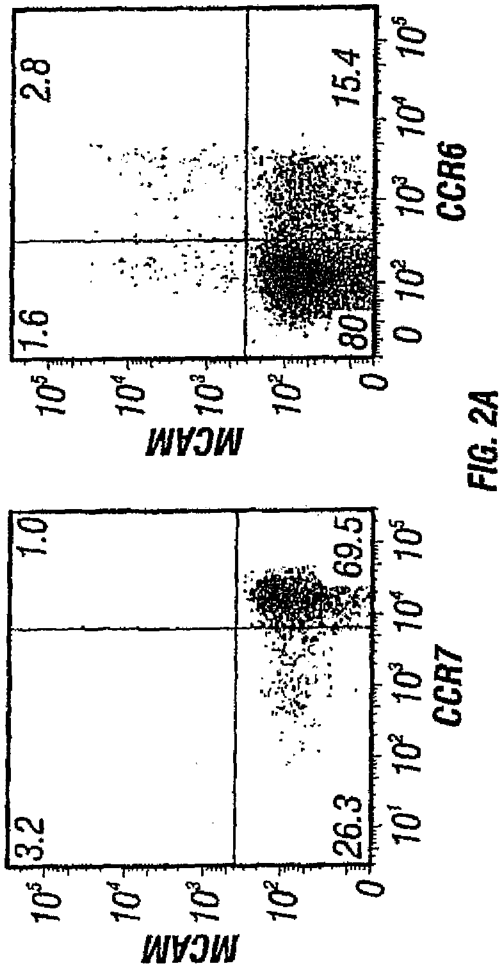
FIGS. 2A, B depict the surface markers of MCAM expressing T cells.

To determine which subpopulation includes the MCAM expressing T cells, MCAM expression in T cells was further characterized by staining peripheral human T cells with various markers (CCR6, CCR7, integrin subunits alpha 4, beta 1, and beta 7) as described in Materials and Methods above. MCAM expressing CD4+ T cells were largely CCR7 negative, indicating that most are effector memory T cells, and would be more likely to home to tissues (FIG. 2A). The TH17 enrichment protocol suggested that MCAM expressing T cells obtained would be disproportionately CCR6+. As shown in FIG. 2A, about 64% of MCAM+ cells (2.8%/(2.8%+1.6%)) express CCR6, while only 16.1% of MCAM negative cells (15.4%/(15.4%+80%)) express CCR6 (FIG. 2A). These data suggest that MCAM positive cells would be largely tropic for areas where the ligand for CCR6, CCL20, is high. See, e.g., Liao et al., *J. Immunol.* 162: 186-194 (1999).

Figure 2B:
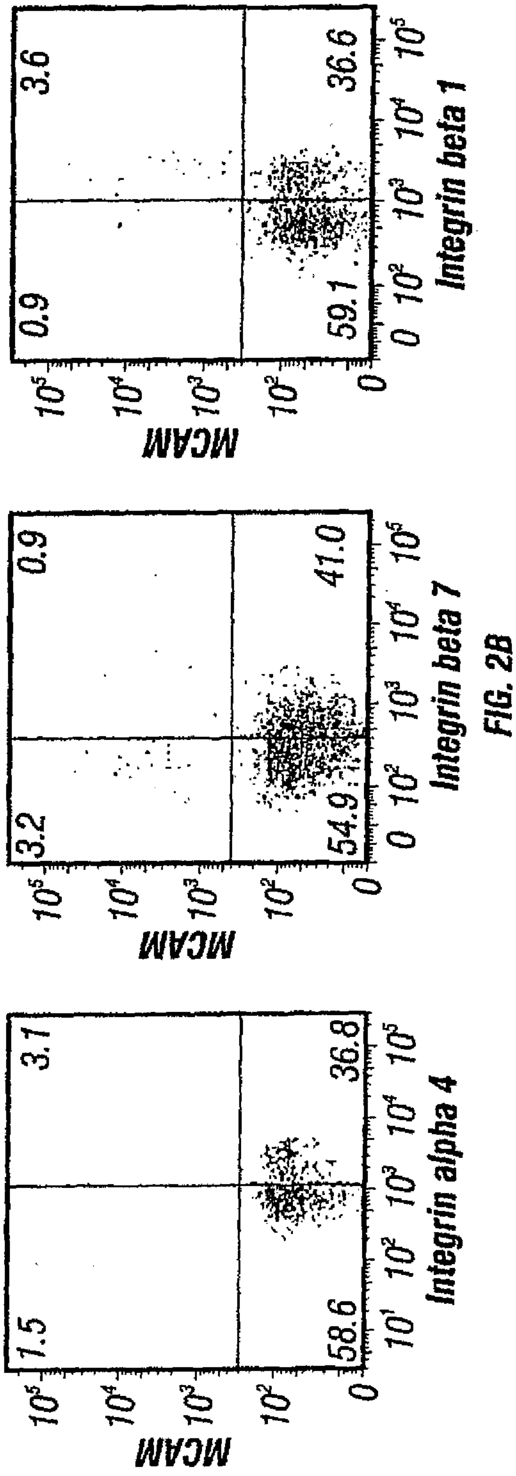
FIG. 2B depicts the integrin expression pattern of MCAM expressing T cells. The majority of MCAM expressing T cells are integrin α4 positive, but are largely integrin β7 negative and β1 positive.

The integrin expression pattern of MCAM expressing T cells was further characterized. The majority of MCAM expressing T cells are integrin α4 positive, but are largely integrin β7 negative and β1 positive (FIG. 2B), which is a phenotype associated with the T cells involved in the pathogenesis of EAE (experimental autoimmune encephalomyelitis). See, e.g., Bauer et al., *Proc. Nat'l Acad. Sci. USA* 106: 1920-1925 (2009).

Figure 3A:
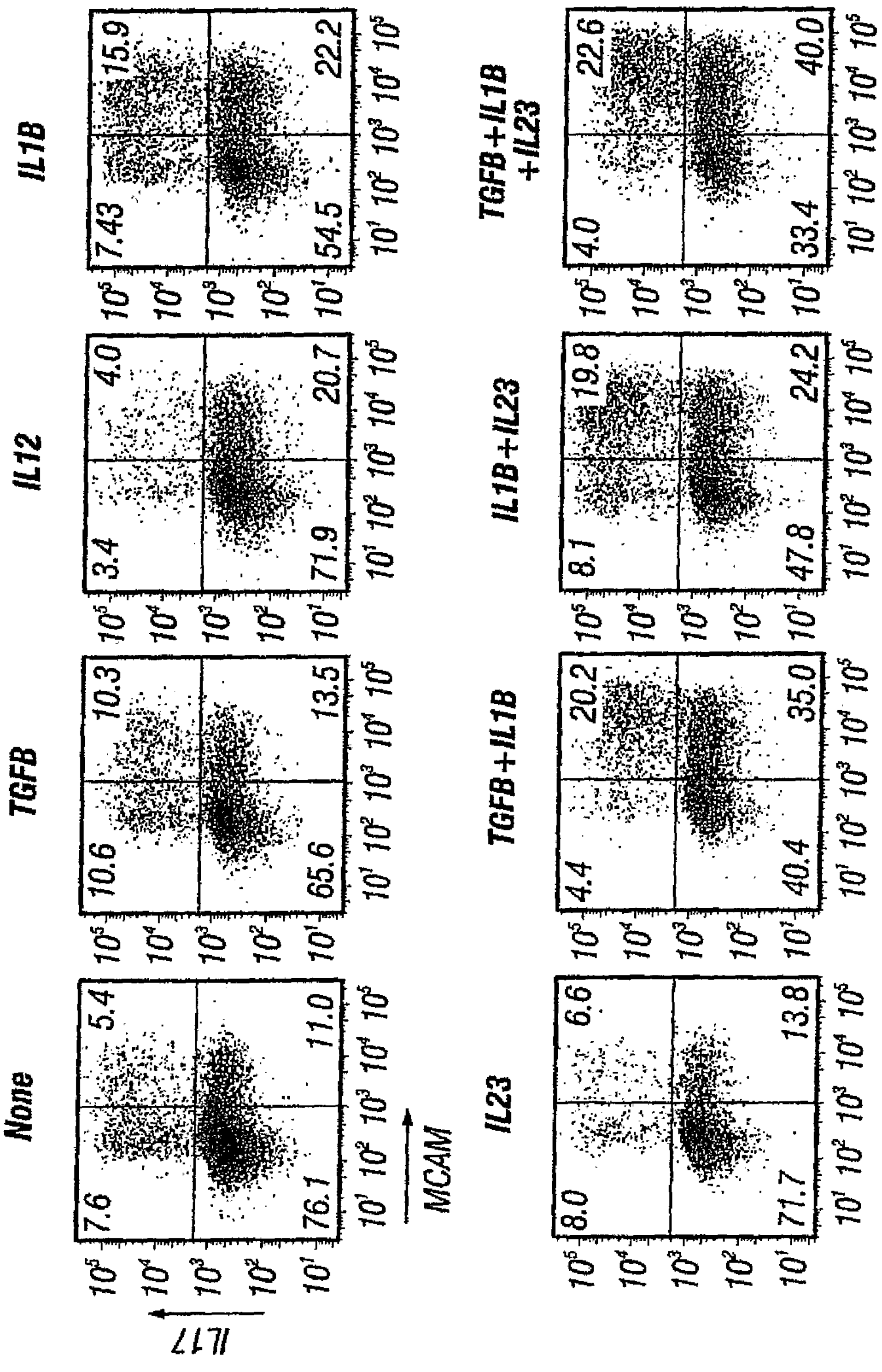
FIGS. 3A-F depict the effects of various cytokines on CD4+/CD45RO+ memory T cells.
Figures 3B, 3C, 3D, 3E, 3F:
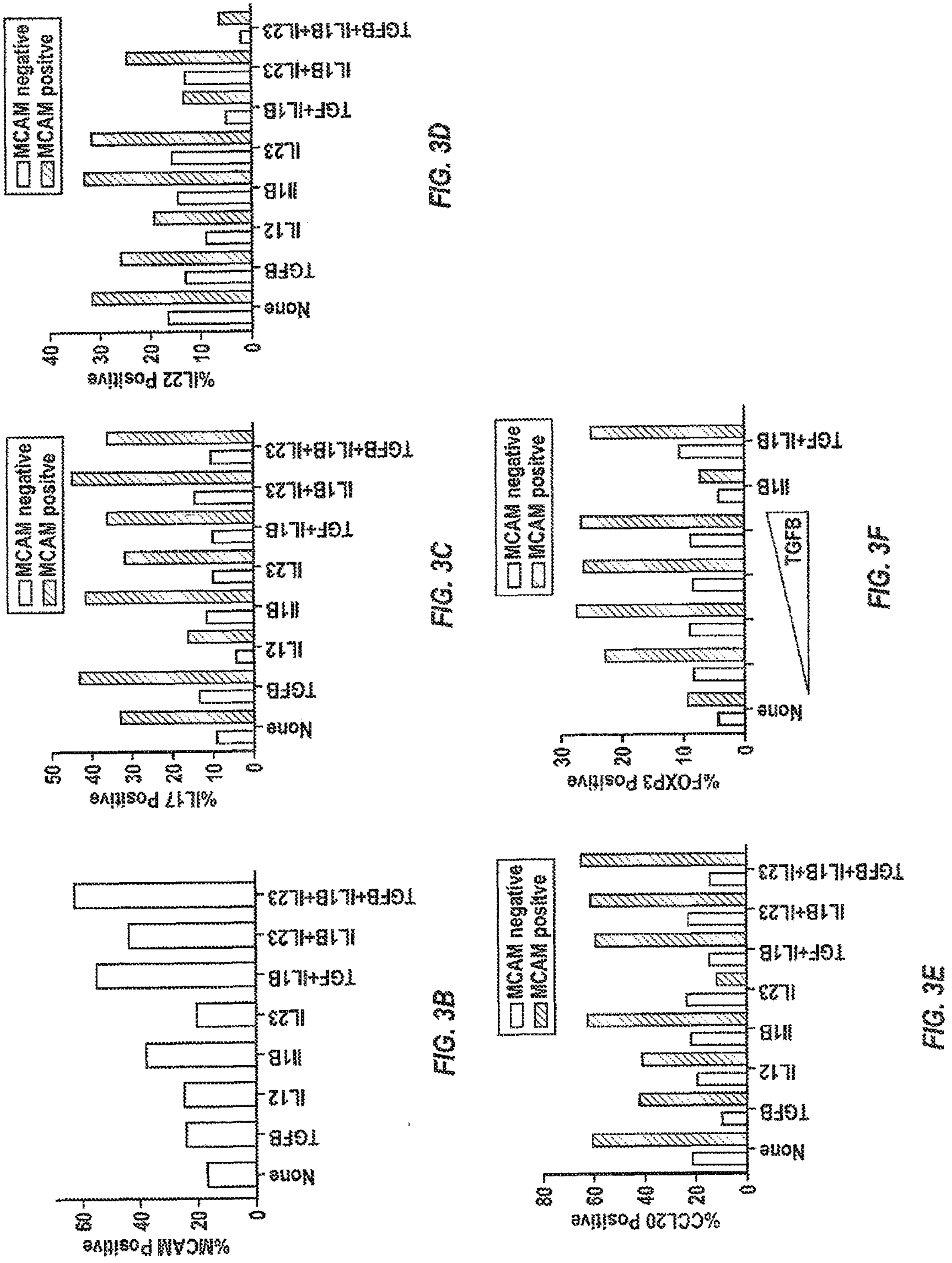

Example 3. MCAM Expressing T Cells are Expanded by IL1β and Produce the Majority of Both IL-17 and IL-22 Under TH17 Conditions MCAM expressing CD4+ T cells, at only 3-5% of cells, is a small minority of the T cell population. It is of interest to determine the conditions under which this population expands and exerts TH17 effector function. For this, human CD4+/CD45RO+ T cells were purified as described in Materials and Methods above and stimulated in vitro with anti-CD3 and anti-CD28 in the presence of a number of cytokine conditions (TGFβ, IL-12, IL-1β, IL-23, and various combinations), and the percentage of MCAM expressing cells, as well as IL-17 expressing cells, was determined by flow cytometry (FIG. 3A). MCAM expression expanded upon stimulation with IL-1β alone (16.4% in the absence of IL-1β vs. 38.1% in the presence of IL-1β, FIG. 3B). Furthermore, while TGFβ alone did not expand the MCAM positive population greatly, it functioned synergistically with IL-1β, as the combination of both cytokines resulted in more than half of the memory T cell population becoming MCAM positive. Under the same conditions that expanded the population of MCAM expressing cells, the population of IL-17 producing cells was concomitantly increased, with considerable enrichment within the MCAM+ population under all cytokine conditions tested (FIG. 3C). In fact, in the presence of TGFβ and IL-1β, more than 80% of the IL-17 producing cells (20.2%/(20.2%+4.4%)) were MCAM positive.

Additional to IL-17, the known TH17 associated cytokine IL-22 (Liang et al., *J. Exp. Med.* 203: 2271-2279 (2006)) was also elevated in MCAM expressing T cells. IL-22 receptor is largely expressed on non-immune cells such as epithelial cells and functions in anti-microbial responses as well as tissue remodeling. See, e.g., Dumoutier et al., *J. Immunol.* 167: 3545-3549 (2001); see also Zenewicz et al., *Int. Immunol.* 23: 159-163 (2011). Although IL-22 has been shown to be involved in blood brain barrier function, it is not absolutely required for induction or progression of EAE. See, e.g., Kreymborg et al., *J. Immunol.* 179: 8098-8104 (2007); see also Kebir et al., *Nat. Med.* 13: 1173-1175 (2007). In a similar fashion to IL-17, a significantly higher percentage of MCAM+ cells expressed IL-22 (FIG. 3D).

TH17 cells have also been reported to express CCL20. See, e.g., Hirota et al., *J. Exp. Med.* 204: 2803-2812 (2007). Similar to IL-17 and IL-22, there was a considerably higher population of MCAM expressing T cells that were positive for CCL20 (FIG. 3E), suggesting a possible positive feedback loop in the migration of CCR6+ T cells.

While the above data are suggestive of a T cell population with a particularly pathogenic phenotype, it was unexpected to observe that MCAM expression was not mutually exclusive with intracellular FOXP3, and in fact, a slightly higher percentage of MCAM+ T cells were FOXP3 positive (FIG. 3F). In the presence of increasing doses of TGFβ, the percentage of MCAM+ cells that were FOXP3+ increased, while the percentage of FOXP3 expressing cells in the MCAM− population remained largely unchanged. These results suggest that MCAM expressing cells have the potential to function in an immunoregulatory role in the presence of TGFβ.

Example 4. MCAM Binds to the ECM at Known Sites of T Cell Infiltration of the CNS, and the MCAM Ligand is Laminin 411

The function of MCAM has been elucidated in tumor models, showing that MCAM expression confers an adhesive, infiltrative, and ultimately metastatic phenotype to tumor cells. See, e.g., Xie et al., *Cancer Res.* 57: 2295-2303 (1997). However, the ligand that MCAM binds remains to be identified. Although the above data indicate that MCAM is enriched in TH17 cells, it is unknown whether MCAM is functionally involved in the T cell infiltration of the CNS. It was thus of great interest to determine (1) where MCAM binds, i.e., the identity of the MCAM ligand, (2) whether MCAM is critical to initial infiltration of TH17 cells into the uninflamed brain, and (3) whether the expression of the MCAM ligand is required at the established points of entry to the CNS.

Figure 4A:
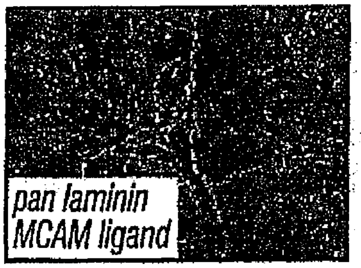
FIGS. 4A-H depict the identification of laminin 411 as the MCAM ligand.
Figure 4B:
Figure 4C:
Figure 4D:
Figure 4E:
Figure 4F:
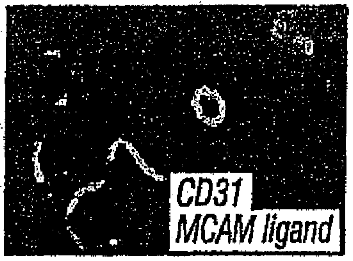

An MCAM-Fc fusion protein was generated (as described in Materials and Methods above) to detect MCAM binding on healthy mouse tissue, particularly those regions known to be involved in T cell infiltration. As the choroid plexus has been suggested as a route of entry for TH17 cells into the uninflamed brain, healthy choroid plexus tissue was stained with MCAM-Fc and anti-laminin. As shown in FIGS. 4A and 4B, the choroid plexus widely expresses the MCAM ligand, but is negative for MCAM. These results strongly suggest that (1) MCAM unlikely mediates adhesion to the choroid plexus tissue through a homotypic MCAM/MCAM interaction; and (2) there is an additional MCAM ligand with considerably more widespread expression than MCAM, whose expression was limited to vascular endothelium within healthy tissues (FIG. 4C). It was unexpected that MCAM-Fc bound nearly ubiquitously to healthy mouse spinal cord (FIG. 4D) in a pattern that was suggestive of an extracellular matrix (ECM) protein, and specifically laminin. MCAM-Fc and anti-laminin co-localized on healthy mouse spinal cord (FIG. 4E), suggesting that the ligand for MCAM might be a form of laminin. MCAM ligand was confirmed to be in the ECM, as it was exterior to the endothelial cell layer within the vasculature, as determined by CD31 co-staining (FIG. 4F).

Figure 4G:
Figure 4H:

While MCAM co-localized with laminin within healthy mouse tissues, the identity of the MCAM ligand was further confirmed by co-staining EAE tissues with laminin and MCAM-Fc. In regions of lymphocyte infiltration, it has been found that the basement membrane separates into two distinct membranes, the endothelial basement membrane and the parenchymal basement membrane with important distinctions in laminin isoform composition. See, e.g., Sixt et al., *J. Cell Biol.* 153: 933-945 (2001). When MCAM-Fc was used to stain the MCAM ligand within these regions, it was found that MCAM-Fc stained only the endothelial basement membrane, while pan-laminin stained both the endothelia basement membrane and the parenchymal basement membrane (FIG. 4G). This same expression pattern has been noted for the laminin 411 (laminin 8 ($\alpha4\beta1\gamma1$)). Co-localization of MCAM-Fc protein and laminin alpha 4 was observed by using a laminin alpha 4 specific antibody (FIG. 4H), suggesting that laminin 411 is a ligand for MCAM. Confirmation that a laminin molecule comprising an alpha 4 chain is the ligand for MCAM, and which may contribute to the unique migratory capability of TH17 cells is described by Flanagan et al., PLoS ONE 7(7): e40443. doi:10.1371/journal.pone.0040443 (2012).

Example 5. Anti-MCAM Antibodies Block Binding of MCAM to Laminin 411

Figure 5A:
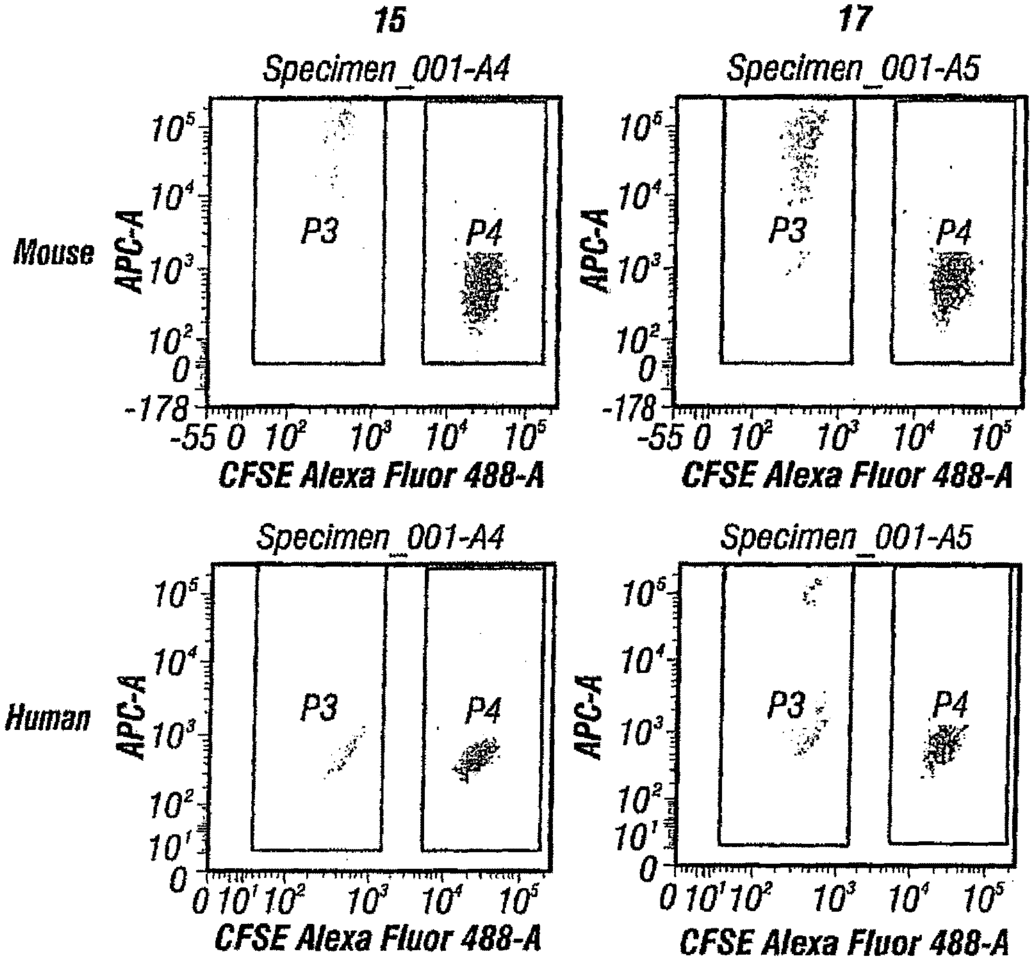
FIGS. 5A-C.

Monoclonal antibodies against mouse MCAM were generated as described in Materials and Methods above. The specific binding between the monoclonal antibody and MCAM was confirmed by assessing the monoclonal antibody's ability to bind to cells transfected with either mouse or human MCAM. For this, untransfected cells were labeled with carboxyfluorescein succinimidyl ester (CFSE) and mixed with unlabeled MCAM transfected cells. Untransfected cells (in blue) could therefore be differentiated. As shown in FIG. 5A, clones 15 and 17 showed specific binding to mouse MCAM (top, orange) while only clone 17 bound to human MCAM (bottom, orange).

Next, the monoclonal antibodies were used to test their ability to block the binding of MCAM to its ligand. Murine or human MCAM-Fc protein (5 μg/mL) was pre-incubated with isotype control antibody, clone 15, or clone 17 (10 μg/mL) for 30 minutes in PBS. The mixture was added to healthy spinal cord tissue sections and subsequently characterized by fluorescence microscopy as described in Materials and Methods above.

Figure 5B:
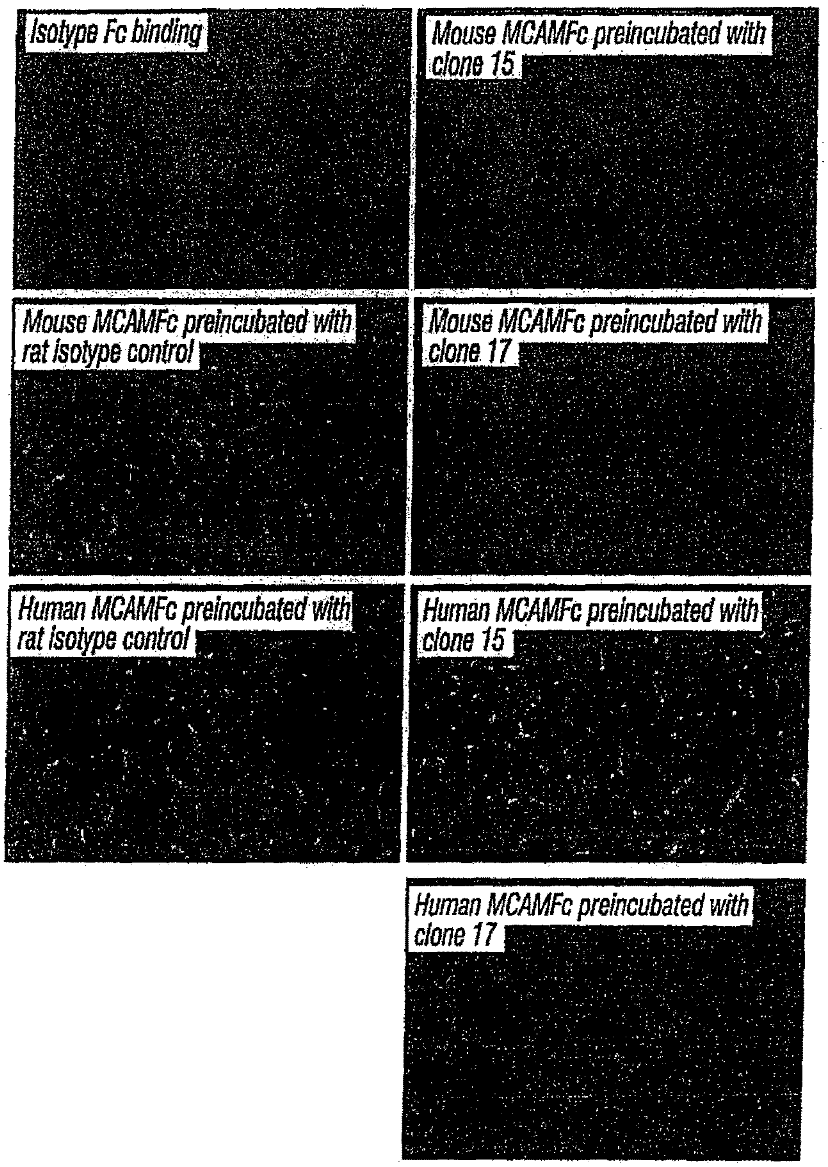
Figure 6A:
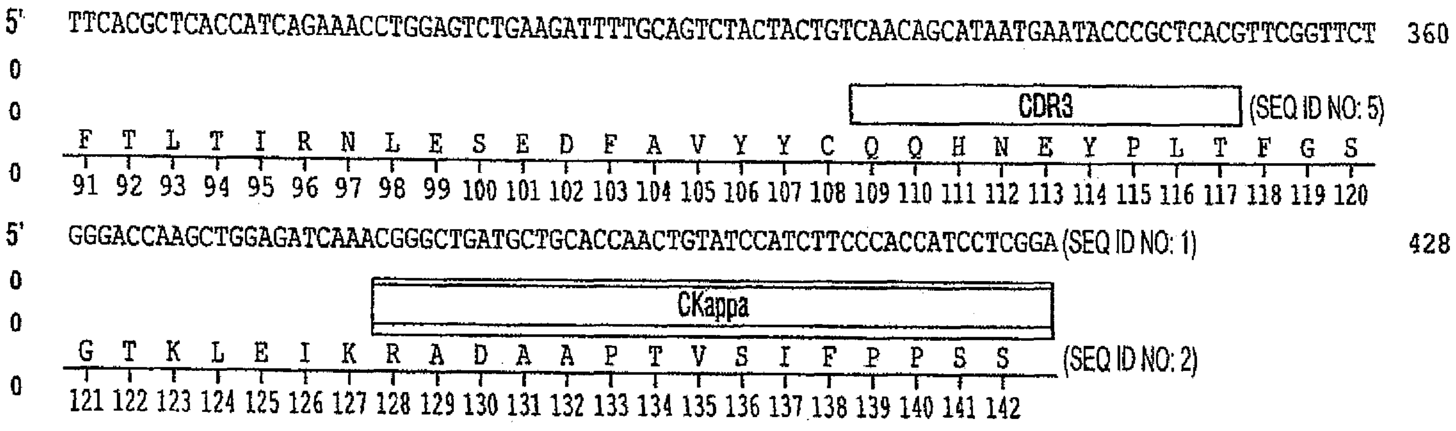
FIGS. 6A, B.
Figure 6B:
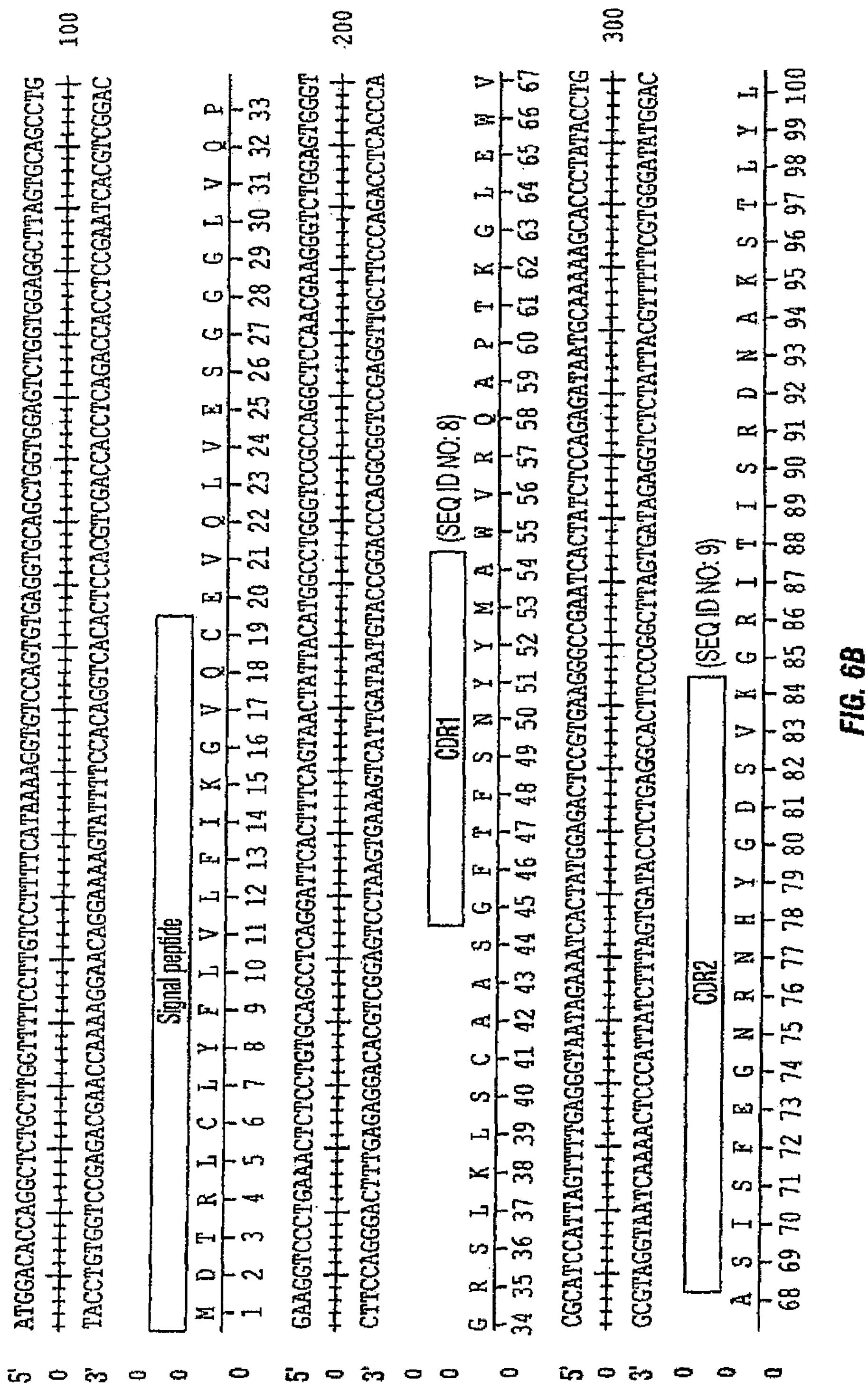
FIG. 6B depicts the heavy chain variable region clone 17 monoclonal antibody.

As shown in FIG. 5B, both clones 15 and 17 could block binding of the murine MCAM-Fc protein to the tissue, while only clone 17 could block human MCAM-Fc protein binding to the tissue. CDRs of clone 17 have been sequenced and are presented in FIGS. 6A (SEQ ID NO:2, light chain) and 6B (SEQ ID NO:7, heavy chain). Non-denaturing Western blot analysis using clone 17 on individual Fc domains of MCAM confirmed that clone 17 binds specifically to a domain comprising amino acid residues 19 to 129 of MCAM. This binding was confirmed by ForteBio analysis.

Figure 5C:
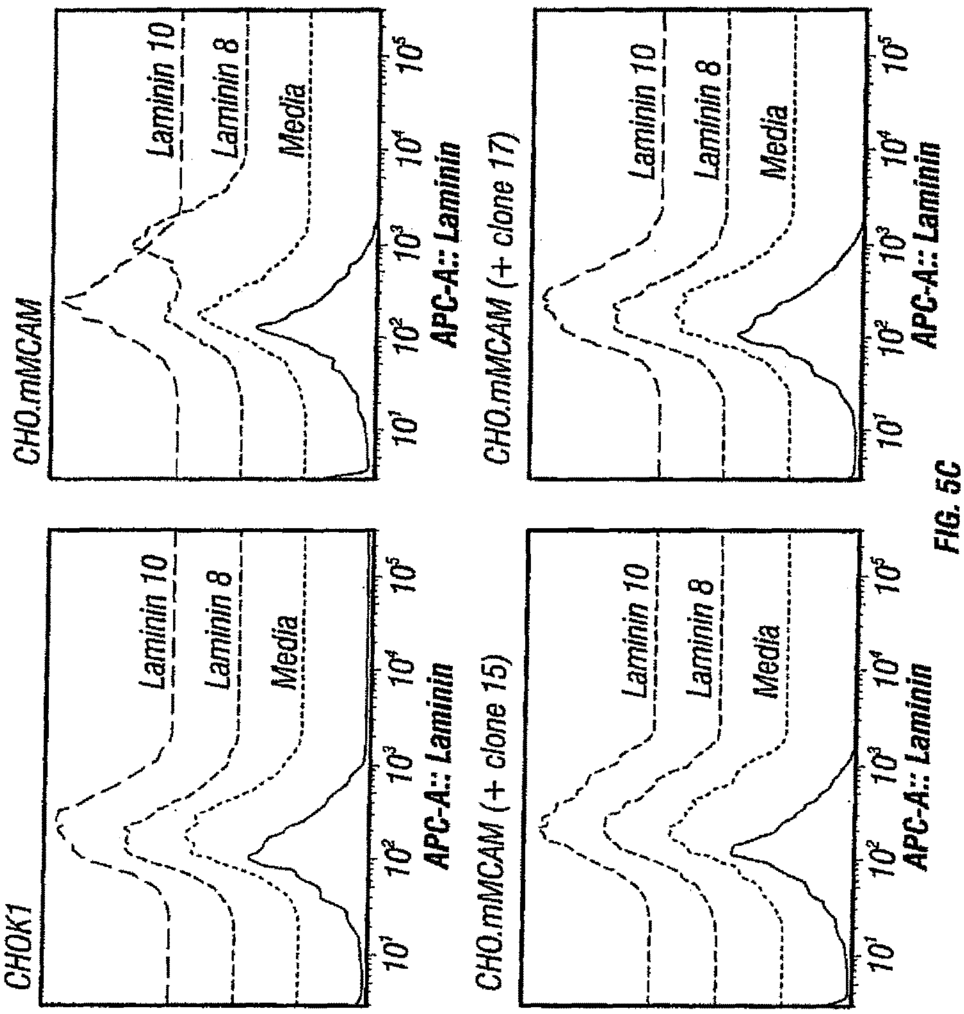

Furthermore, the MCAM monoclonal antibodies were shown to inhibit the interaction between MCAM and its ligand, laminin 411. Parental CHO cells (CHOK1) or CHO cells transfected with mouse MCAM gene were preincubated with CHO culture media (DMEM), recombinant laminin 411 (10 μg/ml), or recombinant laminin 511 (i.e., laminin 10 ($\alpha5\beta1\gamma1$)) (10 μg/ml) at 37° C. for 45 minutes. Cells were washed, and specific binding of laminin 411, but not laminin 511, to MCAM was detected with a pan-laminin antibody by flow cytometry (FIG. 5C, top right panel). Preincubation of mouse MCAM transfected CHO cells with the anti-MCAM antibody (clone 15 or clone 17, each at 20 μg/ml), prior to laminin incubation, abolished the binding of MCAM to laminin 411 (FIG. 5C, bottom panels).

The above-presented data suggest that clone 17, which is capable of specifically blocking the binding of human MCAM to its ligand, might be useful to prevent or treat various TH17-mediated diseases by inhibiting MCAM-mediated adhesion of TH17 cells to the vasculature and blocking the migration of TH17 cells into central nervous system.

Figures 7A, 7B:
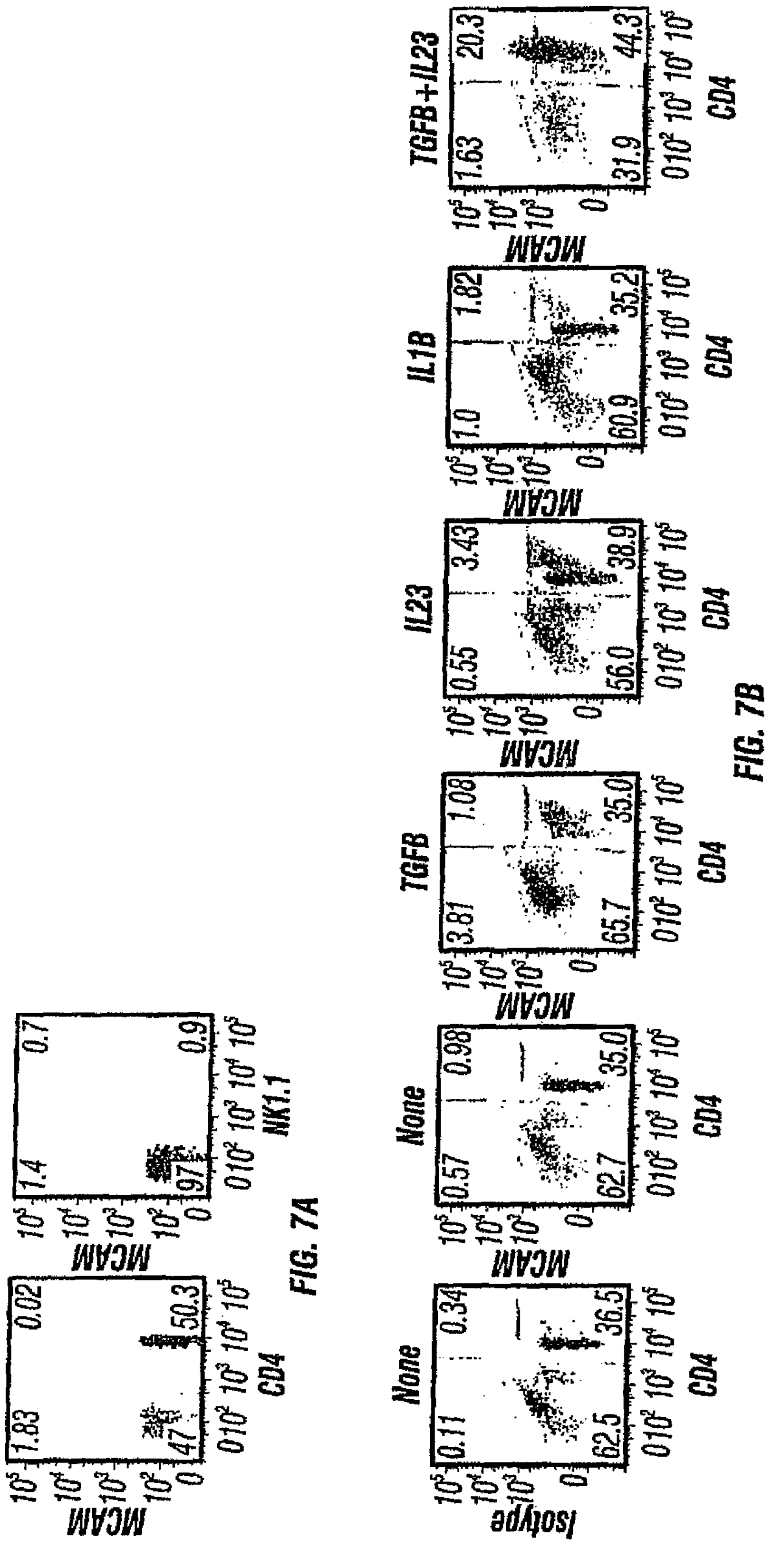
FIGS. 7A, B.
FIG. 7B depicts MCAM expression levels among splenocytes in the presence of various cytokines. Splenocytes were obtained from PLP immunized SJL mice and in vitro restimulated with PLP.

Example 6. MCAM is Not Expressed on Circulating Mouse T Cells, but is Induced Following TH17 Polarization Using the antibodies above, peripheral mouse blood was stained to detect MCAM expressing T cells in mice as described in Materials and Methods above. As previously described, mouse T cells lack expression of MCAM, while expression is noted on a population of NK cells (FIG. 7A). The expression of MCAM solely on memory T cells in humans suggests that mice, if living in a clean environment with limited previous T cell activation, would have to be polarized in order to generate a population of MCAM expressing T cells. Considering the link between MCAM and TH17 cells in humans, experiments were conducted to determine whether it was possible to induce a population of MCAM expressing T cells in mice. Myelin proteolipid protein (PLP) specific T cells were generated by immunizing wild type mice with PLP in the presence of complete Freund's adjuvant (CFA) as described in Materials and Methods above. Splenocytes were restimulated in vitro with 5 μg/mL PLP in the presence of the indicated cytokines and analyzed five days later for MCAM expression (FIG. 7B). In the absence of exogenous cytokines, the restimulation did not induce statistically significant MCAM expression on CD4+ cells (as compared to isotype control). In the presence of IL-23, a small population of MCAM expressing CD4+ T cells was detectable. While TGFβ alone did not induce a sizable population of MCAM expressing T cells, the combination of TGFβ and IL-23 synergistically generated MCAM expression among CD4+ T cells. Both of these cytokines have an important role in the polarization and effector function of mouse TH17 cells. Notably, MCAM was expressed on a population of CD4 high T cells which have been described to exclusively contain the pathogenic T cells in EAE. See, e.g., Li et al., *J. Neuroimmunol.* 192: 57-67 (2007). Thus, unlike humans, mice do not possess a population of circulating CD4+MCAM+ T cells, but polarization under TH17 conditions with TGFβ and IL-23 is sufficient to generate such a population. Mice remain a viable model to study the role of MCAM in the infiltration of CNS by pathogenic T cells.

Example 7. MCAM Blockade by an Anti-MCAM Antibody Inhibits EAE Disease Progression EAE is a disease that is generated laboratory animals to produce symptoms similar to those of multiple sclerosis (MS) in humans. EAE is generally produced by injecting animals with different proteins from the central nervous system of other animals, for example, extracts of myelin basic protein and whole spinal cord or brain tissue, or with T cells that specifically react to myelin. EAE is commonly used to follow the course the relapsing or progressive forms of MS. EAE has been served as a suitable animal model to both develop therapeutic agents for MS and study the specific disease processes of MS. See, e.g., Gold et al., *Brain* 129: 1953-1971 (2006); see also Steinman et al., *Ann. Neurol.* 60: 12-21 (2006).

Figure 8A:
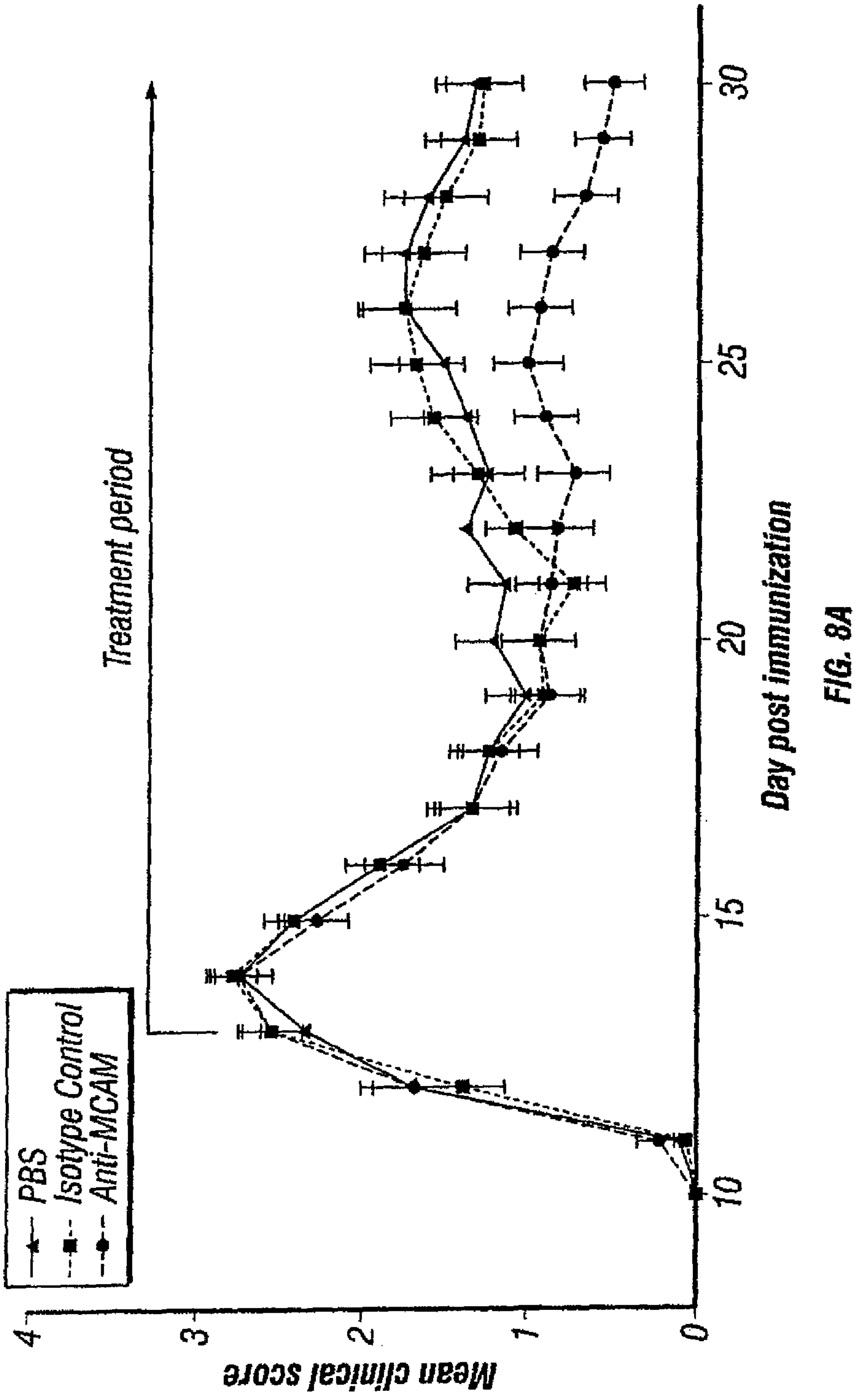
FIGS. 8A, B depicts the effects of MCAM blockade on disease progression in a therapeutic model of EAE. After EAE symptoms appeared, PLP-immunized mice were treated intraperitoneally with (1) anti-MCAM antibody (clone 15) at 10 mg/kg body weight, (2) the isotype control (Bioxcell) at 10 mg/kg body weight, and (3) PBS every day thereafter. The disease progression (FIG. 8A) and body weights (FIG. 8B) were monitored every 2-3 days. Data represent the mean of 15 mice±sem (standard error of the mean).
Figure 8B:
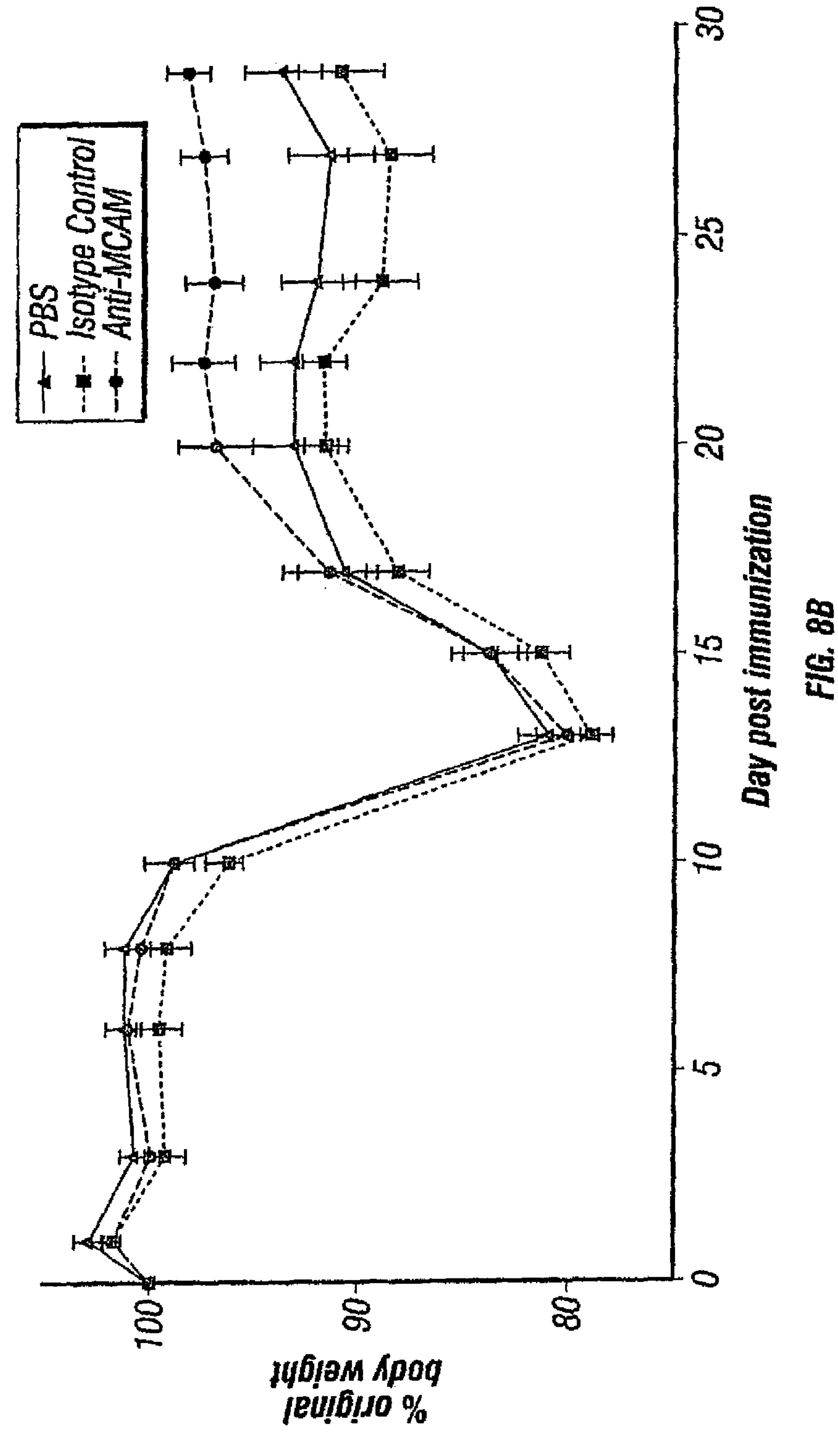
Figure 9A:
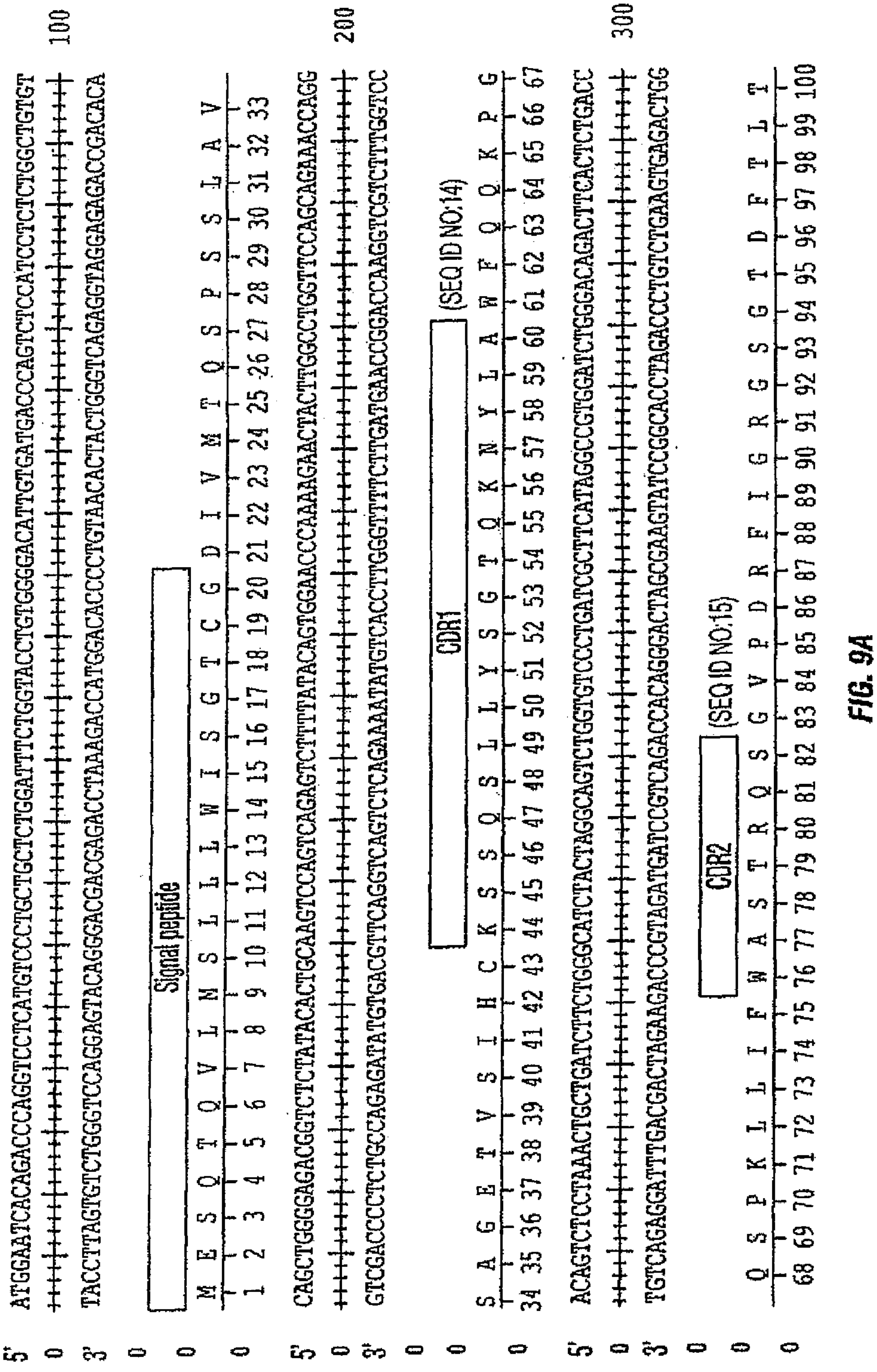
FIGS. 9A, B.

The effects of MCAM blockade on disease progression were further examined in a therapeutic model of EAE, wherein the TH17 polarization occurs in vivo (see Example 6). Mice were immunized with PLP 139-151 peptide as described in Materials and Methods above. Immunized mice were randomized into groups based on clinical scores and day of onset. On the second day following disease onset (EAE symptoms appeared between 12 and 14 days post immunization), mice were treated (N=15 per group) intraperitoneally with either anti-MCAM antibody (clone 15) or isotype control (Bioxcell) at 10 mg/kg body weight, and every day thereafter. Mice were monitored daily and scored for in a blinded manner (FIG. 8A), and body weights were obtained every 2-3 days (FIG. 8B). While MCAM blockade does not appear to affect the severity or duration of the ongoing acute phase of the disease, relapse was delayed and was significantly less severe in mice treated with anti-MCAM antibody (clone 15). These results are consistent with the idea that MCAM may not be essential for infiltration of immune cells during an existing inflammatory process, but may be involved in the subsequent recruitment of antigen experienced pioneer T cells to initiate new inflammatory sites.

Example 8. Domain Binding Test for Murine Anti-MCAM Antibodies

The following protocol was used: ForteBio Domain Mapping Protocol. ForteBio anti-human IgG Fc biosensors were used to immobilize various mouse MCAMhFc domains including full length mouse MCAMhFc protein on to biosensor surface. These sensors were dipped into either clone 15 or 17 MCAM specific antibody for detection of binding to these domains or full length protein. After loading these samples into a black 96 well plate, the Octet Red was programmed as follows: 60 seconds for baseline #1; 180 seconds for loading various domains; 60 seconds for baseline #2; 180 seconds for association of antibody to domain; and 240 seconds for dissociation of antibody from domain.

Figure 10A:
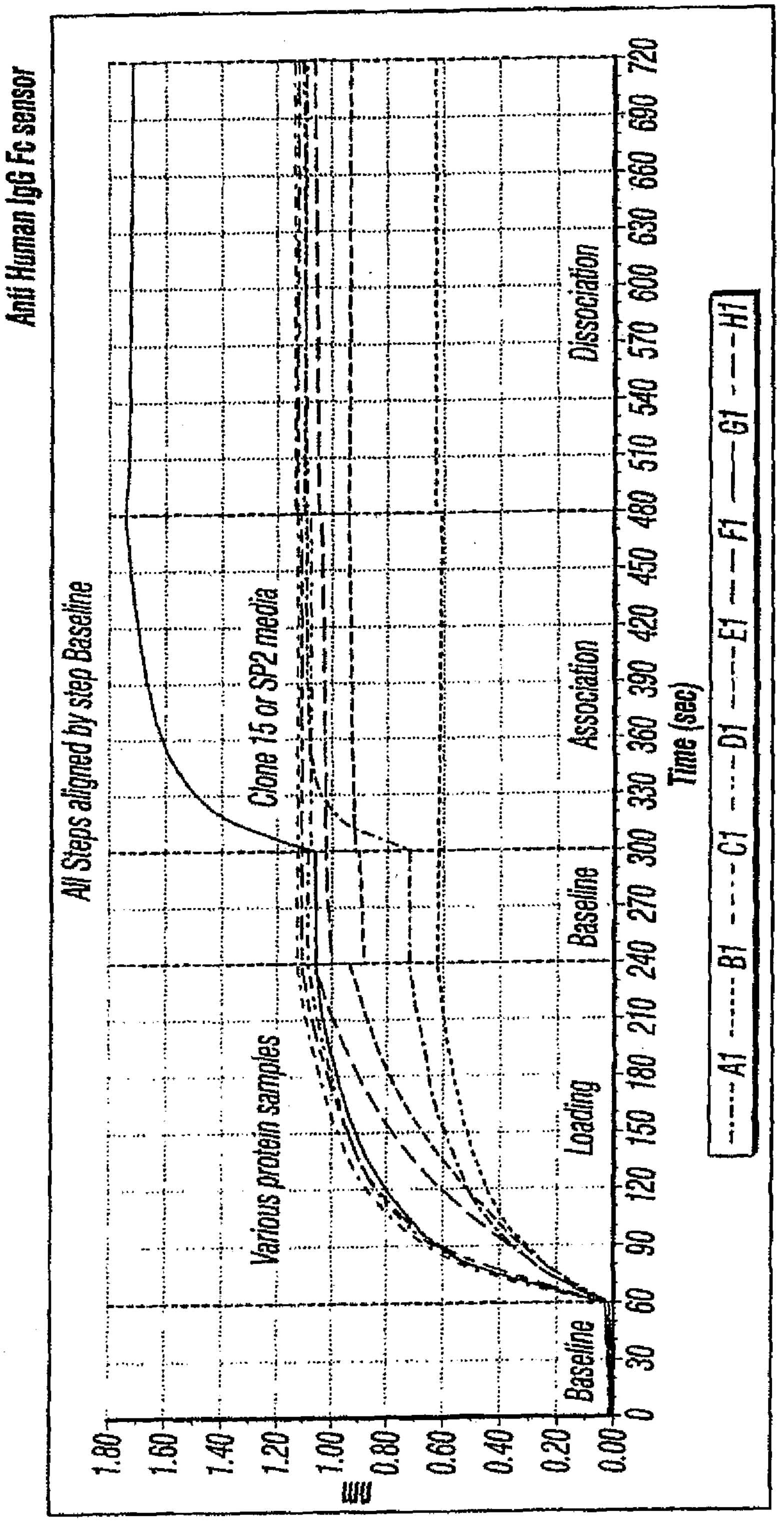
FIGS. 10A, B depict the results of a domain binding test for MCAM antibodies.
Figure 10B:
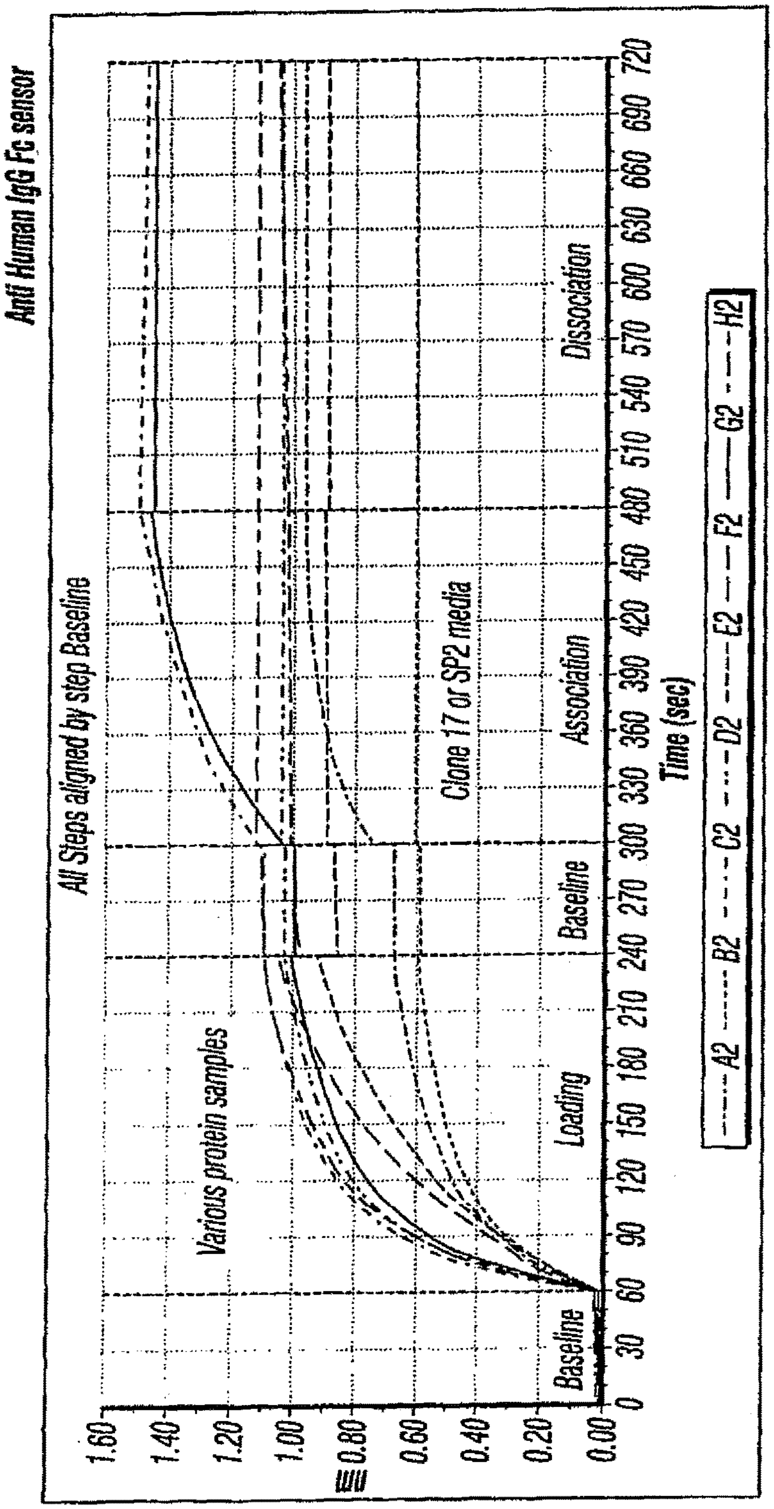

Reagents and Supplies Used:

1. Mouse MCAMhFc final concentration @ 5 ug/ml
2. Antibody clone 15 or 17 @ 5 ug/ml
3. ForteBio anti-human IgG Fc Capture (AHC) biosensors for kinetics experiments, cat #18-5060
4. Block 96 well plate from Greiner Bio-one, cat #655209
5. ForteBio Octet Red machine
6. Fresh tissue culture medium, DMEM with 20% FCS, was used as buffer for dilution FIG. 10A demonstrates that clone 15 binds specifically to MCAM Fc domains 1 and 2, but not Fc domain 1 alone. FIG. 10B demonstrates that clone 17 binds specifically to either MCAM Fc domains 1 and 2, or Fc domain 1 alone. For FIGS. 10A-B, clones 15 and 17 were tested against the following protein samples (all have human IgG Fc tag): Murine MCAM; Human Fc full length protein; Murine MCAM domain 1 (Ig1); Murine MCAM domain 2 (Ig2); and Murine MCAM domain 1 and 2 (Ig1-2A).

Example 9. MCAM Domains Bind Laminin A4 (α4) Chain

The binding affinity of the human laminin-α4 to human MCAM IgG1-2A was measured by Surface Plasmon Resonance on a Biacore T200 machine. Human Fc-specific $F(ab')_2$ IgG (Jackson Laboratories) was immobilized on a CM5 chip using amine coupling. The four flow cells of the CM5 chips dextran surface are activated by a 7 min injection of freshly prepared 1:1 50 mM NHS: EDC at a flow rate of 5 μl/min. 70 μl IgG solution (pH 4.5) was injected for 3 min to a density of up to 3 000 RU. The coupling is then blocked by a 7 min injection of 1M ethanolamine to deactivate residual reactive sites. Recombinant human Fc-tagged MCAM IgG1-2A in degassed and filtered HBS-P buffer containing 12 mg/ml BSA and 12 mg/ml carboxy-methylated dextran sodium salt was captured by anti-Fc IgG to a capture level 1560 RU. Recombinant human Fc-tagged MCAM IgG1-2A was centrifuged at 14 000 rpm for 5 min at 4° C. before injection for 20 min at a flow rate of 5 μl/min over the anti-Fc IgG containing surface. Flow cell 1 was left free of IgG to serve as a control surface. One flow cell was used to capture recombinant human IgG1 Fc (R&D systems) to serve as a negative control. Recombinant human laminin-α4 (R&D systems) or recombinant human laminin 411 (Biolamina) or recombinant human laminin 511 (Biolamina) (negative control) was diluted in degassed and filtered HBS-P buffer containing 12 mg/ml BSA and 12 mg/ml carboxy-methylated dextran sodium salt to concentrations spanning 5-175 nM and injected (1 min association, 3 min dissociation) over the MCAM IgG1-2A surfaces and control surfaces at a flow rate of 10 μl/min. Buffer injections served as negative control. Data evaluation: Data from the buffer injections and the control surface were subtracted to remove artifacts. The data was fitted globally to a 1:1 interaction model using the Biaevaluation software or Scrubber.

The laminin α-4 chain was found to bind specifically to the MCAM Fc domains 1 and 2, but not to Fc domain 1 alone (data not shown). The negative controls included: a lack of binding of laminin 511 to either domain, and a lack of binding of laminin 411 to hIgG1-Fc. Recombinant human laminin-α4 (R&D systems) binds to human Fc-tagged MCAM IgG1-2A (data not shown) at an affinity of 60 nM, but not to recombinant human IgG1 Fc (R&D systems) (data not shown). Recombinant human laminin 411 (Biolamina) binds to human Fc-tagged MCAM IgG1-2A at an affinity of 66 nM as measured by steady state kinetics (data not shown) but not to recombinant human IgG1 Fc (R&D systems) (data not shown). The negative control, recombinant human laminin 511 (Biolamina) does not bind to human Fc-tagged MCAM IgG1-2A (data not shown).

Example 10. Generation of New Anti-MCAM Monoclonal Antibodies

Mouse and rat monoclonal antibodies directed against human MCAM protein were generated as described in Materials and Methods above. The specific binding between the monoclonal antibody and human MCAM was confirmed by assessing the monoclonal antibody's ability to bind to cells transfected with human MCAM. For this, untransfected cells were labeled with carboxyfluorescein succinimidyl ester (CFSE) and mixed with unlabeled human MCAM transfected cells. Untransfected cells could, therefore, be differentiated.

Using these techniques, 823 independent mouse fusions clones were isolated and shown to express an antibody capable of binding to human MCAM. Additionally, 152 independent rat fusions clones were isolated and shown to express an antibody capable of binding to human MCAM.

Next, the anti-human MCAM monoclonal antibodies were used to test their ability to block the binding of human MCAM to its ligand. Human MCAM-Fc protein (5 μg/mL) was pre-incubated with isotype control antibody, or 10 μg/mL of the test monoclonal antibody for 30 minutes in PBS. The mixture was added to healthy spinal cord tissue sections and subsequently characterized by fluorescence microscopy as described in Materials and Methods above. Furthermore, parental CHO cells (CHOK1) or CHO cells transfected with a human MCAM gene were preincubated with CHO culture media (DMEM), recombinant laminin 411 (10 μg/ml), or recombinant laminin 511 (i.e., laminin 10 (α5β1γ1)) (10 μg/ml) at 37° C. for 45 minutes. Cells were washed, and specific binding of laminin 411, but not laminin 511, to MCAM was detected with a pan-laminin antibody by flow cytometry. Preincubation of human MCAM transfected CHO cells with the anti-MCAM antibody (at 20 μg/ml), prior to laminin incubation, abolished the binding of human MCAM to laminin 411.

Using this technique, it was shown that 87 of the 823 independent mouse fusion clones and 26 of the 152 independent rat fusion clones described above expressed an antibody that was capable of blocking the interaction between human MCAM protein and its ligand, α-4 chain of laminin.

Example 11. Further Characterization of New Anti-MCAM Monoclonal Antibodies

The 87 independent mouse fusion clones and 26 independent rat fusion clones described in Example 10 above as being capable of (i) binding to human MCAM, and (ii) blocking the interaction between human MCAM and the α-4 chain of laminin were further characterized as follows. First, IC50 quantitation for the ability of the monoclonal antibody to block the binding of human MCAM to the α-4 chain of laminin was determined as follows. CHO cells expressing human MCAM were incubated with an anti-human MCAM antibody (at various concentrations) for 30 minutes at 4 degrees Celsius. Unbound antibody was then washed away, and the cells were incubated with recombinant human laminin 411 at 20 ug/ml for 45 minutes at 37 degrees Celsius. Unbound laminin was then washed away, and the laminin bound to the surface of the cells was detected with fluorescently labeled anti-laminin antibodies. After washing, the amount of laminin bound to the surface was detected by flow cytometry, and IC50s were calculated based on the mean fluorescent intensity.

Using the above described assay, six independent anti-human MCAM monoclonal antibody clones were identified as binding to human MCAM and having the greatest ability to block the interaction between human MCAM expressed on the surface of cells and its binding ligand, human laminin 411. These six anti-MCAM monoclonal antibody clones are herein referred to as (i) the mouse anti-human MCAM monoclonal clones 1174.1.3, 1414.1.2, 1415.1.1, and 1749.1.3, and (ii) the rat anti-human MCAM monoclonal antibody clones 2120.4.19 and 2107.4.10. Amino acid and nucleic acid sequences of the heavy and light chains of these antibodies are provided in FIGS. 13-24. More specifically, in the above assay, IC50s for the monoclonal antibody clones 1174.1.3, 1414.1.2, 1415.1.1, 1749.1.3, 2120.4.19, and 2107.4.10 were determined to be 0.469 ug/ml, 0.431 ug/ml, 0.307 ug/ml, 0.545 ug/ml, 0.888 ug/ml, and 0.290 ug/ml, respectively. Moreover, experiments performed to determine the specific binding affinity of each monoclonal antibody demonstrated that each was capable of binding to human MCAM protein with high affinity (data not shown). As such, each of these specific monoclonal antibodies was very capable of binding to human MCAM and inhibiting the interaction of cell-expressed human MCAM with its α-4 laminin binding ligand. In contrast, two control antibodies, a non-specific human IgG1 antibody and a previously described, fully human anti-MCAM antibody referred to as ABX-MA1 (e.g., see Mills et al., Cancer Res. 62:5106 (2002), and U.S. Pat. Nos. 6,924,360, 7,067,131, and 7,090,844) were both incapable of blocking the binding interaction between human MCAM and its laminin 411 counterpart. As such, the six specific monoclonal antibodies identified above possess the novel ability to both (i) bind with high affinity to human MCAM on the surface of living cells, and (ii) block the interaction of cell expressed human MCAM with a laminin protein comprising an α-4 laminin polypeptide chain.

Example 12. Domain Binding Analysis for New Anti-MCAM Monoclonal Antibodies

The technique described in Example 8 above was employed to determine the location of the antigen epitope on the human MCAM protein that is recognized and bound by monoclonal antibody clones 1174.1.3, 1414.1.2, 1415.1.1, 1749.1.3, 2120.4.19, and 2107.4.10. The results from these analyses are as follows.

Monoclonal antibody clones 1174.1.3, 1414.1.2, 1415.1.1, and 1749.1.3 were all shown to bind to an antigenic epitope found on domain 3 of the human MCAM protein, defined specifically by amino acids 244-321 (SEQ ID NO:24) of the human MCAM protein. These monoclonal antibodies were not capable of binding to human MCAM domain 1 (namely amino acids 19-129, SEQ ID NO:22), domain 2 (namely amino acids 139-242, SEQ ID NO:23), or the combination of domains 1 and 2 (namely, amino acids 19-242). Hence, monoclonal antibody clones 1174.1.3, 1414.1.2, 1415.1.1, and 1749.1.3 define a novel antigenic epitope located within domain 3 of the human MCAM protein.

Monoclonal antibody clones 2120.4.19, and 2107.4.10 were each shown to bind to an antigenic epitope defined by the combination of human MCAM domains 1 (namely amino acids 19-129, SEQ ID NO:22), and domain 2 (namely amino acids 139-242, SEQ ID NO:23). Neither of these two monoclonal antibodies bound to human MCAM domain 1 by itself. Hence, monoclonal antibody clones 2120.4.19, and 2107.4.10 define a novel antigenic epitope determined by the presence of both human MCAM protein domains 1 and 2.

In contrast to the above, the previously described fully human anti-MCAM antibody ABX-MA1 binds to a different antigenic epitope than those described above, namely an antigenic epitope that is fully defined and encompassed within human MCAM domain 1 only.

Given these results, since each of monoclonal antibody clones 1174.1.3, 1414.1.2, 1415.1.1, 1749.1.3, 2120.4.19, and 2107.4.10 are capable of both (i) binding to human MCAM, and (ii) blocking the interaction between human MCAM and an α-4 laminin containing protein, whereas the ABX-MA1 antibody is capable of only binding to human MCAM, but not blocking the interaction between human MCAM and an α-4 laminin containing protein, these results demonstrate that human MCAM domain 2, human MCAM domain 3, and the combination thereof play a role in the binding interaction with α-4 laminin chain. Given this, it is clear that antibodies which bind to human MCAM domain 2, human MCAM domain 3, and/or the combination thereof would find use as agents capable of blocking the interaction between human MCAM and α-4 laminin and, thereby, find use for inhibiting the various consequences described herein resulting from that interaction. In contrast, antibodies that bind to an antigenic epitope defined solely by human MCAM domain 1 (such as the ABX-MA1 antibody described herein) are not useful for blocking the MCAM/α-4 laminin interaction and its various downstream biological consequences.

Example 13. Generation of Humanized Anti-MCAM Antibodies

Various humanized anti-MCAM antibodies were generated according to the following protocol. First, a three-dimensional molecular model of the variable regions was constructed using JN Biosciences' proprietary algorithm. Second, the framework amino acid residues important for the formation of the CDR structure or necessary for the binding to antigen were identified using the molecular model. In parallel, cDNA-derived human VH and VL amino acid sequences with high homology to the VH and VL amino acid sequences, respectively, were selected. Lastly, CDR sequences together with framework amino acid residues important for CDR structure or antigen binding were grafted from VH and VL into the corresponding selected human framework sequences.

FIGS. 25-27 depict the alignment of various 1749, 2107, and 2120 heavy and light chain sequences. Residue numbering is according to Kabat numbering. Different mutations to the framework (FR) amino acid residues involved in CDR formation and antigen binding were identified depending upon the version of antibody. For example, exemplary mutations of the 1749 antibodies are depicted in FIG. 25A (boxed residue between CDR-H2 and CDR-H3 (A93T) affects CDR contact; the A93T mutation combined with mutations of the boxed residue between CDR-H1 and CDR-H2 (G44R) affects VH/VL interface and CDR conformation) and FIG. 25B (Mutations of the boxed residue between CDR-L2 and CDR-L3 (S63T) affects CDR2 and antigen contact). Exemplary mutations of the 2107 antibodies are depicted in FIG. 26A (boxed residues before CDR-H1 (S30T), between CDR-H1 and CDR-H2 (I37V and L48I), and between CDR-H2 and CDR-H3 (K71R) affect CDR contacts; and S30T, I37V, L48I and K71R mutations combined with a mutation of the boxed residue immediately after CDR-H2 (T68S) affect antigen/antibody interactions); and FIG. 26B (boxed residues between CDR-L1 and CDR-L2 (Y36F), and between CDR-L2 and CDR-L3 (V58I) affect CDR contact; and Y36F and V58I mutations combined with (i) an additional mutation of the boxed residue between CDR-L1 and CDR-L2 (Q38L) affect CDR structure; or (ii) an additional mutation before CDR-L1 (T22N) affect antibody antigen interaction). Exemplary mutations of the 2120 antibodies are depicted in FIG. 27A (boxed residues in CDR-H1 (S30T), between CDR-H1 and CDR-H2 (I37V and L48I), and between CDR-H2 and CDR-H3 (K71R) affect CDR contact; and S30T, I37V, L48I, and K71R mutations combined with an additional mutation after CDR-H2 (T68S) affect CDR contact); and FIG. 27B (boxed residues between CDR-L1 and CDR-L2 (L46V and Y49F) and between CDR-L2 and CDR-L3 (V58I) affect CDR contact; boxed residues between CDR-L1 and CDR-L2 (L46V and Y49F) affect CDR contact; and L46V, Y49F, and V58I mutations combined with an additional mutation before CDR-L1 (T22N) affect antibody/antigen interaction).

Several versions of each chain were designed (standard vs. aggressive or conservative). For those antibodies that contained N-deamidation motifs (NG), mutations to the asparagines or glycine were introduced into the standard version. The various humanized V regions were synthesized with a heterologous signal sequence and cloned into expression vectors containing human CK (VL) or human IgG1 (VH).

The heavy and light chain plasmids were co-transfected into 293F cells with the FreeStyle™ MAX transfection regent (Invitrogen) according to the manufacturer's protocol. The expressed antibody was purified with protein A PhyTip columns (Phynexus) and quantified via OD280.

The apparent affinities of the humanized antibodies were compared to the parental rodent or chimeric antibody in a competitive ELISA according to the following protocol.

ELISA plates were coated with recombinant hMCAM-His, and blocked with casein buffer to prevent non-specific binding. Biotinylated rodent or chimeric antibody was added at a subsaturating concentration, in the presence or absence of 3× increasing concentrations of unlabeled competitor (humanized antibody, rodent, or chimeric). After washing to remove unbound antibody, streptavidin HRP was added to allow detection of the biotinylated antibody. The ELISA was developed with TMB substrate and the OD450 was measured. The IC50 of the unlabeled competitor was determined using the GraphPad Prism5 software.

Table 2 summarizes the design of humanized sequences (see also FIGS. 25-27 and 30-32).

TABLE 2

| | Donor Framework | Mutations |
|---|---|---|
| 1749 | | |
| VH1 | U96282 IGHV3-7*02 | A93T |
| VH2 | U96282 IGHV3-7*02 | VH1 + G44R |
| VL1 | X02990 IGKV4-1*01 | None |
| VL2 | X02990 IGHKV-1*01 | VL1 + S63T |
| 2107 | | |
| VH1 | AF062133 IGHV2-26*01 | S30T*, I37V, L48I and K71R |
| VH2 | AF062133 IGHV2-26*01 | VH1 mutations + T68S |
| VH3 | AF062133 IGHV2-26*01 | VH1 mutations + D72N |
| VH4 | AF062133 IGHV2-26*01 | VH1 mutations + N32S |
| VH5 | AF062133 IGHV2-26*01 | VH1 mutations + N32Q |
| VH6 | AF062133 IGHV2-26*01 | VH1 mutations + G33A |
| VL1 | U86803 IGKV1-27*01 | Y36F, V58I |
| VL2 | U86803 IGKV1-27*01 | VL1 mutations + Q38L |
| VL3 | U86803 IGKV1-27*01 | VL1 mutations + T22N |
| 2120 | | |
| VH1 | AF062133 IGHV2-26*01 | S30T*, I37V, L48I and K71R |
| VH2 | AF062133 IGHV2-26*01 | VH1 mutations + T68S |
| VH3 | AF062133 IGHV2-26*01 | VH1 mutations + N32S |
| VH4 | AF062133 IGHV2-26*01 | VH1 mutations + N32Q |
| VH5 | AF062133 IGHV2-26*01 | VH1 mutations + G33A |
| VL1 | X84343 IGKV1-39*01 | L46V, Y49F and V58I |
| VL2 | X84343 IGKV1-39*01 | L46V, Y49F |
| VL3 | X84343 IGKV1-39*01 | VL1 + T22N |

The heavy and light chain plasmids were co-transfected into 293F cells with the FreeStyle™ MAX transfection regent (Invitrogen) according to the manufacturer's protocol. The expressed antibody was purified with protein A PhyTip columns (Phynexus) and quantified via OD280.

The apparent affinities of the humanized antibodies were compared to the parental rodent or chimeric antibody in a competitive ELISA according to the following protocol:

ELISA plates were coated with recombinant hMCAM-His, and blocked with casein buffer to prevent non-specific binding. Biotinylated rodent or chimeric antibody was added at a subsaturating concentration, in the presence or absence of 3× increasing concentrations of unlabeled competitor (humanized antibody, rodent, or chimeric). After washing to remove unbound antibody, streptavidin HRP was added to allow detection of the biotinylated antibody. The ELISA was developed with TMB substrate and the OD450 was measured. The IC50 of the unlabeled competitor was determined using the GraphPad Prism5 software.

The affinities were measured using the ForteBio Octet Red. Anti-human Fc sensors were used to capture the humanized antibodies, and several concentrations of hMCAMHis analyte were used to determine the affinity using a 1:1 fitting model.

The potencies of the antibodies were measured in the laminin/FACS assay according to the following protocol: recombinant laminin 411 (Biolaminate) was added to hMCAM expressing CHO cells in the presence or absence of varying concentrations of the humanized, rodent, or chimeric antibodies. Following incubation for 30-45 minutes, the cells were washed and anti-laminin conjugated to AF650 (NovusBio) was added to detect the bound laminin. The cells were run on a flow cytometer to measure the laminin binding signal.

Table 3 provides the constructs used for transfection.

TABLE 3

| Construct | Description |
|---|---|
| h1749VH1 | Standard |
| h1749VH2 | Conservative |
| h1749VL1 | Standard |
| h1749VL2 | Conservative |
| h2120_VH1 | Standard |
| h2120_VH2 | Conservative |
| h2120_VH3 | Standard + N-S |
| h2120_VH4 | Standard + N-Q |
| h2120_VH5 | Standard + G-A |
| h2120_VL1 | Standard |
| h2120_VL2 | Aggressive |
| h2120_VL3 | Conservative |
| h2107_VH1 | Standard |
| h2107_VH2 | Conservative |
| h2107_VH3 | Standard + glyc |
| h2107_VH4 | Standard + N-S |
| h2107_VH5 | Standard + N-Q |
| h2107_VH6 | Standard + G-A |
| h2107_VL1 | Standard |
| h2107_VL2 | Conservative--rec |
| h2107_VL3 | Conservative |

Table 4 describes the specific transfection experiments.

TABLE 4

| | |
|---|---|
| Transfection--round 1 | |
| h1749VH1 + h1749VL1 | Standard VH and VL |
| h1749VH2 + h1749VL2 | Conservative VH and VL |
| h2120_VH1 + h2120_VL3 | Standard VH + conservative VL |
| h2120_VH2 + h2120_VL3 | Conservative VH + conservative VL |
| h2120_VH3 + h2120_VL3 | N-S deamidate VH + conservative VL |
| h2107_VH1 + h2107_VL2 | Standard VH + conservative VL |
| h2107_VH2 + h2107_VL2 | Conservative VH + conservative VL |
| h2107_VH3 + h2107_VL2 | Standard VH/restore N-gly + conservative VL |
| h2107_VH4 + h2107_VL2 | N-S deamidate mut VH + conservative VL |
| Transfection--round 2 | |
| h1749VH1 + h1749VL2 | Standard VH and conservative VL |
| h1749VH2 + h1749VL1 | Conservative VH and standard VL |
| h2120_VH4 + h2120_VL3 | N-Q deamidate VH + conservative VL |
| h2120_VH5 + h2120_VL3 | G-A deamidate VH + conservative VL |
| h2120_VH1 + h2120_VL1 | Standard VH + standard VL |
| h2120_VH1 + h2120_VL2 | Standard VH + aggressive VL |
| h2107_VH1 + h2107_VL1 | Standard VH and standard VL |
| h2107_VH1 + h2107_VL3 | Standard VH and other VL |
| h2107_VH5 + h2107_VL2 | N-Q deamidate VH + conservative VL |
| h2107_VH6 + h2107_VL2 | G-A deamidate VH + conservative VL |
| h2107_VH5 + h2107_VL3 | N-Q deamidate VH + other VL |
| h2107_VH6 + h2107_VL3 | G-A deamidate VH + other VL |
| h2107_VH5 + h2107_VL1 | N-Q deamidate VH + standard VL |
| h2107_VH6 + h2107_VL1 | G-A deamidate VH + standard VL |

Table 5 shows the relative affinities of the humanized antibodies compared to the rodent parent as measured by ForteBio and competitive ELISA, as well as the expression levels for the first round of transfections. FIG. 28A-C compares the blocking of various 1749, 2120, and 2107 antibodies of MCAM binding to laminin from the first round of transfections.

TABLE 5

| | Forte | | ELISA | | |
|---|---|---|---|---|---|
| Transfection--round 1 | Expt. #1 Fold over rodent | Expt. #2 Fold over rodent | Expt. #1 Fold over rodent | Expt. #2 Fold over rodent | Expression level |
| rodent 1749 | 1.00 | 1.00 | 1.00 | 1.00 | |
| h1749VH1 + h1749VL1 | 2.50 | 2.41 | 1.26 | 1.35 | 7.2 mg/L |
| h1749VH2 + h1749VL2 | 0.73 | 1.09 | 1.28 | 1.46 | 7.2 mg/L |
| chimeric 1749 | | 0.79 | 0.81 | 0.97 | |
| chimeric 1749 TM | | | | 1.07 | |
| rodent 2120 | 1.00 | 1.00 | 1.00 | 1.00 | |
| h2120_VH1 + h2120_VL3 | 5.64 | 6.21 | 2.23 | 2.42 | 22 mg/L |
| h2120_VH2 + h2120_VL3 | 6.57 | 6.43 | 1.93 | 2.62 | 16 mg/L |
| h2120_VH3 + h2120_VL3 | 16.14 | | 3.47 | | 22 mg/L |
| chimeric 2120 | | | 0.97 | 1.72 | |
| rodent 2107 | 1.00 | 1.00 | 1.00 | 1.00 | |
| h2107_VH1 + h2107_VL2 | 2.37 | 3.40 | 1.29 | 1.32 | 12 mg/L |
| h2107_VH2 + h2107_VL2 | 2.54 | 3.58 | 1.32 | 1.48 | 26.7 mg/L |
| h2107_VH3 + h2107_VL2 | 2.54 | | 1.62 | | 14.6 mg/L |
| h2107_VH4 + h2107_VL2 | 5.59 | | 11.72 | | 26.7 mg/L |
| chimeric 2107 | | | 0.68 | 1.01 | |
| chimeric 2107 TM | | | | 0.96 | |

Table 6 shows the measured affinity by ForteBio, competitive ELISA, and functional blocking data (laminin/FACS assay) compared to the rodent parent, as well as the expression levels, from the second round of transfections.

TABLE 6

| Transfection--round 2 | Forte Fold over rodent | Forte Fold over rodent | ELISA Fold over rodent | Blocking Expt#1 fold over rodent | Blocking Expt#2 fold over rodent | Expression level |
|---|---|---|---|---|---|---|
| h1749VH1 + h1749VL2 | 2.5 | | 1.0 | 1.1 | 1.2 | 6.9 mg/L |
| **h1749VH2 +h1749VL1** | 1.2 | | 1.0 | 1.5 | 1.8 | 3.2 mg/L |
| h1749VH1 + h1749VL1 | 2.5 | | 1.0 | 1.4 | 1.4 | 7.2 mg/L |
| h1749VH2 + h1749VL2 | 0.7 | | 1.1 | 1.8 | 1.7 | 7.2 mg/L |
| chimeric 1749 | 0.6 | | | 1.4 | 1.4 | |
| rodent 1749 | 1.0 | | 1.0 | 1.0 | 1.0 | |
| h2120_VH4 + h2120_VL3 | 17.4 | | 5.0 | 3.8 | 5.6 | 15 mgL |
| **h2120_VH5 +h2120_VL3** | **1.1** | **1.2** | **2.4** | **1.2** | 1.5 | **22 mg/L** |
| h2120_VH1 + h2120_VL1 | 8.8 | | 3.1 | 2.0 | 3.5 | 17 mg/L |
| h2120_VH1 + h2120_VL2 | 10.8 | | 3.1 | 4.6 | 12.6 | 2 mg/L |
| h2120_VH1 + h2120_VL3 | 5.9 | 5.8 | 1.8 | 1.7 | 2.8 | 22 mg/L |
| rodent 2120 | 1.0 | 1.0 | 1.0 | 1.0 | 1.0 | |
| h2107_VH1 + h2107_VL1 | 12.9 | | 2.1 | 2.3 | 2.1 | 25 mg/L |
| h2107_VH1 + h2107_VL3 | 16.3 | | 2.3 | 2.6 | 2.0 | 22 mg/L |
| **h2107_VH5 + h2107_VL2** | **5.9** | **6.0** | **1.3** | **1.6** | 1.5 | **19 mg/L** |
| h2107_VH6 + h2107_VL2 | 5.2 | 5.5 | 3.5 | 4.8 | 2.3 | 3 mg/L |
| h2107_VH5 + h2107_VL3 | 33.2 | | 3.4 | | | 19 mg/L |
| h2107_VH6 + h2107_VL3 | 22.1 | | 9.9 | | | 3 mg/L |
| h2107_VH5 + h2107_VL1 | 28.2 | | 3.7 | | | 18 mg/L |
| h2107_VH6 + h2107_VL1 | 36.8 | | 15.3 | | | 3 mg/L |
| h2107_VH1 + h2107_VL2 | 3.0 | 2.8 | 1.4 | 1.9 | 1.4 | 12 mg/L |
| **h2107_VH2 +h2107_VL2** | **2.7** | **2.9** | **1.3** | **1.4** | 1.5 | **26.7 mg/L** |
| rodent 2107 | 1.0 | 1.0 | 1.0 | 1.0 | | |
| chimeric 2107 | | | | | 1.0 | |

Overall, the data demonstrates that the various 1749 humanized antibodies have <2× reduction in potency and affinity compared to the rodent. The various 2120 humanized antibodies have a >5× reduction in affinity as measured by ForteBio, and most have a >2-3× reduction in apparent affinity and potency as measured by the competitive ELISA and laminin blocking assay, with the exception of VH5VL3 (G-A N-deamidation mutant VH/conservative VL), which had a <2× reduction in affinity and potency. Many of the 2107 humanized antibodies have a significant loss of affinity and potency, with the exception of VH1VL2, VH2VL2, and VH3VL2 (conservative light chain with standard, conservative, and the restored N-glycosylation site D72N heavy chains); these generally had <3× reduction and affinity and potency while retaining the N-deamidation site.

Figure 29B:
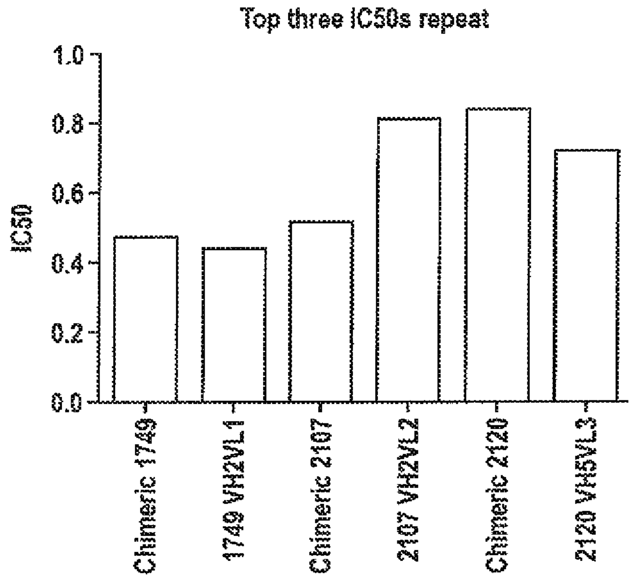

Certain candidate antibodies were re-expressed and tested for their affinity by ForteBio and their $IC_{50}$. The results are provided in Table 7 below and in FIG. 29.

TABLE 7

| | Forte kD | Blocking IC50 | Expression |
|---|---|---|---|
| h2120VH5VL3 | 1.3 | 0.7 | 12.7 mg/L |
| h2107VH2VL2 | 1.4 | 0.8 | 20 mg/L |
| h1749VH2VL1 | 0.67 | 0.4 | 3.3 mg/L |

Example 14. Analysis of MCAM Blockade by a Humanized Anti-MCAM Antibody and Inhibition of EAE Disease Progression The humanized antibodies described herein, e.g., Example 13, are tested for their effect on EAE disease progression according to the protocol provided in Example 7.

Example 15. Use of Humanized Antibodies to Analyze MCAM Expression Following TH17 Polarization The humanized antibodies described herein, e.g., Example 13, are used to analyze MCAM expression following TH17 polarization according to the protocol provided in Example 6.

Example 16. DNFB-Induced Skin Inflammation in Mice

DNFB (2,4-dinitrofluorobezene, Sigma) was diluted in acetone and olive oil (4/1). Abdomen of BALB/c mice (6-10 weeks old) were shaved and sensitized with 25 ul of 0.5% DNFB solution on days 0 and 1 as a model of allergic contact dermatitis and psoriasis. Animals received intraperitoneal treatment of antibodies (Anti-MCAM Clone 15 and Isotype, 10 mg/kg) on days 6 and 7. Right mouse ear was challenge with 5 ul of 0.2% DNFB and the left ear received vehicle (acetone/olive oil) on day 7 (Nakae et al., Immunity. 2002 September; 17(3):375-871). Mice were euthanized on day 8 and ear thickness or swelling was monitored using a micrometer (Mitutoyo, USA). The ear swelling was calculated as [(T1+T2+T3+T4)/4 left ear]−[(T1+T2+T3+T4)/4 right ear], where T represent four different values of ear thickness. FIG. 30 shows the antibody significantly inhibited inflammation.

Figure 31B:
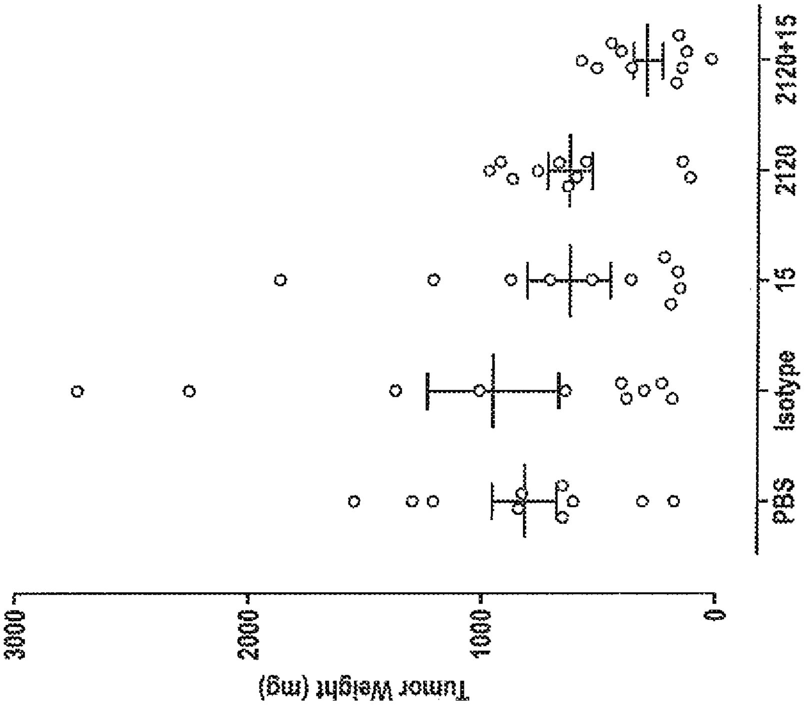

Example 17. Inhibition of Tumor Growth Nude SCID Mice $5\times10^5$ human MCAM expressing melanoma cells (WM2664) were injected subcutaneously into male nude severe combined immunodeficiency (SCID) mice. Mice were treated weekly with 1 mg of total antibody (0.5 mg of each antibody in the combination group) weekly beginning on day 4 post tumor implantation. The antibodies used were anti-mouse MCAM clone 15 or anti-human MCAM clone 2120.4.19 or a combination thereof. Tumors were measured in a blinded fashion with calipers 2× per week and tumor volume was determined by standard formula (Volume=(width)2×length/2) (FIG. 31A). On day 40 post tumor implantation, mice were euthanized, and tumors were removed intact, and weighed (FIG. 31B). Each antibody inhibited tumor growth and inhibition was most notable in the combination treatment. It is believed the combination treatment is more efficient in mice containing human cancer cells. The human cancer cells express human MCAM and human laminin, and the mice express mouse MCAM and mouse laminin Because mouse and human MCAM/laminin bind to each other, antibodies with specificity for human and mouse MCAM act synergistically to inhibit tumor growth. In a human, where all MCAM and laminin are human, human anti-MCAM clone 2120.4.19 (or similar antibody) is expected to be similarly effective as the combination treatment in mice.

What is claimed is:

1. An isolated anti-MCAM antibody, or antigen binding fragment thereof, said antibody or antigen binding fragment thereof comprising three light chain hypervariable regions (HVR-L1, HVR-L2, and HVR-L3) and three heavy chain hypervariable regions (HVR-H1, HVR-H2, and HVR-H3), wherein:

(a) HVR-L1 comprises the amino acid sequence of SEQ ID NO:61, HVR-L2 comprises the amino acid sequence of SEQ ID NO:62, HVR-L3 comprises the amino acid sequence of SEQ ID NO:63, HVR-H1 comprises the amino acid sequence of SEQ ID NO:66, HVR-H2 comprises the amino acid sequence of SEQ ID NO:67, and HVR-H3 comprises the amino acid sequence of SEQ ID NO:68;

(b) HVR-L1 comprises the amino acid sequence of SEQ ID NO:41, HVR-L2 comprises the amino acid sequence of SEQ ID NO:42, HVR-L3 comprises the amino acid sequence of SEQ ID NO:43, HVR-H1 comprises the amino acid sequence of SEQ ID NO:46, HVR-H2 comprises the amino acid sequence of SEQ ID NO:47, and HVR-H3 comprises the amino acid sequence of SEQ ID NO:48;

(c) HVR-L1 comprises the amino acid sequence of SEQ ID NO:51, HVR-L2 comprises the amino acid sequence of SEQ ID NO:52, HVR-L3 comprises the amino acid sequence of SEQ ID NO:53, HVR-H1 comprises the amino acid sequence of SEQ ID NO:56, HVR-H2 comprises the amino acid sequence of SEQ ID NO:57, and HVR-H3 comprises the amino acid sequence of SEQ ID NO:58;

(d) HVR-L1 comprises the amino acid sequence of SEQ ID NO:31, HVR-L2 comprises the amino acid sequence of SEQ ID NO:32, HVR-L3 comprises the amino acid sequence of SEQ ID NO:33, HVR-H1 comprises the amino acid sequence of SEQ ID NO:36, HVR-H2 comprises the amino acid sequence of SEQ ID NO:37, and HVR-H3 comprises the amino acid sequence of SEQ ID NO:38; or (e) HVR-L1 comprises the amino acid sequence of SEQ ID NO:85, HVR-L2 comprises the amino acid sequence of SEQ ID NO:86, HVR-L3 comprises the amino acid sequence of SEQ ID NO:87, HVR-H1 comprises the amino acid sequence of SEQ ID NO:90, HVR-H2 comprises the amino acid sequence of SEQ ID NO:91, and HVR-H3 comprises the amino acid sequence of SEQ ID NO:92.

2. The isolated antibody of claim 1 which is a chimeric or humanized antibody.

3. The isolated antibody of claim 1 which is an IgG1 antibody.

4. The isolated antibody of claim 1 which is produced in bacteria or CHO cells.

5. The isolated anti-MCAM antibody, or antigen binding fragment thereof of claim 1, said antibody or antigen binding fragment thereof comprising a light chain variable region and a heavy chain variable region, wherein:

(a) the light chain variable region comprises the amino acid sequence of SEQ ID NO:97, SEQ ID NO:98 or SEQ ID NO:99; and (b) the heavy chain variable region comprises the amino acid sequence of SEQ ID NO:93, SEQ ID NO:94 or SEQ ID NO:95.

6. The isolated anti-MCAM antibody, or antigen binding fragment thereof, of claim 5, wherein the light chain variable region comprises the amino acid sequence of SEQ ID NO:98 and the heavy chain variable region comprises the amino acid sequence of SEQ ID NO:94.

7. The isolated anti-MCAM antibody, or antigen binding fragment thereof, of claim 5, wherein the light chain variable region comprises the amino acid sequence of SEQ ID NO:98 and the heavy chain variable region comprises the amino acid sequence of SEQ ID NO:95.

8. The isolated anti-MCAM antibody, or antigen binding fragment thereof, of claim 5, wherein the light chain variable region comprises the amino acid sequence of SEQ ID NO:99 and the heavy chain variable region comprises the amino acid sequence of SEQ ID NO:94.

9. The isolated anti-MCAM antibody, or antigen binding fragment thereof, of claim 5, wherein the light chain variable region comprises the amino acid sequence of SEQ ID NO:99 and the heavy chain variable region comprises the amino acid sequence of SEQ ID NO:95.

10. The isolated antibody of claim 5 which is a chimeric or humanized antibody.

11. The isolated antibody of claim 5 which is an IgG1 antibody.

12. The isolated antibody of claim 5 which is produced in bacteria or CHO cells.

13. The isolated anti-MCAM antibody, or antigen binding fragment thereof, of claim 5, wherein the light chain variable region comprises the amino acid sequence of SEQ ID NO:97 and the heavy chain variable region comprises the amino acid sequence of SEQ ID NO:93.

14. The isolated anti-MCAM antibody, or antigen binding fragment thereof of claim 1, said antibody or antigen binding fragment thereof comprising a light chain variable region and a heavy chain variable region, wherein:

(a) the light chain variable region comprises the amino acid sequence of SEQ ID NO:109, SEQ ID NO:110, SEQ ID NO:111 or SEQ ID NO:112; and (b) the heavy chain variable region comprises the amino acid sequence of SEQ ID NO:101, SEQ ID NO:102, SEQ ID NO:103, SEQ ID NO:104, SEQ ID NO:105 or SEQ ID NO: 106.

15. The isolated anti-MCAM antibody, or antigen binding fragment thereof, of claim 14, wherein the light chain variable region comprises the amino acid sequence of SEQ ID NO:109 and the heavy chain variable region comprises the amino acid sequence of SEQ ID NO:101.

16. The isolated anti-MCAM antibody, or antigen binding fragment thereof, of claim 14, wherein the light chain variable region comprises the amino acid sequence of SEQ ID NO:111 and the heavy chain variable region comprises the amino acid sequence of SEQ ID NO:102.

17. The isolated anti-MCAM antibody, or antigen binding fragment thereof, of claim 14, wherein the light chain variable region comprises the amino acid sequence of SEQ ID NO:111 and the heavy chain variable region comprises the amino acid sequence of SEQ ID NO:103.

18. The isolated anti-MCAM antibody, or antigen binding fragment thereof, of claim 14, wherein the light chain variable region comprises the amino acid sequence of SEQ ID NO:111 and the heavy chain variable region comprises the amino acid sequence of SEQ ID NO:104.

19. The isolated anti-MCAM antibody, or antigen binding fragment thereof of claim 1, said antibody or antigen binding fragment thereof comprising a light chain variable region and a heavy chain variable region, wherein:

(a) the light chain variable region comprises the amino acid sequence of SEQ ID NO:30; and (b) the heavy chain variable region comprises the amino acid sequence of SEQ ID NO:35.

20. The isolated anti-MCAM antibody, or antigen binding fragment thereof of claim 1, said antibody or antigen binding fragment thereof comprising a light chain variable region and a heavy chain variable region, wherein:

(a) the light chain variable region comprises the amino acid sequence of SEQ ID NO:40; and (b) the heavy chain variable region comprises the amino acid sequence of SEQ ID NO:45.

21. The isolated anti-MCAM antibody, or antigen binding fragment thereof of claim 1, said antibody or antigen binding fragment thereof comprising a light chain variable region and a heavy chain variable region, wherein:

(a) the light chain variable region comprises the amino acid sequence of SEQ ID NO:50; and (b) the heavy chain variable region comprises the amino acid sequence of SEQ ID NO:55.

22. The isolated anti-MCAM antibody, or antigen binding fragment thereof of claim 1, said antibody or antigen binding fragment thereof comprising a light chain variable region and a heavy chain variable region, wherein the light chain variable region has at least 95% sequence identity to SEQ ID NO:111 with any variation from SEQ ID NO:111 occurring outside the hypervariable regions of the light chain variable region; and the heavy chain variable region has at least 95% sequence identity to SEQ ID NO:103 with any variation from SEQ ID NO:103 occurring outside the hypervariable regions of the heavy chain variable region.

23. The isolated anti-MCAM antibody, or antigen binding fragment thereof of claim 1, said antibody or antigen binding fragment thereof comprising a light chain variable region and a heavy chain variable region, wherein the light chain variable region has at least 95% sequence identity to SEQ ID NO: 95 with any variation from SEQ ID NO:95 occurring outside the hypervariable regions of the light chain variable region and the heavy chain variable region has at least 95% sequence identity to SEQ ID NO:98 with any variation occurring outside the hypervariable regions of the heavy chain variable region.

24. A pharmaceutical composition comprising an antibody, or antigen binding fragment thereof, according to any of claim 1, 5, 6, 7, 8, 9, 14, 16, 17, or 18.

25. An article of manufacture comprising the pharmaceutical composition of claim 24.

* * * * *

SEQUENCE LISTING

```
<160> NUMBER OF SEQ ID NOS: 155

<210> SEQ ID NO 1
<211> LENGTH: 428
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: CDS
<222> LOCATION: (1)...(426)

<400> SEQUENCE: 1

atg agg gtc cag att cag ttt ctg ggg ctc ctt ctg ctc tgg aca tca       48
Met Arg Val Gln Ile Gln Phe Leu Gly Leu Leu Leu Leu Trp Thr Ser
 1               5                  10                  15

gtt gtc cag tgt gat gtc cag atg acc cag tct cca tct tat ctt gct       96
Val Val Gln Cys Asp Val Gln Met Thr Gln Ser Pro Ser Tyr Leu Ala
            20                  25                  30

acg tct cct gga gag agt gtt tcc atc agt tgc aag gca agt aaa aac      144
Thr Ser Pro Gly Glu Ser Val Ser Ile Ser Cys Lys Ala Ser Lys Asn
        35                  40                  45

att gac aca tac tta gcc tgg tat cag gag aaa cct ggg aaa acg aat      192
Ile Asp Thr Tyr Leu Ala Trp Tyr Gln Glu Lys Pro Gly Lys Thr Asn
    50                  55                  60

aag ctt ctt atc tac tct ggg tca act ttg caa tct gga act cca tcg      240
Lys Leu Leu Ile Tyr Ser Gly Ser Thr Leu Gln Ser Gly Thr Pro Ser
 65                  70                  75                  80

aga ttc agt ggc agt gga tct ggt aca gat ttc acg ctc acc atc aga      288
Arg Phe Ser Gly Ser Gly Ser Gly Thr Asp Phe Thr Leu Thr Ile Arg
                85                  90                  95

aac ctg gag tct gaa gat ttt gca gtc tac tac tgt caa cag cat aat      336
Asn Leu Glu Ser Glu Asp Phe Ala Val Tyr Tyr Cys Gln Gln His Asn
            100                 105                 110

gaa tac ccg ctc acg ttc ggt tct ggg acc aag ctg gag atc aaa cgg      384
Glu Tyr Pro Leu Thr Phe Gly Ser Gly Thr Lys Leu Glu Ile Lys Arg
        115                 120                 125

gct gat gct gca cca act gta tcc atc ttc cca cca tcc tcg              426
Ala Asp Ala Ala Pro Thr Val Ser Ile Phe Pro Pro Ser Ser
    130                 135                 140

ga                                                                   428

<210> SEQ ID NO 2
<211> LENGTH: 142
<212> TYPE: PRT
```

<213> ORGANISM: Artificial Sequence
<220> FEATURE:
<223> OTHER INFORMATION: Synthetic Construct

<400> SEQUENCE: 2

```
Met Arg Val Gln Ile Gln Phe Leu Gly Leu Leu Leu Leu Trp Thr Ser
1               5                   10                  15

Val Val Gln Cys Asp Val Gln Met Thr Gln Ser Pro Ser Tyr Leu Ala
            20                  25                  30

Thr Ser Pro Gly Glu Ser Val Ser Ile Ser Cys Lys Ala Ser Lys Asn
        35                  40                  45

Ile Asp Thr Tyr Leu Ala Trp Tyr Gln Glu Lys Pro Gly Lys Thr Asn
    50                  55                  60

Lys Leu Leu Ile Tyr Ser Gly Ser Thr Leu Gln Ser Gly Thr Pro Ser
65                  70                  75                  80

Arg Phe Ser Gly Ser Gly Ser Gly Thr Asp Phe Thr Leu Thr Ile Arg
                85                  90                  95

Asn Leu Glu Ser Glu Asp Phe Ala Val Tyr Tyr Cys Gln Gln His Asn
            100                 105                 110

Glu Tyr Pro Leu Thr Phe Gly Ser Gly Thr Lys Leu Glu Ile Lys Arg
        115                 120                 125

Ala Asp Ala Ala Pro Thr Val Ser Ile Phe Pro Pro Ser Ser
    130                 135                 140
```

<210> SEQ ID NO 3
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 3

```
Lys Ala Ser Lys Asn Ile Asp Thr Tyr Leu Ala
1               5                   10
```

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 4

```
Ser Gly Ser Thr Leu
1               5
```

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

```
Gln Gln His Asn Glu Tyr Pro Leu Thr
1               5
```

<210> SEQ ID NO 6
<211> LENGTH: 483
<212> TYPE: DNA
<213> ORGANISM: Artificial Sequence
<220> FEATURE:
<223> OTHER INFORMATION: Synthetic Polynucleotide

```
<220> FEATURE:
<221> NAME/KEY: CDS
<222> LOCATION: (1)...(483)

<400> SEQUENCE: 6

atg gac acc agg ctc tgc ttg gtt ttc ctt gtc ctt ttc ata aaa ggt       48
Met Asp Thr Arg Leu Cys Leu Val Phe Leu Val Leu Phe Ile Lys Gly
 1               5                  10                  15

gtc cag tgt gag gtg cag ctg gtg gag tct ggt gga ggc tta gtg cag       96
Val Gln Cys Glu Val Gln Leu Val Glu Ser Gly Gly Gly Leu Val Gln
            20                  25                  30

cct gga agg tcc ctg aaa ctc tcc tgt gca gcc tca gga ttc act ttc      144
Pro Gly Arg Ser Leu Lys Leu Ser Cys Ala Ala Ser Gly Phe Thr Phe
        35                  40                  45

agt aac tat tac atg gcc tgg gtc cgc cag gct cca acg aag ggt ctg      192
Ser Asn Tyr Tyr Met Ala Trp Val Arg Gln Ala Pro Thr Lys Gly Leu
    50                  55                  60

gag tgg gtc gca tcc att agt ttt gag ggt aat aga aat cac tat gga      240
Glu Trp Val Ala Ser Ile Ser Phe Glu Gly Asn Arg Asn His Tyr Gly
 65                  70                  75                  80

gac tcc gtg aag ggc cga atc act atc tcc aga gat aat gca aaa agc      288
Asp Ser Val Lys Gly Arg Ile Thr Ile Ser Arg Asp Asn Ala Lys Ser
                85                  90                  95

acc cta tac ctg caa atg acc agt ctg agg cct gag gac acg gcc act      336
Thr Leu Tyr Leu Gln Met Thr Ser Leu Arg Pro Glu Asp Thr Ala Thr
            100                 105                 110

tat tat tgt gca aga cat cgg ggg tat agt acg aat ttt tat cac gac      384
Tyr Tyr Cys Ala Arg His Arg Gly Tyr Ser Thr Asn Phe Tyr His Asp
        115                 120                 125

gtt ttg gat gcc tgg ggt caa gga gct tta gtc act gtc tcc tca gct      432
Val Leu Asp Ala Trp Gly Gln Gly Ala Leu Val Thr Val Ser Ser Ala
    130                 135                 140

gaa aca aca gcc cca tct gtc tat cca ctg gct cct gga act gct ctc      480
Glu Thr Thr Ala Pro Ser Val Tyr Pro Leu Ala Pro Gly Thr Ala Leu
145                 150                 155                 160

aaa                                                                  483
Lys


<210> SEQ ID NO 7
<211> LENGTH: 161
<212> TYPE: PRT
<213> ORGANISM: Artificial Sequence
<220> FEATURE:
<223> OTHER INFORMATION: Synthetic Construct

<400> SEQUENCE: 7

Met Asp Thr Arg Leu Cys Leu Val Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45

Ser Asn Tyr Tyr Met Ala Trp Val Arg Gln Ala Pro Thr Lys Gly Leu
    50                  55                  60

Glu Trp Val Ala Ser Ile Ser Phe Glu Gly Asn Arg Asn His Tyr Gly
65                  70                  75                  80

Asp Ser Val Lys Gly Arg Ile Thr Ile Ser Arg Asp Asn Ala Lys Ser
                85                  90                  95

Thr Leu Tyr Leu Gln Met Thr Ser Leu Arg Pro Glu Asp Thr Ala Thr
            100                 105                 110
```

```
Tyr Tyr Cys Ala Arg His Arg Gly Tyr Ser Thr Asn Phe Tyr His Asp
        115                 120                 125

Val Leu Asp Ala Trp Gly Gln Gly Ala Leu Val Thr Val Ser Ser Ala
    130                 135                 140

Glu Thr Thr Ala Pro Ser Val Tyr Pro Leu Ala Pro Gly Thr Ala Leu
145                 150                 155                 160

Lys


<210> SEQ ID NO 8
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 8

Gly Phe Thr Phe Ser Asn Tyr Tyr Met Ala
1               5                   10


<210> SEQ ID NO 9
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 9

Ser Ile Ser Phe Glu Gly Asn Arg Asn His Tyr Gly Asp Ser Val Lys
1               5                   10                  15


<210> SEQ ID NO 10
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 10

His Arg Gly Tyr Ser Thr Asn Phe Tyr His Asp Val Leu Asp Ala Trp
1               5                   10                  15

Gly Gln Gly


<210> SEQ ID NO 11
<211> LENGTH: 646
<212> TYPE: PRT
<213> ORGANISM: Homo sapiens

<400> SEQUENCE: 11

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
        35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95
```

-continued

```
Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
        195                 200                 205

Lys Ala Gln Leu Val Lys Glu Asp Lys Asp Ala Gln Phe Tyr Cys Glu
    210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro Pro His Phe Ser Ile Ser Lys Gln Asn
        275                 280                 285

Pro Ser Thr Arg Glu Ala Glu Glu Glu Thr Thr Asn Asp Asn Gly Val
    290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
        355                 360                 365

Ser Ser Gln Asp Leu Glu Phe Gln Trp Leu Arg Glu Glu Thr Asp Gln
    370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
            420                 425                 430

Met Ala Phe Lys Glu Arg Lys Val Trp Val Lys Glu Asn Met Val Leu
        435                 440                 445

Asn Leu Ser Cys Glu Ala Ser Gly His Pro Arg Pro Thr Ile Ser Trp
    450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
```

```
        515                 520                 525

Thr Thr Gly Leu Ser Thr Ser Thr Ala Ser Pro His Thr Arg Ala Asn
    530                 535                 540

Ser Thr Ser Thr Glu Arg Lys Leu Pro Glu Pro Glu Ser Arg Gly Val
545                 550                 555                 560

Val Ile Val Ala Val Ile Val Cys Ile Leu Val Leu Ala Val Leu Gly
                565                 570                 575

Ala Val Leu Tyr Phe Leu Tyr Lys Lys Gly Lys Leu Pro Cys Arg Arg
            580                 585                 590

Ser Gly Lys Gln Glu Ile Thr Leu Pro Pro Ser Arg Lys Thr Glu Leu
        595                 600                 605

Val Val Glu Val Lys Ser Asp Lys Leu Pro Glu Glu Met Gly Leu Leu
    610                 615                 620

Gln Gly Ser Ser Gly Asp Lys Arg Ala Pro Gly Asp Gln Gly Glu Lys
625                 630                 635                 640

Tyr Ile Asp Leu Arg His
                645


<210> SEQ ID NO 12
<211> LENGTH: 474
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: CDS
<222> LOCATION: (1)...(474)

<400> SEQUENCE: 12

atg gaa tca cag acc cag gtc ctc atg tcc ctg ctg ctc tgg att tct       48
Met Glu Ser Gln Thr Gln Val Leu Met Ser Leu Leu Leu Trp Ile Ser
 1               5                  10                  15

ggt acc tgt ggg gac att gtg atg acc cag tct cca tcc tct ctg gct       96
Gly Thr Cys Gly Asp Ile Val Met Thr Gln Ser Pro Ser Ser Leu Ala
            20                  25                  30

gtg tca gct ggg gag acg gtc tct ata cac tgc aag tcc agt cag agt      144
Val Ser Ala Gly Glu Thr Val Ser Ile His Cys Lys Ser Ser Gln Ser
        35                  40                  45

ctt tta tac agt gga acc caa aag aac tac ttg gcc tgg ttc cag cag      192
Leu Leu Tyr Ser Gly Thr Gln Lys Asn Tyr Leu Ala Trp Phe Gln Gln
     50                  55                  60

aaa cca gga cag tct cct aaa ctg ctg atc ttc tgg gca tct act agg      240
Lys Pro Gly Gln Ser Pro Lys Leu Leu Ile Phe Trp Ala Ser Thr Arg
 65                  70                  75                  80

cag tct ggt gtc cct gat cgc ttc ata ggc cgt gga tct ggg aca gac      288
Gln Ser Gly Val Pro Asp Arg Phe Ile Gly Arg Gly Ser Gly Thr Asp
                 85                  90                  95

ttc act ctg acc atc agc ggt gtg cag gca gaa gat ctg gca att tat      336
Phe Thr Leu Thr Ile Ser Gly Val Gln Ala Glu Asp Leu Ala Ile Tyr
            100                 105                 110

tac tgt caa caa tat tat gat act ctc acg gac acg ttt gga gcg ggg      384
Tyr Cys Gln Gln Tyr Tyr Asp Thr Leu Thr Asp Thr Phe Gly Ala Gly
        115                 120                 125

acc aag ctg gaa ctg aaa cgg gct gat gct gca cca act gta tct atc      432
Thr Lys Leu Glu Leu Lys Arg Ala Asp Ala Ala Pro Thr Val Ser Ile
    130                 135                 140

ttc cca cca tcc acg gaa cag tta gca act gga ggt gcc tca              474
Phe Pro Pro Ser Thr Glu Gln Leu Ala Thr Gly Gly Ala Ser
145                 150                 155
```

<210> SEQ ID NO 13
<211> LENGTH: 158
<212> TYPE: PRT
<213> ORGANISM: Artificial Sequence
<220> FEATURE:
<223> OTHER INFORMATION: Synthetic Construct

<400> SEQUENCE: 13

```
Met Glu Ser Gln Thr Gln Val Leu Met Ser Leu Leu Leu Trp Ile Ser
1               5                   10                  15

Gly Thr Cys Gly Asp Ile Val Met Thr Gln Ser Pro Ser Ser Leu Ala
            20                  25                  30

Val Ser Ala Gly Glu Thr Val Ser Ile His Cys Lys Ser Ser Gln Ser
        35                  40                  45

Leu Leu Tyr Ser Gly Thr Gln Lys Asn Tyr Leu Ala Trp Phe Gln Gln
    50                  55                  60

Lys Pro Gly Gln Ser Pro Lys Leu Leu Ile Phe Trp Ala Ser Thr Arg
65                  70                  75                  80

Gln Ser Gly Val Pro Asp Arg Phe Ile Gly Arg Gly Ser Gly Thr Asp
                85                  90                  95

Phe Thr Leu Thr Ile Ser Gly Val Gln Ala Glu Asp Leu Ala Ile Tyr
            100                 105                 110

Tyr Cys Gln Gln Tyr Tyr Asp Thr Leu Thr Asp Thr Phe Gly Ala Gly
        115                 120                 125

Thr Lys Leu Glu Leu Lys Arg Ala Asp Ala Ala Pro Thr Val Ser Ile
    130                 135                 140

Phe Pro Pro Ser Thr Glu Gln Leu Ala Thr Gly Gly Ala Ser
145                 150                 155
```

<210> SEQ ID NO 14
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 14

```
Lys Ser Ser Gln Ser Leu Leu Tyr Ser Gly Thr Gln Lys Asn Tyr Leu
1               5                   10                  15

Ala
```

<210> SEQ ID NO 15
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 15

```
Trp Ala Ser Thr Arg Gln Ser
1               5
```

<210> SEQ ID NO 16
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 16

```
Gln Gln Tyr Tyr Asp Thr Leu Thr Asp Thr
```

```
1               5                   10


<210> SEQ ID NO 17
<211> LENGTH: 469
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: CDS
<222> LOCATION: (1)...(468)

<400> SEQUENCE: 17

atg gac atc agg ctc agc ttg gct ttc ctg gtc ctt ttc ata aaa ggt       48
Met Asp Ile Arg Leu Ser Leu Ala Phe Leu Val Leu Phe Ile Lys Gly
 1               5                  10                  15

gtc cag tgt gag gtg cgg ctg gtg gag tct ggg gga ggc tta gtg cag       96
Val Gln Cys Glu Val Arg Leu Val Glu Ser Gly Gly Gly Leu Val Gln
            20                  25                  30

cct gga aag tcc atg aaa ctc tcc tgt gta gcc tcg gga ttc aaa ttc      144
Pro Gly Lys Ser Met Lys Leu Ser Cys Val Ala Ser Gly Phe Lys Phe
        35                  40                  45

agt aac tat tac atg tcc tgg gtc cgc cag gct cca gcg aag ggt ctg      192
Ser Asn Tyr Tyr Met Ser Trp Val Arg Gln Ala Pro Ala Lys Gly Leu
     50                  55                  60

gag tgg gtc gca tcc att agt gat ggt ggt ggt gac act ttc tgt cga      240
Glu Trp Val Ala Ser Ile Ser Asp Gly Gly Gly Asp Thr Phe Cys Arg
 65                  70                  75                  80

gac ttg gtg aag ggc cga ttc act atc tcc aga gat aat gca aaa agt      288
Asp Leu Val Lys Gly Arg Phe Thr Ile Ser Arg Asp Asn Ala Lys Ser
                 85                  90                  95

acc ctt tac ctg caa atg gac agt ctg agg cct gag gac acg gcc act      336
Thr Leu Tyr Leu Gln Met Asp Ser Leu Arg Pro Glu Asp Thr Ala Thr
            100                 105                 110

tat tac tgt gca aga cgg gga gca gct atg ggg ggt gtt atg gat gcc      384
Tyr Tyr Cys Ala Arg Arg Gly Ala Ala Met Gly Gly Val Met Asp Ala
        115                 120                 125

tgg ggt caa gga act tca gtc act gtc tcc tca gct gaa aca aca gcc      432
Trp Gly Gln Gly Thr Ser Val Thr Val Ser Ser Ala Glu Thr Thr Ala
    130                 135                 140

cca tct gtc tat cca ctg gct cct gga act gct ctc a                    469
Pro Ser Val Tyr Pro Leu Ala Pro Gly Thr Ala Leu
145                 150                 155


<210> SEQ ID NO 18
<211> LENGTH: 156
<212> TYPE: PRT
<213> ORGANISM: Artificial Sequence
<220> FEATURE:
<223> OTHER INFORMATION: Synthetic Construct

<400> SEQUENCE: 18

Met Asp Ile Arg Leu Ser Leu Ala Phe Leu Val Leu Phe Ile Lys Gly
1               5                   10                  15

Val Gln Cys Glu Val Arg Leu Val Glu Ser Gly Gly Gly Leu Val Gln
            20                  25                  30

Pro Gly Lys Ser Met Lys Leu Ser Cys Val Ala Ser Gly Phe Lys Phe
        35                  40                  45

Ser Asn Tyr Tyr Met Ser Trp Val Arg Gln Ala Pro Ala Lys Gly Leu
    50                  55                  60

Glu Trp Val Ala Ser Ile Ser Asp Gly Gly Gly Asp Thr Phe Cys Arg
65                  70                  75                  80
```

```
Asp Leu Val Lys Gly Arg Phe Thr Ile Ser Arg Asp Asn Ala Lys Ser
                85                  90                  95

Thr Leu Tyr Leu Gln Met Asp Ser Leu Arg Pro Glu Asp Thr Ala Thr
            100                 105                 110

Tyr Tyr Cys Ala Arg Arg Gly Ala Ala Met Gly Gly Val Met Asp Ala
        115                 120                 125

Trp Gly Gln Gly Thr Ser Val Thr Val Ser Ser Ala Glu Thr Thr Ala
    130                 135                 140

Pro Ser Val Tyr Pro Leu Ala Pro Gly Thr Ala Leu
145                 150                 155


<210> SEQ ID NO 19
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 19

Gly Phe Lys Phe Ser Asn Tyr Tyr Met Ser
1               5                   10


<210> SEQ ID NO 20
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 20

Ser Ile Ser Asp Gly Gly Gly Asp Thr Phe Cys Arg Asp Leu Val Lys
1               5                   10                  15

Gly


<210> SEQ ID NO 21
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 21

Arg Gly Ala Ala Met Gly Gly Val Met Asp Ala Trp Gly Gln Gly
1               5                   10                  15


<210> SEQ ID NO 22
<211> LENGTH: 111
<212> TYPE: PRT
<213> ORGANISM: Homo sapiens

<400> SEQUENCE: 22

Pro Arg Val Ala Gly Val Pro Gly Glu Ala Glu Gln Pro Ala Pro Glu
1               5                   10                  15

Leu Val Glu Val Glu Val Gly Ser Thr Ala Leu Leu Lys Cys Gly Leu
            20                  25                  30

Ser Gln Ser Gln Gly Asn Leu Ser His Val Asp Trp Phe Ser Val His
        35                  40                  45

Lys Glu Lys Arg Thr Leu Ile Phe Arg Val Arg Gln Gly Gln Gly Gln
    50                  55                  60

Ser Glu Pro Gly Glu Tyr Glu Gln Arg Leu Ser Leu Gln Asp Arg Gly
65                  70                  75                  80
```

```
Ala Thr Leu Ala Leu Thr Gln Val Thr Pro Gln Asp Glu Arg Ile Phe
                85                  90                  95

Leu Cys Gln Gly Lys Arg Pro Arg Ser Gln Glu Tyr Arg Ile Gln
            100                 105                 110


<210> SEQ ID NO 23
<211> LENGTH: 104
<212> TYPE: PRT
<213> ORGANISM: Homo sapiens

<400> SEQUENCE: 23

Pro Asn Ile Gln Val Asn Pro Leu Gly Ile Pro Val Asn Ser Lys Glu
1               5                   10                  15

Pro Glu Glu Val Ala Thr Cys Val Gly Arg Asn Gly Tyr Pro Ile Pro
            20                  25                  30

Gln Val Ile Trp Tyr Lys Asn Gly Arg Pro Leu Lys Glu Glu Lys Asn
        35                  40                  45

Arg Val His Ile Gln Ser Ser Gln Thr Val Glu Ser Ser Gly Leu Tyr
    50                  55                  60

Thr Leu Gln Ser Ile Leu Lys Ala Gln Leu Val Lys Glu Asp Lys Asp
65                  70                  75                  80

Ala Gln Phe Tyr Cys Glu Leu Asn Tyr Arg Leu Pro Ser Gly Asn His
                85                  90                  95

Met Lys Glu Ser Arg Glu Val Thr
            100


<210> SEQ ID NO 24
<211> LENGTH: 78
<212> TYPE: PRT
<213> ORGANISM: Homo sapiens

<400> SEQUENCE: 24

Pro Val Phe Tyr Pro Thr Glu Lys Val Trp Leu Glu Val Glu Pro Val
1               5                   10                  15

Gly Met Leu Lys Glu Gly Asp Arg Val Glu Ile Arg Cys Leu Ala Asp
            20                  25                  30

Gly Asn Pro Pro Pro His Phe Ser Ile Ser Lys Gln Asn Pro Ser Thr
        35                  40                  45

Arg Glu Ala Glu Glu Glu Thr Thr Asn Asp Asn Gly Val Leu Val Leu
    50                  55                  60

Glu Pro Ala Arg Lys Glu His Ser Gly Arg Tyr Glu Cys Gln
65                  70                  75


<210> SEQ ID NO 25
<211> LENGTH: 90
<212> TYPE: PRT
<213> ORGANISM: Homo sapiens

<400> SEQUENCE: 25

Pro Gln Glu Leu Leu Val Asn Tyr Val Ser Asp Val Arg Val Ser Pro
1               5                   10                  15

Ala Ala Pro Glu Arg Gln Glu Gly Ser Ser Leu Thr Leu Thr Cys Glu
            20                  25                  30

Ala Glu Ser Ser Gln Asp Leu Glu Phe Gln Trp Leu Arg Glu Glu Thr
        35                  40                  45

Asp Gln Val Leu Glu Arg Gly Pro Val Leu Gln Leu His Asp Leu Lys
    50                  55                  60
```

Arg Glu Ala Gly Gly Gly Tyr Arg Cys Val Ala Ser Val Pro Ser Ile
65 70 75 80

Pro Gly Leu Asn Arg Thr Gln Leu Val Lys
85 90

<210> SEQ ID NO 26
<211> LENGTH: 81
<212> TYPE: PRT
<213> ORGANISM: Homo sapiens

<400> SEQUENCE: 26

Pro Pro Trp Met Ala Phe Lys Glu Arg Lys Val Trp Val Lys Glu Asn
1 5 10 15

Met Val Leu Asn Leu Ser Cys Glu Ala Ser Gly His Pro Arg Pro Thr
20 25 30

Ile Ser Trp Asn Val Asn Gly Thr Ala Ser Glu Gln Asp Gln Asp Pro
35 40 45

Gln Arg Val Leu Ser Thr Leu Asn Val Leu Val Thr Pro Glu Leu Leu
50 55 60

Glu Thr Gly Val Glu Cys Thr Ala Ser Asn Asp Leu Gly Lys Asn Thr
65 70 75 80

Ser

<210> SEQ ID NO 27
<211> LENGTH: 1823
<212> TYPE: PRT
<213> ORGANISM: Homo sapiens

<400> SEQUENCE: 27

Met Ala Leu Ser Ser Ala Trp Arg Ser Val Leu Pro Leu Trp Leu Leu
1 5 10 15

Trp Ser Ala Ala Cys Ser Arg Ala Ala Ser Gly Asp Asp Asn Ala Phe
20 25 30

Pro Phe Asp Ile Glu Gly Ser Ser Ala Val Gly Arg Gln Asp Pro Pro
35 40 45

Glu Thr Ser Glu Pro Arg Val Ala Leu Gly Arg Leu Pro Pro Ala Ala
50 55 60

Glu Lys Cys Asn Ala Gly Phe Phe His Thr Leu Ser Gly Glu Cys Val
65 70 75 80

Pro Cys Asp Cys Asn Gly Asn Ser Asn Glu Cys Leu Asp Gly Ser Gly
85 90 95

Tyr Cys Val His Cys Gln Arg Asn Thr Thr Gly Glu His Cys Glu Lys
100 105 110

Cys Leu Asp Gly Tyr Ile Gly Asp Ser Ile Arg Gly Ala Pro Gln Phe
115 120 125

Cys Gln Pro Cys Pro Cys Pro Leu Pro His Leu Ala Asn Phe Ala Glu
130 135 140

Ser Cys Tyr Arg Lys Asn Gly Ala Val Arg Cys Ile Cys Asn Glu Asn
145 150 155 160

Tyr Ala Gly Pro Asn Cys Glu Arg Cys Ala Pro Gly Tyr Tyr Gly Asn
165 170 175

Pro Leu Leu Ile Gly Ser Thr Cys Lys Lys Cys Asp Cys Ser Gly Asn
180 185 190

Ser Asp Pro Asn Leu Ile Phe Glu Asp Cys Asp Glu Val Thr Gly Gln
195 200 205

Cys Arg Asn Cys Leu Arg Asn Thr Thr Gly Phe Lys Cys Glu Arg Cys

```
    210                 215                 220

Ala Pro Gly Tyr Tyr Gly Asp Ala Arg Ile Ala Lys Asn Cys Ala Val
225                 230                 235                 240

Cys Asn Cys Gly Gly Gly Pro Cys Asp Ser Val Thr Gly Glu Cys Leu
                245                 250                 255

Glu Glu Gly Phe Glu Pro Pro Thr Gly Met Asp Cys Pro Thr Ile Ser
            260                 265                 270

Cys Asp Lys Cys Val Trp Asp Leu Thr Asp Asp Leu Arg Leu Ala Ala
        275                 280                 285

Leu Ser Ile Glu Glu Gly Lys Ser Gly Val Leu Ser Val Ser Ser Gly
    290                 295                 300

Ala Ala Ala His Arg His Val Asn Glu Ile Asn Ala Thr Ile Tyr Leu
305                 310                 315                 320

Leu Lys Thr Lys Leu Ser Glu Arg Glu Asn Gln Tyr Ala Leu Arg Lys
                325                 330                 335

Ile Gln Ile Asn Asn Ala Glu Asn Thr Met Lys Ser Leu Leu Ser Asp
            340                 345                 350

Val Glu Glu Leu Val Glu Lys Glu Asn Gln Ala Ser Arg Lys Gly Gln
        355                 360                 365

Leu Val Gln Lys Glu Ser Met Asp Thr Ile Asn His Ala Ser Gln Leu
    370                 375                 380

Val Glu Gln Ala His Asp Met Arg Asp Lys Ile Gln Glu Ile Asn Asn
385                 390                 395                 400

Lys Met Leu Tyr Tyr Gly Glu Glu His Glu Leu Ser Pro Lys Glu Ile
                405                 410                 415

Ser Glu Lys Leu Val Leu Ala Gln Lys Met Leu Glu Glu Ile Arg Ser
            420                 425                 430

Arg Gln Pro Phe Phe Thr Gln Arg Glu Leu Val Asp Glu Glu Ala Asp
        435                 440                 445

Glu Ala Tyr Glu Leu Leu Ser Gln Ala Glu Ser Trp Gln Arg Leu His
    450                 455                 460

Asn Glu Thr Arg Thr Leu Phe Pro Val Val Leu Glu Gln Leu Asp Asp
465                 470                 475                 480

Tyr Asn Ala Lys Leu Ser Asp Leu Gln Glu Ala Leu Asp Gln Ala Leu
                485                 490                 495

Asn Tyr Val Arg Asp Ala Glu Asp Met Asn Arg Ala Thr Ala Ala Arg
            500                 505                 510

Gln Arg Asp His Glu Lys Gln Gln Glu Arg Val Arg Glu Gln Met Glu
        515                 520                 525

Val Val Asn Met Ser Leu Ser Thr Ser Ala Asp Ser Leu Thr Thr Pro
    530                 535                 540

Arg Leu Thr Leu Ser Glu Leu Asp Asp Ile Ile Lys Asn Ala Ser Gly
545                 550                 555                 560

Ile Tyr Ala Glu Ile Asp Gly Ala Lys Ser Glu Leu Gln Val Lys Leu
                565                 570                 575

Ser Asn Leu Ser Asn Leu Ser His Asp Leu Val Gln Glu Ala Ile Asp
            580                 585                 590

His Ala Gln Asp Leu Gln Gln Glu Ala Asn Glu Leu Ser Arg Lys Leu
        595                 600                 605

His Ser Ser Asp Met Asn Gly Leu Val Gln Lys Ala Leu Asp Ala Ser
    610                 615                 620

Asn Val Tyr Glu Asn Ile Val Asn Tyr Val Ser Glu Ala Asn Glu Thr
625                 630                 635                 640
```

```
Ala Glu Phe Ala Leu Asn Thr Thr Asp Arg Ile Tyr Asp Ala Val Ser
                645                 650                 655

Gly Ile Asp Thr Gln Ile Ile Tyr His Lys Asp Glu Ser Glu Asn Leu
            660                 665                 670

Leu Asn Gln Ala Arg Glu Leu Gln Ala Lys Ala Glu Ser Ser Ser Asp
        675                 680                 685

Glu Ala Val Ala Asp Thr Ser Arg Arg Val Gly Gly Ala Leu Ala Arg
    690                 695                 700

Lys Ser Ala Leu Lys Thr Arg Leu Ser Asp Ala Val Lys Gln Leu Gln
705                 710                 715                 720

Ala Ala Glu Arg Gly Asp Ala Gln Gln Arg Leu Gly Gln Ser Arg Leu
                725                 730                 735

Ile Thr Glu Glu Ala Asn Arg Thr Thr Met Glu Val Gln Gln Ala Thr
            740                 745                 750

Ala Pro Met Ala Asn Asn Leu Thr Asn Trp Ser Gln Asn Leu Gln His
        755                 760                 765

Phe Asp Ser Ser Ala Tyr Asn Thr Ala Val Asn Ser Ala Arg Asp Ala
    770                 775                 780

Val Arg Asn Leu Thr Glu Val Val Pro Gln Leu Leu Asp Gln Leu Arg
785                 790                 795                 800

Thr Val Glu Gln Lys Arg Pro Ala Ser Asn Val Ser Ala Ser Ile Gln
                805                 810                 815

Arg Ile Arg Glu Leu Ile Ala Gln Thr Arg Ser Val Ala Ser Lys Ile
            820                 825                 830

Gln Val Ser Met Met Phe Asp Gly Gln Ser Ala Val Glu Val His Ser
        835                 840                 845

Arg Thr Ser Met Asp Asp Leu Lys Ala Phe Thr Ser Leu Ser Leu Tyr
    850                 855                 860

Met Lys Pro Pro Val Lys Arg Pro Glu Leu Thr Glu Thr Ala Asp Gln
865                 870                 875                 880

Phe Ile Leu Tyr Leu Gly Ser Lys Asn Ala Lys Lys Glu Tyr Met Gly
                885                 890                 895

Leu Ala Ile Lys Asn Asp Asn Leu Val Tyr Val Tyr Asn Leu Gly Thr
            900                 905                 910

Lys Asp Val Glu Ile Pro Leu Asp Ser Lys Pro Val Ser Ser Trp Pro
        915                 920                 925

Ala Tyr Phe Ser Ile Val Lys Ile Glu Arg Val Gly Lys His Gly Lys
    930                 935                 940

Val Phe Leu Thr Val Pro Ser Leu Ser Ser Thr Ala Glu Glu Lys Phe
945                 950                 955                 960

Ile Lys Lys Gly Glu Phe Ser Gly Asp Asp Ser Leu Leu Asp Leu Asp
                965                 970                 975

Pro Glu Asp Thr Val Phe Tyr Val Gly Gly Val Pro Ser Asn Phe Lys
            980                 985                 990

Leu Pro Thr Ser Leu Asn Leu Pro Gly Phe Val Gly Cys Leu Glu Leu
        995                 1000                1005

Ala Thr Leu Asn Asn Asp Val Ile Ser Leu Tyr Asn Phe Lys His Ile
    1010                1015                1020

Tyr Asn Met Asp Pro Ser Thr Ser Val Pro Cys Ala Arg Asp Lys Leu
1025                1030                1035                1040

Ala Phe Thr Gln Ser Arg Ala Ala Ser Tyr Phe Phe Asp Gly Ser Gly
                1045                1050                1055
```

-continued

```
Tyr Ala Val Val Arg Asp Ile Thr Arg Arg Gly Lys Phe Gly Gln Val
            1060                1065                1070

Thr Arg Phe Asp Ile Glu Val Arg Thr Pro Ala Asp Asn Gly Leu Ile
        1075                1080                1085

Leu Leu Met Val Asn Gly Ser Met Phe Phe Arg Leu Glu Met Arg Asn
    1090                1095                1100

Gly Tyr Leu His Val Phe Tyr Asp Phe Gly Phe Ser Gly Gly Pro Val
1105                1110                1115                1120

His Leu Glu Asp Thr Leu Lys Lys Ala Gln Ile Asn Asp Ala Lys Tyr
                1125                1130                1135

His Glu Ile Ser Ile Ile Tyr His Asn Asp Lys Lys Met Ile Leu Val
            1140                1145                1150

Val Asp Arg Arg His Val Lys Ser Met Asp Asn Glu Lys Met Lys Ile
        1155                1160                1165

Pro Phe Thr Asp Ile Tyr Ile Gly Gly Ala Pro Pro Glu Ile Leu Gln
    1170                1175                1180

Ser Arg Ala Leu Arg Ala His Leu Pro Leu Asp Ile Asn Phe Arg Gly
1185                1190                1195                1200

Cys Met Lys Gly Phe Gln Phe Gln Lys Lys Asp Phe Asn Leu Leu Glu
                1205                1210                1215

Gln Thr Glu Thr Leu Gly Val Gly Tyr Gly Cys Pro Glu Asp Ser Leu
            1220                1225                1230

Ile Ser Arg Arg Ala Tyr Phe Asn Gly Gln Ser Phe Ile Ala Ser Ile
        1235                1240                1245

Gln Lys Ile Ser Phe Phe Asp Gly Phe Glu Gly Gly Phe Asn Phe Arg
    1250                1255                1260

Thr Leu Gln Pro Asn Gly Leu Leu Phe Tyr Tyr Ala Ser Gly Ser Asp
1265                1270                1275                1280

Val Phe Ser Ile Ser Leu Asp Asn Gly Thr Val Ile Met Asp Val Lys
                1285                1290                1295

Gly Ile Lys Val Gln Ser Val Asp Lys Gln Tyr Asn Asp Gly Leu Ser
            1300                1305                1310

His Phe Val Ile Ser Ser Val Ser Pro Thr Arg Tyr Glu Leu Ile Val
        1315                1320                1325

Asp Lys Ser Arg Val Gly Ser Lys Asn Pro Thr Lys Gly Lys Ile Glu
    1330                1335                1340

Gln Thr Gln Ala Ser Glu Lys Lys Phe Tyr Phe Gly Gly Ser Pro Ile
1345                1350                1355                1360

Ser Ala Gln Tyr Ala Asn Phe Thr Gly Cys Ile Ser Asn Ala Tyr Phe
                1365                1370                1375

Thr Arg Val Asp Arg Asp Val Glu Val Glu Asp Phe Gln Arg Tyr Thr
            1380                1385                1390

Glu Lys Val His Thr Ser Leu Tyr Glu Cys Pro Ile Glu Ser Ser Pro
        1395                1400                1405

Leu Phe Leu Leu His Lys Lys Gly Lys Asn Leu Ser Lys Pro Lys Ala
    1410                1415                1420

Ser Gln Asn Lys Lys Gly Gly Lys Ser Lys Asp Ala Pro Ser Trp Asp
1425                1430                1435                1440

Pro Val Ala Leu Lys Leu Pro Glu Arg Asn Thr Pro Arg Asn Ser His
                1445                1450                1455

Cys His Leu Ser Asn Ser Pro Arg Ala Ile Glu His Ala Tyr Gln Tyr
            1460                1465                1470

Gly Gly Thr Ala Asn Ser Arg Gln Glu Phe Glu His Leu Lys Gly Asp
```

```
        1475                1480                1485

Phe Gly Ala Lys Ser Gln Phe Ser Ile Arg Leu Arg Thr Arg Ser Ser
    1490                1495                1500

His Gly Met Ile Phe Tyr Val Ser Asp Gln Glu Glu Asn Asp Phe Met
1505                1510                1515                1520

Thr Leu Phe Leu Ala His Gly Arg Leu Val Tyr Met Phe Asn Val Gly
                1525                1530                1535

His Lys Lys Leu Lys Ile Arg Ser Gln Glu Lys Tyr Asn Asp Gly Leu
            1540                1545                1550

Trp His Asp Val Ile Phe Ile Arg Glu Arg Ser Ser Gly Arg Leu Val
        1555                1560                1565

Ile Asp Gly Leu Arg Val Leu Glu Glu Ser Leu Pro Pro Thr Glu Ala
    1570                1575                1580

Thr Trp Lys Ile Lys Gly Pro Ile Tyr Leu Gly Gly Val Ala Pro Gly
1585                1590                1595                1600

Lys Ala Val Lys Asn Val Gln Ile Asn Ser Ile Tyr Ser Phe Ser Gly
                1605                1610                1615

Cys Leu Ser Asn Leu Gln Leu Asn Gly Ala Ser Ile Thr Ser Ala Ser
            1620                1625                1630

Gln Thr Phe Ser Val Thr Pro Cys Phe Glu Gly Pro Met Glu Thr Gly
        1635                1640                1645

Thr Tyr Phe Ser Thr Glu Gly Gly Tyr Val Val Leu Asp Glu Ser Phe
    1650                1655                1660

Asn Ile Gly Leu Lys Phe Glu Ile Ala Phe Glu Val Arg Pro Arg Ser
1665                1670                1675                1680

Ser Ser Gly Thr Leu Val His Gly His Ser Val Asn Gly Glu Tyr Leu
                1685                1690                1695

Asn Val His Met Lys Asn Gly Gln Val Ile Val Lys Val Asn Asn Gly
            1700                1705                1710

Ile Arg Asp Phe Ser Thr Ser Val Thr Pro Lys Gln Ser Leu Cys Asp
        1715                1720                1725

Gly Arg Trp His Arg Ile Thr Val Ile Arg Asp Ser Asn Val Val Gln
    1730                1735                1740

Leu Asp Val Asp Ser Glu Val Asn His Val Val Gly Pro Leu Asn Pro
1745                1750                1755                1760

Lys Pro Ile Asp His Arg Glu Pro Val Phe Val Gly Gly Val Pro Glu
                1765                1770                1775

Ser Leu Leu Thr Pro Arg Leu Ala Pro Ser Lys Pro Phe Thr Gly Cys
            1780                1785                1790

Ile Arg His Phe Val Ile Asp Gly His Pro Val Ser Phe Ser Lys Ala
        1795                1800                1805

Ala Leu Val Ser Gly Ala Val Ser Ile Asn Ser Cys Pro Ala Ala
    1810                1815                1820


<210> SEQ ID NO 28
<211> LENGTH: 1816
<212> TYPE: PRT
<213> ORGANISM: Homo sapiens

<400> SEQUENCE: 28

Met Ala Leu Ser Ser Ala Trp Arg Ser Val Leu Pro Leu Trp Leu Leu
1               5                   10                  15

Trp Ser Ala Ala Cys Ser Arg Ala Ala Ser Gly Asp Asp Asn Ala Phe
            20                  25                  30
```

```
Pro Phe Asp Ile Glu Gly Ser Ser Ala Val Gly Arg Gln Asp Pro Pro
        35                  40                  45

Glu Thr Ser Glu Pro Arg Val Ala Leu Gly Arg Leu Pro Pro Ala Ala
    50                  55                  60

Glu Lys Cys Asn Ala Gly Phe Phe His Thr Leu Ser Gly Glu Cys Val
65                  70                  75                  80

Pro Cys Asp Cys Asn Gly Asn Ser Asn Glu Cys Leu Asp Gly Ser Gly
                85                  90                  95

Tyr Cys Val His Cys Gln Arg Asn Thr Thr Gly Glu His Cys Glu Lys
            100                 105                 110

Cys Leu Asp Gly Tyr Ile Gly Asp Ser Ile Arg Gly Ala Pro Gln Phe
        115                 120                 125

Cys Gln Pro Cys Pro Cys Pro Leu Pro His Leu Ala Asn Phe Ala Glu
    130                 135                 140

Ser Cys Tyr Arg Lys Asn Gly Ala Val Arg Cys Ile Cys Asn Glu Asn
145                 150                 155                 160

Tyr Ala Gly Pro Asn Cys Glu Arg Cys Ala Pro Gly Tyr Tyr Gly Asn
                165                 170                 175

Pro Leu Leu Ile Gly Ser Thr Cys Lys Lys Cys Asp Cys Ser Gly Asn
            180                 185                 190

Ser Asp Pro Asn Leu Ile Phe Glu Asp Cys Asp Glu Val Thr Gly Gln
        195                 200                 205

Cys Arg Asn Cys Leu Arg Asn Thr Thr Gly Phe Lys Cys Glu Arg Cys
    210                 215                 220

Ala Pro Gly Tyr Tyr Gly Asp Ala Arg Ile Ala Lys Asn Cys Ala Val
225                 230                 235                 240

Cys Asn Cys Gly Gly Gly Pro Cys Asp Ser Val Thr Gly Glu Cys Leu
                245                 250                 255

Glu Glu Gly Phe Glu Pro Pro Thr Gly Cys Asp Lys Cys Val Trp Asp
            260                 265                 270

Leu Thr Asp Asp Leu Arg Leu Ala Ala Leu Ser Ile Glu Glu Gly Lys
        275                 280                 285

Ser Gly Val Leu Ser Val Ser Ser Gly Ala Ala Ala His Arg His Val
    290                 295                 300

Asn Glu Ile Asn Ala Thr Ile Tyr Leu Leu Lys Thr Lys Leu Ser Glu
305                 310                 315                 320

Arg Glu Asn Gln Tyr Ala Leu Arg Lys Ile Gln Ile Asn Asn Ala Glu
                325                 330                 335

Asn Thr Met Lys Ser Leu Leu Ser Asp Val Glu Glu Leu Val Glu Lys
            340                 345                 350

Glu Asn Gln Ala Ser Arg Lys Gly Gln Leu Val Gln Lys Glu Ser Met
        355                 360                 365

Asp Thr Ile Asn His Ala Ser Gln Leu Val Glu Gln Ala His Asp Met
    370                 375                 380

Arg Asp Lys Ile Gln Glu Ile Asn Asn Lys Met Leu Tyr Tyr Gly Glu
385                 390                 395                 400

Glu His Glu Leu Ser Pro Lys Glu Ile Ser Glu Lys Leu Val Leu Ala
                405                 410                 415

Gln Lys Met Leu Glu Glu Ile Arg Ser Arg Gln Pro Phe Phe Thr Gln
            420                 425                 430

Arg Glu Leu Val Asp Glu Glu Ala Asp Glu Ala Tyr Glu Leu Leu Ser
        435                 440                 445

Gln Ala Glu Ser Trp Gln Arg Leu His Asn Glu Thr Arg Thr Leu Phe
```

```
    450                 455                 460

Pro Val Val Leu Glu Gln Leu Asp Asp Tyr Asn Ala Lys Leu Ser Asp
465                 470                 475                 480

Leu Gln Glu Ala Leu Asp Gln Ala Leu Asn Tyr Val Arg Asp Ala Glu
                485                 490                 495

Asp Met Asn Arg Ala Thr Ala Ala Arg Gln Arg Asp His Glu Lys Gln
            500                 505                 510

Gln Glu Arg Val Arg Glu Gln Met Glu Val Val Asn Met Ser Leu Ser
        515                 520                 525

Thr Ser Ala Asp Ser Leu Thr Thr Pro Arg Leu Thr Leu Ser Glu Leu
    530                 535                 540

Asp Asp Ile Ile Lys Asn Ala Ser Gly Ile Tyr Ala Glu Ile Asp Gly
545                 550                 555                 560

Ala Lys Ser Glu Leu Gln Val Lys Leu Ser Asn Leu Ser Asn Leu Ser
                565                 570                 575

His Asp Leu Val Gln Glu Ala Ile Asp His Ala Gln Asp Leu Gln Gln
            580                 585                 590

Glu Ala Asn Glu Leu Ser Arg Lys Leu His Ser Ser Asp Met Asn Gly
        595                 600                 605

Leu Val Gln Lys Ala Leu Asp Ala Ser Asn Val Tyr Glu Asn Ile Val
    610                 615                 620

Asn Tyr Val Ser Glu Ala Asn Glu Thr Ala Glu Phe Ala Leu Asn Thr
625                 630                 635                 640

Thr Asp Arg Ile Tyr Asp Ala Val Ser Gly Ile Asp Thr Gln Ile Ile
                645                 650                 655

Tyr His Lys Asp Glu Ser Glu Asn Leu Leu Asn Gln Ala Arg Glu Leu
            660                 665                 670

Gln Ala Lys Ala Glu Ser Ser Ser Asp Glu Ala Val Ala Asp Thr Ser
        675                 680                 685

Arg Arg Val Gly Gly Ala Leu Ala Arg Lys Ser Ala Leu Lys Thr Arg
    690                 695                 700

Leu Ser Asp Ala Val Lys Gln Leu Gln Ala Ala Glu Arg Gly Asp Ala
705                 710                 715                 720

Gln Gln Arg Leu Gly Gln Ser Arg Leu Ile Thr Glu Glu Ala Asn Arg
                725                 730                 735

Thr Thr Met Glu Val Gln Gln Ala Thr Ala Pro Met Ala Asn Asn Leu
            740                 745                 750

Thr Asn Trp Ser Gln Asn Leu Gln His Phe Asp Ser Ser Ala Tyr Asn
        755                 760                 765

Thr Ala Val Asn Ser Ala Arg Asp Ala Val Arg Asn Leu Thr Glu Val
    770                 775                 780

Val Pro Gln Leu Leu Asp Gln Leu Arg Thr Val Glu Gln Lys Arg Pro
785                 790                 795                 800

Ala Ser Asn Val Ser Ala Ser Ile Gln Arg Ile Arg Glu Leu Ile Ala
                805                 810                 815

Gln Thr Arg Ser Val Ala Ser Lys Ile Gln Val Ser Met Met Phe Asp
            820                 825                 830

Gly Gln Ser Ala Val Glu Val His Ser Arg Thr Ser Met Asp Asp Leu
        835                 840                 845

Lys Ala Phe Thr Ser Leu Ser Leu Tyr Met Lys Pro Pro Val Lys Arg
    850                 855                 860

Pro Glu Leu Thr Glu Thr Ala Asp Gln Phe Ile Leu Tyr Leu Gly Ser
865                 870                 875                 880
```

```
Lys Asn Ala Lys Lys Glu Tyr Met Gly Leu Ala Ile Lys Asn Asp Asn
            885                 890                 895

Leu Val Tyr Val Tyr Asn Leu Gly Thr Lys Asp Val Glu Ile Pro Leu
            900                 905                 910

Asp Ser Lys Pro Val Ser Ser Trp Pro Ala Tyr Phe Ser Ile Val Lys
        915                 920                 925

Ile Glu Arg Val Gly Lys His Gly Lys Val Phe Leu Thr Val Pro Ser
    930                 935                 940

Leu Ser Ser Thr Ala Glu Glu Lys Phe Ile Lys Lys Gly Glu Phe Ser
945                 950                 955                 960

Gly Asp Asp Ser Leu Leu Asp Leu Asp Pro Glu Asp Thr Val Phe Tyr
            965                 970                 975

Val Gly Gly Val Pro Ser Asn Phe Lys Leu Pro Thr Ser Leu Asn Leu
            980                 985                 990

Pro Gly Phe Val Gly Cys Leu Glu Leu Ala Thr Leu Asn Asn Asp Val
        995                 1000                1005

Ile Ser Leu Tyr Asn Phe Lys His Ile Tyr Asn Met Asp Pro Ser Thr
    1010                1015                1020

Ser Val Pro Cys Ala Arg Asp Lys Leu Ala Phe Thr Gln Ser Arg Ala
1025                1030                1035                1040

Ala Ser Tyr Phe Phe Asp Gly Ser Gly Tyr Ala Val Val Arg Asp Ile
                1045                1050                1055

Thr Arg Arg Gly Lys Phe Gly Gln Val Thr Arg Phe Asp Ile Glu Val
            1060                1065                1070

Arg Thr Pro Ala Asp Asn Gly Leu Ile Leu Leu Met Val Asn Gly Ser
        1075                1080                1085

Met Phe Phe Arg Leu Glu Met Arg Asn Gly Tyr Leu His Val Phe Tyr
    1090                1095                1100

Asp Phe Gly Phe Ser Gly Gly Pro Val His Leu Glu Asp Thr Leu Lys
1105                1110                1115                1120

Lys Ala Gln Ile Asn Asp Ala Lys Tyr His Glu Ile Ser Ile Ile Tyr
                1125                1130                1135

His Asn Asp Lys Lys Met Ile Leu Val Val Asp Arg Arg His Val Lys
            1140                1145                1150

Ser Met Asp Asn Glu Lys Met Lys Ile Pro Phe Thr Asp Ile Tyr Ile
        1155                1160                1165

Gly Gly Ala Pro Pro Glu Ile Leu Gln Ser Arg Ala Leu Arg Ala His
    1170                1175                1180

Leu Pro Leu Asp Ile Asn Phe Arg Gly Cys Met Lys Gly Phe Gln Phe
1185                1190                1195                1200

Gln Lys Lys Asp Phe Asn Leu Leu Glu Gln Thr Glu Thr Leu Gly Val
                1205                1210                1215

Gly Tyr Gly Cys Pro Glu Asp Ser Leu Ile Ser Arg Arg Ala Tyr Phe
            1220                1225                1230

Asn Gly Gln Ser Phe Ile Ala Ser Ile Gln Lys Ile Ser Phe Phe Asp
        1235                1240                1245

Gly Phe Glu Gly Gly Phe Asn Phe Arg Thr Leu Gln Pro Asn Gly Leu
    1250                1255                1260

Leu Phe Tyr Tyr Ala Ser Gly Ser Asp Val Phe Ser Ile Ser Leu Asp
1265                1270                1275                1280

Asn Gly Thr Val Ile Met Asp Val Lys Gly Ile Lys Val Gln Ser Val
                1285                1290                1295
```

```
Asp Lys Gln Tyr Asn Asp Gly Leu Ser His Phe Val Ile Ser Ser Val
            1300                1305                1310

Ser Pro Thr Arg Tyr Glu Leu Ile Val Asp Lys Ser Arg Val Gly Ser
        1315                1320                1325

Lys Asn Pro Thr Lys Gly Lys Ile Glu Gln Thr Gln Ala Ser Glu Lys
    1330                1335                1340

Lys Phe Tyr Phe Gly Gly Ser Pro Ile Ser Ala Gln Tyr Ala Asn Phe
1345                1350                1355                1360

Thr Gly Cys Ile Ser Asn Ala Tyr Phe Thr Arg Val Asp Arg Asp Val
                1365                1370                1375

Glu Val Glu Asp Phe Gln Arg Tyr Thr Glu Lys Val His Thr Ser Leu
            1380                1385                1390

Tyr Glu Cys Pro Ile Glu Ser Ser Pro Leu Phe Leu Leu His Lys Lys
        1395                1400                1405

Gly Lys Asn Leu Ser Lys Pro Lys Ala Ser Gln Asn Lys Lys Gly Gly
    1410                1415                1420

Lys Ser Lys Asp Ala Pro Ser Trp Asp Pro Val Ala Leu Lys Leu Pro
1425                1430                1435                1440

Glu Arg Asn Thr Pro Arg Asn Ser His Cys His Leu Ser Asn Ser Pro
                1445                1450                1455

Arg Ala Ile Glu His Ala Tyr Gln Tyr Gly Gly Thr Ala Asn Ser Arg
            1460                1465                1470

Gln Glu Phe Glu His Leu Lys Gly Asp Phe Gly Ala Lys Ser Gln Phe
        1475                1480                1485

Ser Ile Arg Leu Arg Thr Arg Ser Ser His Gly Met Ile Phe Tyr Val
    1490                1495                1500

Ser Asp Gln Glu Glu Asn Asp Phe Met Thr Leu Phe Leu Ala His Gly
1505                1510                1515                1520

Arg Leu Val Tyr Met Phe Asn Val Gly His Lys Lys Leu Lys Ile Arg
                1525                1530                1535

Ser Gln Glu Lys Tyr Asn Asp Gly Leu Trp His Asp Val Ile Phe Ile
            1540                1545                1550

Arg Glu Arg Ser Ser Gly Arg Leu Val Ile Asp Gly Leu Arg Val Leu
        1555                1560                1565

Glu Glu Ser Leu Pro Pro Thr Glu Ala Thr Trp Lys Ile Lys Gly Pro
    1570                1575                1580

Ile Tyr Leu Gly Gly Val Ala Pro Gly Lys Ala Val Lys Asn Val Gln
1585                1590                1595                1600

Ile Asn Ser Ile Tyr Ser Phe Ser Gly Cys Leu Ser Asn Leu Gln Leu
                1605                1610                1615

Asn Gly Ala Ser Ile Thr Ser Ala Ser Gln Thr Phe Ser Val Thr Pro
            1620                1625                1630

Cys Phe Glu Gly Pro Met Glu Thr Gly Thr Tyr Phe Ser Thr Glu Gly
        1635                1640                1645

Gly Tyr Val Val Leu Asp Glu Ser Phe Asn Ile Gly Leu Lys Phe Glu
    1650                1655                1660

Ile Ala Phe Glu Val Arg Pro Arg Ser Ser Ser Gly Thr Leu Val His
1665                1670                1675                1680

Gly His Ser Val Asn Gly Glu Tyr Leu Asn Val His Met Lys Asn Gly
                1685                1690                1695

Gln Val Ile Val Lys Val Asn Asn Gly Ile Arg Asp Phe Ser Thr Ser
            1700                1705                1710

Val Thr Pro Lys Gln Ser Leu Cys Asp Gly Arg Trp His Arg Ile Thr
```

```
        1715                1720                1725

Val Ile Arg Asp Ser Asn Val Val Gln Leu Asp Val Asp Ser Glu Val
    1730                1735                1740

Asn His Val Val Gly Pro Leu Asn Pro Lys Pro Ile Asp His Arg Glu
1745                1750                1755                1760

Pro Val Phe Val Gly Gly Val Pro Glu Ser Leu Leu Thr Pro Arg Leu
                1765                1770                1775

Ala Pro Ser Lys Pro Phe Thr Gly Cys Ile Arg His Phe Val Ile Asp
            1780                1785                1790

Gly His Pro Val Ser Phe Ser Lys Ala Ala Leu Val Ser Gly Ala Val
        1795                1800                1805

Ser Ile Asn Ser Cys Pro Ala Ala
    1810                1815
```

<210> SEQ ID NO 29
<211> LENGTH: 334
<212> TYPE: DNA
<213> ORGANISM: Artificial Sequence
<220> FEATURE:
<223> OTHER INFORMATION: Synthetic Polynucleotide
<220> FEATURE:
<223> OTHER INFORMATION: Clone 1174.1.3 - variable Light Chain
<220> FEATURE:
<221> NAME/KEY: CDS
<222> LOCATION: (1)...(333)

<400> SEQUENCE: 29

```
gac att gtg ctg aca cag tct cct gct tcc tta gct gta tct ctg ggg       48
Asp Ile Val Leu Thr Gln Ser Pro Ala Ser Leu Ala Val Ser Leu Gly
 1               5                  10                  15

cag agg gcc acc atc tca tgc agg gcc agc aaa agt gtc agt aca tct       96
Gln Arg Ala Thr Ile Ser Cys Arg Ala Ser Lys Ser Val Ser Thr Ser
             20                  25                  30

ggc tat agt tat atg tac tgg tac caa cag aaa cca gga cag cca ccc      144
Gly Tyr Ser Tyr Met Tyr Trp Tyr Gln Gln Lys Pro Gly Gln Pro Pro
         35                  40                  45

aaa ctc ctc atc tat ctt gca tcc aac cta gaa tct ggg gtc cct gcc      192
Lys Leu Leu Ile Tyr Leu Ala Ser Asn Leu Glu Ser Gly Val Pro Ala
     50                  55                  60

agg ttc agt ggc agt ggg tct ggg aca gac ttc acc ctc aac atc cat      240
Arg Phe Ser Gly Ser Gly Ser Gly Thr Asp Phe Thr Leu Asn Ile His
 65                  70                  75                  80

cct gtg gag gag gag gat gct gca acc tat tac tgt caa cac agt agg      288
Pro Val Glu Glu Glu Asp Ala Ala Thr Tyr Tyr Cys Gln His Ser Arg
                 85                  90                  95

gag ctt cca ttc acg ttc ggc tcg ggg aca aag ttg gaa ata aaa          333
Glu Leu Pro Phe Thr Phe Gly Ser Gly Thr Lys Leu Glu Ile Lys
            100                 105                 110

c                                                                    334
```

<210> SEQ ID NO 30
<211> LENGTH: 111
<212> TYPE: PRT
<213> ORGANISM: Artificial Sequence
<220> FEATURE:
<223> OTHER INFORMATION: Synthetic Construct

<400> SEQUENCE: 30

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
```

```
            20                  25                  30

Gly Tyr Ser Tyr Met Tyr Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys
            100                 105                 110


<210> SEQ ID NO 31
<211> LENGTH: 15
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: clone 1174.1.3 - CDR-L1

<400> SEQUENCE: 31

Arg Ala Ser Lys Ser Val Ser Thr Ser Gly Tyr Ser Tyr Met Tyr
1               5                   10                  15


<210> SEQ ID NO 32
<211> LENGTH: 6
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1174.1.3 - CDR-L2

<400> SEQUENCE: 32

Ala Ser Asn Leu Glu Ser
1               5


<210> SEQ ID NO 33
<211> LENGTH: 9
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1174.1.3 - CDR-L3

<400> SEQUENCE: 33

Gln His Ser Arg Glu Leu Pro Phe Thr
1               5


<210> SEQ ID NO 34
<211> LENGTH: 363
<212> TYPE: DNA
<213> ORGANISM: Artificial Sequence
<220> FEATURE:
<223> OTHER INFORMATION: Synthetic Polynucleotide
<220> FEATURE:
<223> OTHER INFORMATION: clone 1174.1.3 - Variable Heavy chain
<220> FEATURE:
<221> NAME/KEY: CDS
<222> LOCATION: (1)...(363)

<400> SEQUENCE: 34

cag att cag ttg gtg cag tct gga cct gag ctg aag aag cct gga gag       48
Gln Ile Gln Leu Val Gln Ser Gly Pro Glu Leu Lys Lys Pro Gly Glu
```

-continued

```
 1               5                   10                  15

aca gtc aag atc tcc tgc aag gct tct ggg tat acc ttc aca aac tat       96
Thr Val Lys Ile Ser Cys Lys Ala Ser Gly Tyr Thr Phe Thr Asn Tyr
             20                  25                  30

gga atg aac tgg gtg aag cag gct cca gga aag ggt tta aag tgg atg      144
Gly Met Asn Trp Val Lys Gln Ala Pro Gly Lys Gly Leu Lys Trp Met
         35                  40                  45

ggc tgg ata aac acc tac act gga gag cca aca tat gct gat gac ttc      192
Gly Trp Ile Asn Thr Tyr Thr Gly Glu Pro Thr Tyr Ala Asp Asp Phe
     50                  55                  60

aag gga cgg ttt gcc ttg tct ttg gaa acc tct gcc agc act gcc tat      240
Lys Gly Arg Phe Ala Leu Ser Leu Glu Thr Ser Ala Ser Thr Ala Tyr
 65                  70                  75                  80

ttg cag atc aac aac ctc aaa aat gag gac atg gct aca tat ttc tgt      288
Leu Gln Ile Asn Asn Leu Lys Asn Glu Asp Met Ala Thr Tyr Phe Cys
                 85                  90                  95

gca aga tat agg tat aat aaa tac gag agg gct atg gac tac tgg ggt      336
Ala Arg Tyr Arg Tyr Asn Lys Tyr Glu Arg Ala Met Asp Tyr Trp Gly
            100                 105                 110

caa gga acc tca gtc acc gtc tcc tca                                  363
Gln Gly Thr Ser Val Thr Val Ser Ser
        115                 120


<210> SEQ ID NO 35
<211> LENGTH: 121
<212> TYPE: PRT
<213> ORGANISM: Artificial Sequence
<220> FEATURE:
<223> OTHER INFORMATION: Synthetic Construct

<400> SEQUENCE: 35

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Leu Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Tyr Arg Tyr Asn Lys Tyr Glu Arg Ala Met Asp Tyr Trp Gly
            100                 105                 110

Gln Gly Thr Ser Val Thr Val Ser Ser
        115                 120


<210> SEQ ID NO 36
<211> LENGTH: 10
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1174.1.3 - CDR-H1

<400> SEQUENCE: 36

Gly Tyr Thr Phe Thr Asn Tyr Gly Met Asn
1               5                   10
```

<210> SEQ ID NO 37
<211> LENGTH: 17
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1174.1.3 - CDR-H2

<400> SEQUENCE: 37

```
Trp Ile Asn Thr Tyr Thr Gly Glu Pro Thr Tyr Ala Asp Asp Phe Lys
1               5                   10                  15

Gly
```

<210> SEQ ID NO 38
<211> LENGTH: 12
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1174.1.3 - CDR-H3

<400> SEQUENCE: 38

```
Tyr Arg Tyr Asn Lys Tyr Glu Arg Ala Met Asp Tyr
1               5                   10
```

<210> SEQ ID NO 39
<211> LENGTH: 338
<212> TYPE: DNA
<213> ORGANISM: Artificial Sequence
<220> FEATURE:
<223> OTHER INFORMATION: Synthetic Polynucleotide
<220> FEATURE:
<223> OTHER INFORMATION: Clone 1414.1.2 - variable Light Chain
<220> FEATURE:
<221> NAME/KEY: CDS
<222> LOCATION: (1)...(336)

<400> SEQUENCE: 39

```
gac att gtg atg tca cag tct cca tcc tcc ctg gct gtg tca gca gga       48
Asp Ile Val Met Ser Gln Ser Pro Ser Ser Leu Ala Val Ser Ala Gly
 1               5                  10                  15

gag aag gtc act atg agc tgc aaa tcc agt cag agt ctg ctc aac agt       96
Glu Lys Val Thr Met Ser Cys Lys Ser Ser Gln Ser Leu Leu Asn Ser
             20                  25                  30

agc acc cga aag aac ttc ttg gct tgg tac cag cag aaa cca ggg cag      144
Ser Thr Arg Lys Asn Phe Leu Ala Trp Tyr Gln Gln Lys Pro Gly Gln
         35                  40                  45

tct cct aaa ctg ctg atc tac tgg gca tcc act agg gaa tct ggg gtc      192
Ser Pro Lys Leu Leu Ile Tyr Trp Ala Ser Thr Arg Glu Ser Gly Val
     50                  55                  60

cct gat cgc ttc aca ggc agt gga tct ggg aca gat ttc act ctc acc      240
Pro Asp Arg Phe Thr Gly Ser Gly Ser Gly Thr Asp Phe Thr Leu Thr
 65                  70                  75                  80

atc agc agt gtg cag gct gaa gac ctg gca gtt tat tac tgc aag caa      288
Ile Ser Ser Val Gln Ala Glu Asp Leu Ala Val Tyr Tyr Cys Lys Gln
                 85                  90                  95

tct tat aat cgg tac acg ttc gga ggg ggg acc aag ctg gaa ata aaa      336
Ser Tyr Asn Arg Tyr Thr Phe Gly Gly Gly Thr Lys Leu Glu Ile Lys
            100                 105                 110

cg                                                                   338
```

<210> SEQ ID NO 40

```
<211> LENGTH: 112
<212> TYPE: PRT
<213> ORGANISM: Artificial Sequence
<220> FEATURE:
<223> OTHER INFORMATION: Synthetic Construct

<400> SEQUENCE: 40

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Ser Thr Arg Lys Asn Phe Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Arg Tyr Thr Phe Gly Gly Gly Thr Lys Leu Glu Ile Lys
            100                 105                 110


<210> SEQ ID NO 41
<211> LENGTH: 17
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: clone 1414.1.2 - CDR-L1

<400> SEQUENCE: 41

Lys Ser Ser Gln Ser Leu Leu Asn Ser Ser Thr Arg Lys Asn Phe Leu
1               5                   10                  15

Ala


<210> SEQ ID NO 42
<211> LENGTH: 7
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: clone 1414.1.2 - CDR-L2

<400> SEQUENCE: 42

Trp Ala Ser Thr Arg Glu Ser
1               5


<210> SEQ ID NO 43
<211> LENGTH: 8
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1414.1.2 - CDR-L3

<400> SEQUENCE: 43

Lys Gln Ser Tyr Asn Arg Tyr Thr
1               5


<210> SEQ ID NO 44
<211> LENGTH: 351
```

```
<212> TYPE: DNA
<213> ORGANISM: Artificial Sequence
<220> FEATURE:
<223> OTHER INFORMATION: Synthetic Polynucleotide
<220> FEATURE:
<223> OTHER INFORMATION: Clone 1414.1.2 - variable Heavy chain
<220> FEATURE:
<221> NAME/KEY: CDS
<222> LOCATION: (1)...(351)

<400> SEQUENCE: 44

gag atc cag ctg cag cag act gga cct gag ctg gtg aag cct ggg gct       48
Glu Ile Gln Leu Gln Gln Thr Gly Pro Glu Leu Val Lys Pro Gly Ala
 1               5                  10                  15

tca gtg aag ata tcc tgc aag gct tct ggt tat tca ttc act gac tac       96
Ser Val Lys Ile Ser Cys Lys Ala Ser Gly Tyr Ser Phe Thr Asp Tyr
            20                  25                  30

atc atg ctc tgg gtg aag cag agc cat gga aag agc ctt gag tgg att      144
Ile Met Leu Trp Val Lys Gln Ser His Gly Lys Ser Leu Glu Trp Ile
        35                  40                  45

gga aat att aat cct tac tct ggt agt agt ggc tac aat ctg aag ttc      192
Gly Asn Ile Asn Pro Tyr Ser Gly Ser Ser Gly Tyr Asn Leu Lys Phe
    50                  55                  60

aag ggc aag gcc aca ttg act gta gac aaa tct tcc agc aca gcc tac      240
Lys Gly Lys Ala Thr Leu Thr Val Asp Lys Ser Ser Ser Thr Ala Tyr
 65                  70                  75                  80

atg cag ctc aac agt ctg aca tct gag gac tct gca gtc tat tac tgt      288
Met Gln Leu Asn Ser Leu Thr Ser Glu Asp Ser Ala Val Tyr Tyr Cys
                85                  90                  95

gca aga ggg aag gac ttt gct atg gac tac tgg ggt caa gga acc tca      336
Ala Arg Gly Lys Asp Phe Ala Met Asp Tyr Trp Gly Gln Gly Thr Ser
            100                 105                 110

gtc acc gtc tcc tca                                                  351
Val Thr Val Ser Ser
        115


<210> SEQ ID NO 45
<211> LENGTH: 117
<212> TYPE: PRT
<213> ORGANISM: Artificial Sequence
<220> FEATURE:
<223> OTHER INFORMATION: Synthetic Construct

<400> SEQUENCE: 45

Glu Ile Gln Leu Gln Gln Thr Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Ile Met Leu Trp Val Lys Gln Ser His Gly Lys Ser Leu Glu Trp Ile
        35                  40                  45

Gly Asn Ile Asn Pro Tyr Ser Gly Ser Ser Gly Tyr Asn Leu Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Lys Asp Phe Ala Met Asp Tyr Trp Gly Gln Gly Thr Ser
            100                 105                 110

Val Thr Val Ser Ser
        115
```

<210> SEQ ID NO 46
<211> LENGTH: 10
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1414.1.2 - CDR-H1

<400> SEQUENCE: 46

```
Gly Tyr Ser Phe Thr Asp Tyr Ile Met Leu
1               5                   10
```

<210> SEQ ID NO 47
<211> LENGTH: 17
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1414.1.2 - CDR-H2

<400> SEQUENCE: 47

```
Asn Ile Asn Pro Tyr Ser Gly Ser Ser Gly Tyr Asn Leu Lys Phe Lys
1               5                   10                  15

Gly
```

<210> SEQ ID NO 48
<211> LENGTH: 7
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1414.1.2 - CDR-H3

<400> SEQUENCE: 48

```
Gly Lys Asp Phe Ala Met Asp
1               5
```

<210> SEQ ID NO 49
<211> LENGTH: 322
<212> TYPE: DNA
<213> ORGANISM: Artificial Sequence
<220> FEATURE:
<223> OTHER INFORMATION: Synthetic Polynucleotide
<220> FEATURE:
<223> OTHER INFORMATION: Clone 1415.1.1 - variable Light Chain
<220> FEATURE:
<221> NAME/KEY: CDS
<222> LOCATION: (1)...(321)

<400> SEQUENCE: 49

```
gac att gtg atg act cag tct cca gcc acc ctg tct gtg act cca gga       48
Asp Ile Val Met Thr Gln Ser Pro Ala Thr Leu Ser Val Thr Pro Gly
 1               5                  10                  15

gat aga gtc tct ctt tca tgc agg gcc agc cag agt att agc gac tac       96
Asp Arg Val Ser Leu Ser Cys Arg Ala Ser Gln Ser Ile Ser Asp Tyr
             20                  25                  30

tta cac tgg tat caa caa aaa tca cat gag tct cca agg ctt ctc atc      144
Leu His Trp Tyr Gln Gln Lys Ser His Glu Ser Pro Arg Leu Leu Ile
        35                  40                  45

aaa tat gct tcc caa tcc atc tct ggg atc ccc tcc agg ttc agt ggc      192
Lys Tyr Ala Ser Gln Ser Ile Ser Gly Ile Pro Ser Arg Phe Ser Gly
     50                  55                  60

agt gga tca ggg tca gat ttc act ctc agt atc aac agt gtg gaa cct      240
Ser Gly Ser Gly Ser Asp Phe Thr Leu Ser Ile Asn Ser Val Glu Pro
```

```
 65                  70                  75                  80

gaa gat gtt gga gtg tat tac tgt caa aat ggt cac aac ttt cct cgg      288
Glu Asp Val Gly Val Tyr Tyr Cys Gln Asn Gly His Asn Phe Pro Arg
                85                  90                  95

acg ttc ggt gga ggc acc aag ctg gaa atc aaa c                        322
Thr Phe Gly Gly Gly Thr Lys Leu Glu Ile Lys
            100                 105


<210> SEQ ID NO 50
<211> LENGTH: 107
<212> TYPE: PRT
<213> ORGANISM: Artificial Sequence
<220> FEATURE:
<223> OTHER INFORMATION: Synthetic Construct

<400> SEQUENCE: 50

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Asn Phe Pro Arg
                85                  90                  95

Thr Phe Gly Gly Gly Thr Lys Leu Glu Ile Lys
            100                 105


<210> SEQ ID NO 51
<211> LENGTH: 11
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1415.1.1 - CDR-L1

<400> SEQUENCE: 51

Arg Ala Ser Gln Ser Ile Ser Asp Tyr Leu His
1               5                   10


<210> SEQ ID NO 52
<211> LENGTH: 7
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1415.1.1 - CDR-L2

<400> SEQUENCE: 52

Tyr Ala Ser Gln Ser Ile Ser
1               5


<210> SEQ ID NO 53
<211> LENGTH: 9
<212> TYPE: PRT
<213> ORGANISM: Artificial Sequence
<220> FEATURE:
<223> OTHER INFORMATION: Synthetic Peptide
<220> FEATURE:
```

<223> OTHER INFORMATION: Clone 1415.1.1 - CDR-L3

<400> SEQUENCE: 53

```
Gln Asn Gly His Asn Phe Pro Arg Thr
1               5
```

<210> SEQ ID NO 54
<211> LENGTH: 366
<212> TYPE: DNA
<213> ORGANISM: Artificial Sequence
<220> FEATURE:
<223> OTHER INFORMATION: Synthetic Polynucleotide
<220> FEATURE:
<223> OTHER INFORMATION: Clone 1415.1.1 - variable Heavy chain
<220> FEATURE:
<221> NAME/KEY: CDS
<222> LOCATION: (1)...(366)

<400> SEQUENCE: 54

```
cag gtc caa ctg cag cag cct ggg gct gag ctt gtg cag cct ggg gct       48
Gln Val Gln Leu Gln Gln Pro Gly Ala Glu Leu Val Gln Pro Gly Ala
 1               5                  10                  15

cca gtg aag ctg tcc tgc aag gct tct ggc tac att ttc acc agc tac       96
Pro Val Lys Leu Ser Cys Lys Ala Ser Gly Tyr Ile Phe Thr Ser Tyr
            20                  25                  30

tgg atg aac tgg gtg aag cag agg cct gga cga ggc ctc gag tgg att      144
Trp Met Asn Trp Val Lys Gln Arg Pro Gly Arg Gly Leu Glu Trp Ile
        35                  40                  45

gga agg att gat cct tcc gat agt aaa att cac tac aat caa aag ttc      192
Gly Arg Ile Asp Pro Ser Asp Ser Lys Ile His Tyr Asn Gln Lys Phe
    50                  55                  60

aaa gac aag gcc aca ctg act gta gac aga tcc tcc agc aca gcc tac      240
Lys Asp Lys Ala Thr Leu Thr Val Asp Arg Ser Ser Ser Thr Ala Tyr
 65                  70                  75                  80

atc caa ctc ggc agc ctg aca tct gag gac tct gcg gtc tat tat tgt      288
Ile Gln Leu Gly Ser Leu Thr Ser Glu Asp Ser Ala Val Tyr Tyr Cys
                85                  90                  95

gca aaa gag ggg ggt tta cga cgg ggg gac tat gct atg gac tac tgg      336
Ala Lys Glu Gly Gly Leu Arg Arg Gly Asp Tyr Ala Met Asp Tyr Trp
            100                 105                 110

ggt caa gga acc tca gtc acc gtc tcc tca                              366
Gly Gln Gly Thr Ser Val Thr Val Ser Ser
        115                 120
```

<210> SEQ ID NO 55
<211> LENGTH: 122
<212> TYPE: PRT
<213> ORGANISM: Artificial Sequence
<220> FEATURE:
<223> OTHER INFORMATION: Synthetic Construct

<400> SEQUENCE: 55

```
Gln Val Gln Leu Gln Gln Pro Gly Ala Glu Leu Val Gln Pro Gly Ala
1               5                   10                  15

Pro Val Lys Leu Ser Cys Lys Ala Ser Gly Tyr Ile Phe Thr Ser Tyr
            20                  25                  30

Trp Met Asn Trp Val Lys Gln Arg Pro Gly Arg Gly Leu Glu Trp Ile
        35                  40                  45

Gly Arg Ile Asp Pro Ser Asp Ser Lys Ile His Tyr Asn Gln Lys Phe
    50                  55                  60

Lys Asp Lys Ala Thr Leu Thr Val Asp Arg Ser Ser Ser Thr Ala Tyr
65                  70                  75                  80
```

```
Ile Gln Leu Gly Ser Leu Thr Ser Glu Asp Ser Ala Val Tyr Tyr Cys
                85                  90                  95

Ala Lys Glu Gly Gly Leu Arg Arg Gly Asp Tyr Ala Met Asp Tyr Trp
            100                 105                 110

Gly Gln Gly Thr Ser Val Thr Val Ser Ser
        115                 120


<210> SEQ ID NO 56
<211> LENGTH: 10
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: clone 1415.1.1 - CDR-H1

<400> SEQUENCE: 56

Gly Tyr Ile Phe Thr Ser Tyr Trp Met Asn
1               5                   10


<210> SEQ ID NO 57
<211> LENGTH: 17
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1415.1.1 - CDR-H2

<400> SEQUENCE: 57

Arg Ile Asp Pro Ser Asp Ser Lys Ile His Tyr Asn Gln Lys Phe Lys
1               5                   10                  15

Asp


<210> SEQ ID NO 58
<211> LENGTH: 13
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1415.1.1 - CDR-H3

<400> SEQUENCE: 58

Glu Gly Gly Leu Arg Arg Gly Asp Tyr Ala Met Asp Tyr
1               5                   10


<210> SEQ ID NO 59
<211> LENGTH: 337
<212> TYPE: DNA
<213> ORGANISM: Artificial Sequence
<220> FEATURE:
<223> OTHER INFORMATION: Synthetic Polynucleotide
<220> FEATURE:
<223> OTHER INFORMATION: Clone 1749.1.3 - Variable Light Chain
<220> FEATURE:
<221> NAME/KEY: CDS
<222> LOCATION: (1)...(336)

<400> SEQUENCE: 59

gac att gtg atg tca cag tct cca tcc tcc ctg gct gtg tca gca gga       48
Asp Ile Val Met Ser Gln Ser Pro Ser Ser Leu Ala Val Ser Ala Gly
 1               5                  10                  15

gag aag gtc act atg aac tgc aaa tcc agt cgg agt ctg ctc aac agt       96
Glu Lys Val Thr Met Asn Cys Lys Ser Ser Arg Ser Leu Leu Asn Ser
             20                  25                  30
```

```
aga atc cga aag aac tac ttg gct tgg tac cag cag aaa cca ggg cag      144
Arg Ile Arg Lys Asn Tyr Leu Ala Trp Tyr Gln Gln Lys Pro Gly Gln
        35                  40                  45

tct cct aaa ctg ctg atc tac tgg gca tcc act agg gaa tct ggg gtc      192
Ser Pro Lys Leu Leu Ile Tyr Trp Ala Ser Thr Arg Glu Ser Gly Val
    50                  55                  60

cct gat cgc ttc aca ggc agt gga tct ggg aca gat ttc act ctc acc      240
Pro Asp Arg Phe Thr Gly Ser Gly Ser Gly Thr Asp Phe Thr Leu Thr
65                  70                  75                  80

atc agc agt gtg cag gct gaa gac ctg gca gtt tat tac tgc aag caa      288
Ile Ser Ser Val Gln Ala Glu Asp Leu Ala Val Tyr Tyr Cys Lys Gln
                85                  90                  95

tct tat aat ctg ctc acg ttc ggt gct ggg acc aag ctg gag ctg aaa      336
Ser Tyr Asn Leu Leu Thr Phe Gly Ala Gly Thr Lys Leu Glu Leu Lys
            100                 105                 110

c                                                                    337


<210> SEQ ID NO 60
<211> LENGTH: 112
<212> TYPE: PRT
<213> ORGANISM: Artificial Sequence
<220> FEATURE:
<223> OTHER INFORMATION: Synthetic Construct

<400> SEQUENCE: 60

Asp Ile Val Met Ser Gln Ser Pro Ser Ser Leu Ala Val Ser Ala Gly
1               5                   10                  15

Glu Lys Val Thr Met Asn Cys Lys Ser Ser Arg Ser Leu Leu Asn Ser
            20                  25                  30

Arg Ile Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
            100                 105                 110


<210> SEQ ID NO 61
<211> LENGTH: 17
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1749.1.3 - CDR-L1

<400> SEQUENCE: 61

Lys Ser Ser Arg Ser Leu Leu Asn Ser Arg Ile Arg Lys Asn Tyr Leu
1               5                   10                  15

Ala


<210> SEQ ID NO 62
<211> LENGTH: 7
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: clone 1749.1.3 - CDR-L2
```

```
<400> SEQUENCE: 62

Trp Ala Ser Thr Arg Glu Ser
1               5


<210> SEQ ID NO 63
<211> LENGTH: 8
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1749.1.3 - CDR-L3

<400> SEQUENCE: 63

Lys Gln Ser Tyr Asn Leu Leu Thr
1               5


<210> SEQ ID NO 64
<211> LENGTH: 360
<212> TYPE: DNA
<213> ORGANISM: Artificial Sequence
<220> FEATURE:
<223> OTHER INFORMATION: Synthetic Polynucleotide
<220> FEATURE:
<223> OTHER INFORMATION: Clone 1749.1.3 - variable Heavy chain
<220> FEATURE:
<221> NAME/KEY: CDS
<222> LOCATION: (1)...(360)

<400> SEQUENCE: 64

gac gtg aag ctg gtg gag tct ggg gga gac tta gtg aag cct gga ggg       48
Asp Val Lys Leu Val Glu Ser Gly Gly Asp Leu Val Lys Pro Gly Gly
 1               5                  10                  15

tcc ctg aaa ctc tcc tgt gca gcc tct gga ttc act ttc agt agc tat       96
Ser Leu Lys Leu Ser Cys Ala Ala Ser Gly Phe Thr Phe Ser Ser Tyr
            20                  25                  30

atc atg tct tgg gtt cgt cag act ccg gag aag agg ctg gag tgg gtc      144
Ile Met Ser Trp Val Arg Gln Thr Pro Glu Lys Arg Leu Glu Trp Val
        35                  40                  45

gca acc att agt agt ggt ggt agt tcc acc tac tat cca gac agt gtg      192
Ala Thr Ile Ser Ser Gly Gly Ser Ser Thr Tyr Tyr Pro Asp Ser Val
    50                  55                  60

aag ggc cga ttc acc atc tcc aga gac aat gcc aag aac acc ctg tac      240
Lys Gly Arg Phe Thr Ile Ser Arg Asp Asn Ala Lys Asn Thr Leu Tyr
 65                  70                  75                  80

ctg caa atg agc agt ctg aag tct gag gac aca gcc atg tat tac tgt      288
Leu Gln Met Ser Ser Leu Lys Ser Glu Asp Thr Ala Met Tyr Tyr Cys
                85                  90                  95

aca aga gat gat gat tac gac gta aag gta ttt gct tac tgg ggc caa      336
Thr Arg Asp Asp Asp Tyr Asp Val Lys Val Phe Ala Tyr Trp Gly Gln
            100                 105                 110

ggg act ctg gtc act gtc tct gca                                      360
Gly Thr Leu Val Thr Val Ser Ala
        115                 120


<210> SEQ ID NO 65
<211> LENGTH: 120
<212> TYPE: PRT
<213> ORGANISM: Artificial Sequence
<220> FEATURE:
<223> OTHER INFORMATION: Synthetic Construct

<400> SEQUENCE: 65

Asp Val Lys Leu Val Glu Ser Gly Gly Asp Leu Val Lys Pro Gly Gly
```

-continued

```
1               5                   10                  15

Ser Leu Lys Leu Ser Cys Ala Ala Ser Gly Phe Thr Phe Ser Ser Tyr
            20                  25                  30

Ile Met Ser Trp Val Arg Gln Thr Pro Glu Lys Arg Leu Glu Trp Val
        35                  40                  45

Ala Thr Ile Ser Ser Gly Gly Ser Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Asp Asp Asp Tyr Asp Val Lys Val Phe Ala Tyr Trp Gly Gln
            100                 105                 110

Gly Thr Leu Val Thr Val Ser Ala
        115                 120


<210> SEQ ID NO 66
<211> LENGTH: 10
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1749.1.3 - CDR-H1

<400> SEQUENCE: 66

Gly Phe Thr Phe Ser Ser Tyr Ile Met Ser
1               5                   10


<210> SEQ ID NO 67
<211> LENGTH: 17
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1749.1.3 - CDR-H2

<400> SEQUENCE: 67

Thr Ile Ser Ser Gly Gly Ser Ser Thr Tyr Tyr Pro Asp Ser Val Lys
1               5                   10                  15

Gly


<210> SEQ ID NO 68
<211> LENGTH: 11
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 1749.1.3 - CDR-H3

<400> SEQUENCE: 68

Asp Asp Asp Tyr Asp Val Lys Val Phe Ala Tyr
1               5                   10


<210> SEQ ID NO 69
<211> LENGTH: 319
<212> TYPE: DNA
<213> ORGANISM: Artificial Sequence
<220> FEATURE:
<223> OTHER INFORMATION: Synthetic Polynucleotide
<220> FEATURE:
<223> OTHER INFORMATION: Clone 2120.4.19 - variable Light Chain
```

<220> FEATURE:
<221> NAME/KEY: CDS
<222> LOCATION: (1)...(318)

<400> SEQUENCE: 69

```
gat atc cgg atg act cag tct cct tca ctc ctg tct gca tct gtg ggg       48
Asp Ile Arg Met Thr Gln Ser Pro Ser Leu Leu Ser Ala Ser Val Gly
 1               5                  10                  15

gac aga gtc act ctc aac tgc aaa gca agt cag aat att tat aac agc       96
Asp Arg Val Thr Leu Asn Cys Lys Ala Ser Gln Asn Ile Tyr Asn Ser
             20                  25                  30

tta gcc tgg tat cag caa aag ctt gga gaa ggt ccc aaa gtc ctg att      144
Leu Ala Trp Tyr Gln Gln Lys Leu Gly Glu Gly Pro Lys Val Leu Ile
         35                  40                  45

ttt aat gca aac agt ttg caa acg ggc atc cca tca agg ttc agt ggc      192
Phe Asn Ala Asn Ser Leu Gln Thr Gly Ile Pro Ser Arg Phe Ser Gly
     50                  55                  60

agt gga tct ggt aca gat ttc aca ctc acc atc agc agc ctg cag cct      240
Ser Gly Ser Gly Thr Asp Phe Thr Leu Thr Ile Ser Ser Leu Gln Pro
 65                  70                  75                  80

gaa gat ttt gcc aca tat ttc tgc cag cag ttt tat agc ggg tac acg      288
Glu Asp Phe Ala Thr Tyr Phe Cys Gln Gln Phe Tyr Ser Gly Tyr Thr
                 85                  90                  95

ttt gga gct ggg acc aag ctg gaa ctg aaa c                            319
Phe Gly Ala Gly Thr Lys Leu Glu Leu Lys
            100                 105
```

<210> SEQ ID NO 70
<211> LENGTH: 106
<212> TYPE: PRT
<213> ORGANISM: Artificial Sequence
<220> FEATURE:
<223> OTHER INFORMATION: Synthetic Construct

<400> SEQUENCE: 70

```
Asp Ile Arg Met Thr Gln Ser Pro Ser Leu Leu Ser Ala Ser Val Gly
1               5                   10                  15

Asp Arg Val Thr Leu Asn Cys Lys Ala Ser Gln Asn Ile Tyr Asn Ser
            20                  25                  30

Leu Ala Trp Tyr Gln Gln Lys Leu Gly Glu Gly Pro Lys Val Leu Ile
        35                  40                  45

Phe Asn Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Phe Tyr Ser Gly Tyr Thr
                85                  90                  95

Phe Gly Ala Gly Thr Lys Leu Glu Leu Lys
            100                 105
```

<210> SEQ ID NO 71
<211> LENGTH: 106
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: clone 2120.4.19 - variable Light Chain

<400> SEQUENCE: 71

```
Asp Ile Gln Val Thr Gln Ser Pro Ser Leu Leu Ser Ala Ser Val Gly
1               5                   10                  15
```

```
Asp Arg Val Thr Leu Asn Cys Lys Ala Ser Gln Asn Ile Tyr Asn Ser
            20                  25                  30

Leu Ala Trp Tyr Gln Gln Lys Leu Gly Glu Gly Pro Lys Val Leu Ile
        35                  40                  45

Phe Asn Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Phe Tyr Ser Gly Tyr Thr
                85                  90                  95

Phe Gly Ala Gly Thr Lys Leu Glu Leu Lys
            100                 105


<210> SEQ ID NO 72
<211> LENGTH: 106
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 2120.4.19 - variable Light chain

<400> SEQUENCE: 72

Asp Ile Val Leu Thr Gln Ser Pro Ser Leu Leu Ser Ala Ser Val Gly
1               5                   10                  15

Asp Arg Val Thr Leu Asn Cys Lys Ala Ser Gln Asn Ile Tyr Asn Ser
            20                  25                  30

Leu Ala Trp Tyr Gln Gln Lys Leu Gly Glu Gly Pro Lys Val Leu Ile
        35                  40                  45

Phe Asn Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Phe Tyr Ser Gly Tyr Thr
                85                  90                  95

Phe Gly Ala Gly Thr Lys Leu Glu Leu Lys
            100                 105


<210> SEQ ID NO 73
<211> LENGTH: 11
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 2120.4.19 - CDR-L1

<400> SEQUENCE: 73

Lys Ala Ser Gln Asn Ile Tyr Asn Ser Leu Ala
1               5                   10


<210> SEQ ID NO 74
<211> LENGTH: 7
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 2120.4.19 - CDR-L2

<400> SEQUENCE: 74
```

```
Asn Ala Asn Ser Leu Gln Thr
1               5


<210> SEQ ID NO 75
<211> LENGTH: 8
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 2120.4.19 - CDR-L3

<400> SEQUENCE: 75

Gln Gln Phe Tyr Ser Gly Tyr Thr
1               5


<210> SEQ ID NO 76
<211> LENGTH: 354
<212> TYPE: DNA
<213> ORGANISM: Artificial Sequence
<220> FEATURE:
<223> OTHER INFORMATION: Synthetic Polynucleotide
<220> FEATURE:
<223> OTHER INFORMATION: Clone 2120.4.19 - variable Heavy Chain
<220> FEATURE:
<221> NAME/KEY: CDS
<222> LOCATION: (1)...(354)

<400> SEQUENCE: 76

cag gtg cag ctg aag gag tca gga cct ggt ctg gtg cag ccc tca cag       48
Gln Val Gln Leu Lys Glu Ser Gly Pro Gly Leu Val Gln Pro Ser Gln
 1               5                  10                  15

acc ctg tct ctc acc tgc act gtc tct gga ttc tca tta acc agc aat       96
Thr Leu Ser Leu Thr Cys Thr Val Ser Gly Phe Ser Leu Thr Ser Asn
            20                  25                  30

ggt gta agc tgg gtt cgc cag cct cca gga aag ggt ctg gag tgg att      144
Gly Val Ser Trp Val Arg Gln Pro Pro Gly Lys Gly Leu Glu Trp Ile
        35                  40                  45

gca gca ata tca tct ggt gga acc aca tat tat aat tca gcg ttc aaa      192
Ala Ala Ile Ser Ser Gly Gly Thr Thr Tyr Tyr Asn Ser Ala Phe Lys
     50                  55                  60

tcc cga ctg agc atc agc agg aac acc tcc aag agc caa gtt ctc tta      240
Ser Arg Leu Ser Ile Ser Arg Asn Thr Ser Lys Ser Gln Val Leu Leu
 65                  70                  75                  80

aaa atg aac agt ctg caa act gaa gac aca gcc atg tac ttc tgt gcc      288
Lys Met Asn Ser Leu Gln Thr Glu Asp Thr Ala Met Tyr Phe Cys Ala
                85                  90                  95

aga cgg tat ggg tac ggg tgg tac ttt gac ttc tgg ggc cca gga acc      336
Arg Arg Tyr Gly Tyr Gly Trp Tyr Phe Asp Phe Trp Gly Pro Gly Thr
            100                 105                 110

atg gtc aca gtc tcc tca                                              354
Met Val Thr Val Ser Ser
        115


<210> SEQ ID NO 77
<211> LENGTH: 118
<212> TYPE: PRT
<213> ORGANISM: Artificial Sequence
<220> FEATURE:
<223> OTHER INFORMATION: Synthetic Construct

<400> SEQUENCE: 77

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
```

```
            20                  25                  30

Gly Val Ser Trp Val Arg Gln Pro Pro Gly Lys Gly Leu Glu Trp Ile
        35                  40                  45

Ala Ala Ile Ser Ser Gly Gly Thr Thr Tyr Tyr Asn Ser Ala Phe Lys
    50                  55                  60

Ser Arg Leu Ser Ile Ser Arg Asn Thr Ser Lys Ser Gln Val Leu Leu
65                  70                  75                  80

Lys Met Asn Ser Leu Gln Thr Glu Asp Thr Ala Met Tyr Phe Cys Ala
                85                  90                  95

Arg Arg Tyr Gly Tyr Gly Trp Tyr Phe Asp Phe Trp Gly Pro Gly Thr
            100                 105                 110

Met Val Thr Val Ser Ser
        115


<210> SEQ ID NO 78
<211> LENGTH: 10
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 2120.4.19 - CDR-H1

<400> SEQUENCE: 78

Gly Phe Ser Leu Thr Ser Asn Gly Val Ser
1               5                   10


<210> SEQ ID NO 79
<211> LENGTH: 16
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 2120.4.19 - CDR-H2

<400> SEQUENCE: 79

Ala Ile Ser Ser Gly Gly Thr Thr Tyr Tyr Asn Ser Ala Phe Lys Ser
1               5                   10                  15


<210> SEQ ID NO 80
<211> LENGTH: 10
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 2120.4.19 - CDR-H3

<400> SEQUENCE: 80

Arg Tyr Gly Tyr Gly Trp Tyr Phe Asp Phe
1               5                   10


<210> SEQ ID NO 81
<211> LENGTH: 318
<212> TYPE: DNA
<213> ORGANISM: Artificial Sequence
<220> FEATURE:
<223> OTHER INFORMATION: Synthetic Polynucleotide
<220> FEATURE:
<223> OTHER INFORMATION: Clone 2107.4.10 - variable Light Chain
<220> FEATURE:
<221> NAME/KEY: CDS
<222> LOCATION: (1)...(318)

<400> SEQUENCE: 81
```

```
gac atc cgg gtg act cag tct cct tca ctc ctg tct gca tct gtg gga       48
Asp Ile Arg Val Thr Gln Ser Pro Ser Leu Leu Ser Ala Ser Val Gly
 1               5                  10                  15

gac aga gtc act ctc aac tgc aaa gga agt cag aat att tat aag agc       96
Asp Arg Val Thr Leu Asn Cys Lys Gly Ser Gln Asn Ile Tyr Lys Ser
            20                  25                  30

tta gcc tgg ttt cgg cta aag cgt gga gaa gct ccc aag ctc ctg att      144
Leu Ala Trp Phe Arg Leu Lys Arg Gly Glu Ala Pro Lys Leu Leu Ile
        35                  40                  45

tat gat gca aac agt ttg caa acg ggc atc cca tca agg ttc agt ggc      192
Tyr Asp Ala Asn Ser Leu Gln Thr Gly Ile Pro Ser Arg Phe Ser Gly
    50                  55                  60

agt gga tct ggt aca gat ttc aca ctc acc atc acc agc cta cag cct      240
Ser Gly Ser Gly Thr Asp Phe Thr Leu Thr Ile Thr Ser Leu Gln Pro
 65                  70                  75                  80

gaa gat gtt gcc aca tat ttc tgc cag cag tat tat agc ggt tac acg      288
Glu Asp Val Ala Thr Tyr Phe Cys Gln Gln Tyr Tyr Ser Gly Tyr Thr
                85                  90                  95

ttt gga gct ggg acc aag ctg gaa ctg aaa                              318
Phe Gly Ala Gly Thr Lys Leu Glu Leu Lys
            100                 105


<210> SEQ ID NO 82
<211> LENGTH: 106
<212> TYPE: PRT
<213> ORGANISM: Artificial Sequence
<220> FEATURE:
<223> OTHER INFORMATION: Synthetic Construct

<400> SEQUENCE: 82

Asp Ile Arg Val Thr Gln Ser Pro Ser Leu Leu Ser Ala Ser Val Gly
1               5                   10                  15

Asp Arg Val Thr Leu Asn Cys Lys Gly Ser Gln Asn Ile Tyr Lys Ser
            20                  25                  30

Leu Ala Trp Phe Arg Leu Lys Arg Gly Glu Ala Pro Lys Leu Leu Ile
        35                  40                  45

Tyr Asp Ala Asn Ser Leu Gln Thr Gly Ile Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Val Ala Thr Tyr Phe Cys Gln Gln Tyr Tyr Ser Gly Tyr Thr
                85                  90                  95

Phe Gly Ala Gly Thr Lys Leu Glu Leu Lys
            100                 105


<210> SEQ ID NO 83
<211> LENGTH: 318
<212> TYPE: DNA
<213> ORGANISM: Artificial Sequence
<220> FEATURE:
<223> OTHER INFORMATION: Synthetic Polynucleotide
<220> FEATURE:
<223> OTHER INFORMATION: Clone 2107.4.10 - variable Light Chain
<220> FEATURE:
<221> NAME/KEY: CDS
<222> LOCATION: (1)...(318)

<400> SEQUENCE: 83

gac atc cag gtg act cag tct cct tca ctc ctg tct gca tct gtg gga       48
Asp Ile Gln Val Thr Gln Ser Pro Ser Leu Leu Ser Ala Ser Val Gly
 1               5                  10                  15
```

-continued

```
gac aga gtc act ctc aac tgc aaa gga agt cag aat att tat aag agc       96
Asp Arg Val Thr Leu Asn Cys Lys Gly Ser Gln Asn Ile Tyr Lys Ser
             20                  25                  30

tta gcc tgg ttt cgg cta aag cgt gga gaa gct ccc aag ctc ctg att      144
Leu Ala Trp Phe Arg Leu Lys Arg Gly Glu Ala Pro Lys Leu Leu Ile
         35                  40                  45

tat gat gca aac agt ttg caa acg ggc atc cca tca agg ttc agt ggc      192
Tyr Asp Ala Asn Ser Leu Gln Thr Gly Ile Pro Ser Arg Phe Ser Gly
     50                  55                  60

agt gga tct ggt aca gat ttc aca ctc acc atc acc agc cta cag cct      240
Ser Gly Ser Gly Thr Asp Phe Thr Leu Thr Ile Thr Ser Leu Gln Pro
 65                  70                  75                  80

gaa gat gtt gcc aca tat ttc tgc cag cag tat tat agc ggt tac acg      288
Glu Asp Val Ala Thr Tyr Phe Cys Gln Gln Tyr Tyr Ser Gly Tyr Thr
                 85                  90                  95

ttt gga gct ggg acc aag ctg gaa ctg aaa                              318
Phe Gly Ala Gly Thr Lys Leu Glu Leu Lys
            100                 105


<210> SEQ ID NO 84
<211> LENGTH: 106
<212> TYPE: PRT
<213> ORGANISM: Artificial Sequence
<220> FEATURE:
<223> OTHER INFORMATION: Synthetic Construct

<400> SEQUENCE: 84

Asp Ile Gln Val Thr Gln Ser Pro Ser Leu Leu Ser Ala Ser Val Gly
1               5                   10                  15

Asp Arg Val Thr Leu Asn Cys Lys Gly Ser Gln Asn Ile Tyr Lys Ser
            20                  25                  30

Leu Ala Trp Phe Arg Leu Lys Arg Gly Glu Ala Pro Lys Leu Leu Ile
        35                  40                  45

Tyr Asp Ala Asn Ser Leu Gln Thr Gly Ile Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Val Ala Thr Tyr Phe Cys Gln Gln Tyr Tyr Ser Gly Tyr Thr
                85                  90                  95

Phe Gly Ala Gly Thr Lys Leu Glu Leu Lys
            100                 105


<210> SEQ ID NO 85
<211> LENGTH: 11
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 2107.4.10 - CDR-L1

<400> SEQUENCE: 85

Lys Gly Ser Gln Asn Ile Tyr Lys Ser Leu Ala
1               5                   10


<210> SEQ ID NO 86
<211> LENGTH: 7
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 2107.4.10 - CDR-L2
```

```
<400> SEQUENCE: 86

Asp Ala Asn Ser Leu Gln Thr
1               5


<210> SEQ ID NO 87
<211> LENGTH: 8
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 2107.4.10 - CDR-L3

<400> SEQUENCE: 87

Gln Gln Tyr Tyr Ser Gly Tyr Thr
1               5


<210> SEQ ID NO 88
<211> LENGTH: 348
<212> TYPE: DNA
<213> ORGANISM: Artificial Sequence
<220> FEATURE:
<223> OTHER INFORMATION: Synthetic Polynucleotide
<220> FEATURE:
<223> OTHER INFORMATION: Clone 2107.4.10 - variable Heavy Chain
<220> FEATURE:
<221> NAME/KEY: CDS
<222> LOCATION: (1)...(348)

<400> SEQUENCE: 88

cag gtg cag ctg aag gag tca gga cct ggt ctg gtg cag tcc tca cag       48
Gln Val Gln Leu Lys Glu Ser Gly Pro Gly Leu Val Gln Ser Ser Gln
 1               5                  10                  15

acc ctg tct ctc acc tgc act gtc tct gga ttc tca tta acc agt aat       96
Thr Leu Ser Leu Thr Cys Thr Val Ser Gly Phe Ser Leu Thr Ser Asn
            20                  25                  30

ggt gta agc tgg gtt cgc cag cct cca gga aag ggt ctg gag tgg att      144
Gly Val Ser Trp Val Arg Gln Pro Pro Gly Lys Gly Leu Glu Trp Ile
        35                  40                  45

gca gca ata tca agt ggt gga agc aca tat tat aat tca gcg ttc aaa      192
Ala Ala Ile Ser Ser Gly Gly Ser Thr Tyr Tyr Asn Ser Ala Phe Lys
    50                  55                  60

tcc cga ctg agc atc agc agg aac acc tcc aag agc caa gtt ctc tta      240
Ser Arg Leu Ser Ile Ser Arg Asn Thr Ser Lys Ser Gln Val Leu Leu
 65                  70                  75                  80

aaa atg aac agt ctg caa act gaa gac aca ggc atg tac ttc tgt gcc      288
Lys Met Asn Ser Leu Gln Thr Glu Asp Thr Gly Met Tyr Phe Cys Ala
                 85                  90                  95

aga cat aga ccg ttc tac ttt gat tac tgg ggc caa gga gtc atg gtc      336
Arg His Arg Pro Phe Tyr Phe Asp Tyr Trp Gly Gln Gly Val Met Val
            100                 105                 110

aca gtc tcc tca                                                      348
Thr Val Ser Ser
        115


<210> SEQ ID NO 89
<211> LENGTH: 116
<212> TYPE: PRT
<213> ORGANISM: Artificial Sequence
<220> FEATURE:
<223> OTHER INFORMATION: Synthetic Construct

<400> SEQUENCE: 89

Gln Val Gln Leu Lys Glu Ser Gly Pro Gly Leu Val Gln Ser Ser Gln
```

```
1               5                   10                  15

Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Ser Thr Tyr Tyr Asn Ser Ala Phe Lys
    50                  55                  60

Ser Arg Leu Ser Ile Ser Arg Asn Thr Ser Lys Ser Gln Val Leu Leu
65                  70                  75                  80

Lys Met Asn Ser Leu Gln Thr Glu Asp Thr Gly Met Tyr Phe Cys Ala
                85                  90                  95

Arg His Arg Pro Phe Tyr Phe Asp Tyr Trp Gly Gln Gly Val Met Val
            100                 105                 110

Thr Val Ser Ser
        115


<210> SEQ ID NO 90
<211> LENGTH: 10
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 2107.4.10 - CDR-H1

<400> SEQUENCE: 90

Gly Phe Ser Leu Thr Ser Asn Gly Val Ser
1               5                   10


<210> SEQ ID NO 91
<211> LENGTH: 16
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 2107.4.10 - CDR-H2

<400> SEQUENCE: 91

Ala Ile Ser Ser Gly Gly Ser Thr Tyr Tyr Asn Ser Ala Phe Lys Ser
1               5                   10                  15


<210> SEQ ID NO 92
<211> LENGTH: 8
<212> TYPE: PRT
<213> ORGANISM: Artificial Sequence
<220> FEATURE:
<223> OTHER INFORMATION: Synthetic Peptide
<220> FEATURE:
<223> OTHER INFORMATION: Clone 2107.4.10 - CDR-H3

<400> SEQUENCE: 92

His Arg Pro Phe Tyr Phe Asp Tyr
1               5


<210> SEQ ID NO 93
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 93

Asp Val Lys Leu Val Glu Ser Gly Gly Asp Leu Val Lys Pro Gly Gly
```

1 5 10 15

Ser Leu Lys Leu Ser Cys Ala Ala Ser Gly Phe Thr Phe Ser Ser Tyr
20 25 30

Ile Met Ser Trp Val Arg Gln Thr Pro Glu Lys Arg Leu Glu Trp Val
35 40 45

Ala Thr Ile Ser Ser Gly Gly Ser Ser Thr Tyr Tyr Pro Asp Ser Val
50 55 60

Lys Gly Arg Phe Thr Ile Ser Arg Asp Asn Ala Lys Asn Thr Leu Tyr
65 70 75 80

Leu Gln Met Ser Ser Leu Lys Ser Glu Asp Thr Ala Met Tyr Tyr Cys
85 90 95

Thr Arg Asp Asp Asp Tyr Asp Val Lys Val Phe Ala Tyr Trp Gly Gln
100 105 110

Gly Thr Leu Val Thr Val Ser Ala
115 120

<210> SEQ ID NO 94
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 94

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ile Met Ser Trp Val Arg Gln Ala Pro Gly Lys Gly Leu Glu Trp Val
35 40 45

Ala Thr Ile Ser Ser Gly Gly Ser Ser Thr Tyr Tyr Pro Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Thr Arg Asp Asp Asp Tyr Asp Val Lys Val Phe Ala Tyr Trp Gly Gln
100 105 110

Gly Thr Met Val Thr Val Ser Ser
115 120

<210> SEQ ID NO 95
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 95

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ile Met Ser Trp Val Arg Gln Ala Pro Gly Lys Arg Leu Glu Trp Val
35 40 45

Ala Thr Ile Ser Ser Gly Gly Ser Ser Thr Tyr Tyr Pro Asp Ser Val
50 55 60

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Asp Asp Asp Tyr Asp Val Lys Val Phe Ala Tyr Trp Gly Gln
            100                 105                 110

Gly Thr Met Val Thr Val Ser Ser
        115                 120


<210> SEQ ID NO 96
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Ile Phe Gly Val Val Ser His Ile Trp Gly Gln
            100                 105                 110

Gly Thr Met Val Thr Val Ser Ser
        115                 120


<210> SEQ ID NO 97
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 97

Asp Ile Val Met Ser Gln Ser Pro Ser Ser Leu Ala Val Ser Ala Gly
1               5                   10                  15

Glu Lys Val Thr Met Asn Cys Lys Ser Ser Arg Ser Leu Leu Asn Ser
            20                  25                  30

Arg Ile Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
            100                 105                 110


<210> SEQ ID NO 98
```

<211> LENGTH: 112
<212> TYPE: PRT
<213> ORGANISM: Artificial Sequence
<220> FEATURE:
<223> OTHER INFORMATION: Synthetic Peptide

<400> SEQUENCE: 98

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Arg Ser Leu Leu Asn Ser
            20                  25                  30

Arg Ile Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Leu Thr Phe Gly Gln Gly Thr Lys Val Glu Ile Lys
            100                 105                 110
```

<210> SEQ ID NO 99
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 99

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Arg Ser Leu Leu Asn Ser
            20                  25                  30

Arg Ile Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Leu Thr Phe Gly Gln Gly Thr Lys Val Glu Ile Lys
            100                 105                 110
```

<210> SEQ ID NO 100
<211> LENGTH: 113
<212> TYPE: PRT
<213> ORGANISM: Artificial Sequence
<220> FEATURE:
<223> OTHER INFORMATION: Synthetic Peptide

<400> SEQUENCE: 100

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asp Asn Lys Asn Tyr Leu Ala Trp Tyr Gln Gln Lys Pro Gly Gln
        35                  40                  45
```

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Asn Leu Pro Trp Thr Phe Gly Gln Gly Thr Lys Val Glu Ile
100 105 110

Lys

<210> SEQ ID NO 101
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 101

Gln Val Gln Leu Lys Glu Ser Gly Pro Gly Leu Val Gln Ser Ser Gln
1 5 10 15

Thr Leu Ser Leu Thr Cys Thr Val Ser Gly Phe Ser Leu Thr Ser Asn
20 25 30

Gly Val Ser Trp Val Arg Gln Pro Pro Gly Lys Gly Leu Glu Trp Ile
35 40 45

Ala Ala Ile Ser Ser Gly Gly Ser Thr Tyr Tyr Asn Ser Ala Phe Lys
50 55 60

Ser Arg Leu Ser Ile Ser Pro Asn Thr Ser Lys Ser Gln Val Leu Leu
65 70 75 80

Lys Met Asn Ser Leu Gln Thr Glu Asp Thr Gly Met Tyr Phe Cys Ala
85 90 95

Arg His Arg Pro Phe Tyr Phe Asp Tyr Trp Gly Gln Gly Val Met Val
100 105 110

Thr Val Ser Ser
115

<210> SEQ ID NO 102
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 102

Gln Val Thr Leu Lys Glu Ser Gly Pro Val Leu Val Lys Pro Thr Glu
1 5 10 15

Thr Leu Thr Leu Thr Cys Thr Val Ser Gly Phe Ser Leu Thr Ser Asn
20 25 30

Gly Val Ser Trp Val Arg Gln Pro Pro Gly Lys Ala Leu Glu Trp Ile
35 40 45

Ala Ala Ile Ser Ser Gly Gly Ser Thr Tyr Tyr Asn Ser Ala Phe Lys
50 55 60

Ser Arg Leu Thr Ile Ser Arg Asp Thr Ser Lys Ser Gln Val Val Leu
65 70 75 80

Thr Met Thr Asn Met Asp Pro Val Asp Thr Ala Thr Tyr Tyr Cys Ala
85 90 95

Arg His Arg Pro Phe Tyr Phe Asp Tyr Trp Gly Gln Gly Thr Leu Val
100 105 110

Thr Val Ser Ser
115

<210> SEQ ID NO 103
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 103

Gln Val Thr Leu Lys Glu Ser Gly Pro Val Leu Val Lys Pro Thr Glu
1 5 10 15

Thr Leu Thr Leu Thr Cys Thr Val Ser Gly Phe Ser Leu Thr Ser Asn
20 25 30

Gly Val Ser Trp Val Arg Gln Pro Pro Gly Lys Ala Leu Glu Trp Ile
35 40 45

Ala Ala Ile Ser Ser Gly Gly Ser Thr Tyr Tyr Asn Ser Ala Phe Lys
50 55 60

Ser Arg Leu Ser Ile Ser Arg Asp Thr Ser Lys Ser Gln Val Val Leu
65 70 75 80

Thr Met Thr Asn Met Asp Pro Val Asp Thr Ala Thr Tyr Tyr Cys Ala
85 90 95

Arg His Arg Pro Phe Tyr Phe Asp Tyr Trp Gly Gln Gly Thr Leu Val
100 105 110

Thr Val Ser Ser
115

<210> SEQ ID NO 104
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 104

Gln Val Thr Leu Lys Glu Ser Gly Pro Val Leu Val Lys Pro Thr Glu
1 5 10 15

Thr Leu Thr Leu Thr Cys Thr Val Ser Gly Phe Ser Leu Thr Ser Asn
20 25 30

Gly Val Ser Trp Val Arg Gln Pro Pro Gly Lys Ala Leu Glu Trp Ile
35 40 45

Ala Ala Ile Ser Ser Gly Gly Ser Thr Tyr Tyr Asn Ser Ala Phe Lys
50 55 60

Ser Arg Leu Thr Ile Ser Arg Asn Thr Ser Lys Ser Gln Val Val Leu
65 70 75 80

Thr Met Thr Asn Met Asp Pro Val Asp Thr Ala Thr Tyr Tyr Cys Ala
85 90 95

Arg His Arg Pro Phe Tyr Phe Asp Tyr Trp Gly Gln Gly Thr Leu Val
100 105 110

Thr Val Ser Ser
115

<210> SEQ ID NO 105
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 105

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Ser
            20                  25                  30

Gly Val Ser Trp Val Arg Gln Pro Pro Gly Lys Ala Leu Glu Trp Ile
        35                  40                  45

Ala Ala Ile Ser Ser Gly Gly Ser Thr Tyr Tyr Asn Ser Ala Phe Lys
    50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg His Arg Pro Phe Tyr Phe Asp Tyr Trp Gly Gln Gly Thr Leu Val
            100                 105                 110

Thr Val Ser Ser
        115

<210> SEQ ID NO 106
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 106

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Gln
            20                  25                  30

Gly Val Ser Trp Val Arg Gln Pro Pro Gly Lys Ala Leu Glu Trp Ile
        35                  40                  45

Ala Ala Ile Ser Ser Gly Gly Ser Thr Tyr Tyr Asn Ser Ala Phe Lys
    50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg His Arg Pro Phe Tyr Phe Asp Tyr Trp Gly Gln Gly Thr Leu Val
            100                 105                 110

Thr Val Ser Ser
        115

<210> SEQ ID NO 107
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 107

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Asn
            20                  25                  30

Ala Val Ser Trp Val Arg Gln Pro Pro Gly Lys Ala Leu Glu Trp Ile
        35                  40                  45

```
Ala Ala Ile Ser Ser Gly Gly Ser Thr Tyr Tyr Asn Ser Ala Phe Lys
    50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg His Arg Pro Phe Tyr Phe Asp Tyr Trp Gly Gln Gly Thr Leu Val
            100                 105                 110

Thr Val Ser Ser
        115


<210> SEQ ID NO 108
<211> LENGTH: 131
<212> TYPE: PRT
<213> ORGANISM: Artificial Sequence
<220> FEATURE:
<223> OTHER INFORMATION: Synthetic Peptide

<400> SEQUENCE: 108

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile Gly Glu Ser Ala Ser Asp Arg Tyr Cys Ser Gly Gly
            100                 105                 110

Ser Cys Phe Gly Trp Phe Asp Pro Trp Gly Gln Gly Thr Leu Val Thr
        115                 120                 125

Val Ser Ser
    130


<210> SEQ ID NO 109
<211> LENGTH: 106
<212> TYPE: PRT
<213> ORGANISM: Artificial Sequence
<220> FEATURE:
<223> OTHER INFORMATION: Synthetic Peptide

<400> SEQUENCE: 109

Asp Ile Gln Val Thr Gln Ser Pro Ser Leu Leu Ser Ala Ser Val Gly
1               5                   10                  15

Asp Arg Val Thr Leu Asn Cys Lys Gly Ser Gln Asn Ile Tyr Lys Ser
            20                  25                  30

Leu Ala Trp Phe Arg Leu Lys Arg Gly Glu Ala Pro Lys Leu Leu Ile
        35                  40                  45

Tyr Asp Ala Asn Ser Leu Gln Thr Gly Ile Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Val Ala Thr Tyr Phe Cys Gln Gln Tyr Tyr Ser Gly Tyr Thr
                85                  90                  95
```

Phe Gly Ala Gly Thr Lys Leu Glu Leu Lys
100 105

<210> SEQ ID NO 110
<211> LENGTH: 106
<212> TYPE: PRT
<213> ORGANISM: Artificial Sequence
<220> FEATURE:
<223> OTHER INFORMATION: Synthetic Peptide

<400> SEQUENCE: 110

Asp Ile Gln Met Thr Gln Ser Pro Ser Ser Leu Ser Ala Ser Val Gly
1 5 10 15

Asp Arg Val Thr Ile Thr Cys Lys Gly Ser Gln Asn Ile Tyr Lys Ser
20 25 30

Leu Ala Trp Phe Gln Gln Lys Pro Gly Lys Val Pro Lys Leu Leu Ile
35 40 45

Tyr Asp Ala Asn Ser Leu Gln Thr Gly Ile Pro Ser Arg Phe Ser Gly
50 55 60

Ser Gly Ser Gly Thr Asp Phe Thr Leu Thr Ile Ser Ser Leu Gln Pro
65 70 75 80

Glu Asp Val Ala Thr Tyr Tyr Cys Gln Gln Tyr Tyr Ser Gly Tyr Thr
85 90 95

Phe Gly Gly Gly Thr Lys Val Glu Ile Lys
100 105

<210> SEQ ID NO 111
<211> LENGTH: 106
<212> TYPE: PRT
<213> ORGANISM: Artificial Sequence
<220> FEATURE:
<223> OTHER INFORMATION: Synthetic Peptide

<400> SEQUENCE: 111

Asp Ile Gln Met Thr Gln Ser Pro Ser Ser Leu Ser Ala Ser Val Gly
1 5 10 15

Asp Arg Val Thr Ile Thr Cys Lys Gly Ser Gln Asn Ile Tyr Lys Ser
20 25 30

Leu Ala Trp Phe Gln Leu Lys Pro Gly Lys Val Pro Lys Leu Leu Ile
35 40 45

Tyr Asp Ala Asn Ser Leu Gln Thr Gly Ile Pro Ser Arg Phe Ser Gly
50 55 60

Ser Gly Ser Gly Thr Asp Phe Thr Leu Thr Ile Ser Ser Leu Gln Pro
65 70 75 80

Glu Asp Val Ala Thr Tyr Tyr Cys Gln Gln Tyr Tyr Ser Gly Tyr Thr
85 90 95

Phe Gly Gly Gly Thr Lys Val Glu Ile Lys
100 105

<210> SEQ ID NO 112
<211> LENGTH: 106
<212> TYPE: PRT
<213> ORGANISM: Artificial Sequence
<220> FEATURE:
<223> OTHER INFORMATION: Synthetic Peptide

<400> SEQUENCE: 112

Asp Ile Gln Met Thr Gln Ser Pro Ser Ser Leu Ser Ala Ser Val Gly
1 5 10 15

-continued

```
Asp Arg Val Thr Ile Asn Cys Lys Gly Ser Gln Asn Ile Tyr Lys Ser
            20                  25                  30

Leu Ala Trp Phe Gln Gln Lys Pro Gly Lys Val Pro Lys Leu Leu Ile
        35                  40                  45

Tyr Asp Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Tyr Ser Gly Tyr Thr
                85                  90                  95

Phe Gly Gly Gly Thr Lys Val Glu Ile Lys
            100                 105


<210> SEQ ID NO 113
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Pro
                85                  90                  95

Leu Phe Gly Gly Gly Thr Lys Val Glu Ile Lys
            100                 105


<210> SEQ ID NO 114
<211> LENGTH: 118
<212> TYPE: PRT
<213> ORGANISM: Artificial Sequence
<220> FEATURE:
<223> OTHER INFORMATION: Synthetic Peptide

<400> SEQUENCE: 114

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Thr Thr Tyr Tyr Asn Ser Ala Phe Lys
    50                  55                  60

Ser Arg Leu Ser Ile Ser Arg Asn Thr Ser Lys Ser Gln Val Leu Leu
65                  70                  75                  80

Lys Met Asn Ser Leu Gln Thr Glu Asp Thr Ala Met Tyr Phe Cys Ala
                85                  90                  95

Arg Arg Tyr Gly Tyr Gly Trp Tyr Phe Asp Phe Trp Gly Pro Gly Thr
            100                 105                 110
```

Met Val Thr Val Ser Ser
115

<210> SEQ ID NO 115
<211> LENGTH: 118
<212> TYPE: PRT
<213> ORGANISM: Artificial Sequence
<220> FEATURE:
<223> OTHER INFORMATION: Synthetic Peptide

<400> SEQUENCE: 115

Gln Val Thr Leu Lys Glu Ser Gly Pro Val Leu Val Lys Pro Thr Glu
1 5 10 15

Thr Leu Thr Leu Thr Cys Thr Val Ser Gly Phe Ser Leu Thr Ser Asn
20 25 30

Gly Val Ser Trp Val Arg Gln Pro Pro Gly Lys Ala Leu Glu Trp Ile
35 40 45

Ala Ala Ile Ser Ser Gly Gly Thr Thr Tyr Tyr Asn Ser Ala Phe Lys
50 55 60

Ser Arg Leu Thr Ile Ser Arg Asp Thr Ser Lys Ser Gln Val Val Leu
65 70 75 80

Thr Met Thr Asn Met Asp Pro Val Asp Thr Ala Thr Tyr Tyr Cys Ala
85 90 95

Arg Arg Tyr Gly Tyr Gly Trp Tyr Phe Asp Phe Trp Gly Gln Gly Thr
100 105 110

Leu Val Thr Val Ser Ser
115

<210> SEQ ID NO 116
<211> LENGTH: 118
<212> TYPE: PRT
<213> ORGANISM: Artificial Sequence
<220> FEATURE:
<223> OTHER INFORMATION: Synthetic Peptide

<400> SEQUENCE: 116

Gln Val Thr Leu Lys Glu Ser Gly Pro Val Leu Val Lys Pro Thr Glu
1 5 10 15

Thr Leu Thr Leu Thr Cys Thr Val Ser Gly Phe Ser Leu Thr Ser Asn
20 25 30

Gly Val Ser Trp Val Arg Gln Pro Pro Gly Lys Ala Leu Glu Trp Ile
35 40 45

Ala Ala Ile Ser Ser Gly Gly Thr Thr Tyr Tyr Asn Ser Ala Phe Lys
50 55 60

Ser Arg Leu Ser Ile Ser Arg Asp Thr Ser Lys Ser Gln Val Val Leu
65 70 75 80

Thr Met Thr Asn Met Asp Pro Val Asp Thr Ala Thr Tyr Tyr Cys Ala
85 90 95

Arg Arg Tyr Gly Tyr Gly Trp Tyr Phe Asp Phe Trp Gly Gln Gly Thr
100 105 110

Leu Val Thr Val Ser Ser
115

<210> SEQ ID NO 117
<211> LENGTH: 118
<212> TYPE: PRT
<213> ORGANISM: Artificial Sequence
<220> FEATURE:
<223> OTHER INFORMATION: Synthetic Peptide

<400> SEQUENCE: 117

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Ser
            20                  25                  30

Gly Val Ser Trp Val Arg Gln Pro Pro Gly Lys Ala Leu Glu Trp Ile
        35                  40                  45

Ala Ala Ile Ser Ser Gly Gly Thr Thr Tyr Tyr Asn Ser Ala Phe Lys
    50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Arg Tyr Gly Tyr Gly Trp Tyr Phe Asp Phe Trp Gly Gln Gly Thr
            100                 105                 110

Leu Val Thr Val Ser Ser
        115

<210> SEQ ID NO 118
<211> LENGTH: 118
<212> TYPE: PRT
<213> ORGANISM: Artificial Sequence
<220> FEATURE:
<223> OTHER INFORMATION: Synthetic Peptide

<400> SEQUENCE: 118

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Gln
            20                  25                  30

Gly Val Ser Trp Val Arg Gln Pro Pro Gly Lys Ala Leu Glu Trp Ile
        35                  40                  45

Ala Ala Ile Ser Ser Gly Gly Thr Thr Tyr Tyr Asn Ser Ala Phe Lys
    50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Arg Tyr Gly Tyr Gly Trp Tyr Phe Asp Phe Trp Gly Gln Gly Thr
            100                 105                 110

Leu Val Thr Val Ser Ser
        115

<210> SEQ ID NO 119
<211> LENGTH: 118
<212> TYPE: PRT
<213> ORGANISM: Artificial Sequence
<220> FEATURE:
<223> OTHER INFORMATION: Synthetic Peptide

<400> SEQUENCE: 119

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Asn
            20                  25                  30

Ala Val Ser Trp Val Arg Gln Pro Pro Gly Lys Ala Leu Glu Trp Ile
        35                  40                  45

Ala Ala Ile Ser Ser Gly Gly Thr Thr Tyr Tyr Asn Ser Ala Phe Lys
50 55 60

Ser Arg Leu Thr Ile Ser Arg Asp Thr Ser Lys Ser Gln Val Val Leu
65 70 75 80

Thr Met Thr Asn Met Asp Pro Val Asp Thr Ala Thr Tyr Tyr Cys Ala
85 90 95

Arg Arg Tyr Gly Tyr Gly Trp Tyr Phe Asp Phe Trp Gly Gln Gly Thr
100 105 110

Leu Val Thr Val Ser Ser
115

<210> SEQ ID NO 120
<211> LENGTH: 106
<212> TYPE: PRT
<213> ORGANISM: Artificial Sequence
<220> FEATURE:
<223> OTHER INFORMATION: Synthetic Peptide

<400> SEQUENCE: 120

Asp Ile Arg Met Thr Gln Ser Pro Ser Leu Leu Ser Ala Ser Val Gly
1 5 10 15

Asp Arg Val Thr Leu Asn Cys Lys Ala Ser Gln Asn Ile Tyr Asn Ser
20 25 30

Leu Ala Trp Tyr Gln Gln Lys Leu Gly Glu Gly Pro Lys Val Leu Ile
35 40 45

Pro Asn Ala Asn Ser Leu Gln Thr Gly Ile Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Phe Cys Gln Gln Phe Tyr Ser Gly Tyr Thr
85 90 95

Phe Gly Ala Gly Thr Lys Leu Glu Leu Lys
100 105

<210> SEQ ID NO 121
<211> LENGTH: 106
<212> TYPE: PRT
<213> ORGANISM: Artificial Sequence
<220> FEATURE:
<223> OTHER INFORMATION: Synthetic Peptide

<400> SEQUENCE: 121

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Ile Tyr Asn Ser
20 25 30

Leu Ala Trp Tyr Gln Gln Lys Pro Gly Lys Ala Pro Lys Val Leu Ile
35 40 45

Phe Asn Ala Asn Ser Leu Gln Thr Gly Ile Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Tyr Ser Gly Tyr Thr
85 90 95

Phe Gly Gln Gly Thr Lys Leu Glu Ile Lys
100 105

<210> SEQ ID NO 122
<211> LENGTH: 106
<212> TYPE: PRT
<213> ORGANISM: Artificial Sequence
<220> FEATURE:
<223> OTHER INFORMATION: Synthetic Peptide

<400> SEQUENCE: 122

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Ile Tyr Asn Ser
20 25 30

Leu Ala Trp Tyr Gln Gln Lys Pro Gly Lys Ala Pro Lys Val Leu Ile
35 40 45

Phe Asn Ala Asn Ser Leu Gln Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Tyr Ser Gly Tyr Thr
85 90 95

Phe Gly Gln Gly Thr Lys Leu Glu Ile Lys
100 105

<210> SEQ ID NO 123
<211> LENGTH: 106
<212> TYPE: PRT
<213> ORGANISM: Artificial Sequence
<220> FEATURE:
<223> OTHER INFORMATION: Synthetic Peptide

<400> SEQUENCE: 123

Asp Ile Gln Met Thr Gln Ser Pro Ser Ser Leu Ser Ala Ser Val Gly
1 5 10 15

Asp Arg Val Thr Ile Asn Cys Lys Ala Ser Gln Asn Ile Tyr Asn Ser
20 25 30

Leu Ala Trp Tyr Gln Gln Lys Pro Gly Lys Ala Pro Lys Val Leu Ile
35 40 45

Phe Asn Ala Asn Ser Leu Gln Thr Gly Ile Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Tyr Ser Gly Tyr Thr
85 90 95

Phe Gly Gln Gly Thr Lys Leu Glu Ile Lys
100 105

<210> SEQ ID NO 124
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 124

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Ser Phe Gly Gln Gly Thr Lys Leu Glu Ile Lys
            100                 105


<210> SEQ ID NO 125
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 125

Trp Val Arg Gln Ala Pro Gly Lys Gly Leu Glu Trp Val Ala
1               5                   10


<210> SEQ ID NO 126
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 126

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Thr Arg
            20                  25                  30


<210> SEQ ID NO 127
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 127

Trp Gly Gln Gly Thr Met Val Thr Val Ser Ser
1               5                   10


<210> SEQ ID NO 128
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 128

Trp Val Arg Gln Ala Pro Gly Lys Arg Leu Glu Trp Val Ala
1               5                   10


<210> SEQ ID NO 129
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 129

Trp Tyr Gln Gln Lys Pro Gly Gln Pro Pro Lys Leu Leu Ile Tyr
```

1 5 10 15

<210> SEQ ID NO 130
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 130

Gly Val Pro Asp Arg Phe Ser Gly Ser Gly Ser Gly Thr Asp Phe Thr
1 5 10 15

Leu Thr Ile Ser Ser Leu Gln Ala Glu Asp Val Ala Val Tyr Tyr Cys
20 25 30

<210> SEQ ID NO 131
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 131

Phe Gly Gln Gly Thr Lys Val Glu Ile Lys
1 5 10

<210> SEQ ID NO 132
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 132

Gly Val Pro Asp Arg Phe Thr Gly Ser Gly Ser Gly Thr Asp Phe Thr
1 5 10 15

Leu Thr Ile Ser Ser Leu Gln Ala Glu Asp Val Ala Val Tyr Tyr Cys
20 25 30

<210> SEQ ID NO 133
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 133

Gln Val Thr Leu Lys Glu Ser Gly Pro Val Leu Val Lys Pro Thr Glu
1 5 10 15

Thr Leu Thr Leu Thr Cys Thr Val Ser
20 25

<210> SEQ ID NO 134
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 134

Trp Val Arg Gln Pro Pro Gly Lys Ala Leu Glu Trp Ile Ala
1 5 10

<210> SEQ ID NO 135
<211> LENGTH: 32

<212> TYPE: PRT
<213> ORGANISM: Artificial Sequence
<220> FEATURE:
<223> OTHER INFORMATION: Synthetic Peptide

<400> SEQUENCE: 135

Arg Leu Thr Ile Ser Arg Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 136
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 136

Trp Gly Gln Gly Thr Leu Val Thr Val Ser Ser
1               5                   10

<210> SEQ ID NO 137
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 137

Arg Leu Ser Ile Ser Arg Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 138
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 138

Arg Leu Thr Ile Ser Arg Asn Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 139
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 139

Gly Phe Ser Leu Thr Ser Ser Gly Val Ser
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 140

Gly Phe Ser Leu Thr Ser Gln Gly Val Ser
1 5 10

<210> SEQ ID NO 141
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 141

Gly Phe Ser Leu Thr Ser Asn Ala Val Ser
1 5 10

<210> SEQ ID NO 142
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 142

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 143
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 143

Trp Phe Gln Gln Lys Pro Gly Lys Val Pro Lys Leu Leu Ile Tyr
1 5 10 15

<210> SEQ ID NO 144
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 144

Gly Ile Pro Ser Arg Phe Ser Gly Ser Gly Ser Gly Thr Asp Phe Thr
1 5 10 15

Leu Thr Ile Ser Ser Leu Gln Pro Glu Asp Val Ala Thr Tyr Tyr Cys
20 25 30

<210> SEQ ID NO 145
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 145

Phe Gly Gly Gly Thr Lys Val Glu Ile Lys
1 5 10

<210> SEQ ID NO 146
<211> LENGTH: 15

<212> TYPE: PRT
<213> ORGANISM: Artificial Sequence
<220> FEATURE:
<223> OTHER INFORMATION: Synthetic Peptide

<400> SEQUENCE: 146

Trp Phe Gln Leu Lys Pro Gly Lys Val Pro Lys Leu Leu Ile Tyr
1 5 10 15

<210> SEQ ID NO 147
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 147

Asp Ile Gln Met Thr Gln Ser Pro Ser Ser Leu Ser Ala Ser Val Gly
1 5 10 15

Asp Arg Val Thr Ile Asn Cys
20

<210> SEQ ID NO 148
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 148

Trp Tyr Gln Gln Lys Pro Gly Lys Ala Pro Lys Val Leu Ile Phe
1 5 10 15

<210> SEQ ID NO 149
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 149

Gly Ile Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 150
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 150

Phe Gly Gln Gly Thr Lys Leu Glu Ile Lys
1 5 10

<210> SEQ ID NO 151
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 151

Ser Asn Gly Val Ser

-continued

```
1               5


<210> SEQ ID NO 152
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 152

Ser Ser Gly Val Ser
1               5


<210> SEQ ID NO 153
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 153

Arg Tyr Gly Tyr Gly Trp Tyr Phe Asp Phe
1               5                   10


<210> SEQ ID NO 154
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 154

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30


<210> SEQ ID NO 155
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 155

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```